(12) United States Patent
Lee et al.

(10) Patent No.: US 11,283,028 B2
(45) Date of Patent: Mar. 22, 2022

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD, Chungcheongnam-do (KR)

(72) Inventors: Su-Hyun Lee, Gyeonggi-do (KR); Chi-Sik Kim, Gyeonggi-do (KR); Hee-Ryong Kang, Gyeonggi-do (KR); Bitnari Kim, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 295 days.

(21) Appl. No.: 16/331,543

(22) PCT Filed: Aug. 22, 2017

(86) PCT No.: PCT/KR2017/009141
§ 371 (c)(1),
(2) Date: Mar. 8, 2019

(87) PCT Pub. No.: WO2018/066812
PCT Pub. Date: Apr. 12, 2018

(65) Prior Publication Data
US 2019/0221752 A1    Jul. 18, 2019

(30) Foreign Application Priority Data

Oct. 5, 2016 (KR) .................. 10-2016-0128230
Aug. 4, 2017 (KR) .................. 10-2017-0098913

(51) Int. Cl.
*C07D 487/04* (2006.01)
*H01L 51/00* (2006.01)
*H01L 51/50* (2006.01)

(52) U.S. Cl.
CPC ........ *H01L 51/0072* (2013.01); *C07D 487/04* (2013.01); *H01L 51/0052* (2013.01); *H01L 51/0067* (2013.01); *H01L 51/5016* (2013.01); *H01L 2251/5384* (2013.01)

(58) Field of Classification Search
CPC .................. C07D 487/04; H01L 51/0072
See application file for complete search history.

(56) References Cited

U.S. PATENT DOCUMENTS

| 9,156,843 | B2 | 10/2015 | Kai et al. |
| 2011/0062429 | A1 † | 3/2011 | Kai |
| 2016/0225992 | A1 * | 8/2016 | Ito .................. C09B 57/001 |

FOREIGN PATENT DOCUMENTS

| JP | 2012520872 A † | 9/2012 |
| KR | 10-2015-0077513 A | 7/2015 |
| WO | 2009136595 A1 | 11/2009 |
| WO | 2017/183859 A1 | 10/2017 |

OTHER PUBLICATIONS

SciFinder Search (Year: 2021).*

* cited by examiner
† cited by third party

Primary Examiner — Vu A Nguyen
(74) Attorney, Agent, or Firm — G. Creston Campbell

(57) ABSTRACT

The present disclosure relates to an organic electroluminescent compound and an organic electroluminescent device comprising the same. The organic electroluminescent compound of the present disclosure can provide an organic electroluminescent device having low driving voltage and/or high power efficiency properties.

4 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

An organic EL device (OLED) changes electric energy into light by applying electricity to an organic light-emitting material, and commonly comprises an anode, a cathode, and an organic layer formed between the two electrodes. The organic layer of the organic EL device may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc, if necessary. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on functions. In the organic EL device, holes from an anode and electrons from a cathode are injected into a light-emitting layer by the application of electric voltage, and an exciton having high energy is produced by the recombination of the holes and electrons. The organic light-emitting compound moves into an excited state by the energy and emits light from energy when the organic light-emitting compound returns to the ground state from the excited state.

The most important factor determining luminous efficiency in an organic EL device is light-emitting materials. The light-emitting materials are required to have the following features: high quantum efficiency, high movement degree of an electron and a hole, and uniformality and stability of the formed light-emitting material layer. The light-emitting material is classified into blue, green, and red light-emitting materials according to the light-emitting color, and further includes yellow or orange light-emitting materials. Furthermore, the light-emitting material is classified into a host material and a dopant material in a functional aspect. Recently, an urgent task is the development of an organic EL device having high efficiency and long lifespan. In particular, the development of highly excellent light-emitting material over conventional materials is urgently required, considering the EL properties necessary for medium- and large-sized OLED panels.

Although the conventional materials provide good luminous characteristics, they have the following disadvantages: (1) Due to their low glass transition temperature and poor thermal stability, their degradation may occur during a high-temperature deposition process in a vacuum, and the lifespan of the device may be shortened. (2) The power efficiency of the organic electroluminescent device is given by [($\pi$/voltage)×current efficiency], and the power efficiency is inversely proportional to the voltage. Although the organic electroluminescent device comprising phosphorescent host materials provides higher current efficiency (cd/A) than one comprising fluorescent materials, a significantly high driving voltage is necessary. Thus, there is no merit in terms of power efficiency (lm/W). (3) Also, the operational lifespan of the organic electroluminescent device is short, and improving luminous efficiency is still necessary. Accordingly, the materials constituting the organic layer in the device, in particular a host or a dopant constituting the light-emitting material, should be selected appropriately in order to realize the excellent characteristics of the organic EL device.

Meanwhile, an indolocarbazole derivative is usually used as a host HOMO component in order to improve the voltage properties of an organic electroluminescent device. However, there is a need to improve the conventional indolocarbazole in order to further lower the driving voltage.

Korean Patent No. 1313730 discloses an indolocarbazole compound as an organic electroluminescent compound, but does not specifically disclose a benzo-indolocarbazole structure.

Korean Patent Application Laid-Open No. 2015-77513 discloses a [c]benzo-indolocarbazole structure as an organic electroluminescent compound from the viewpoint of HOMO, but does not specifically disclose a [a]benzo-indolocarbazole or [b]benzo-indolocarbazole structure.

DISCLOSURE OF THE INVENTION

Problems to be Solved

The object of the present disclosure is to provide an organic electroluminescent compound effective for producing an organic electroluminescent device having low driving voltage and/or high power efficiency properties.

Solution to Problems

As a result of intensive studies to solve the technical problem above, the present inventors found that the organic electroluminescent device can achieve low driving voltage and/or improved power efficiency by comprising a benzo-indolocarbazole derivative, especially a [a]benzo-indolocarbazole or [b]benzo-indolocarbazole derivative. Specifically, the above objective can be achieved by the organic electroluminescent compound represented by the following formula 1:

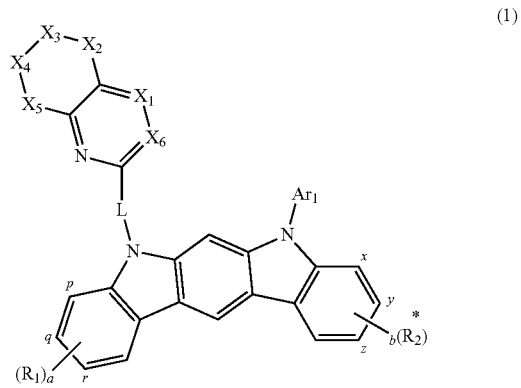

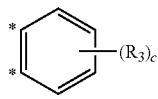
(1-a)

wherein at least one of both x and y, both y and z, both p and q, and both q and r are fused with the * positions in formula 1-a, with the proviso that the case where both x and y, and both y and z are simultaneously fused with the * positions in formula 1-a, and the case where both p and q, and both q and r are simultaneously fused with the * positions in formula 1-a, are excluded;

L represents a single bond, a substituted or unsubstituted (C6-C30)arylene, or a substituted or unsubstituted (5- to 30-membered)heteroarylene;

$X_1$ to $X_6$, each independently, represent N or $CR_4$, with the proviso, at least one of $X_1$ to $X_6$ represents N;

$Ar_1$ represents a substituted or unsubstituted (C6-C30) aryl, or a substituted or unsubstituted (5- to 30-membered) heteroaryl;

$R_1$ to $R_4$, each independently, represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (3- to 7-membered)heterocycloalkyl, a substituted or unsubstituted (C6-C30)aryl(C1-C30)alkyl, $-NR_{11}R_{12}$, $-SiR_{13}R_{14}R_{15}$, $-SR_{16}$, $-OR_{17}$, a cyano, a nitro, or a hydroxyl;

$R_{11}$ to $R_{17}$, each independently, represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; or are linked to an adjacent substituent to form a substituted or unsubstituted, mono- or polycyclic, (3- to 30-membered) alicyclic or aromatic ring, or the combination thereof, which may comprise at least one heteroatom selected from nitrogen, oxygen, and sulfur;

a to c, each independently, represent an integer of 1 to 4, where if a to c, each independently, are an integer of 2 or more, each of $R_1$ to $R_3$ may be the same or different; and the heteroaryl(ene) or the heterocycloalkyl contains at least one heteroatom selected from B, N, O, S, Si, and P.

Effects of the Invention

By comprising the organic electroluminescent compound according to the present disclosure, it is possible to provide an organic electroluminescent device having low driving voltage and/or high power efficiency properties.

EMBODIMENTS OF THE INVENTION

Hereinafter, the present disclosure will be described in detail. However, the following description is intended to explain the disclosure, and is not meant in any way to restrict the scope of the disclosure.

The term "an organic electroluminescent compound" in the present disclosure means a compound that may be used in an organic electroluminescent device, and may be comprised in any layers constituting an organic electroluminescent device, if necessary.

The term "an organic electroluminescent material" in the present disclosure means a material that may be used in an organic electroluminescent device, and may comprise at least one compound. If necessary, the organic electroluminescent material may be comprised in any layers constituting an organic electroluminescent device. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material, etc.

The organic electroluminescent material of the present disclosure may comprise at least one compound represented by formula 1. Although not limited thereto, the compound of formula 1 may be included in the light-emitting layer. In this case, the compound of formula 1 may be included as a host.

Hereinafter, the organic electroluminescent compound represented by formula 1 will be described in more detail.

In formula 1, at least one of both x and y, both y and z, both p and q, and both q and r are fused with the * positions in formula 1-a, with the proviso that the case where both x and y, and both y and z are simultaneously fused with the * positions in formula 1-a, and the case where both p and q, and both q and r are simultaneously fused with the * positions in formula 1-a, are excluded. The meaning of both x and y in formula 1 being fused with the * positions in formula 1-a is that the benzene ring containing x and y in formula 1 and the benzene ring in formula 1-a are fused to at the x and y positions in formula 1 and two * positions in formula 1-a each other to form a naphthalene ring. According to one embodiment of the present disclosure, both x and y, or both y and z; and/or both p and q, or both q and r in formula 1 are fused with the * positions in formula 1-a to form at least one ring. According to another embodiment of the present disclosure, both x and y, both y and z, both p and q, or both q and r in formula 1 are fused with the * positions in formula 1-a to form one ring. According to another embodiment of the present disclosure, both x and y, or both y and z in formula 1 are fused with the * positions in formula 1-a to form one ring.

In formula 1, L represents a single bond, a substituted or unsubstituted (C6-C30)arylene, or a substituted or unsubstituted (5- to 30-membered)heteroarylene; as one embodiment, a single bond, a substituted or unsubstituted (C6-C25) arylene, or a substituted or unsubstituted (5- to 25-membered)heteroarylene; and as another embodiment, a single bond, an unsubstituted (C6-C18)arylene, or an unsubstituted (5- to 18-membered)heteroarylene. For example, L represents a single bond, an unsubstituted phenylene, an unsubstituted naphthylene, or an unsubstituted pyridinylene.

In formula 1,

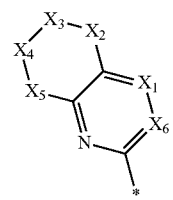

may represent a substituted or unsubstituted quinoxalinyl, a substituted or unsubstituted quinazolinyl, a substituted or unsubstituted naphthyridinyl, a substituted or unsubstituted pyridopyrimidinyl, or a substituted or unsubstituted pyridopyrazinyl; as one embodiment, may represent a substituted or unsubstituted quinoxalinyl, or a substituted or unsubstituted quinazolinyl; and as another embodiment, may represent a substituted or unsubstituted quinoxalinyl.

In formula 1, Ar₁ represents a substituted or unsubstituted (C6-C30)aryl, or a substituted or unsubstituted (5- to 30-membered)heteroaryl; as one embodiment, may represent a substituted or unsubstituted (C6-C25)aryl, or a substituted or unsubstituted (5- to 25-membered)heteroaryl; as another embodiment, may represent a (C6-C18)aryl unsubstituted or substituted with (C1-C6)alkyl, or an unsubstituted (5- to 18-membered)heteroaryl; and for example, may represent an unsubstituted phenyl, an unsubstituted naphthyl, a fluorenyl substituted with dimethyl, an unsubstituted phenanthrenyl, or an unsubstituted pyridyl.

In formula 1, R₁ to R₄, each independently, represent hydrogen, deuterium, a halogen, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (3- to 7-membered)heterocycloalkyl, a substituted or unsubstituted (C6-C30)aryl(C1-C30)alkyl, —NR₁₁R₁₂, —SiR₁₃R₁₄R₁₅, —SR₁₆, —OR₁₇, a cyano, a nitro, or a hydroxyl; as one embodiment, may represent hydrogen, or a substituted or unsubstituted (C6-C25)aryl; as another embodiment, may represent hydrogen, or a (C6-C18)aryl unsubstituted or substituted with (C1-C6)alkyl. According to another embodiment of the present disclosure, R₁ may represent hydrogen, or an unsubstituted (C6-C18)aryl, R₂ and R₃ may represent hydrogen, and R₄ may represent hydrogen, an unsubstituted (C6-C18)aryl, or an unsubstituted (C1-C4)alkyl(C6-C18)aryl. For example, R₁ may represent hydrogen, or an unsubstituted phenyl, R₂ and R₃ may represent hydrogen, R₄ may represent hydrogen, an unsubstituted phenyl, an unsubstituted naphthyl, an unsubstituted biphenyl, an unsubstituted naphthylphenyl, an unsubstituted dimethylfluorenyl, or an unsubstituted phenanthrenyl. Also, when X₁ or X₆ represents CR₄, R₄ may represent (C6-C18) aryl unsubstituted or substituted with (C1-C6)alkyl, and when X₂ to X₅ represent CR₄, R₄ may represent hydrogen. R₁₁ to R₁₇, each independently, represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, a substituted or unsubstituted (3- to 7-membered)heterocycloalkyl, or a substituted or unsubstituted (C3-C30)cycloalkyl; or are linked to an adjacent substituent to form a substituted or unsubstituted, mono- or polycyclic, (3- to 30-membered) alicyclic or aromatic ring, or the combination thereof, which may comprise at least one heteroatom selected from nitrogen, oxygen, and sulfur.

In formula 1, a to c, each independently, represent an integer of 1 to 4, as one embodiment, an integer of 1 or 2; and as another embodiment, an integer of 1. If a to c, each independently, are an integer of 2 or more, each of R₁ to R₃ may be the same or different.

In formula 1, the heteroaryl(ene) or the heterocycloalkyl contains at least one heteroatom selected from B, N, O, S, Si, and P; as one embodiment, at least one heteroatom selected from N, O and S; and as another embodiment, at least one N.

According to one embodiment of the present disclosure, formula 1 may be represented by any one of the following formulas 2 to 5:

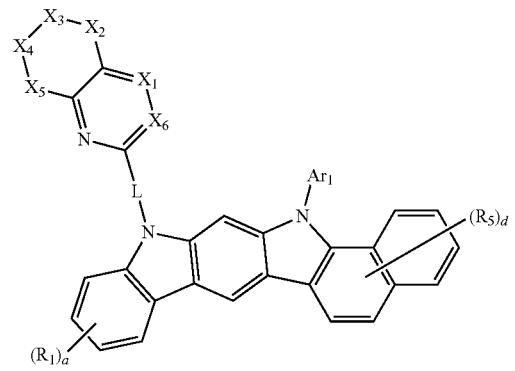

(2)


(3)

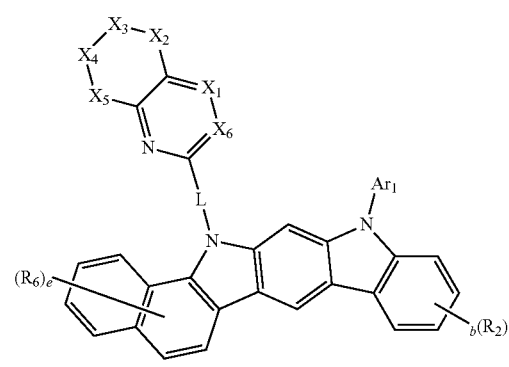

(4)

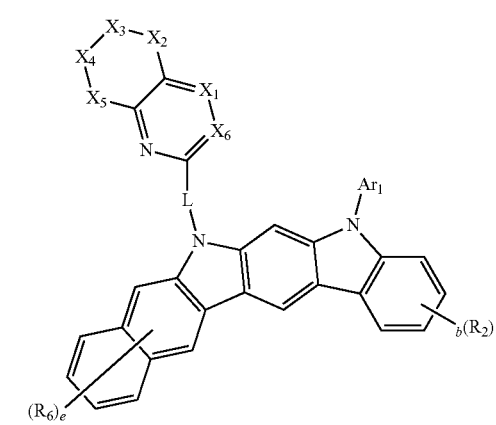

(5)

In formulas 2 to 5, L, Ar₁, R₁, R₂, X₁ to X₆, a and b are as defined in formula 1.

In formulas 2 to 5, $R_5$ and $R_6$, each independently, are as defined in $R_1$ and $R_2$.

In formulas 2 to 5, d and e, each independently, represent an integer of 1 to 6; as one embodiment, an integer of 1 or 2; and as another embodiment, an integer of 1. If d and e, each independently, are an integer of 2 or more, each of $R_5$ and $R_6$ may be the same or different.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, isobutyl, tert-butyl, etc. The term "(C3-C30)cycloalkyl" is a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered) heterocycloalkyl" is a cycloalkyl having 3 to 7, preferably 5 to 7, ring backbone atoms, and including at least one heteroatom selected from the group consisting of the group consisting of B, N, O, S, Si, and P, and preferably the group consisting of the group consisting of O, S, and N. The above heterocycloalkyl may include tetrahydrofuran, pyrrolidine, thiolan, tetrahydropyran, etc. The term "(C6-C30)aryl(ene)" is a monocyclic or fused ring radical derived from an aromatic hydrocarbon having 6 to 30 ring backbone carbon atoms, in which the number of the ring backbone carbon atoms is preferably 6 to 25, more preferably 6 to 18. The above aryl(ene) may be partially saturated, and may comprise a spiro structure. The above aryl may include phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. The term "(5- to 30-membered)heteroaryl(ene)" is an aryl having 5 to 30 ring backbone atoms, and including at least one, preferably 1 to 4 heteroatoms selected from the group consisting of the group consisting of B, N, O, S, Si, and P. The above heteroaryl(ene) may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, naphthyridinyl, carbazolyl, benzocarbazolyl, dibenzocarbazolyl, phenoxazinyl, phenothiazinyl, phenanthridinyl, benzodioxolyl, and dihydroacridinyl. Furthermore, "halogen" includes F, Cl, Br, and I.

Herein, "substituted" in the expression "substituted or unsubstituted" means that a hydrogen atom in a certain functional group is replaced with another atom or another functional group, i.e. a substituent. The substituents of the substituted alkyl, the substituted aryl(ene), the substituted heteroaryl(ene), the substituted cycloalkyl, the substituted heterocycloalkyl, the substituted aralkyl, and the substituted mono- or polycyclic, alicyclic or aromatic ring, or the combination thereof, in L, $Ar_1$, $R_1$ to $R_4$, and $R_{11}$ to $R_{17}$ of formulas 1 and 1-a, each independently, are at least one selected from the group consisting of deuterium, a halogen, a cyano, a carboxyl, a nitro, a hydroxyl, a (C1-C30)alkyl, a halo(C1-C30)alkyl, a (C2-C30)alkenyl, a (C2-C30)alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (C6-C30)aryl, a (5- to 30-membered)heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30)alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl; as one embodiment, each independently, are at least one selected from the group consisting of a (C1-C20)alkyl, a (5- to 25-membered)heteroaryl unsubstituted or substituted with (C6-C25)aryl, a (C6-C25)aryl, and a (C1-C20)alkyl(C6-C25)aryl; as another embodiment, each independently, are at least one selected from the group consisting of a (C1-C10)alkyl and a (C6-C18)aryl; and for example, at least one selected from the group consisting of methyl and naphthyl.

The compound represented by formula 1 includes the following compounds, but is not limited thereto:

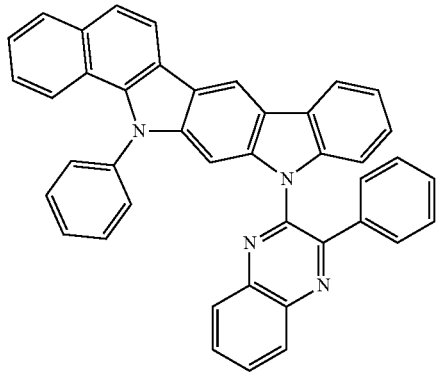

H-1

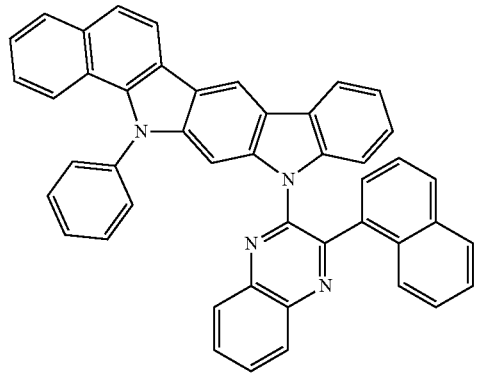

H-2

-continued
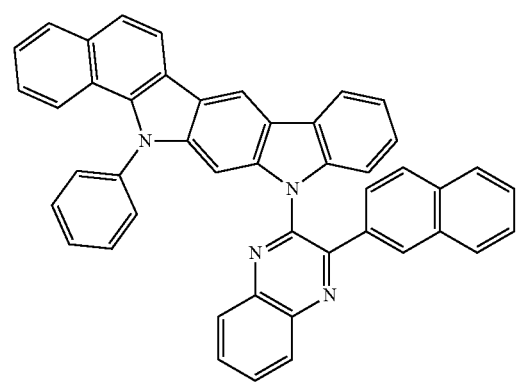
H-3
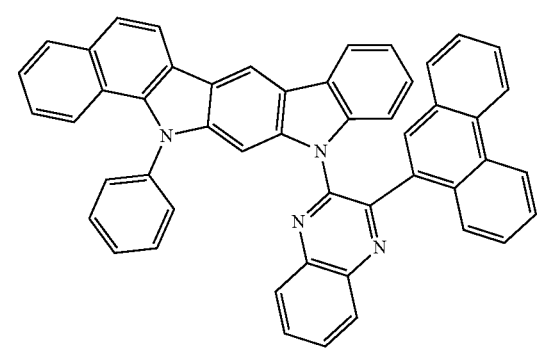
H-4
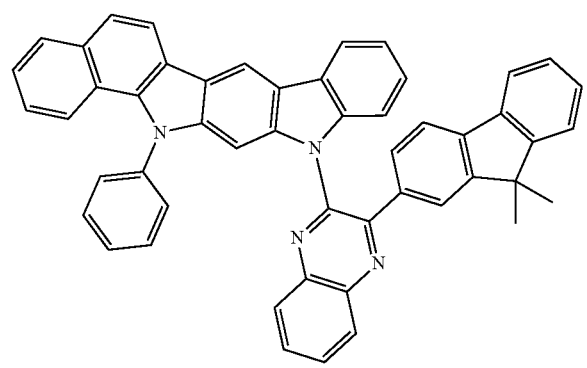
H-5
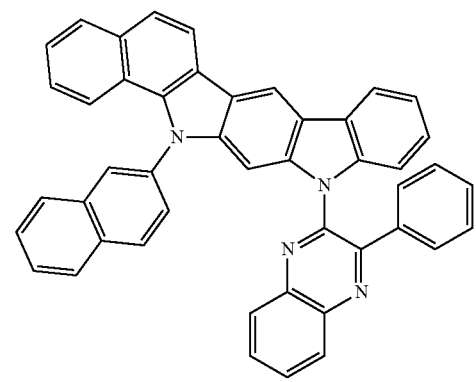
H-6
-continued
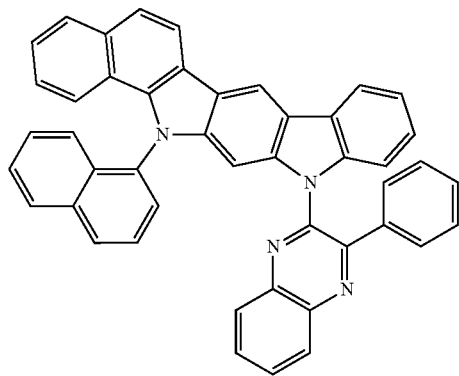
H-7
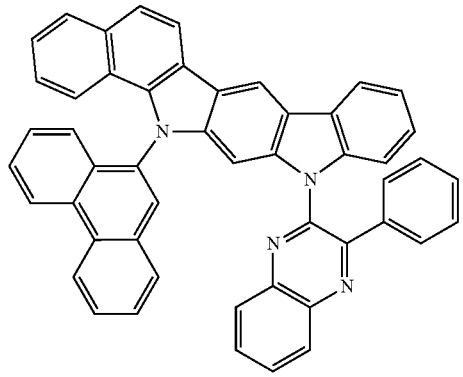
H-8
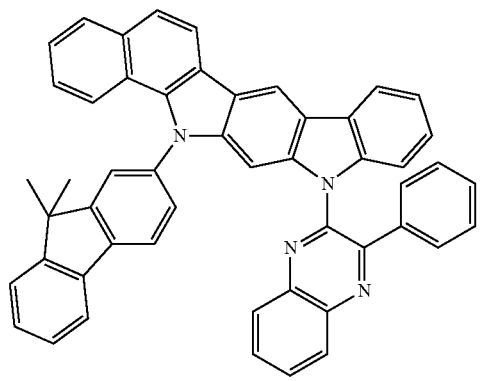
H-9
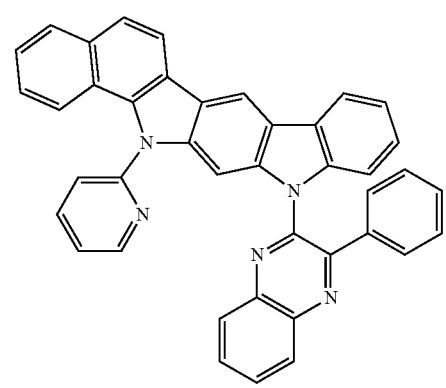
H-10

-continued
H-11
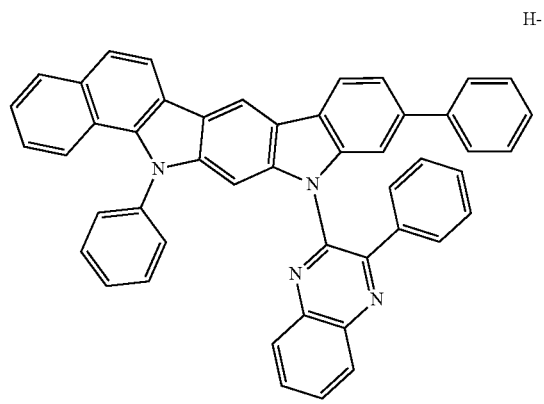
H-12
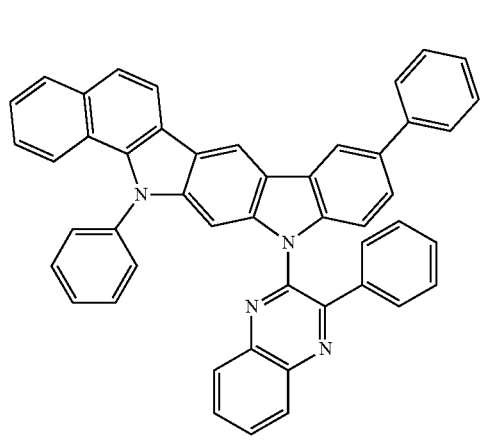
H-13
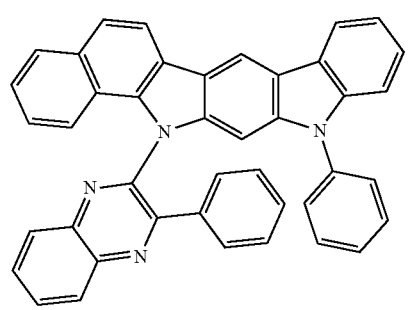
H-14
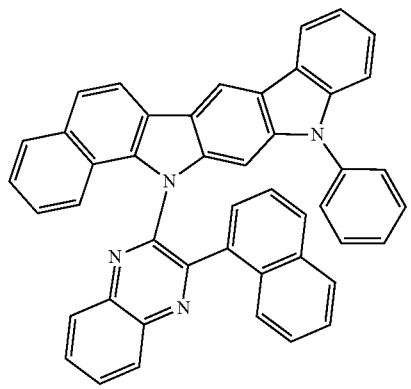
-continued
H-15
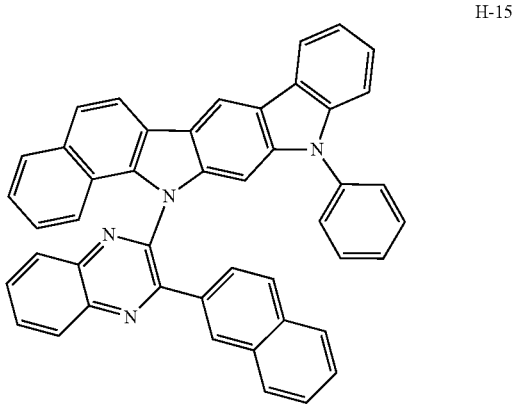
H-16
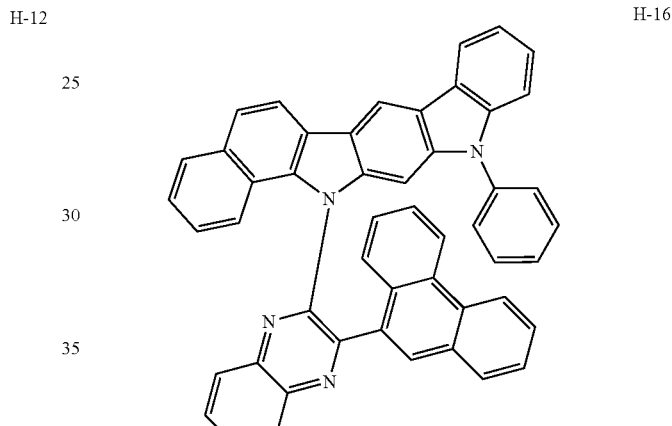
H-17
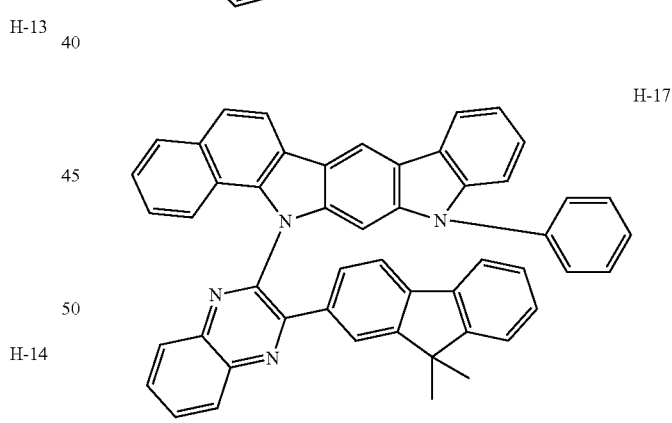
H-18
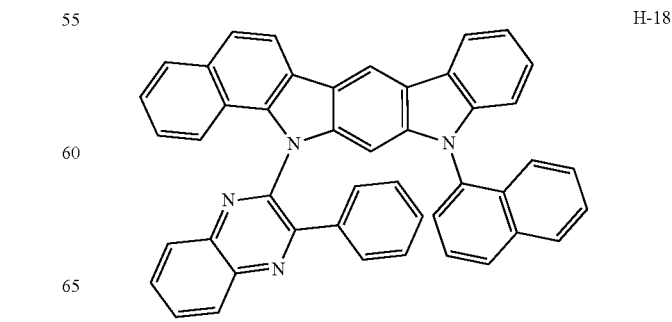

-continued
H-19
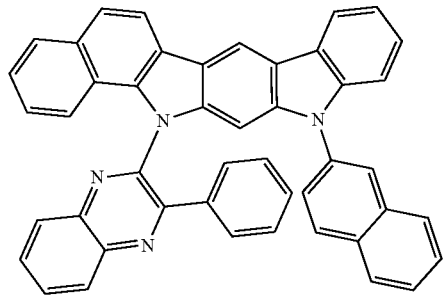
H-20
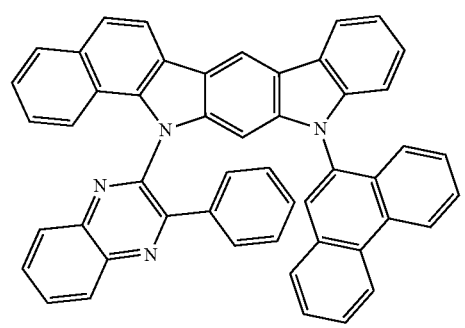
H-21
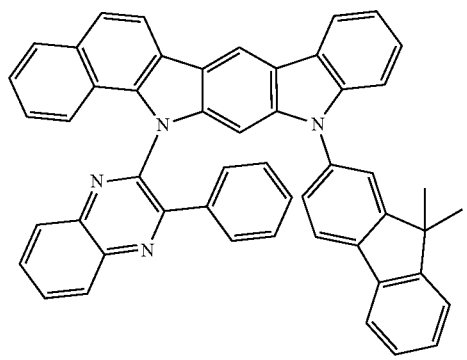
H-22
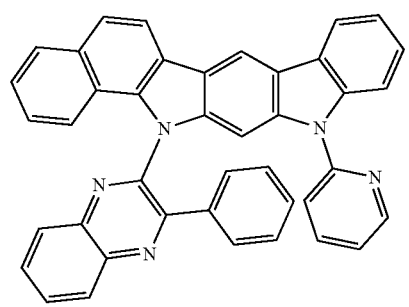
H-23
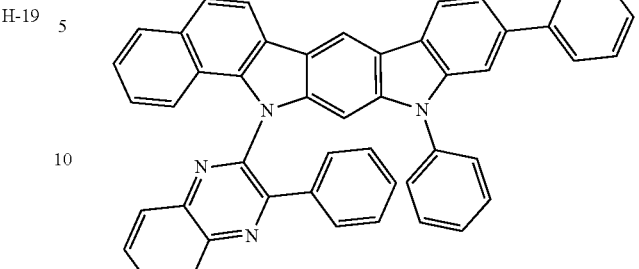
H-24
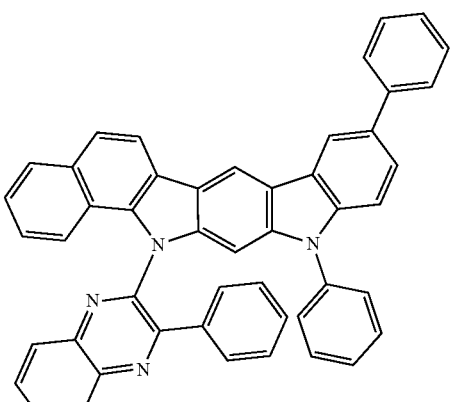
H-25
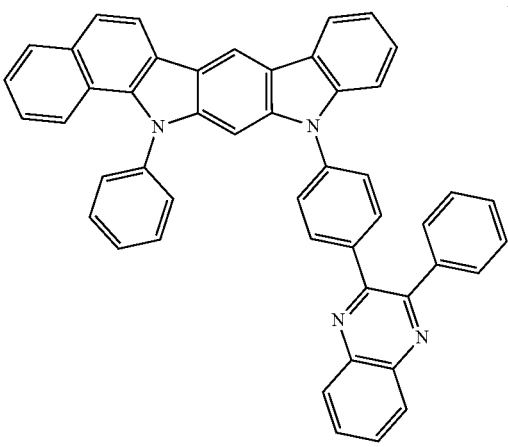
H-26
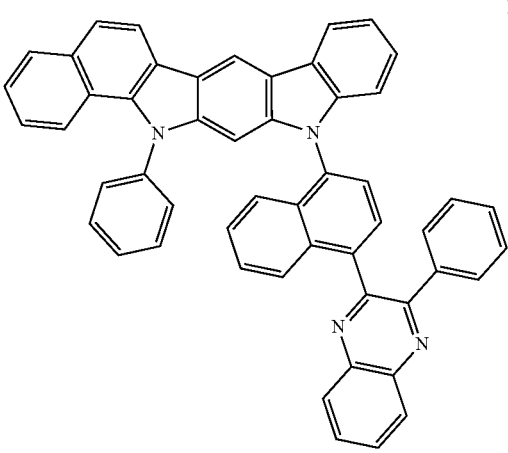

H-27
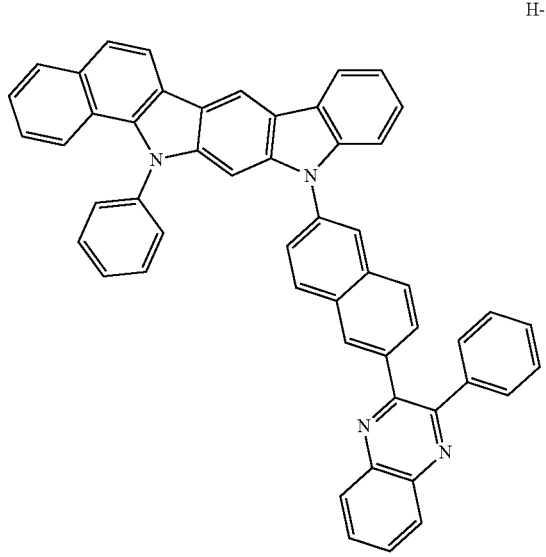
H-28
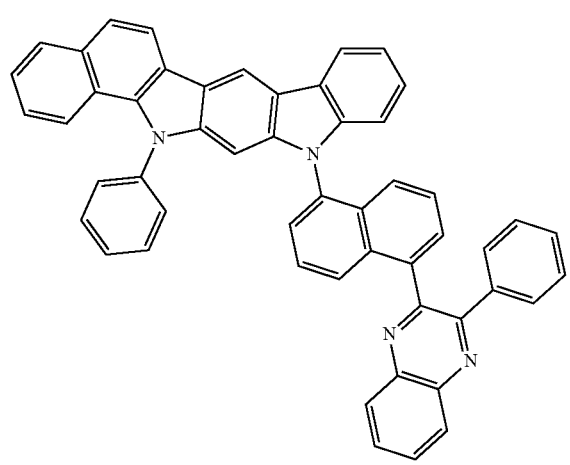
H-29
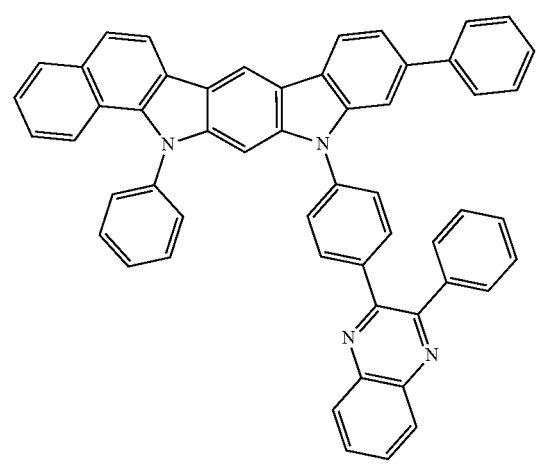
H-30
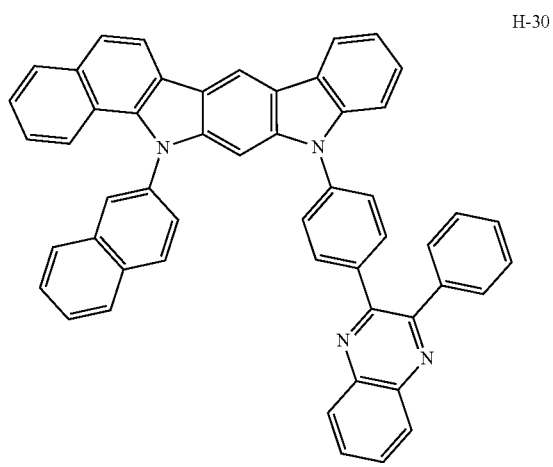
H-31
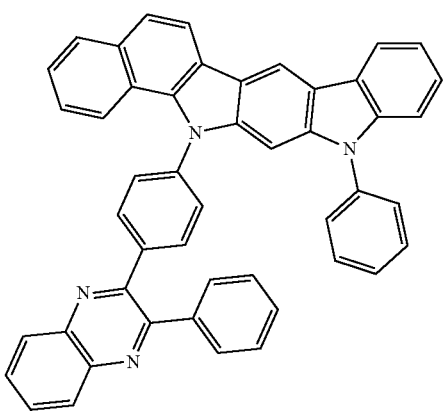
H-32
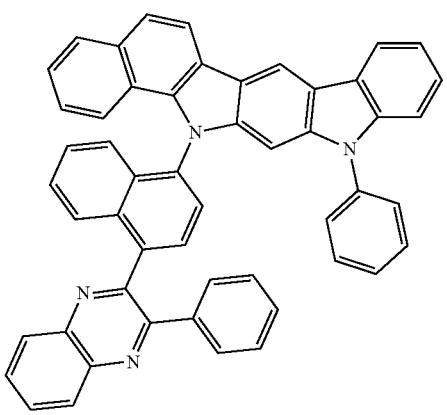

H-33
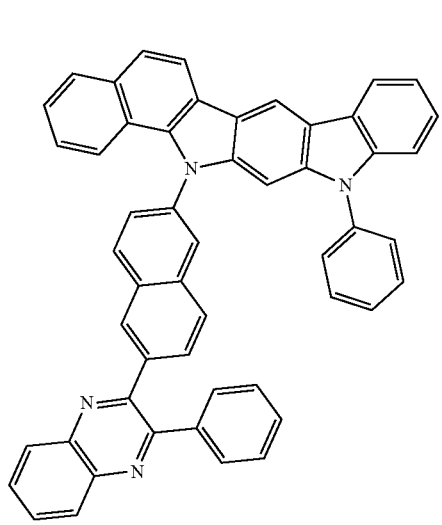
H-34
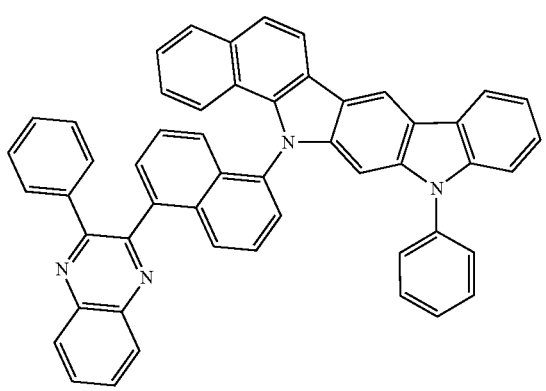
H-35
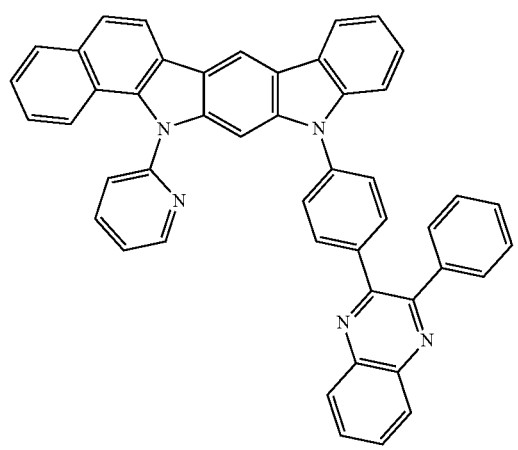
H-36
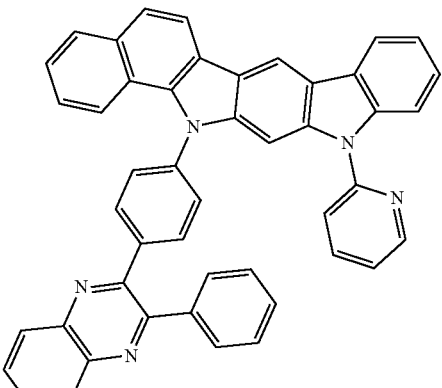
H-37
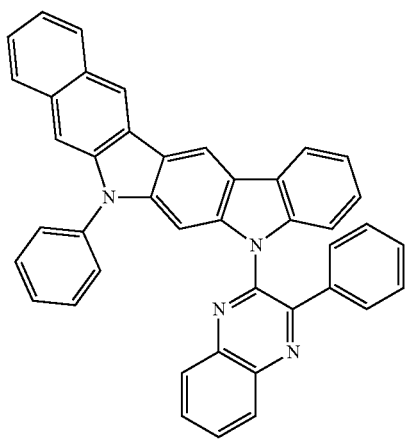
H-38
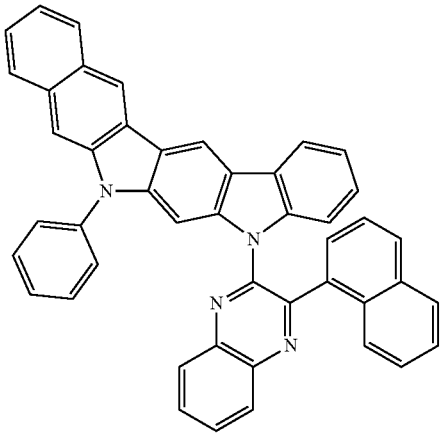

H-39
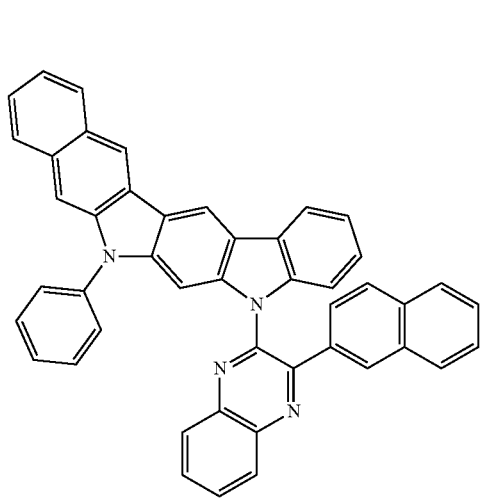
H-40
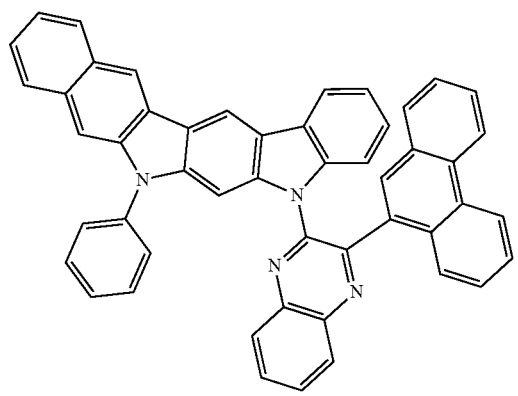
H-41
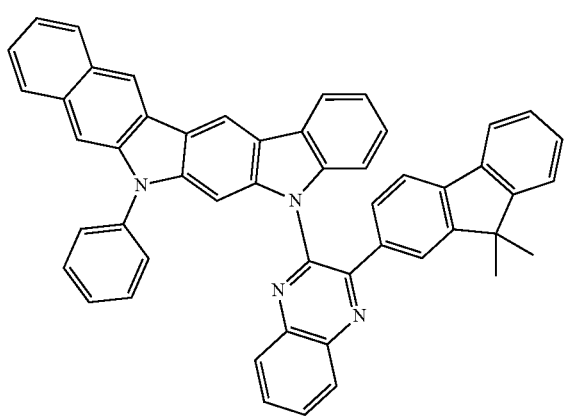
H-42
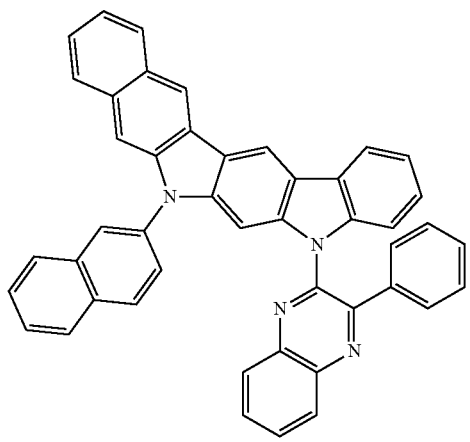
H-43
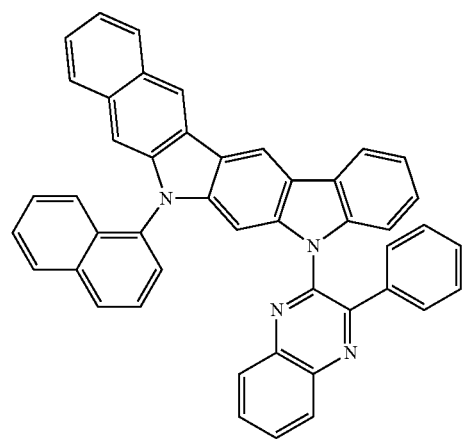
H-44
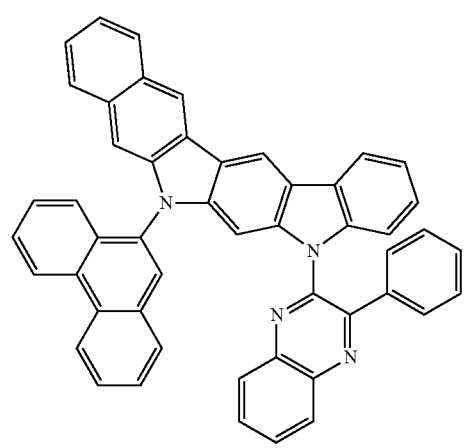

-continued
H-45
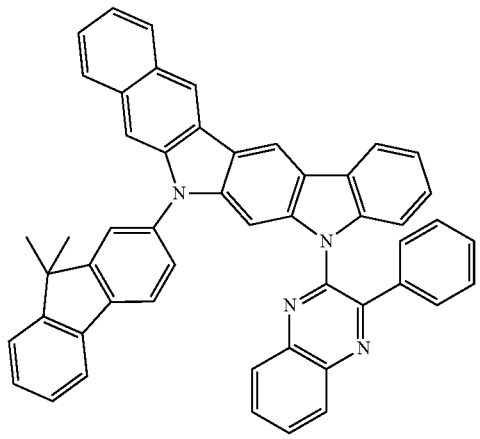
H-46
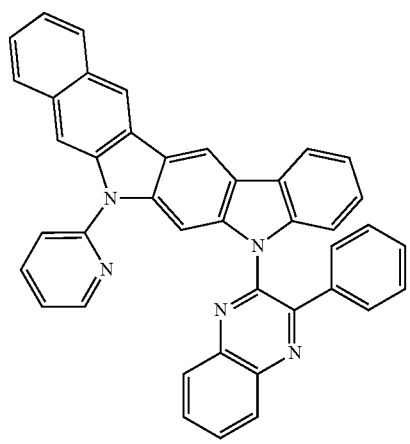
H-47
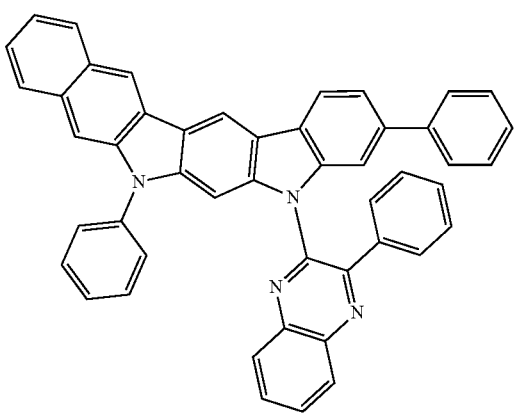
-continued
H-48
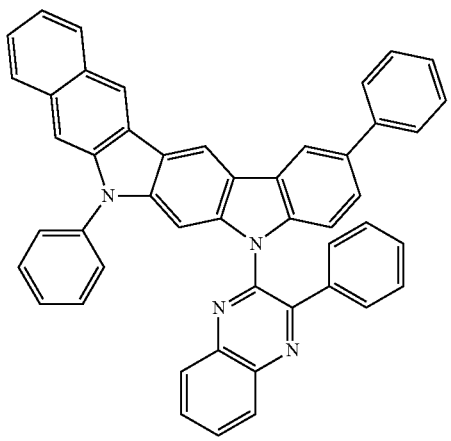
H-49
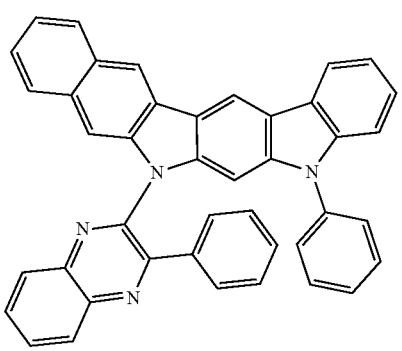
H-50
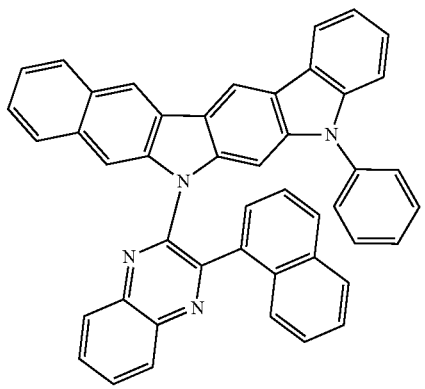
H-51
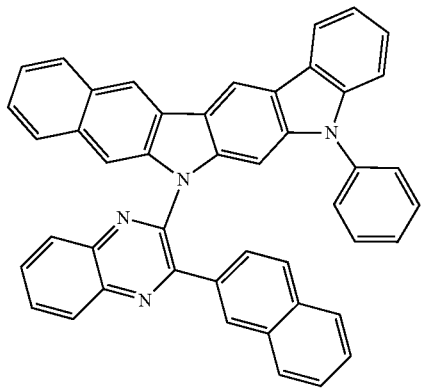

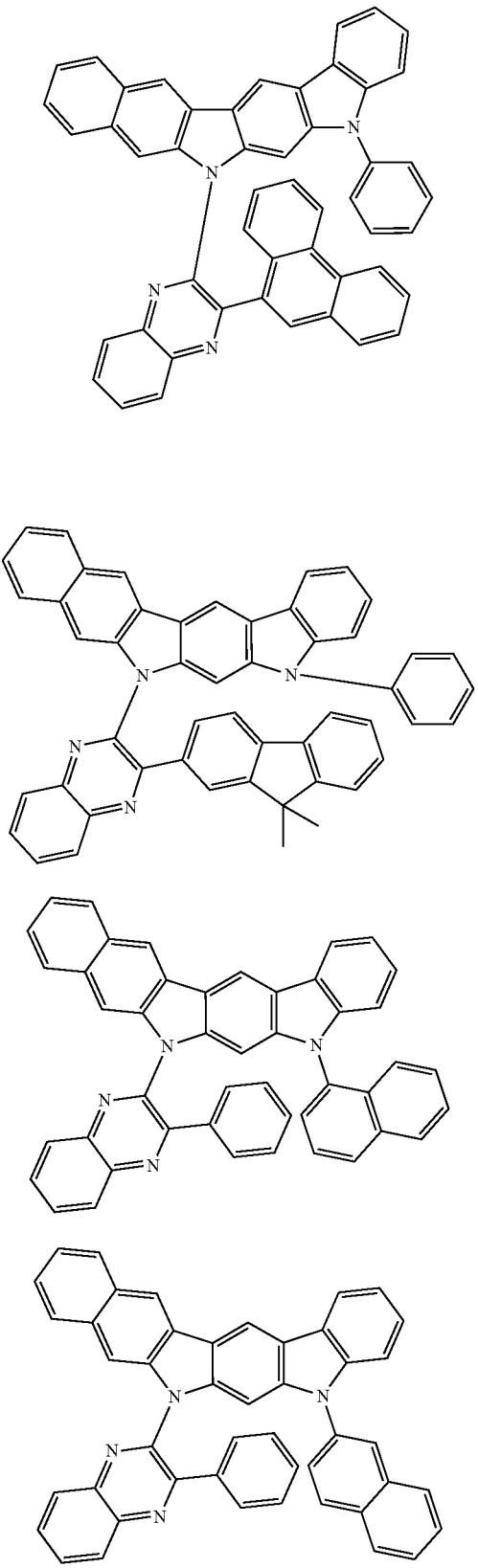
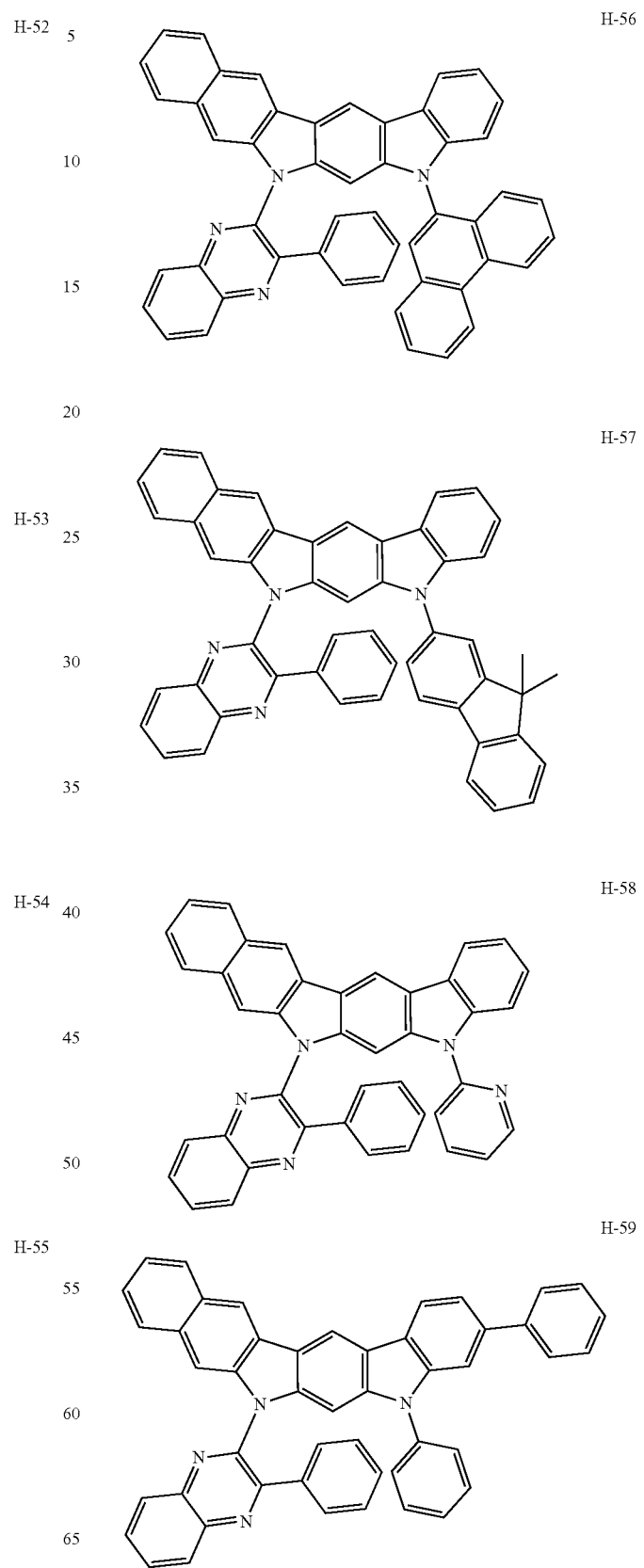

H-60
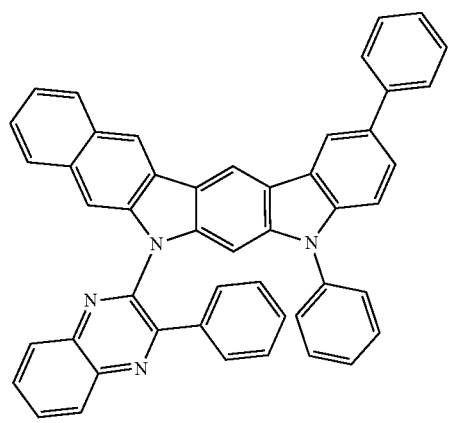
H-63
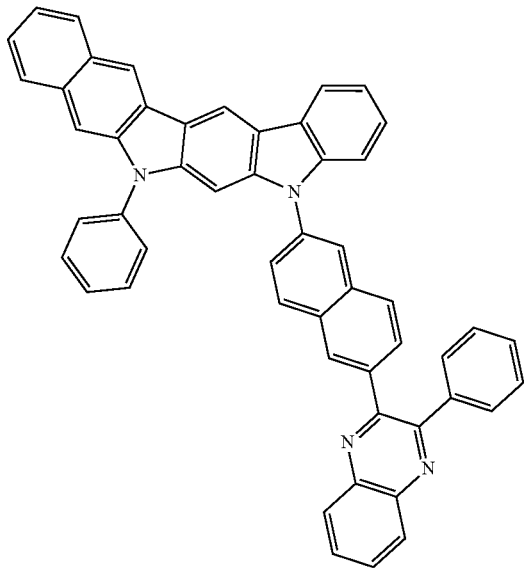
H-61
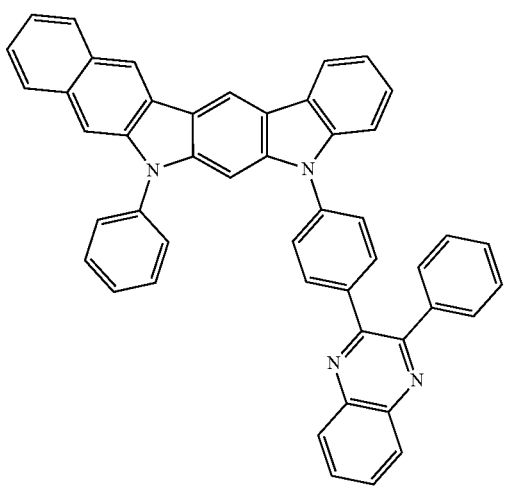
H-64
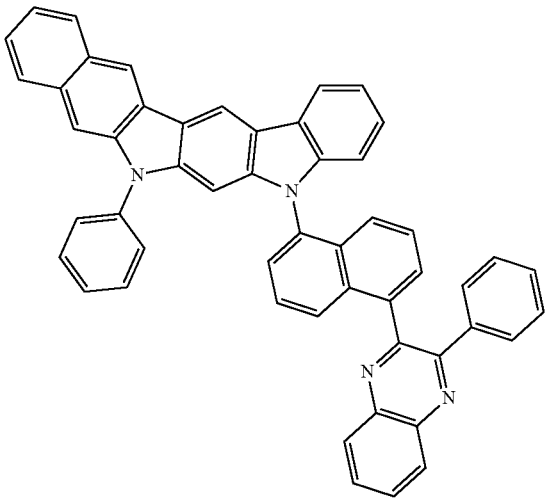
H-62
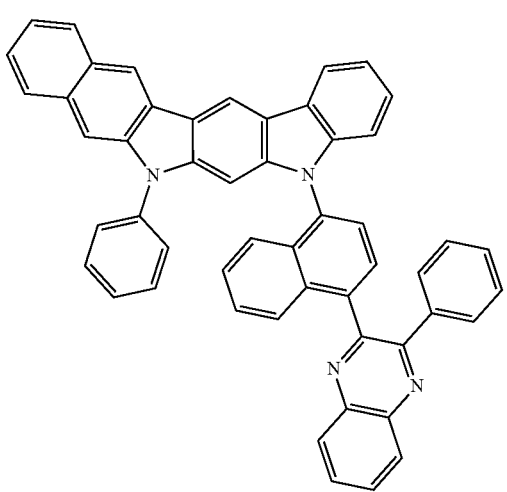
H-65
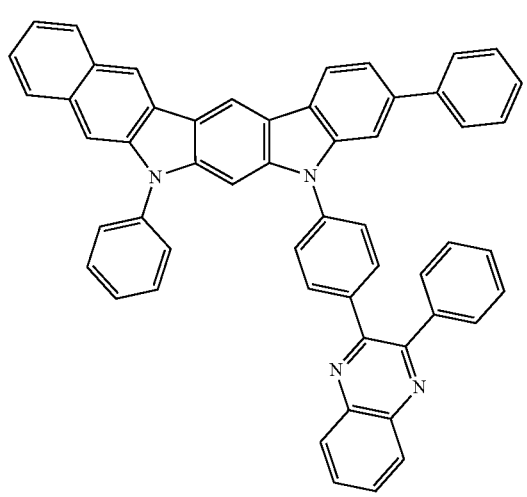

H-66
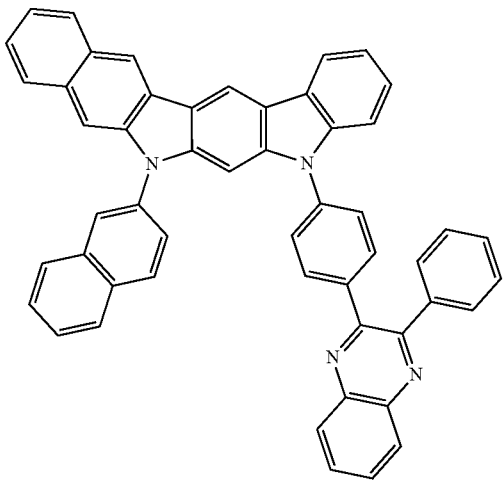
H-67
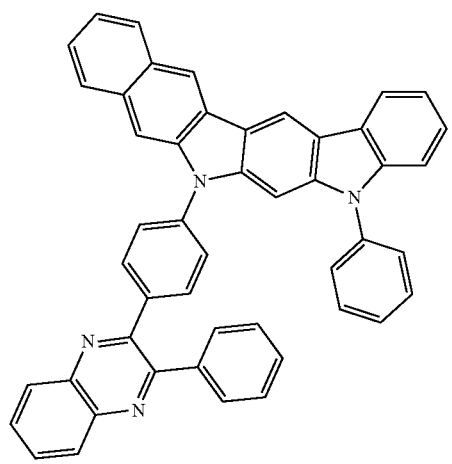
H-68
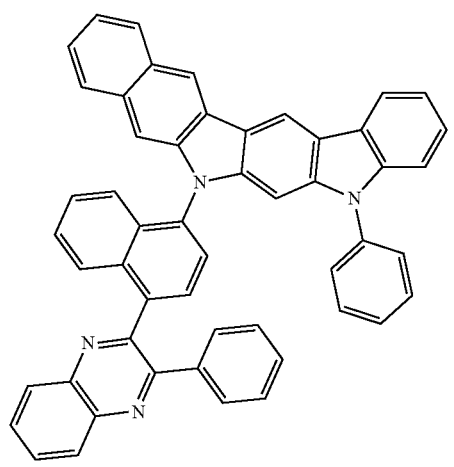
H-69
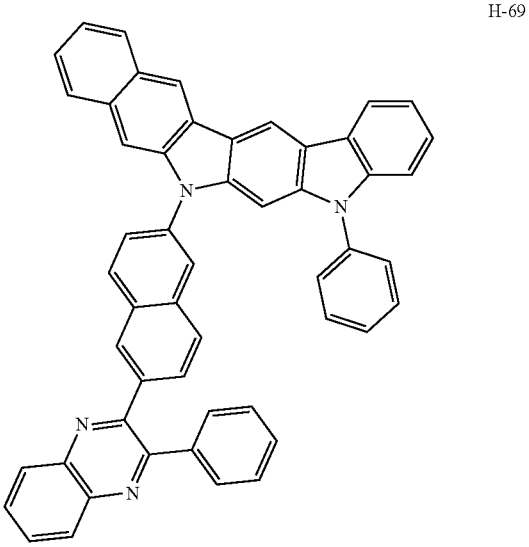
H-70
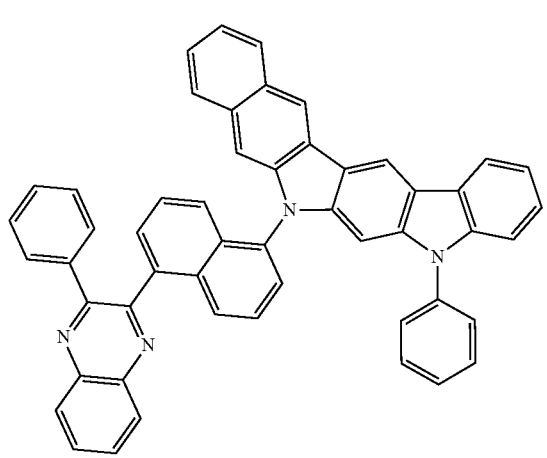
H-71
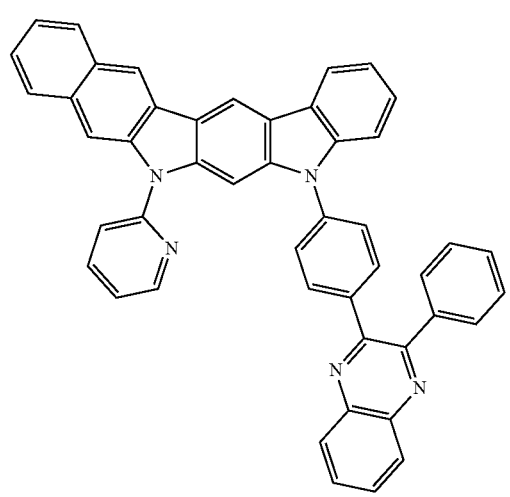

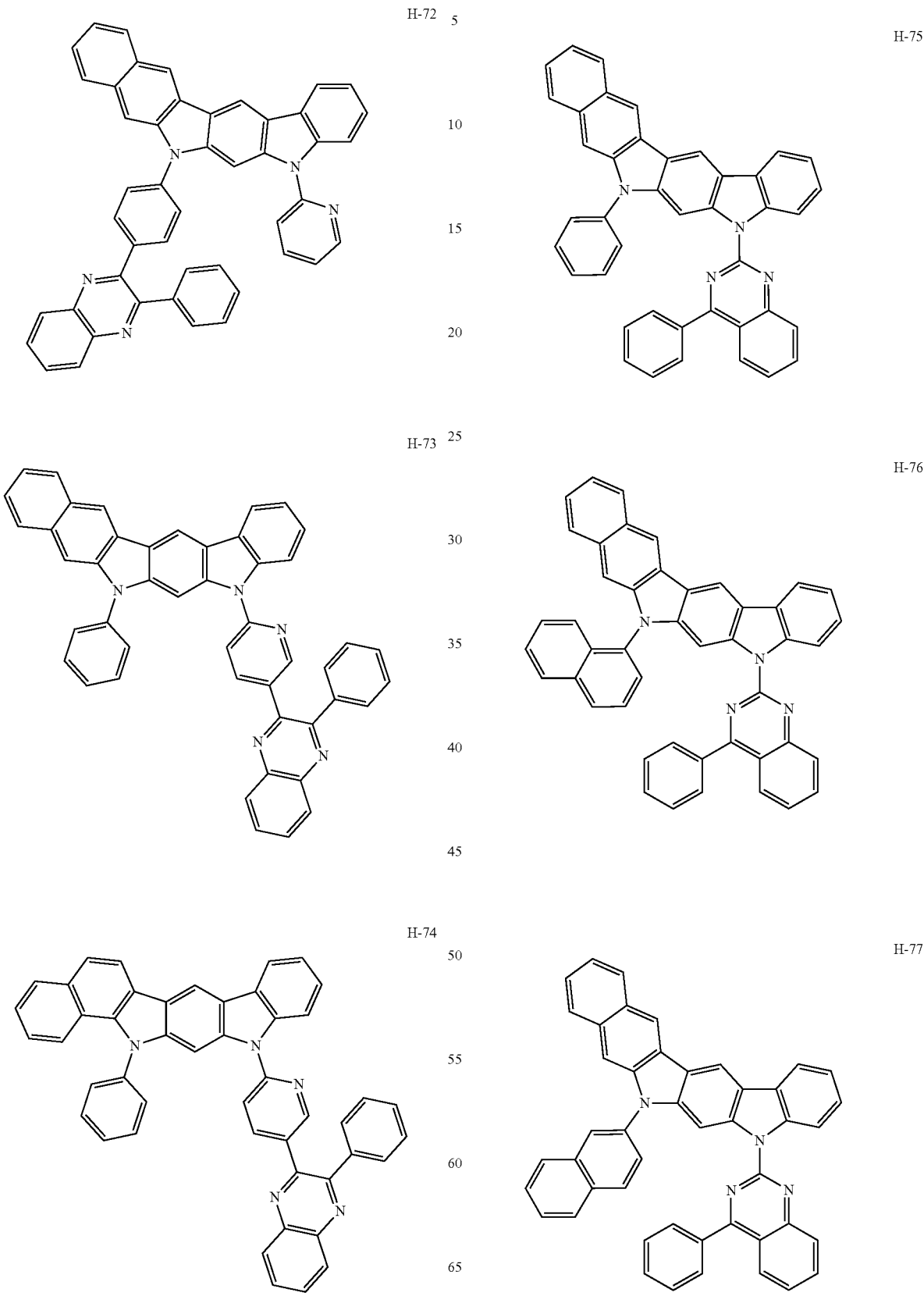

H-78
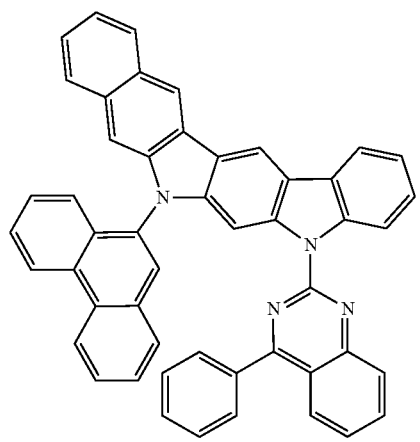
H-79
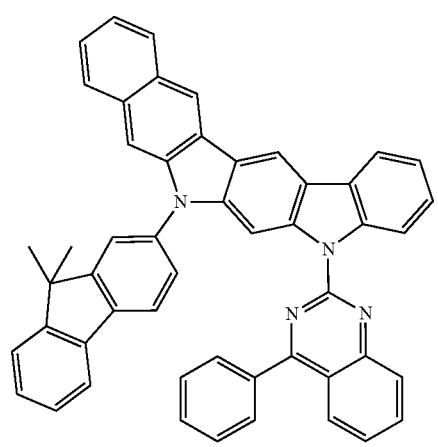
H-80
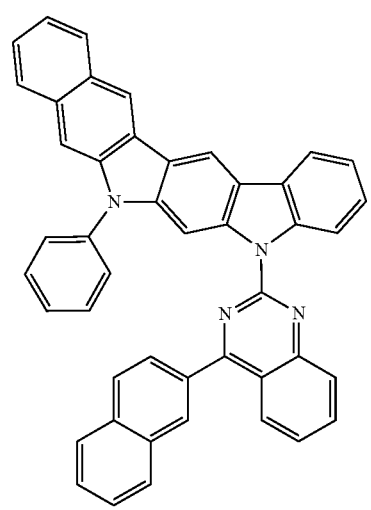
H-81
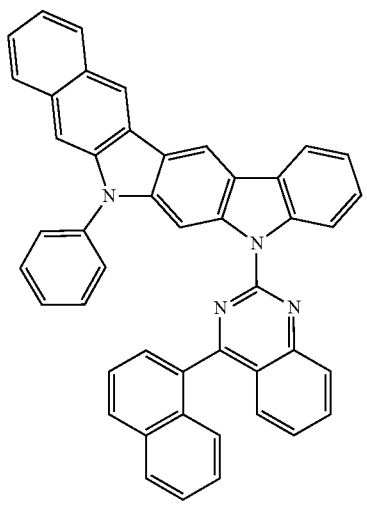
H-82
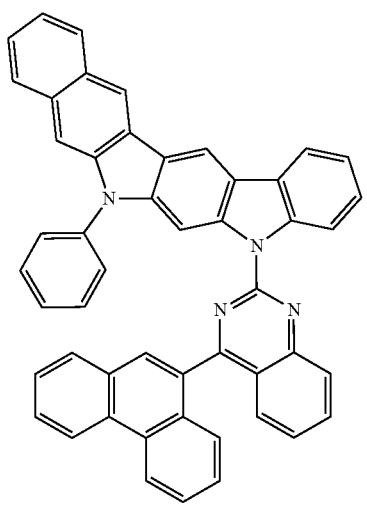
H-83
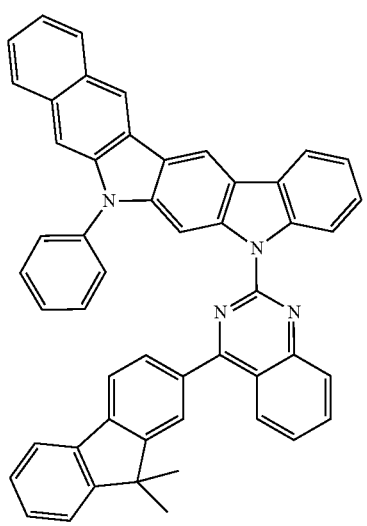

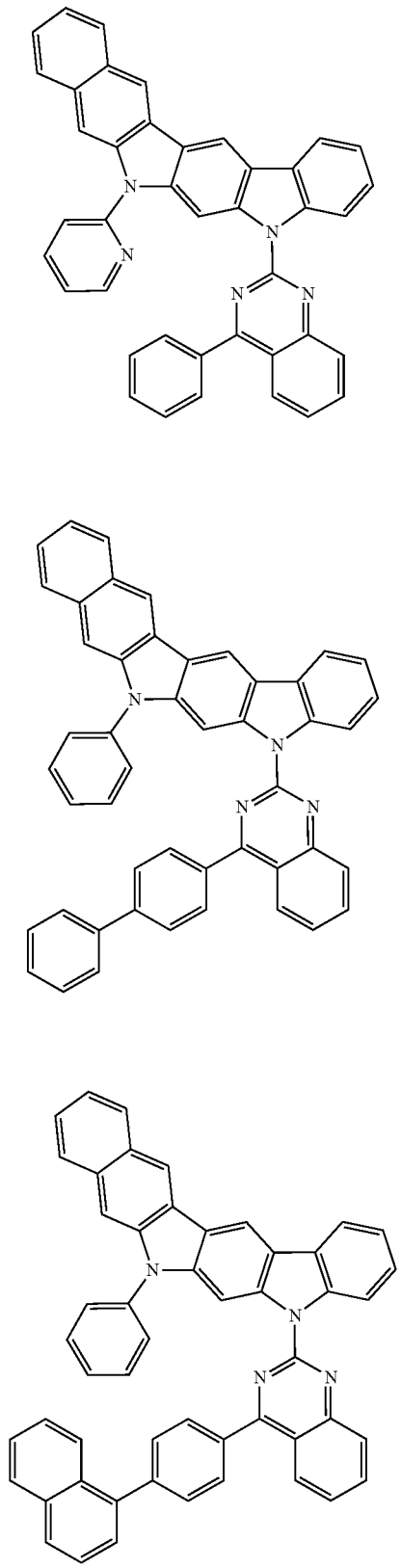
H-84
H-85
H-86
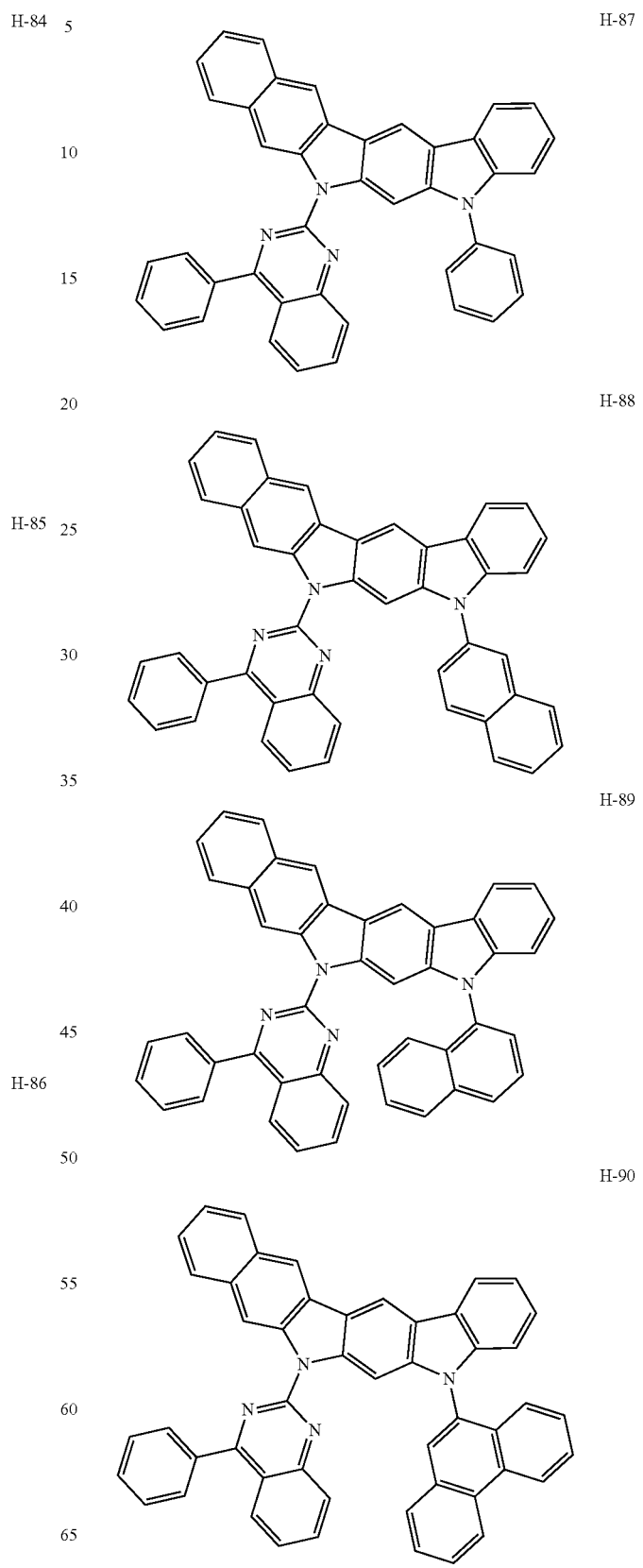
H-87
H-88
H-89
H-90

-continued
H-91
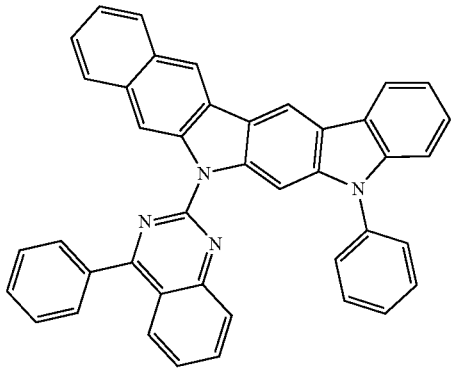
H-92
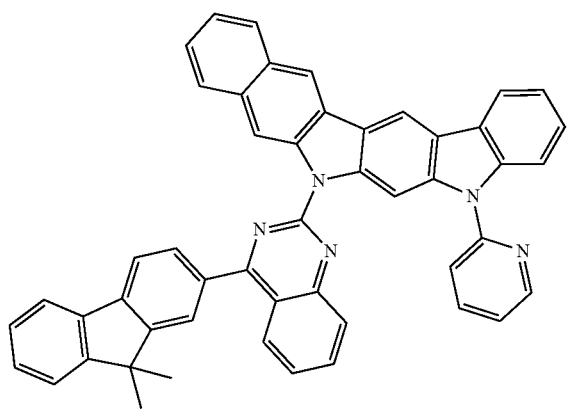
H-93
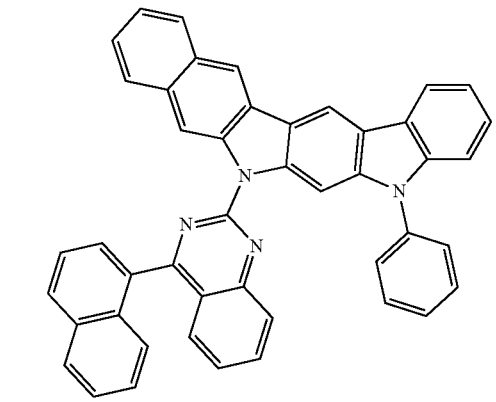
H-94
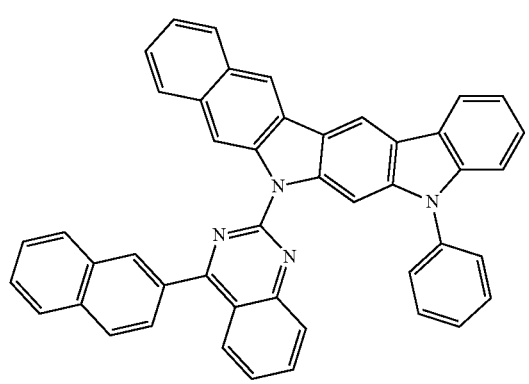
-continued
H-95
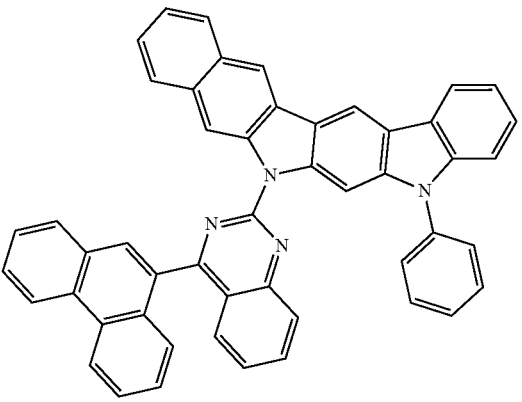
H-96
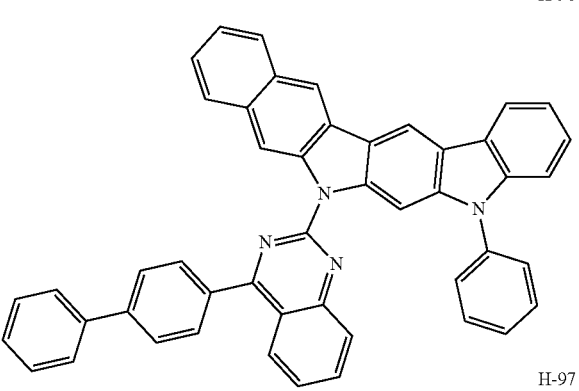
H-97
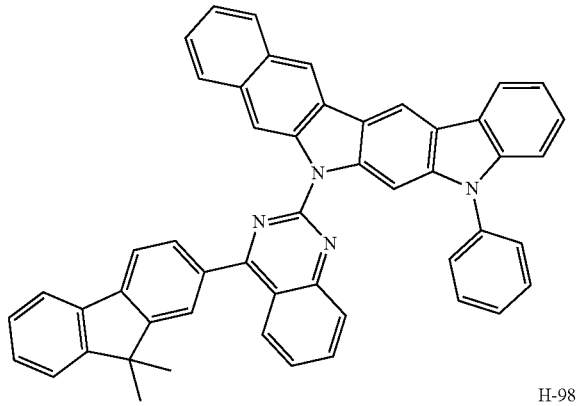
H-98
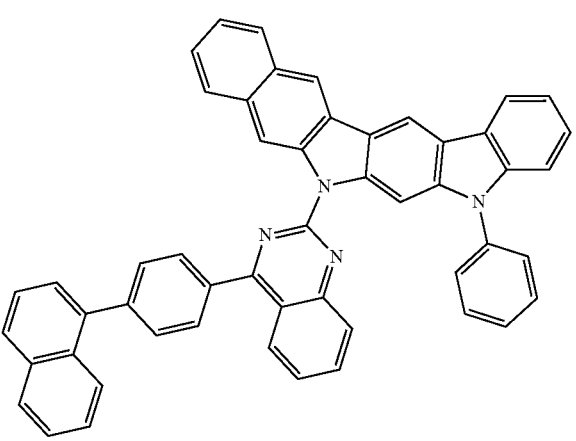

H-99
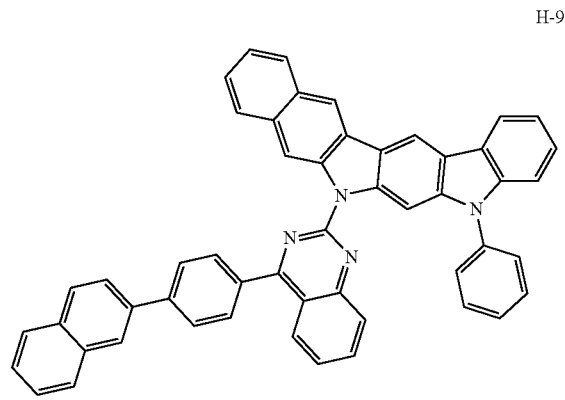
H-100
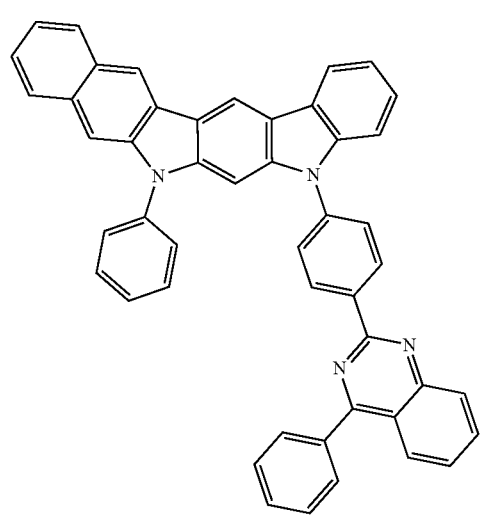
H-101
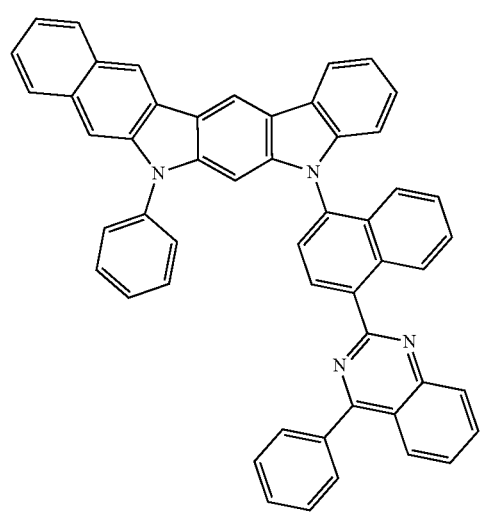
H-102
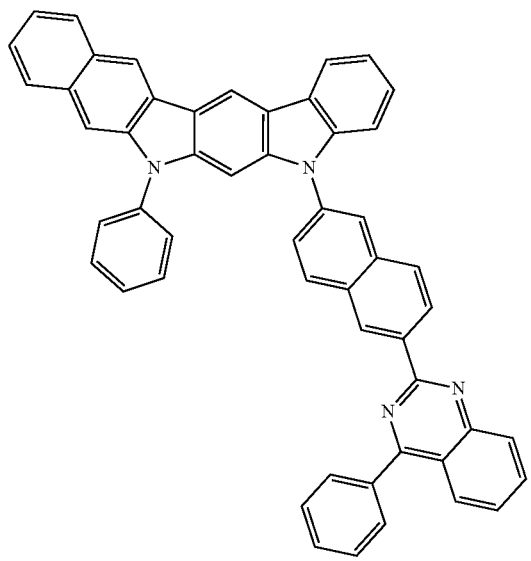
H-103
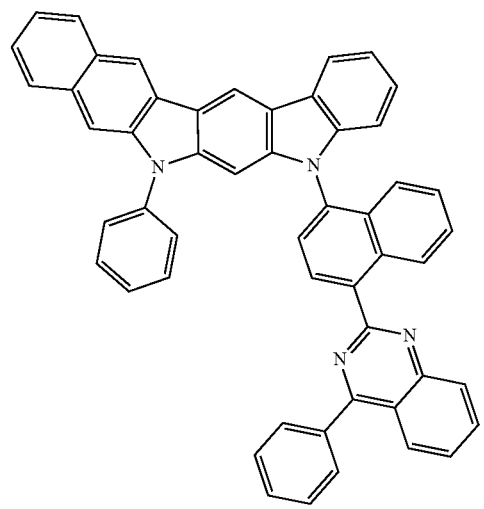
H-104
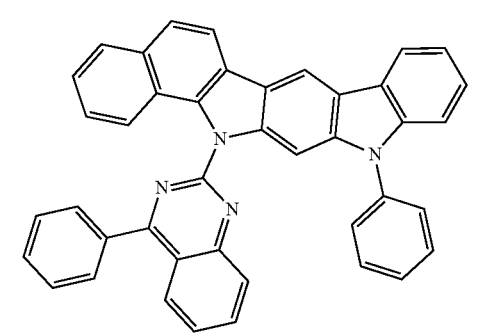

H-105
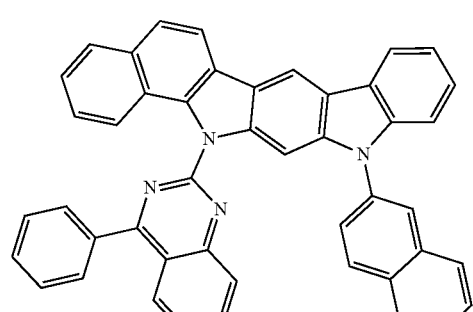
H-106
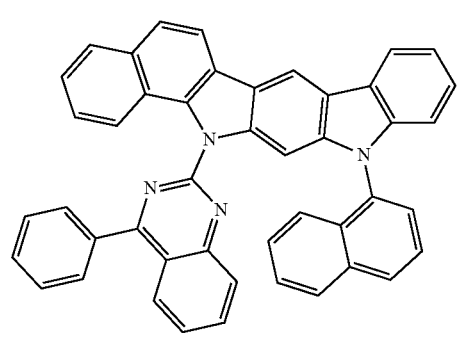
H-107
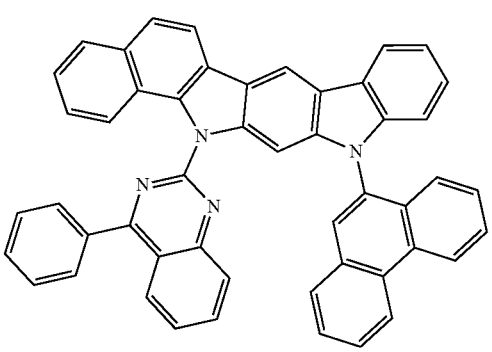
H-108
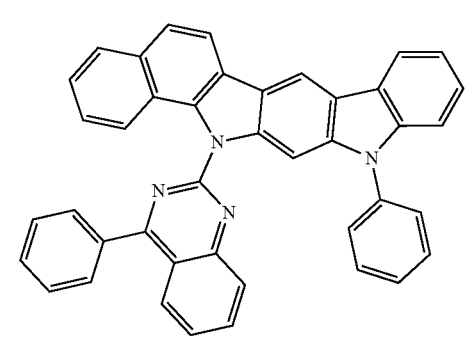
H-109
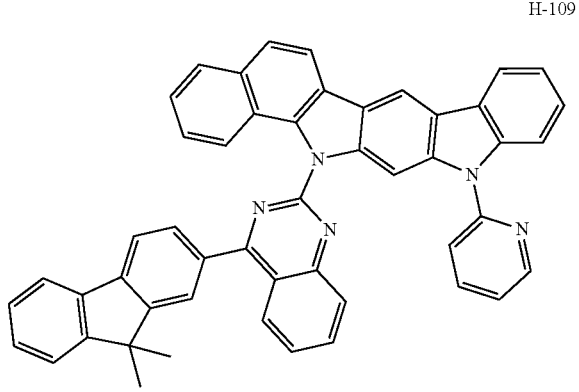
H-110
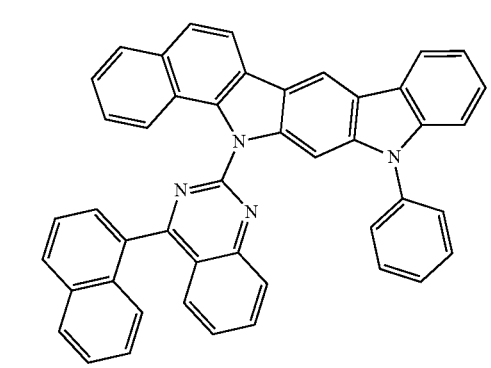
H-111
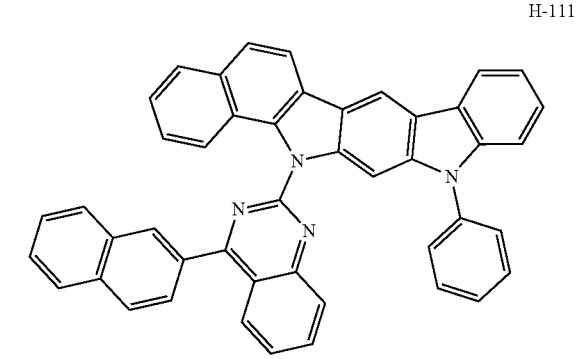
H-112
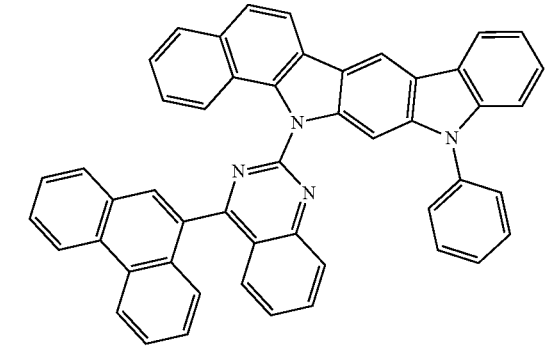

H-113
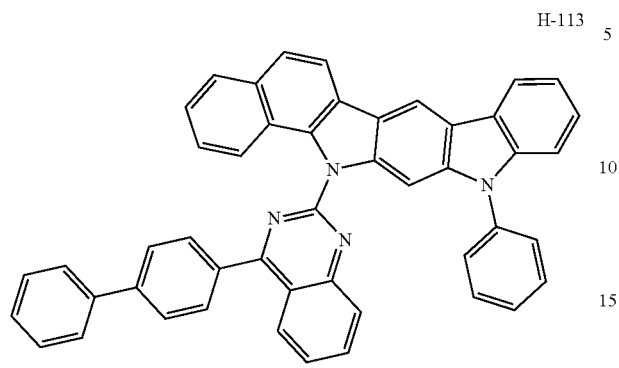
H-114
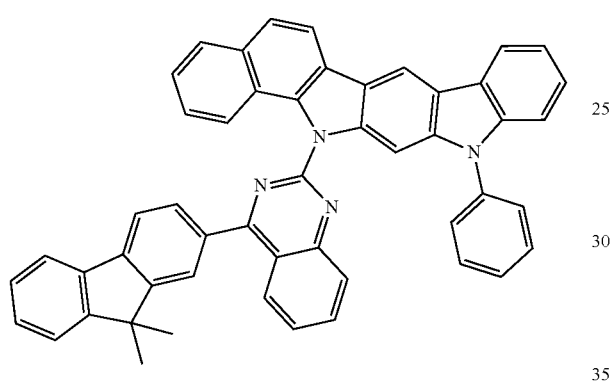
H-115
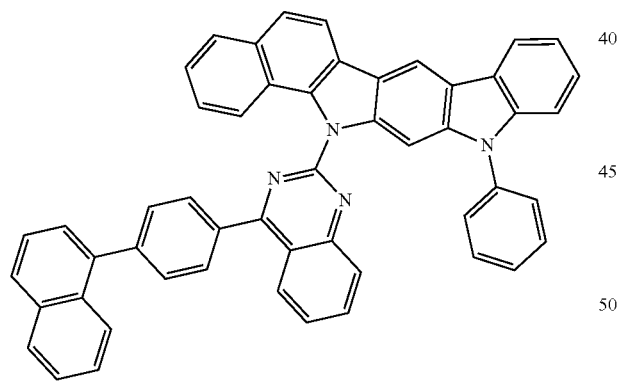
H-116
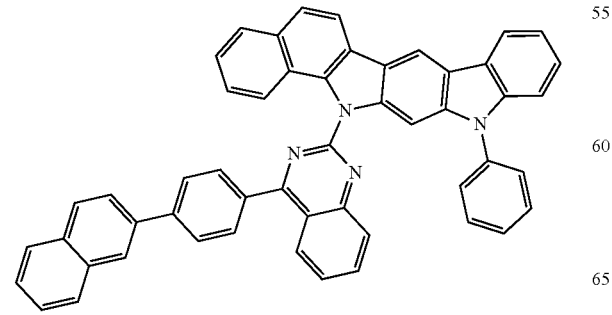
H-117
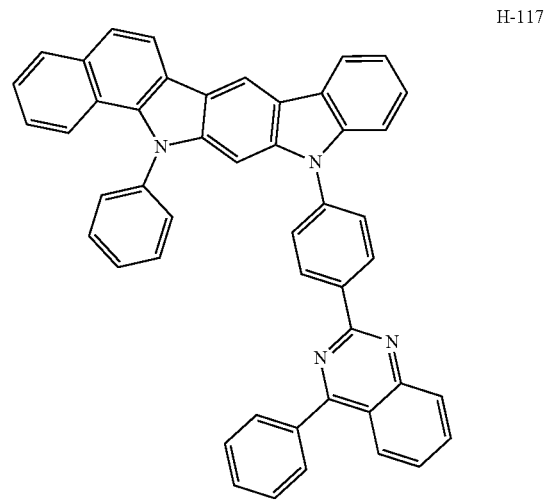
H-118
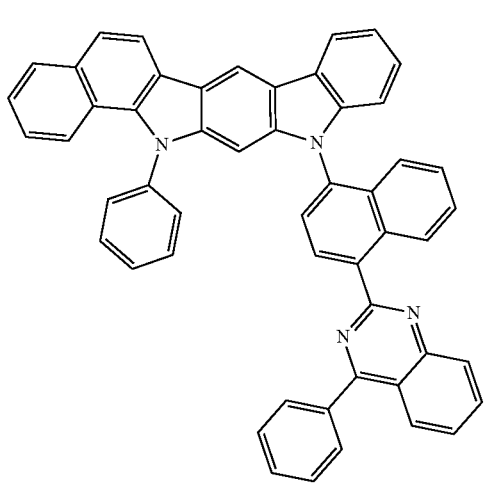
H-119
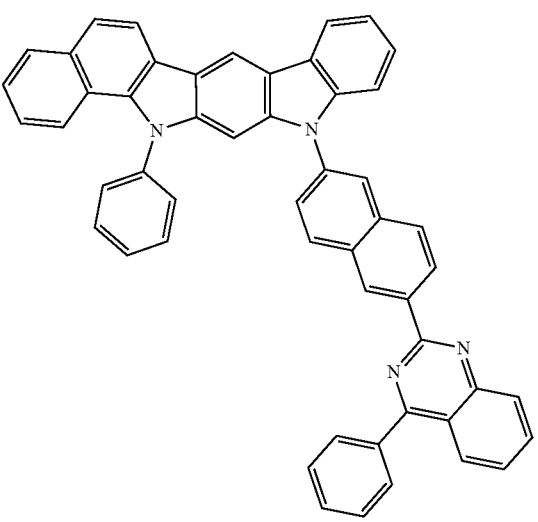

H-120
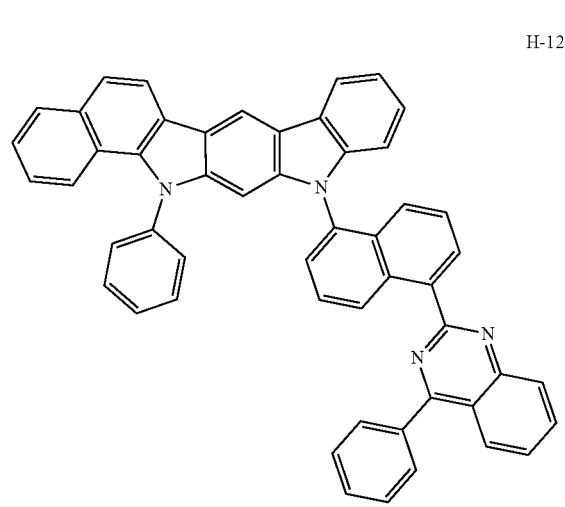
H-121
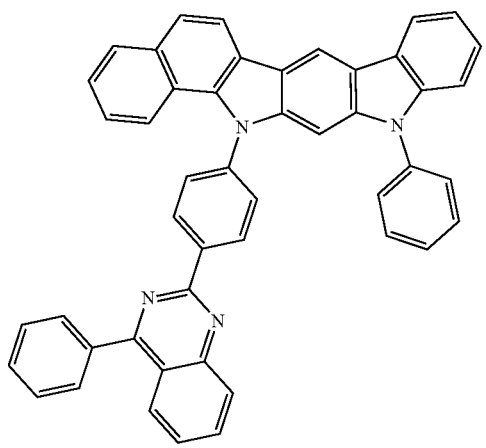
H-122
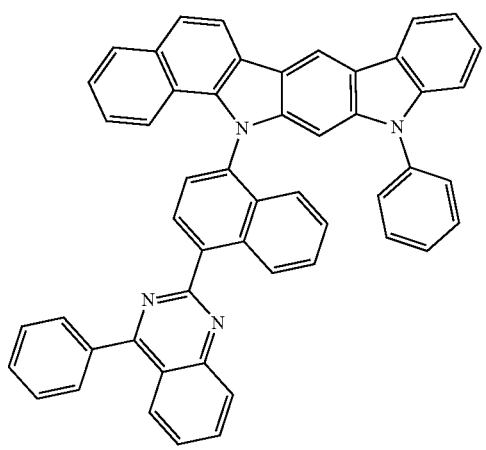
H-123
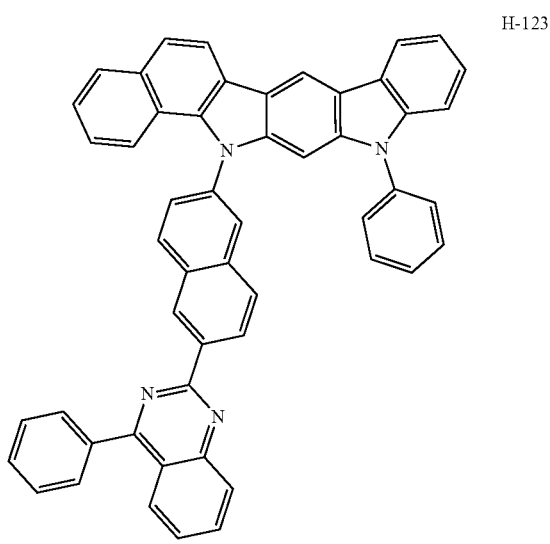
H-124
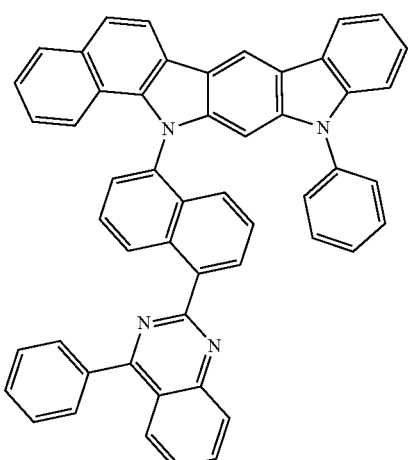
H-125
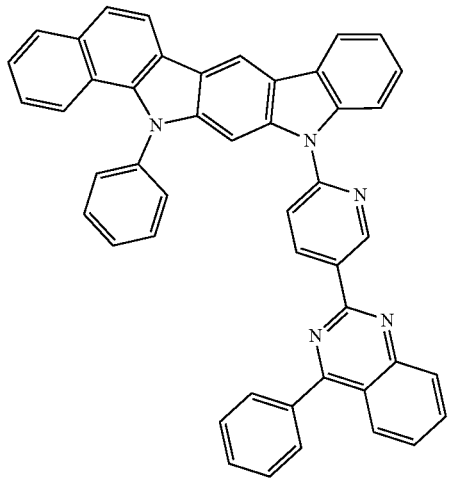

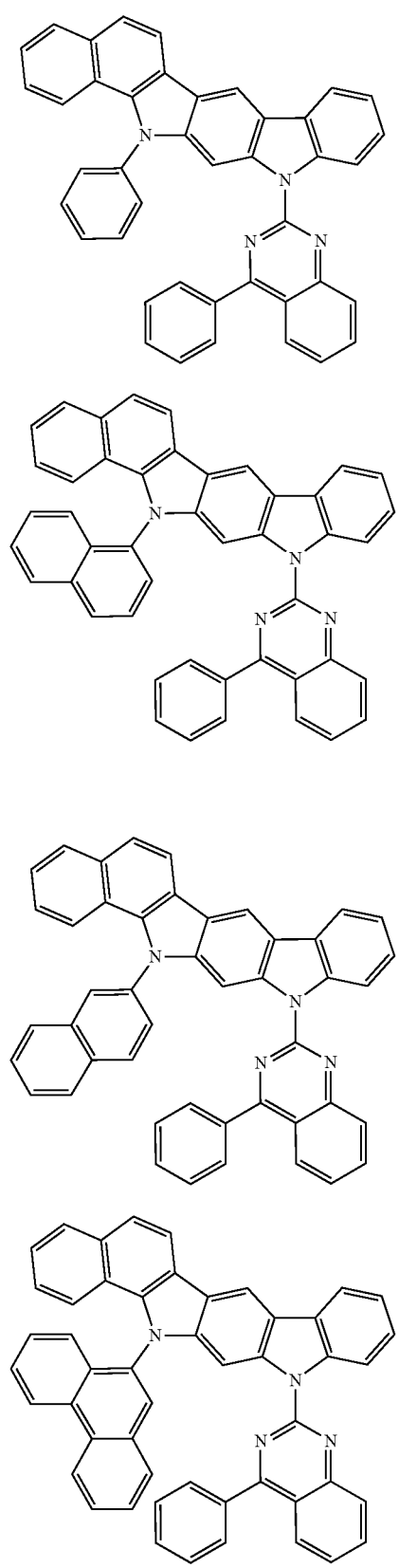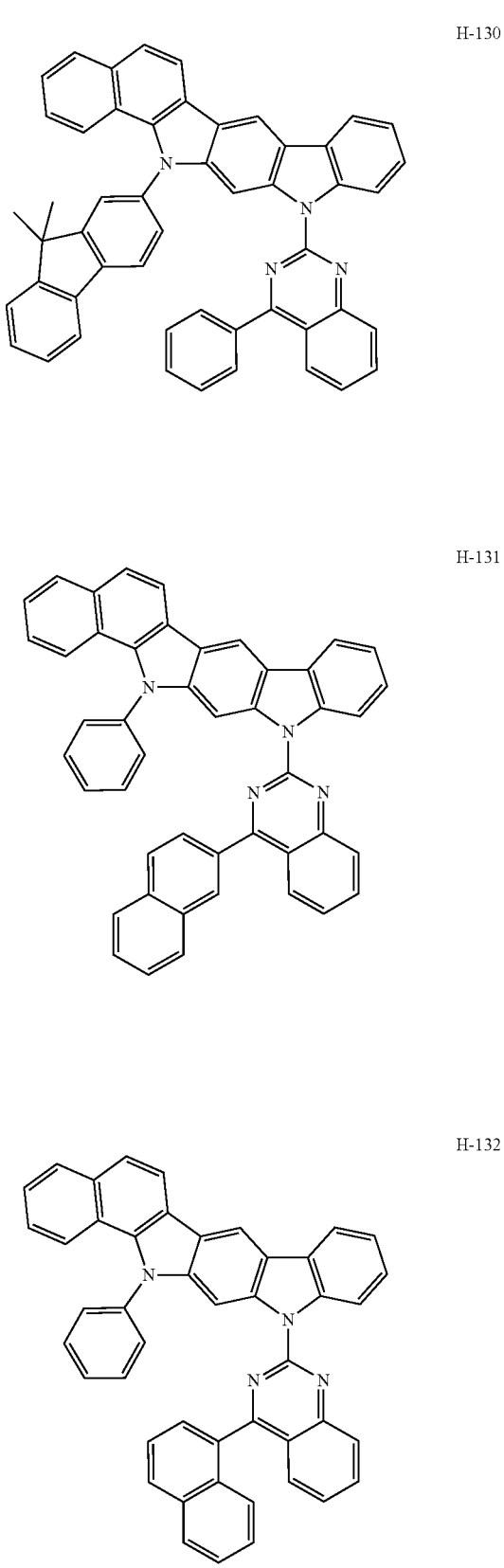

H-133
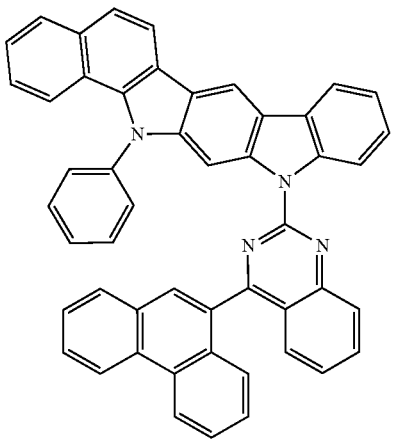
H-134
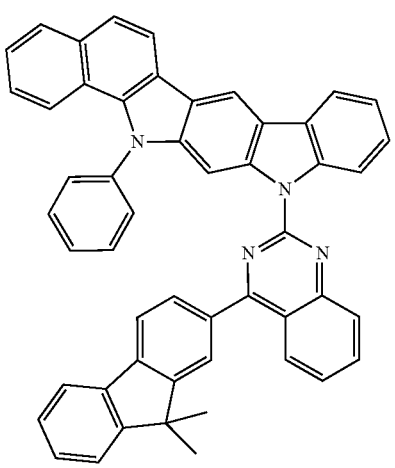
H-135
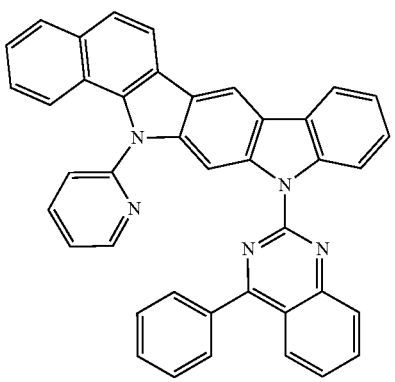
H-136
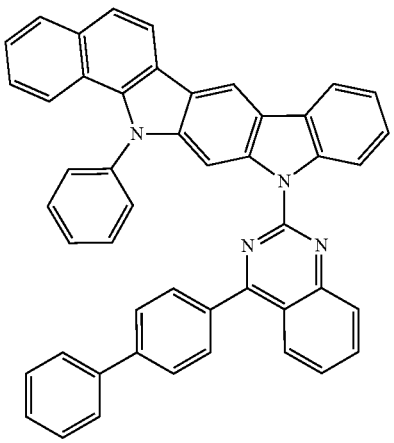
H-137
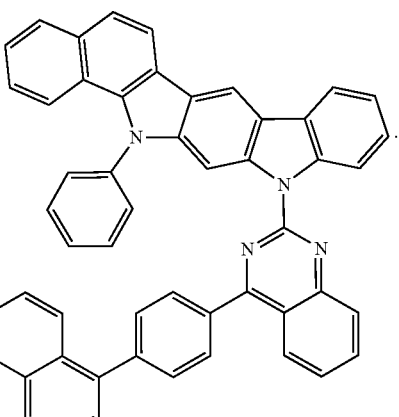
The organic electroluminescent compound of formula 1 according to the present disclosure may be produced by a synthetic method known to a person skilled in the art, and for example referring to the following reaction schemes 1 to 5, but is not limited thereto:
[Reaction Scheme 1]
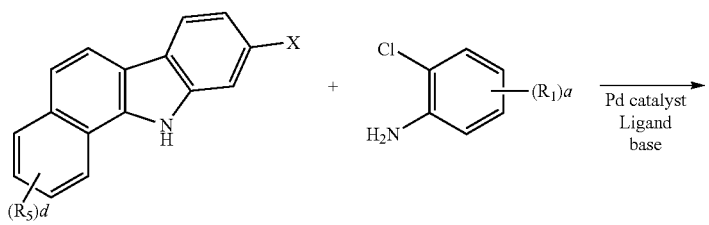

-continued
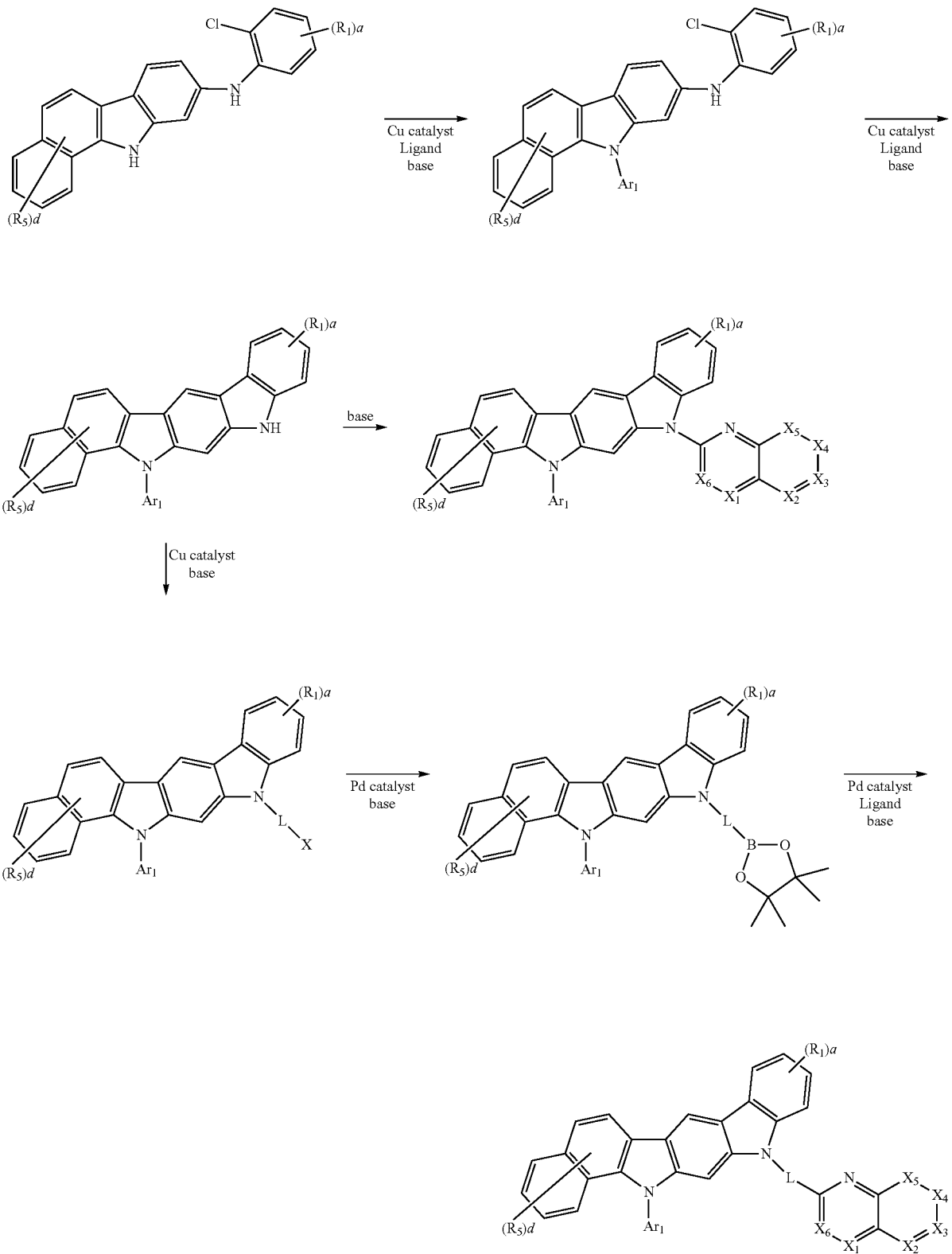

[Reaction Scheme 2]
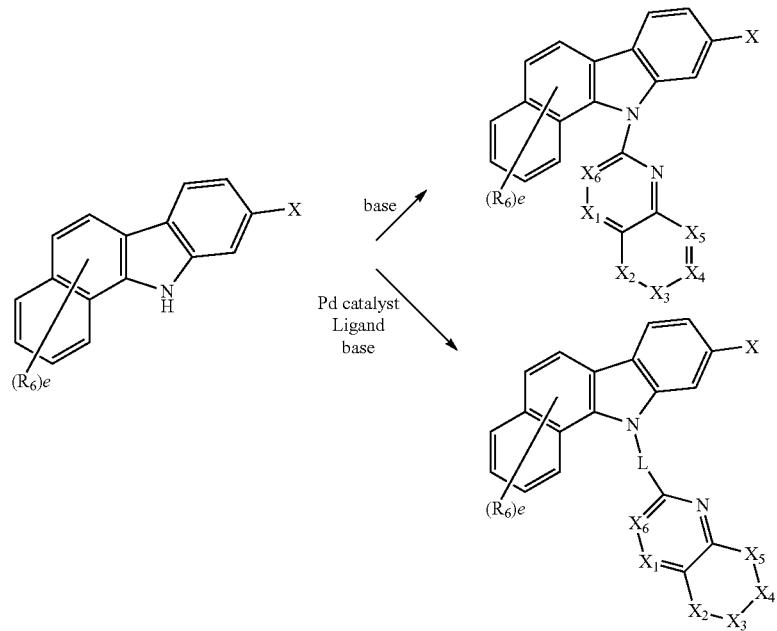
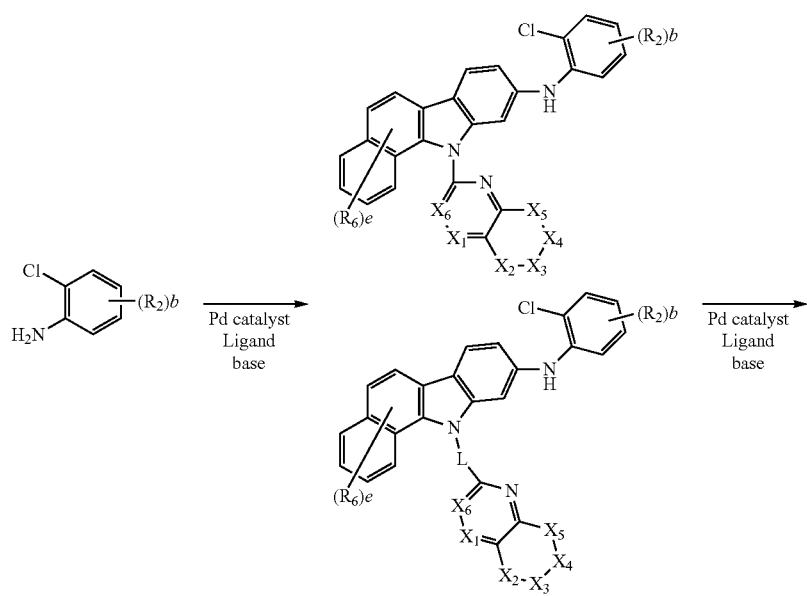

-continued
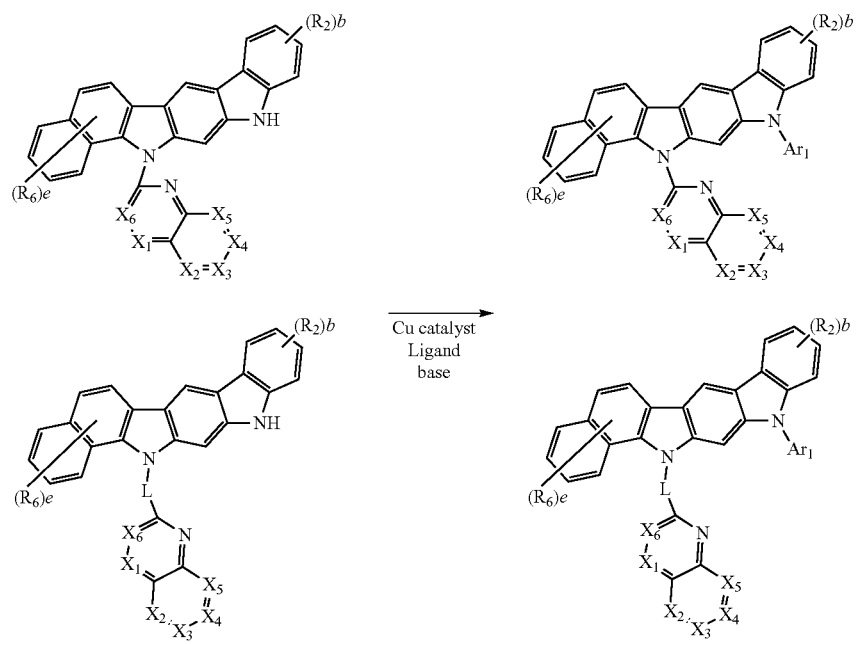
[Reaction Scheme 3]
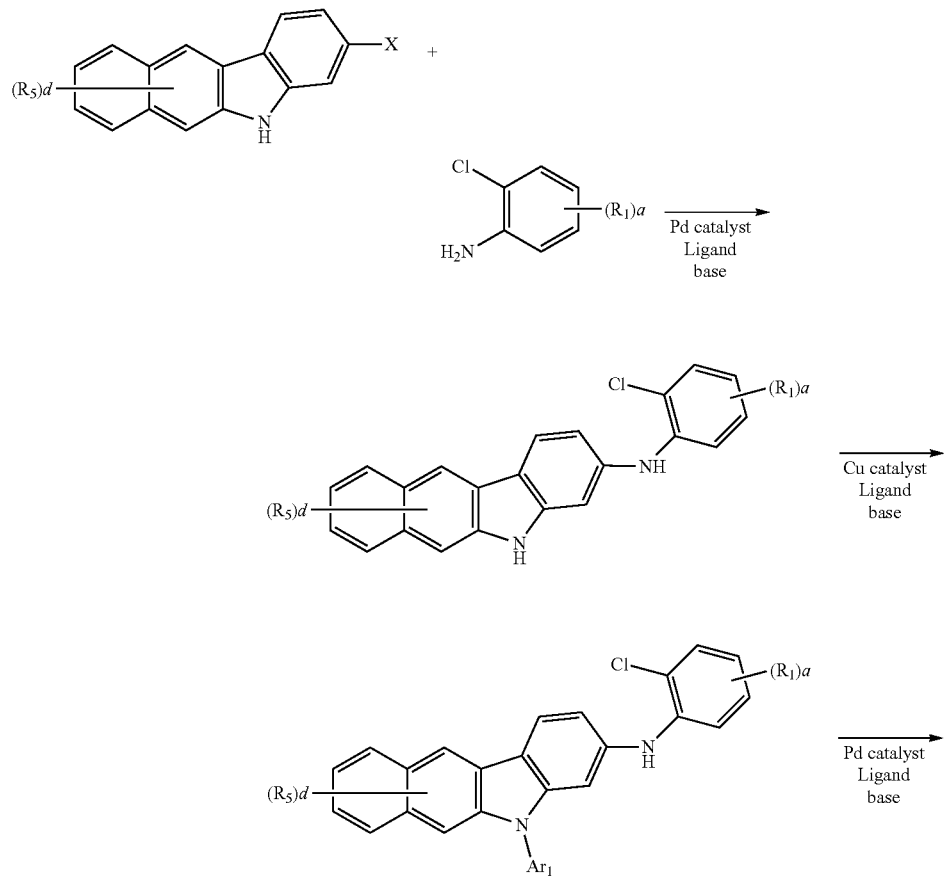

-continued
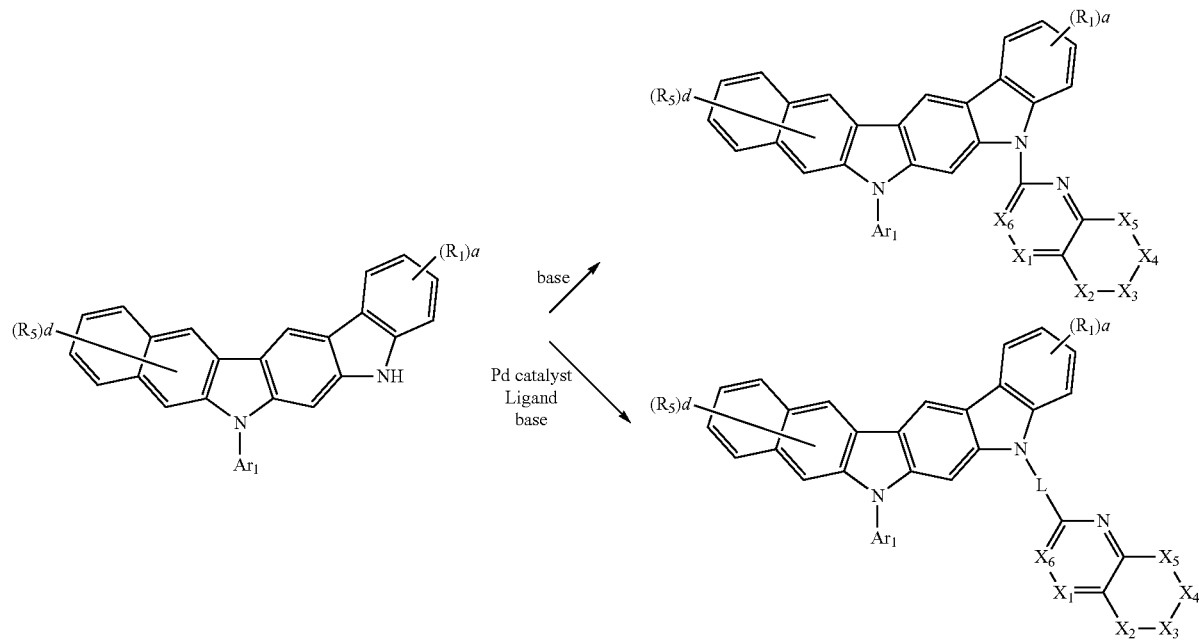
[Reaction Scheme 4]
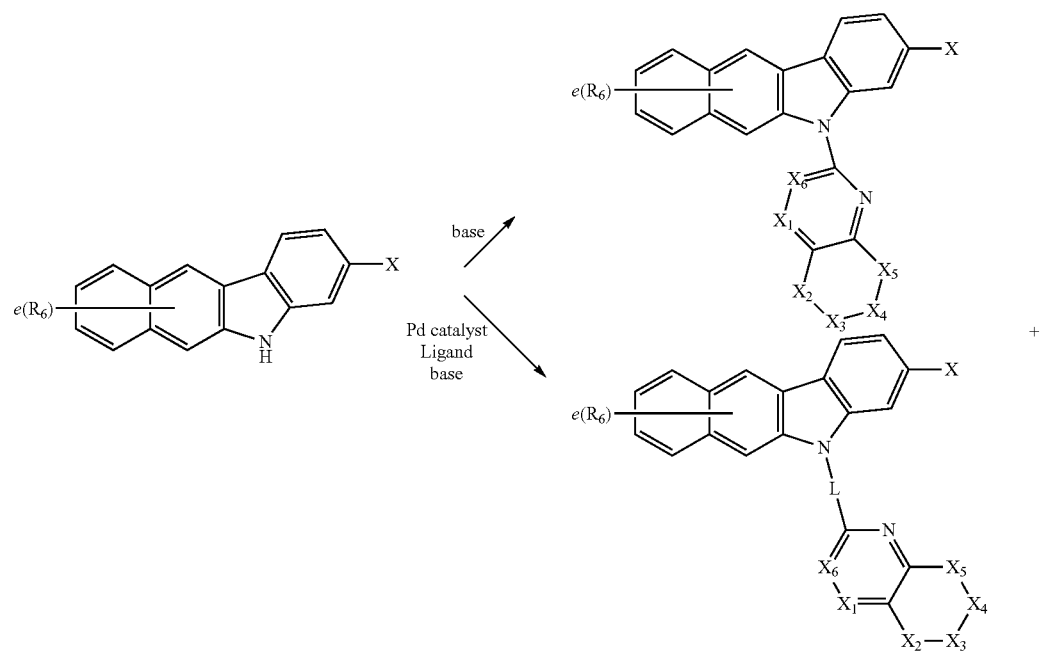

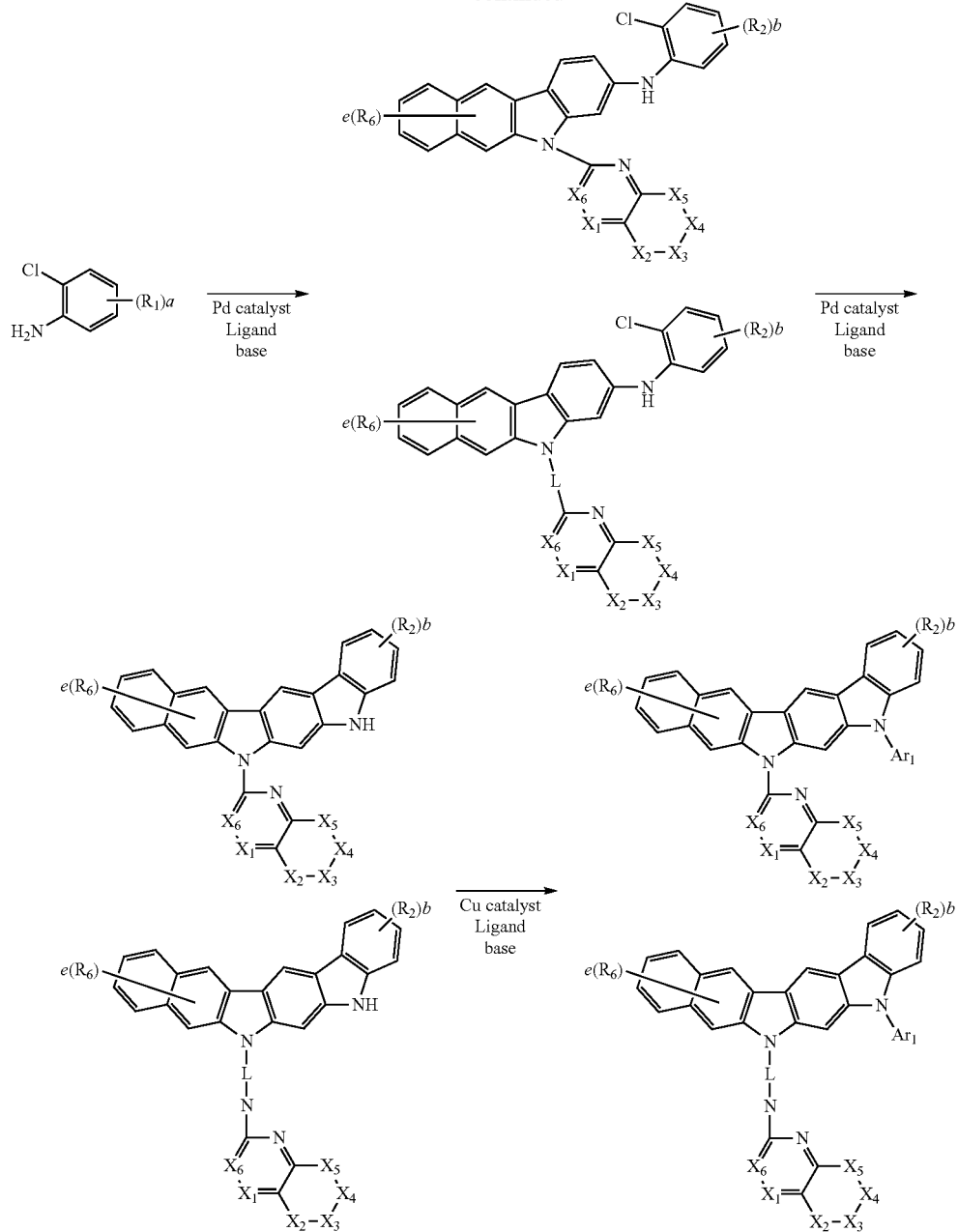

[Reaction Scheme 5]
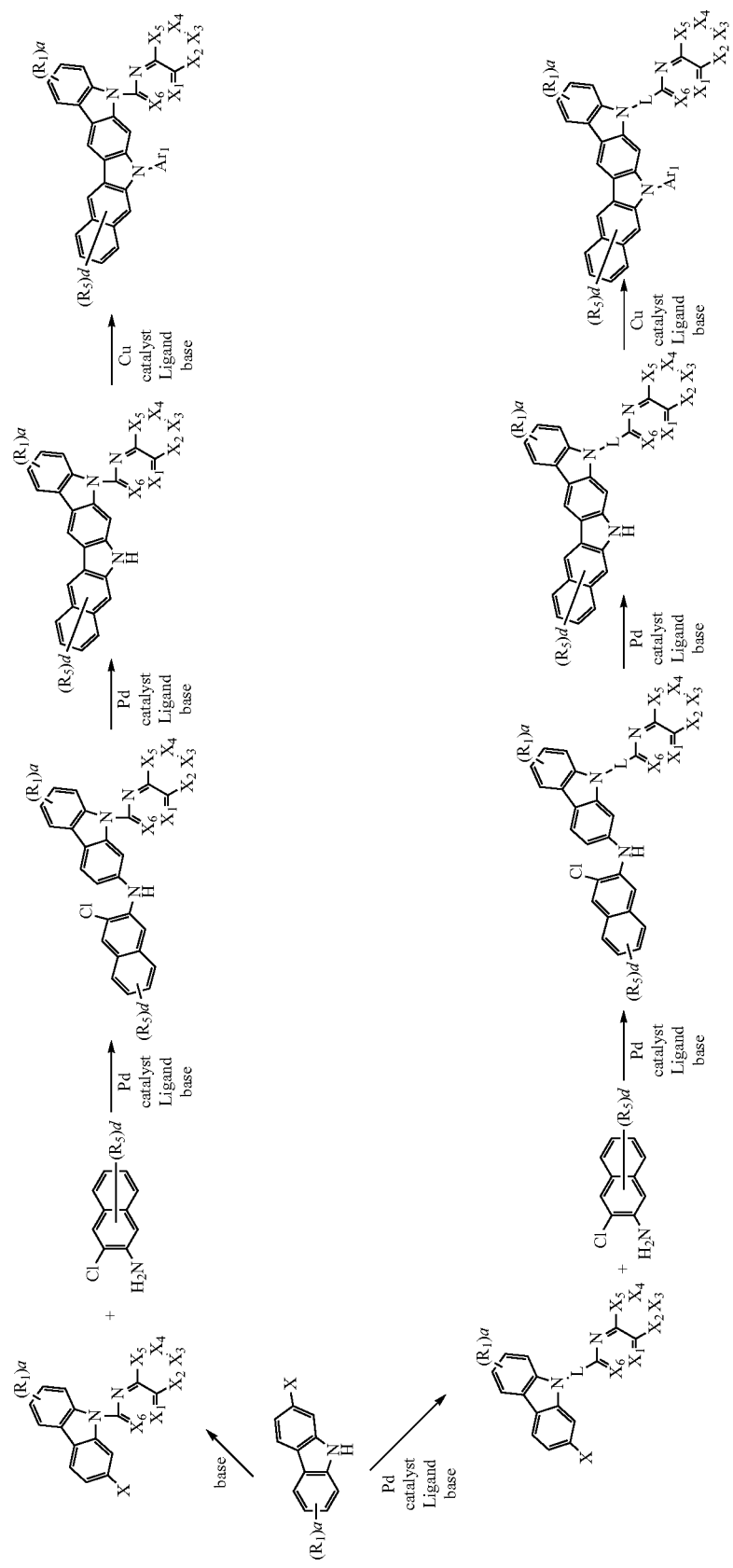

In reaction schemes 1 to 5, L, $Ar_1$, $R_1$, $R_2$, $R_5$, $R_6$, $X_1$ to $X_6$, a, b, d and e are as defined in formulas 1 to 5, and X represents a halogen.

The present disclosure may provide an organic electroluminescent material comprising the organic electroluminescent compound of formula 1, and an organic electroluminescent device comprising the material.

The organic electroluminescent material may consist of the organic electroluminescent compound of the present disclosure as a sole compound, or may further comprise conventional materials generally used in organic electroluminescent materials.

The organic electroluminescent device of the present disclosure may comprise a first electrode, a second electrode, and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron injection layer, an interlayer, a hole blocking layer, an electron blocking layer, and an electron buffer layer.

The hole auxiliary layer or the light-emitting auxiliary layer may be placed between the hole transport layer and the light-emitting layer, and may control the hole transport rate. The hole auxiliary layer or the light-emitting auxiliary layer may have an effect of improving the efficiency and/or the lifespan of the organic electroluminescent device.

The organic electroluminescent compound represented by formula 1 may be comprised in the light-emitting layer. When used in the light-emitting layer, the organic electroluminescent compound of formula 1 may be comprised as a host material. Preferably, the light-emitting layer may further comprise at least one dopant. If necessary, another compound besides the organic electroluminescent compound of formula 1 may be further comprised as a second host material. Herein, the weight ratio of the first host material to the second host material is in the range of 1:99 to 99:1.

The second host material can use any of the known phosphorescent hosts. In terms of luminous efficiency, the second host material may be preferably selected from the group consisting of the compounds represented by the following formulas 11 to 16:

(11)

(12)

(13)

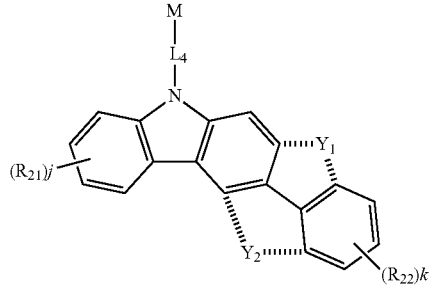

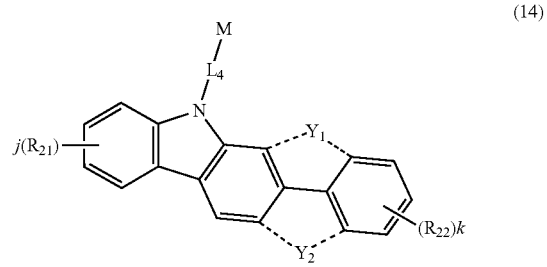
(14)

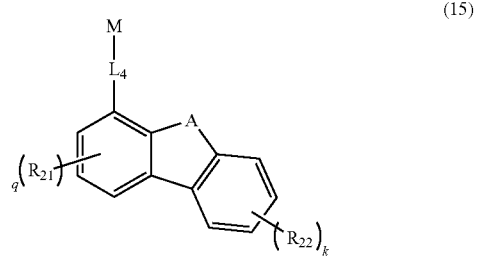
(15)

wherein Cz represents the following structure:

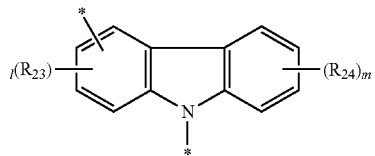

A represents —O— or —S—; and $R_{21}$ to $R_{24}$, each independently, represent hydrogen, deuterium, a halogen, a substituted or unsubstituted (C1-C30) alkyl, a substituted or unsubstituted (C6-C30)aryl, a substituted or unsubstituted (5- to 30-membered)heteroaryl, or —$SiR_{25}R_{26}R_{27}$, in which $R_{25}$ to $R_{27}$, each independently, represent a substituted or unsubstituted (C1-C30)alkyl, or a substituted or unsubstituted (C6-C30)aryl; $L_4$ represents a single bond, a substituted or unsubstituted (C6-C30)arylene, or a substituted or unsubstituted (5- to 30-membered)heteroarylene; M represents a substituted or unsubstituted (C6-C30)aryl, or a substituted or unsubstituted (5- to 30-membered)heteroaryl; $Y_1$ and $Y_2$, each independently, represent —O—, —S—, —$NR_{31}$— or —$CR_{32}R_{33}$—, with the proviso that $Y_1$ and $Y_2$ are not present simultaneously; $R_{31}$ to $R_{33}$, each independently, represent a substituted or unsubstituted (C1-C30)alkyl, a substituted or unsubstituted (C6-C30)aryl, or a substituted or unsubstituted (5- to 30-membered)heteroaryl; $R_{32}$ and $R_{33}$ may be the same or different; h and i, each independently, represent an integer of 1 to 3; j, k, l and m, each independently, represent an integer of 1 to 4; q represents an integer of 1 to 3; where if h, i, j, k, l, m or q represents an integer of 2 or more, each (Cz-$L_4$), each (Cz), each $R_{21}$, each $R_{22}$, each $R_{23}$ or each $R_{24}$ may be the same or different;

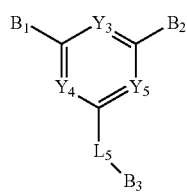
(16)

wherein $Y_3$ to $Y_5$, each independently, represent $CR_{34}$ or N, in which $R_{34}$ represents hydrogen, a substituted or unsubstituted (C1-C30)alkyl, a substituted or unsubstituted (C6-C30)aryl, or a substituted or unsubstituted (5- to 30-membered)heteroaryl;

$B_1$ and $B_2$, each independently, represent hydrogen, a substituted or unsubstituted (C6-C30)aryl, or a substituted or unsubstituted (5- to 30-membered)heteroaryl;

$B_3$ represents a substituted or unsubstituted (C6-C30)aryl, or a substituted or unsubstituted (5- to 30-membered)heteroaryl; and $L_5$ represents a single bond, a substituted or unsubstituted (C6-C30)arylene, or a substituted or unsubstituted (5- to 30-membered)heteroarylene.

Specifically, the preferred examples of the second host material are as follows, but are not limited thereto.

B-1

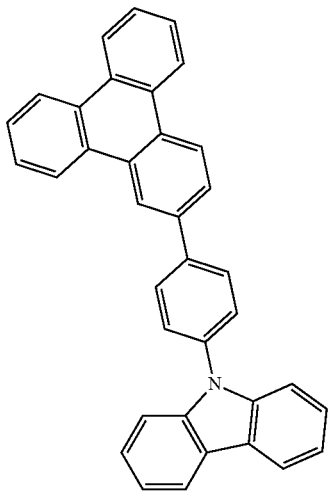

B-2

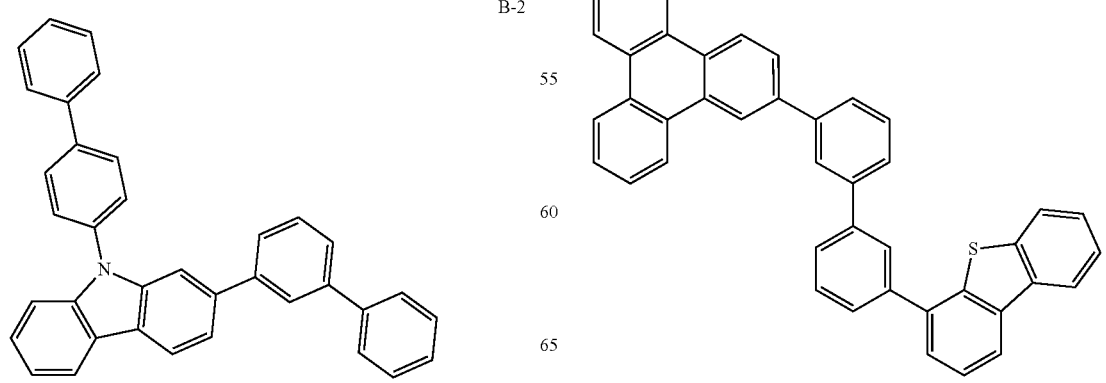

B-3

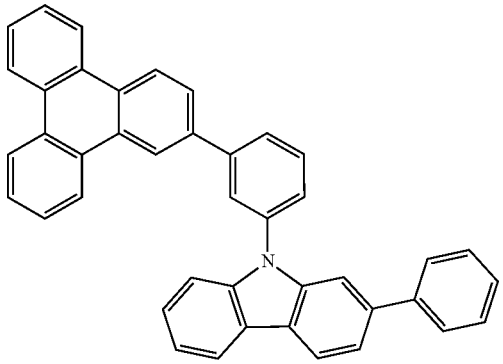

B-4

B-5

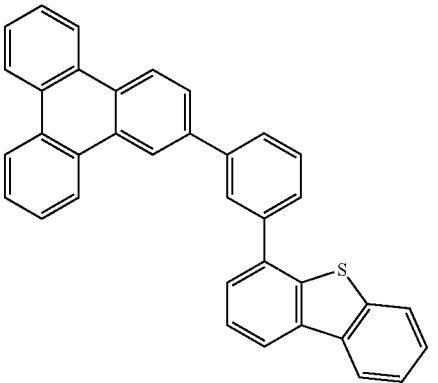

B-6

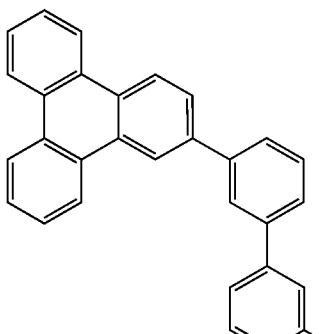

B-7
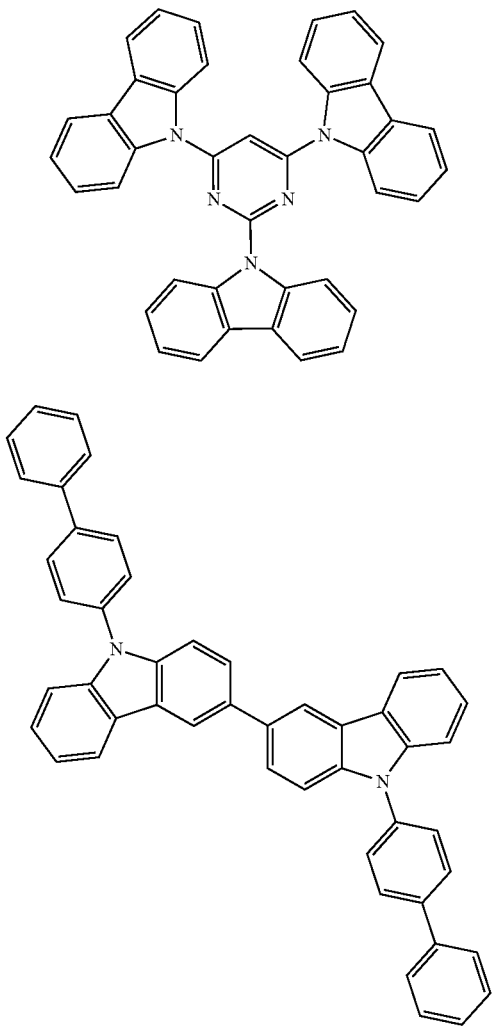
B-8
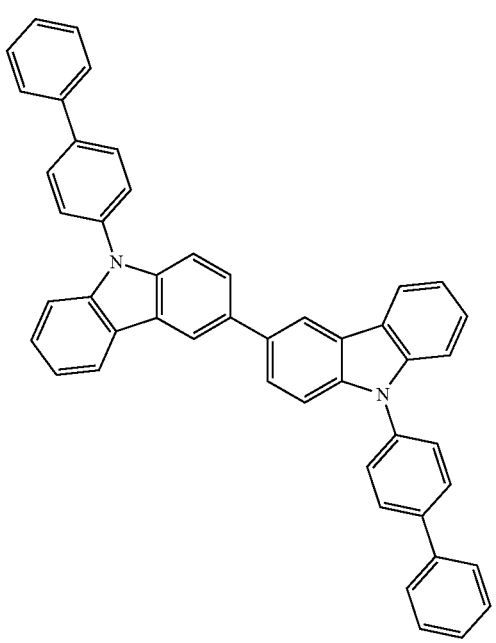
B-9
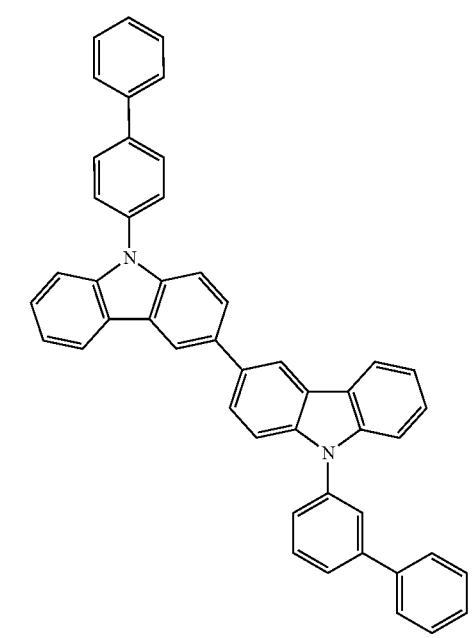
B-10
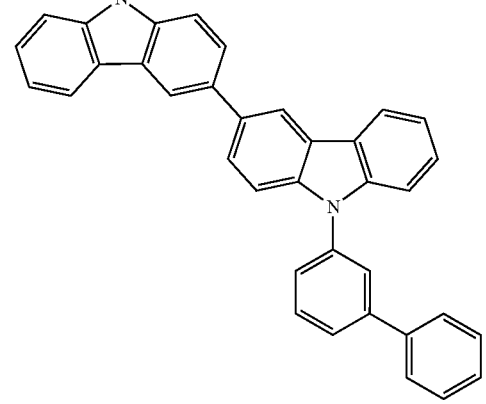
B-11
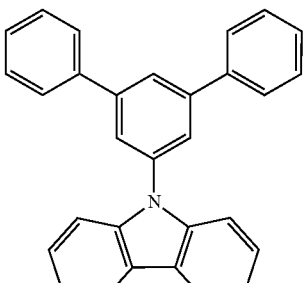

B-12
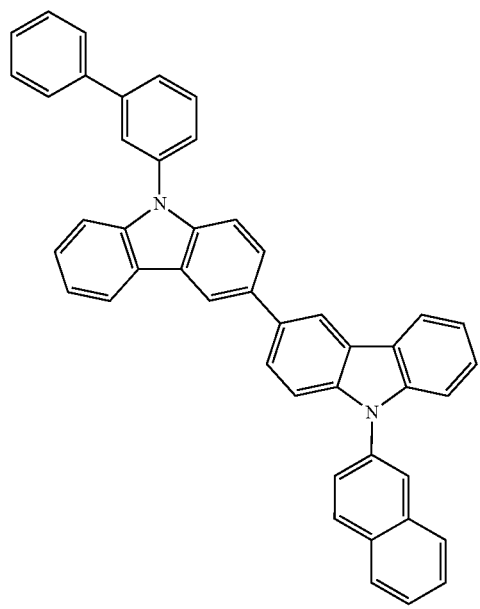
B-13
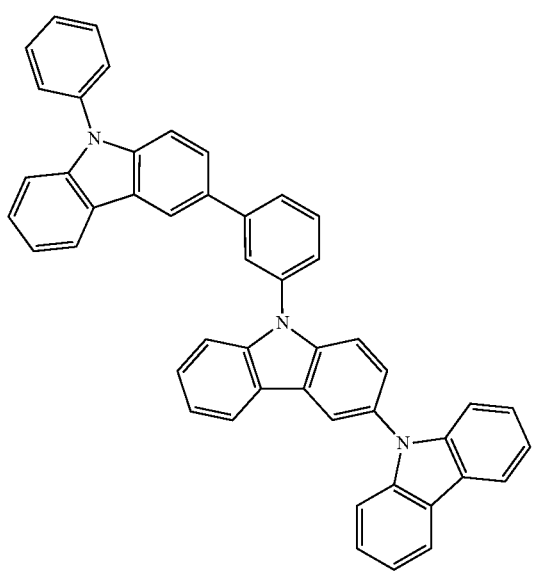
B-14
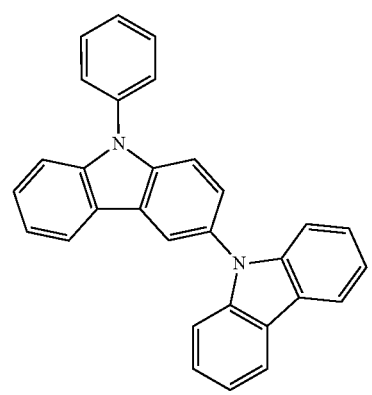
B-15
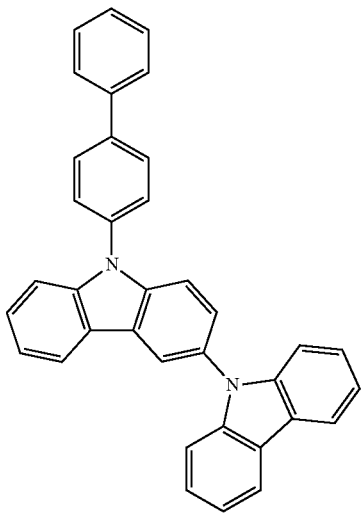
B-16
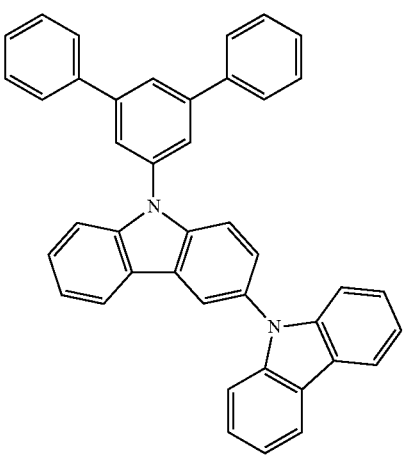
B-17
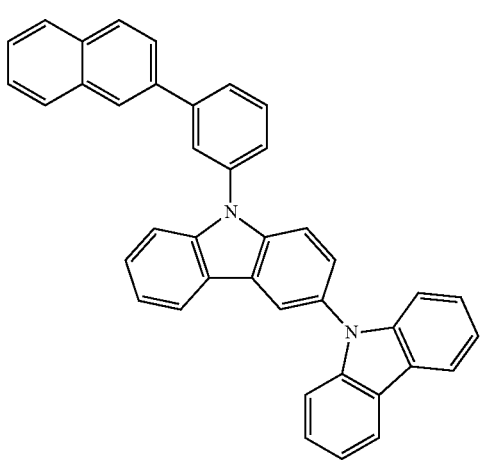

B-18
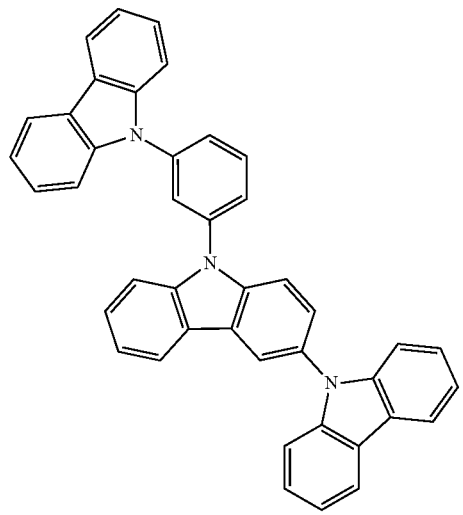
B-19
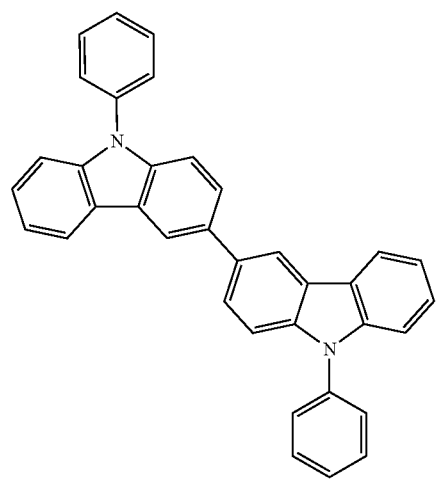
B-20
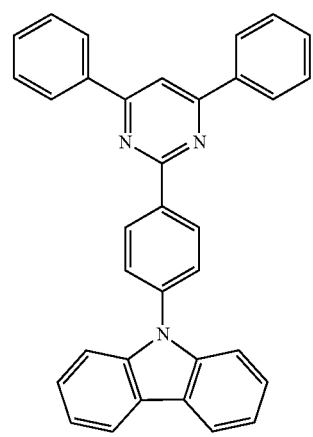
B-21
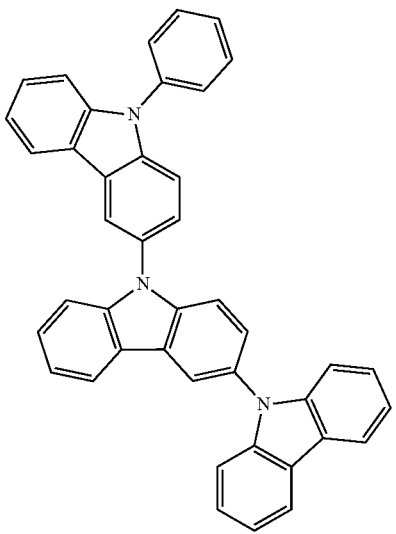
B-22
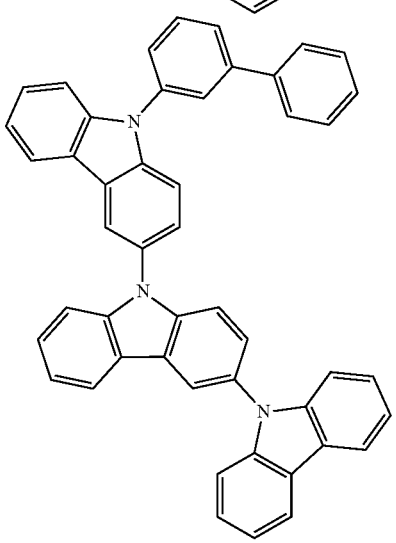
B-23
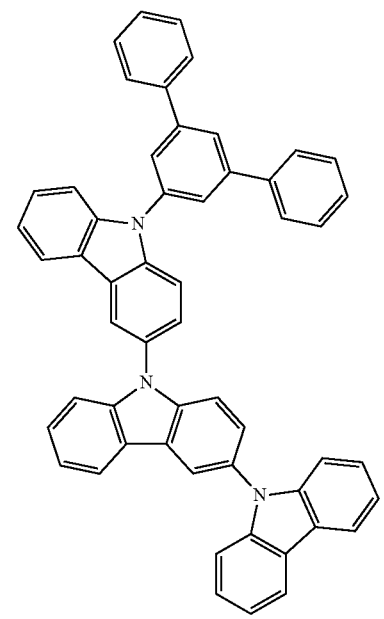

B-24
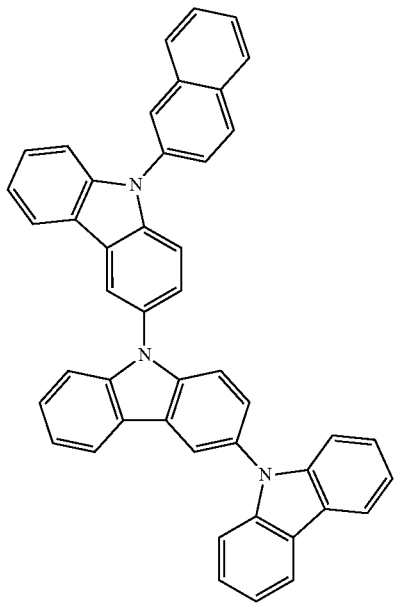
B-25
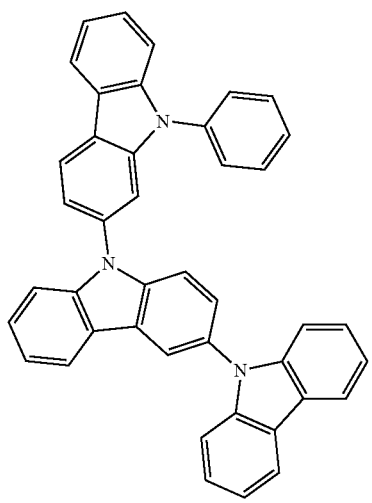
B-26
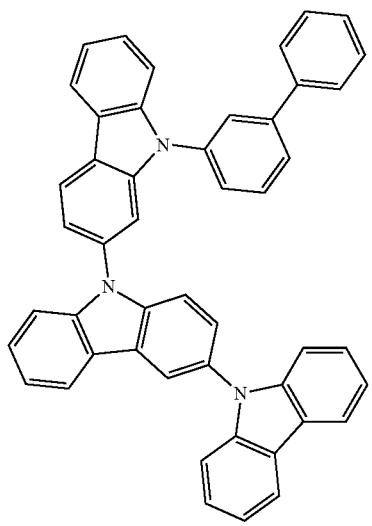
B-27
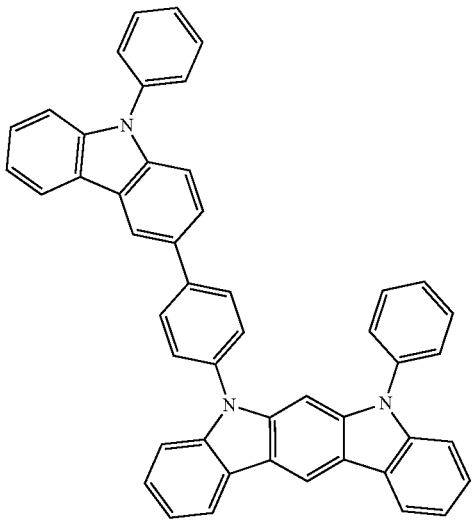
B-28
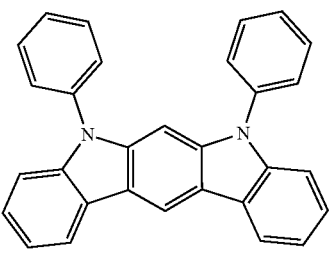
B-29
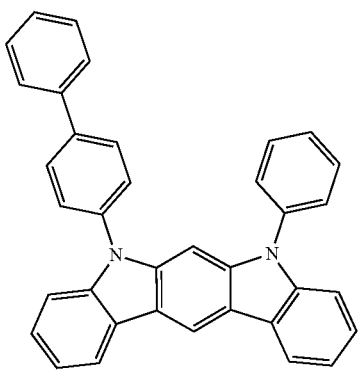
B-30
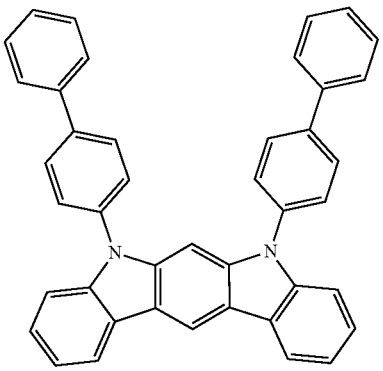

B-31
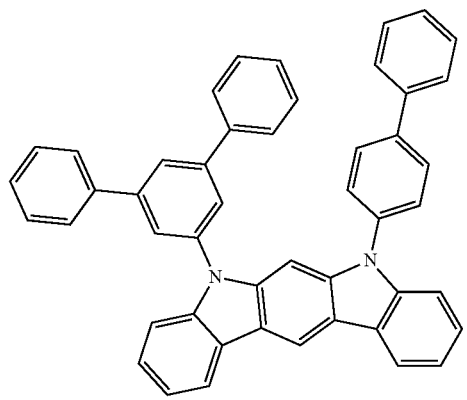
B-32
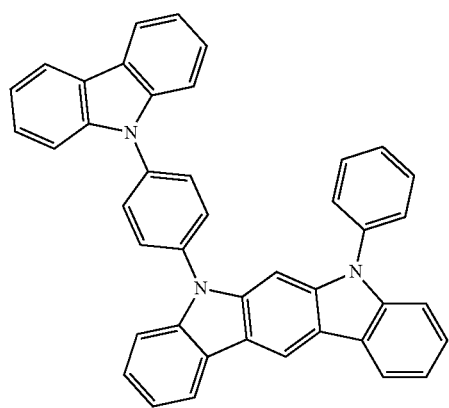
B-33
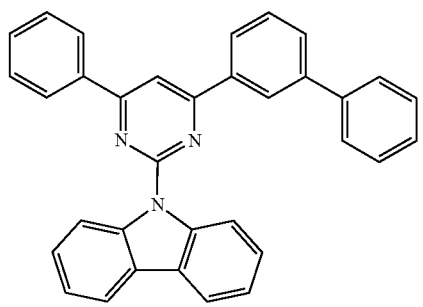
B-34
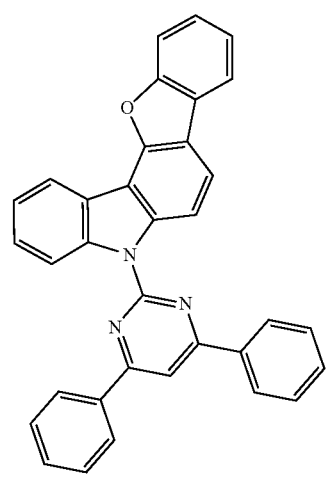
B-35
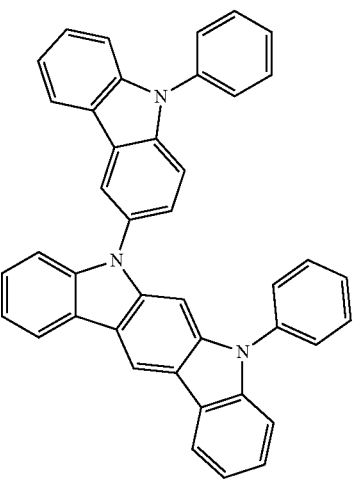
B-36
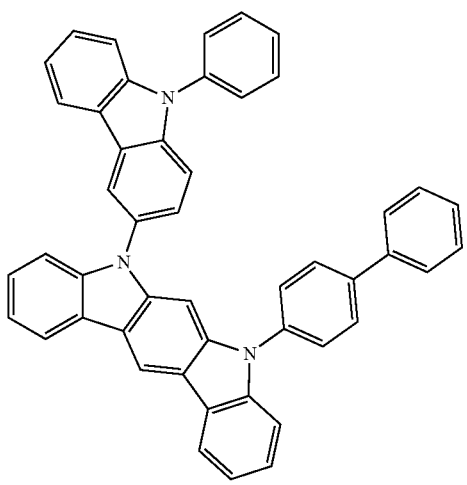
B-37
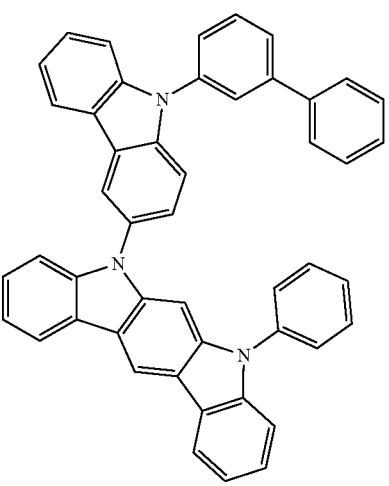

-continued
B-38
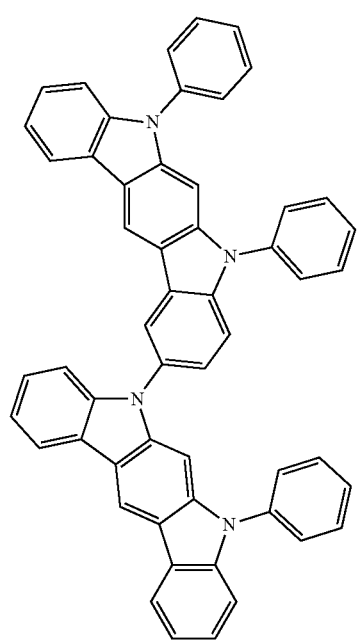
B-39
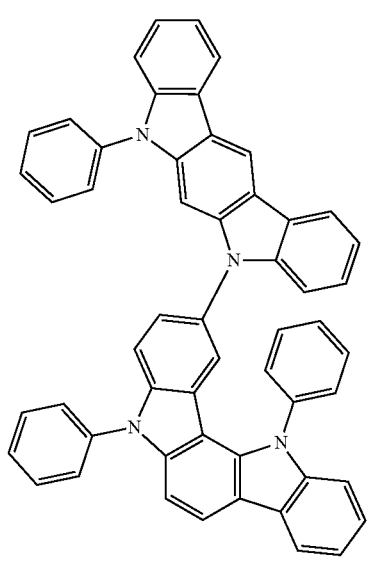
B-40
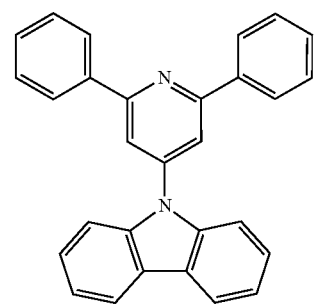
-continued
B-41
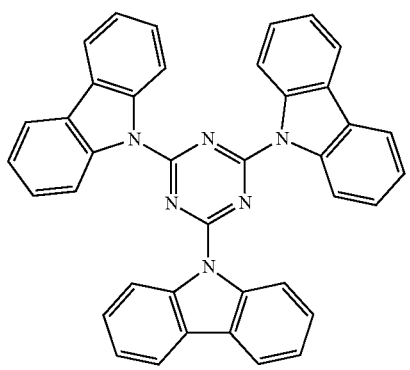
B-42
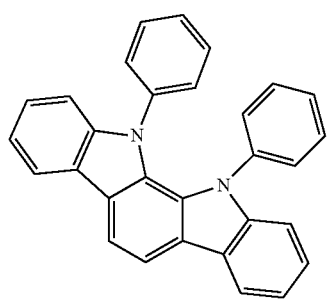
B-43
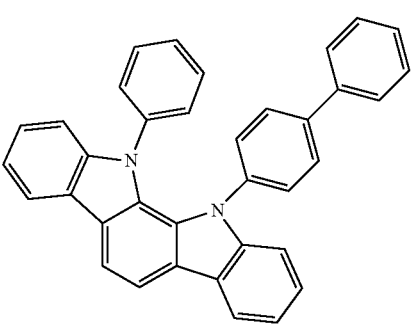
B-44
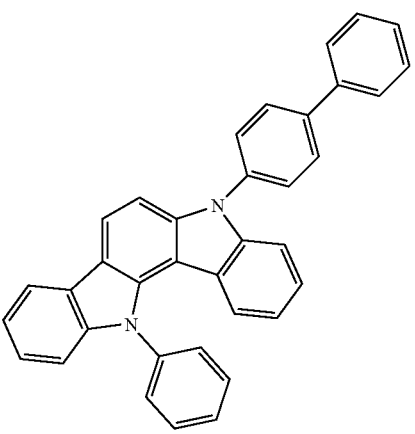

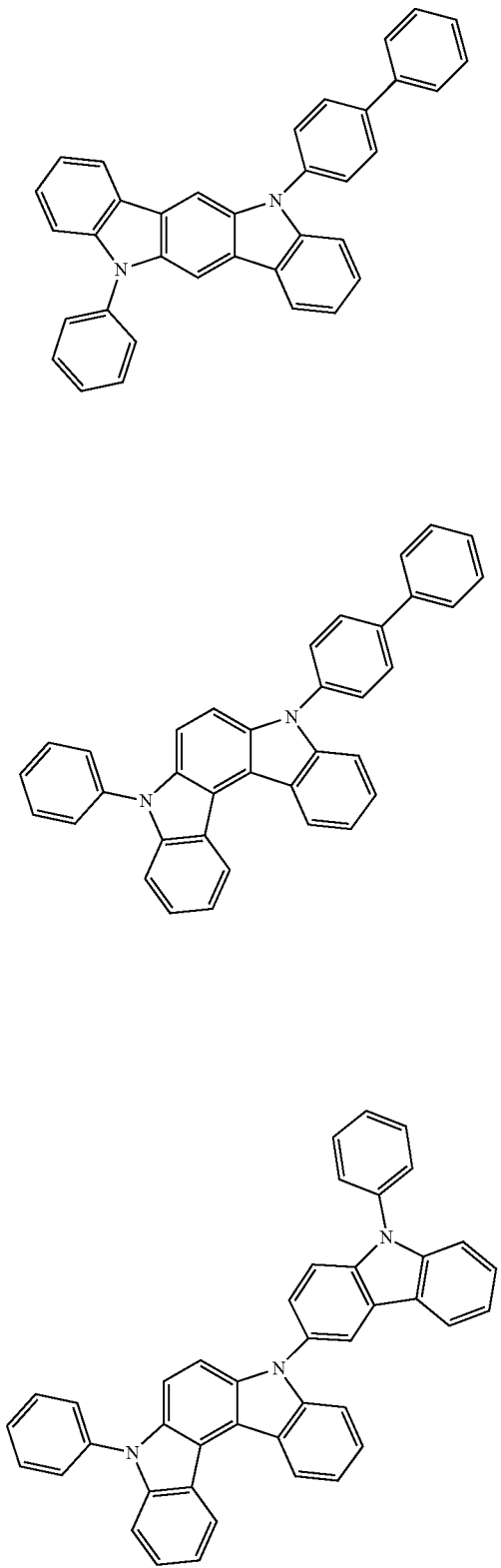
B-45
B-46
B-47
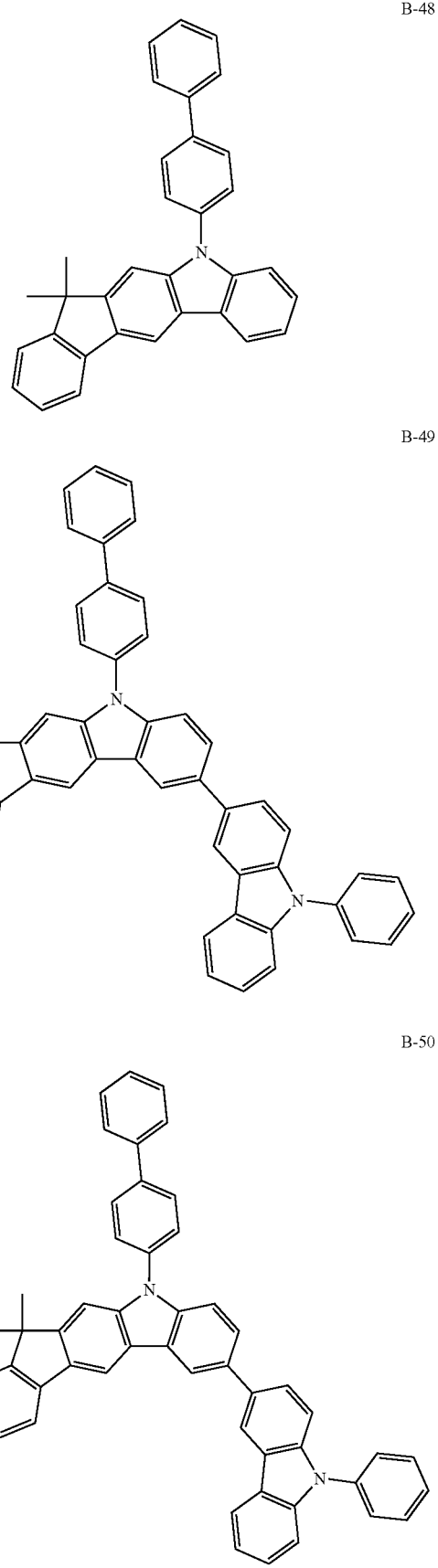
B-48
B-49
B-50

B-51
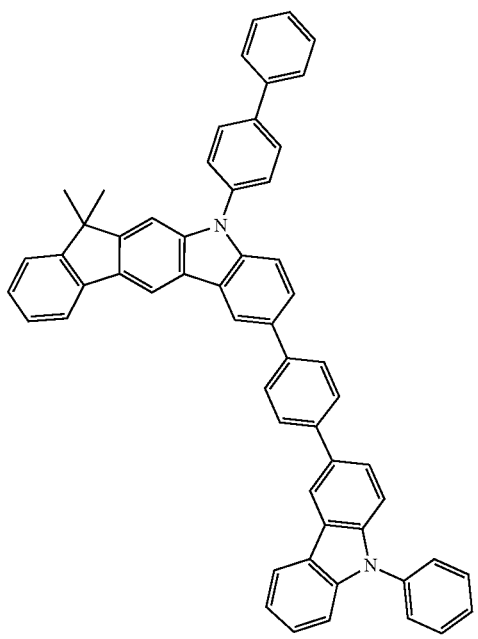
B-52
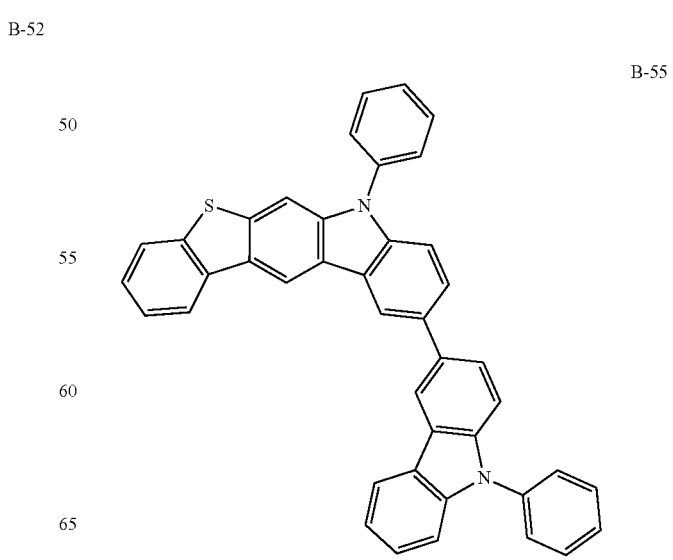
B-53
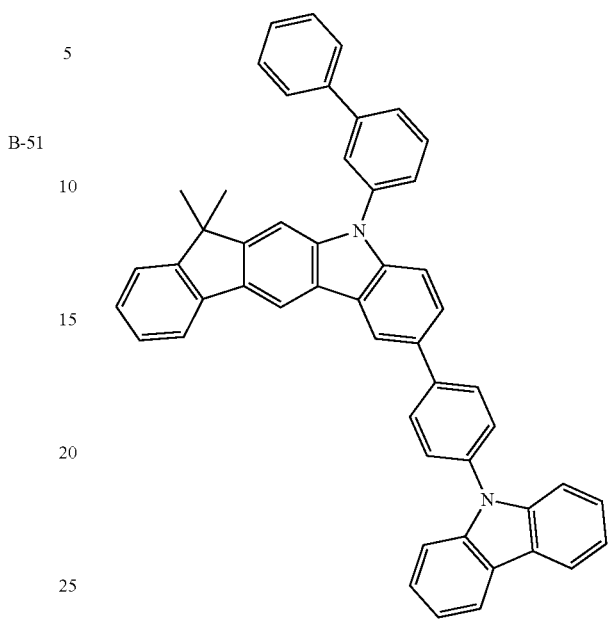
B-54
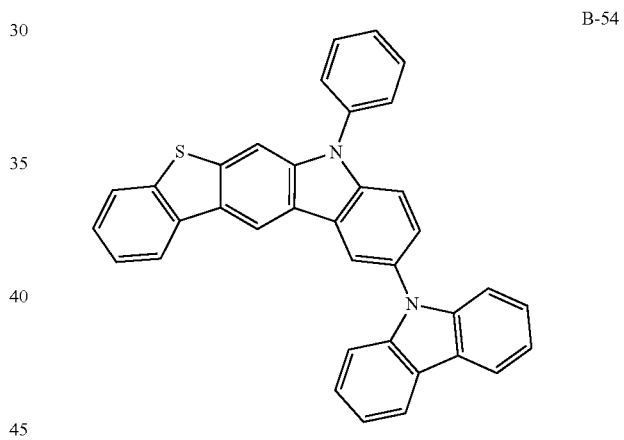
B-55

B-56
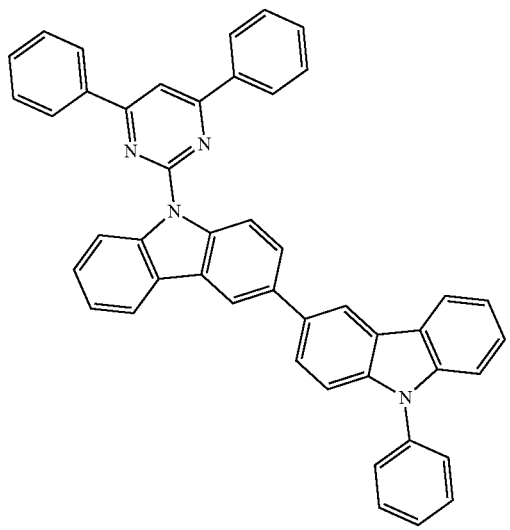
B-57
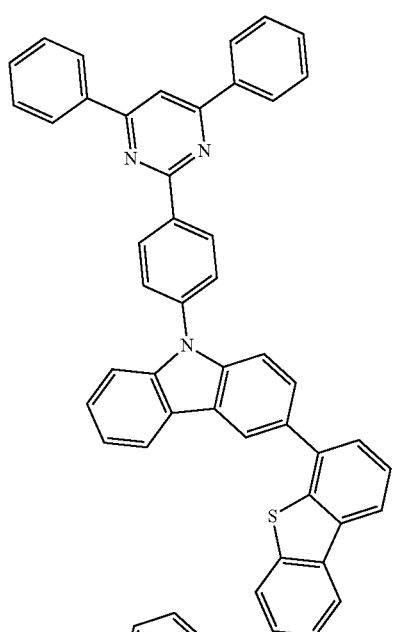
B-58
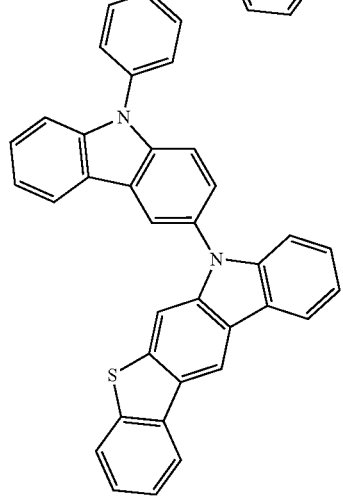
B-59
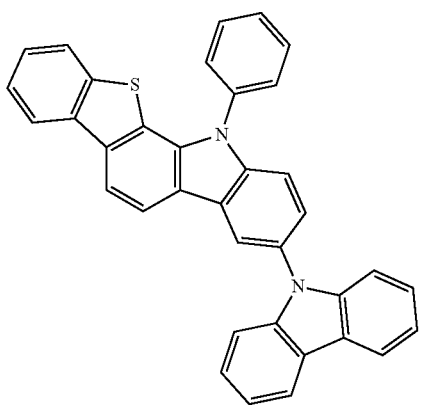
B-60
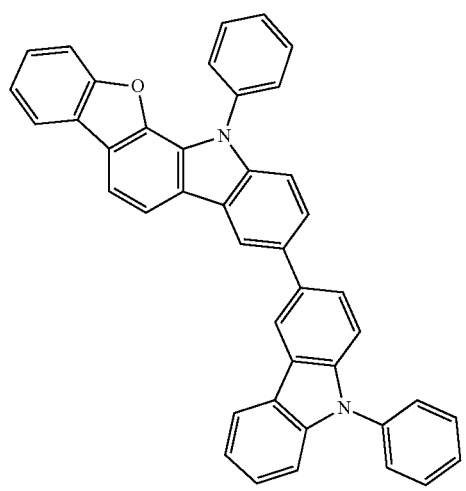
B-61
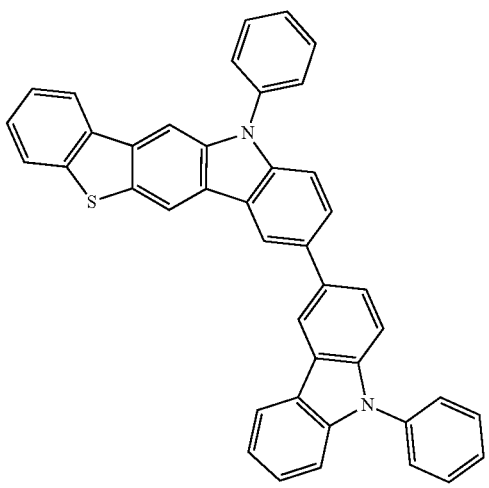

B-62
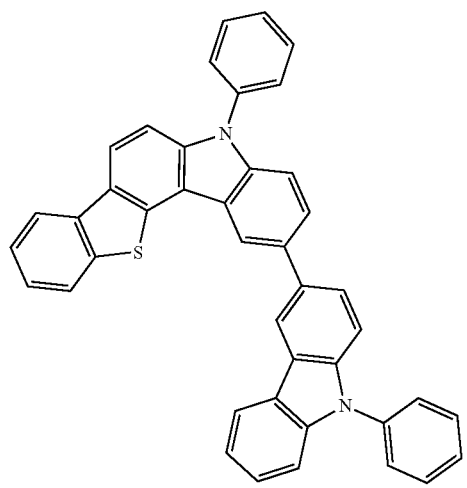
B-63
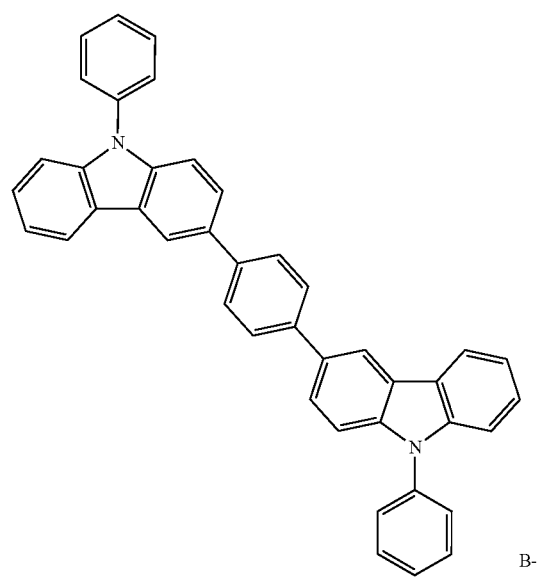
B-64
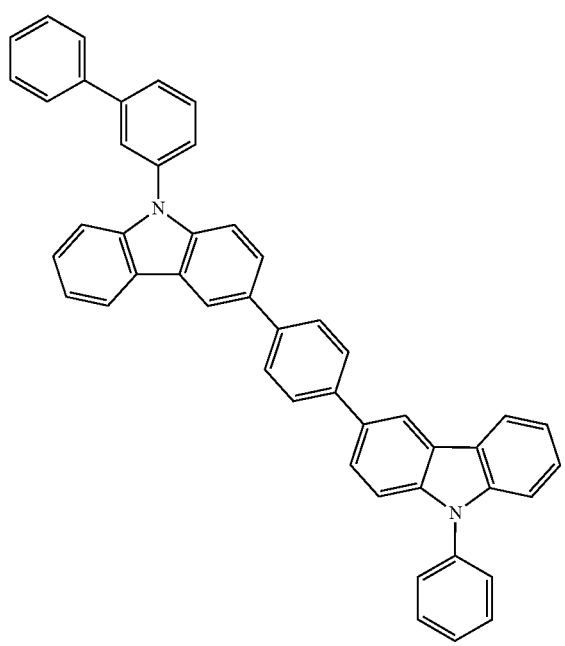
B-65
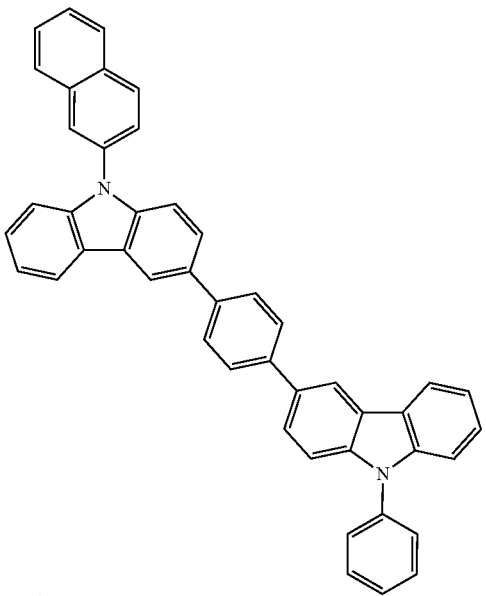
B-66
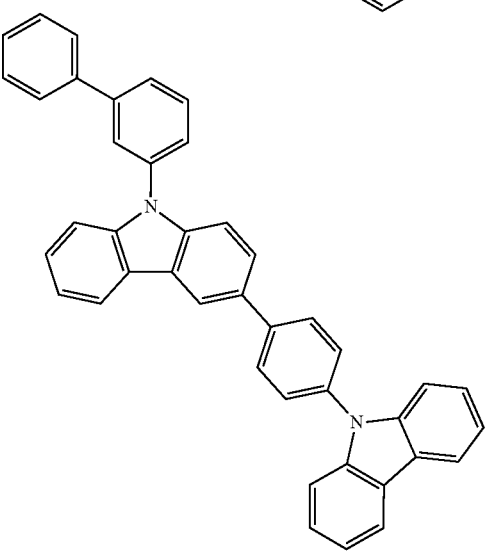
B-67
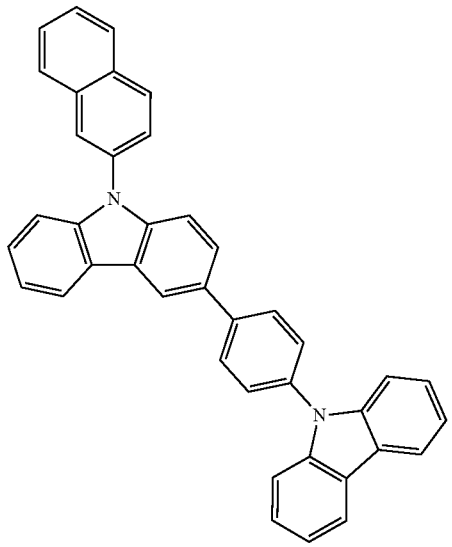

B-68
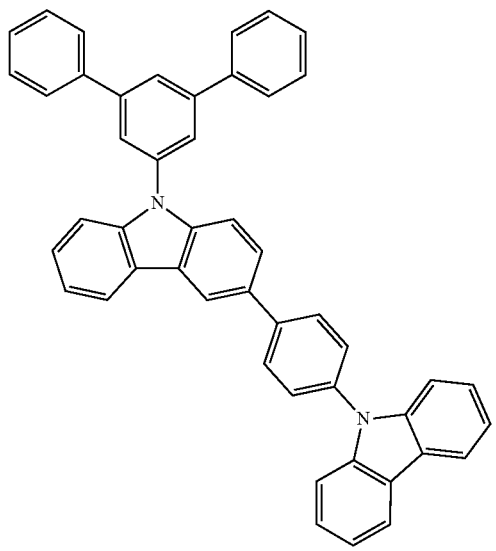
B-69
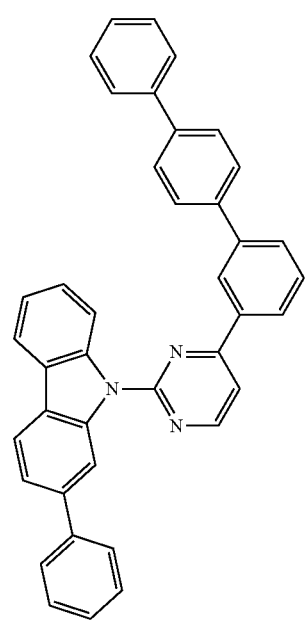
B-70
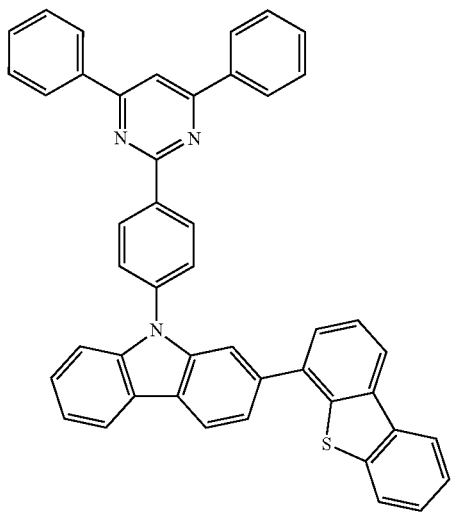
B-71
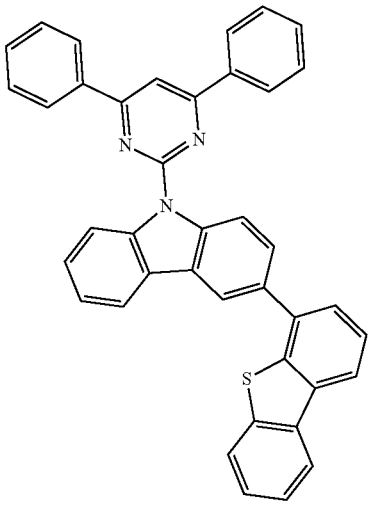
B-72
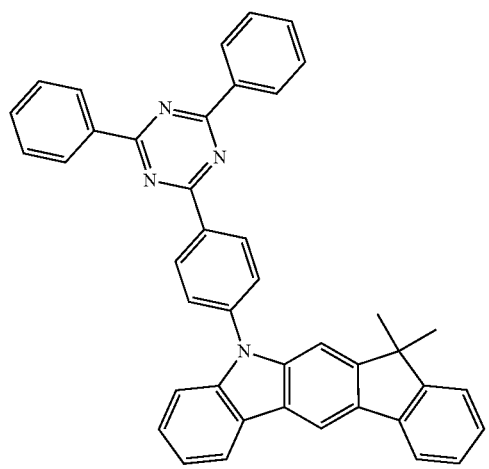
B-73
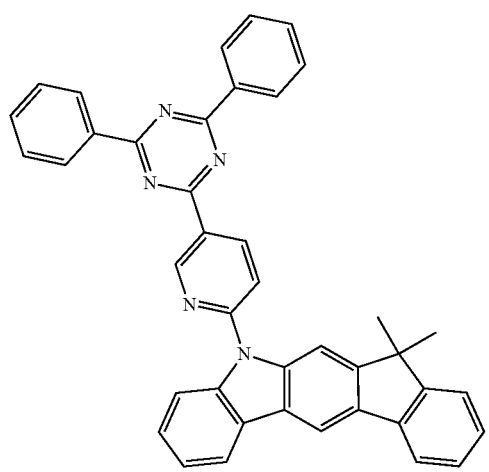

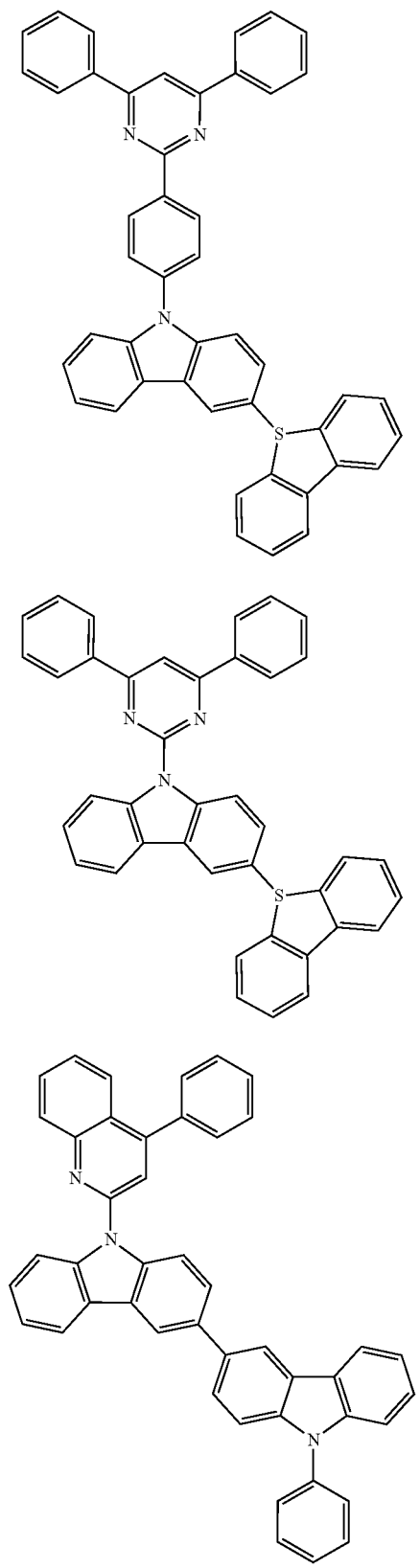
B-74
B-75
B-76
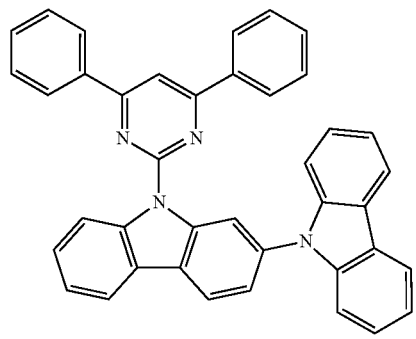
B-77
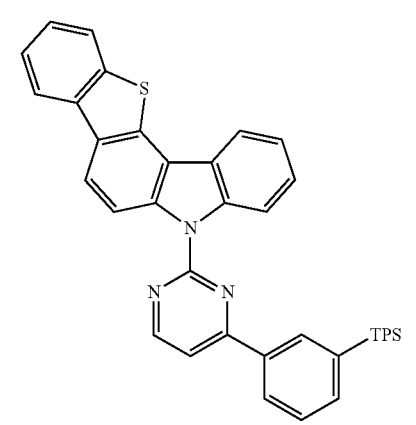
B-78
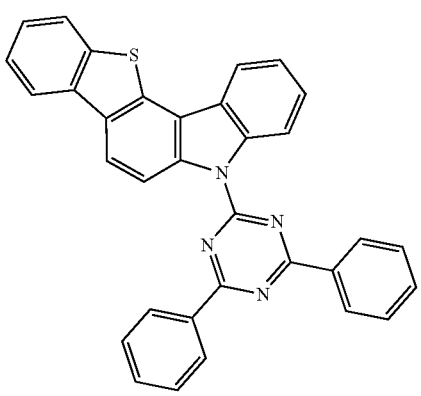
B-79
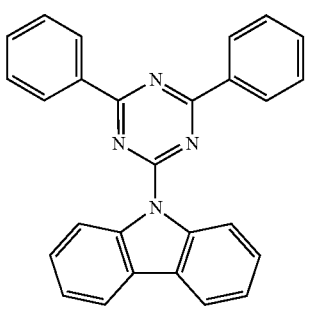
B-80

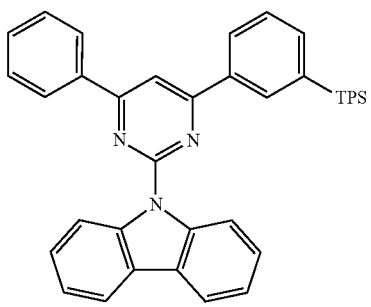
B-81
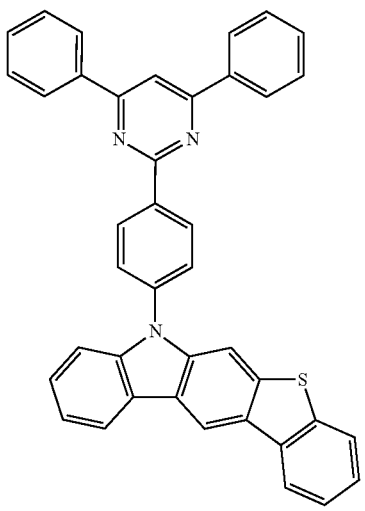
B-85
B-82
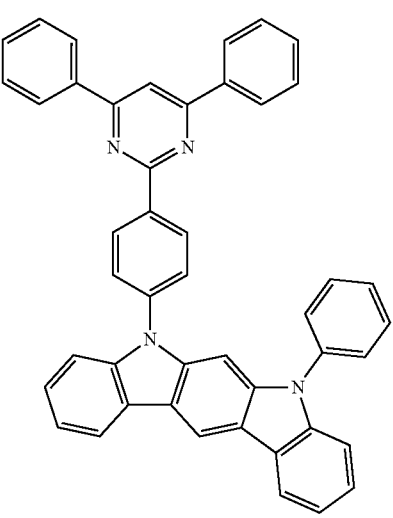
B-86
B-83
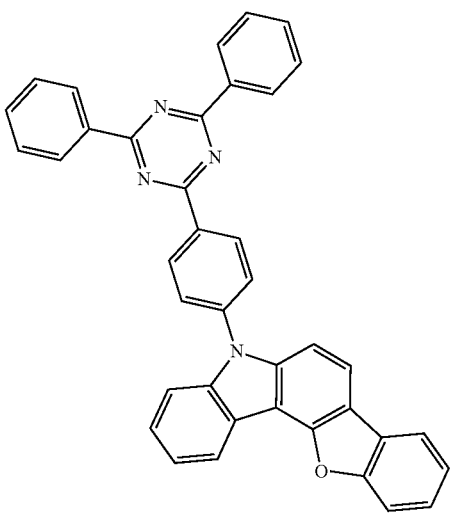
B-87
B-84

B-88
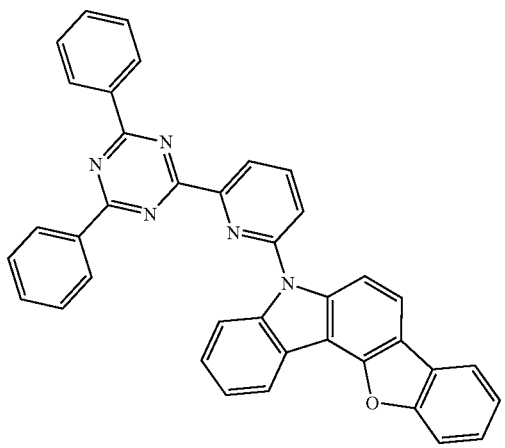
B-91
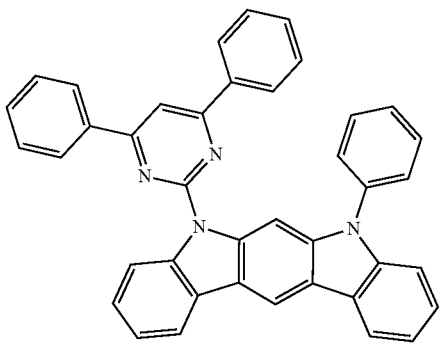
B-89
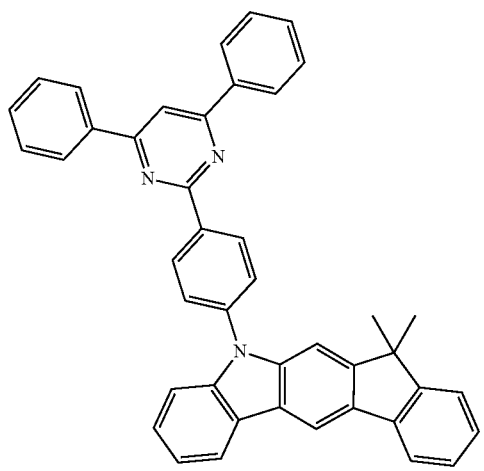
B-92
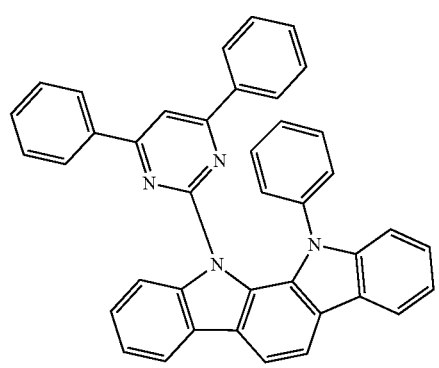
B-93
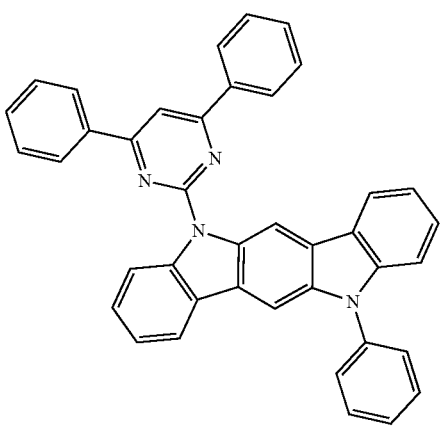
B-90
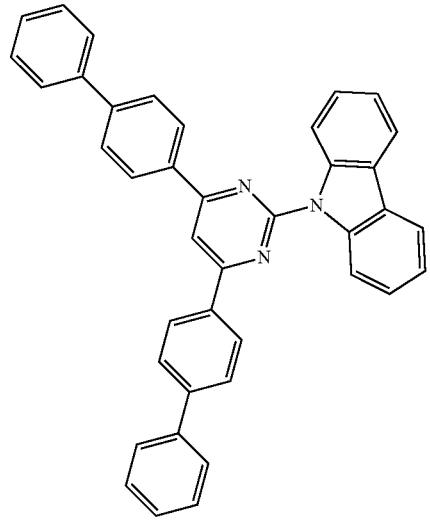
B-94
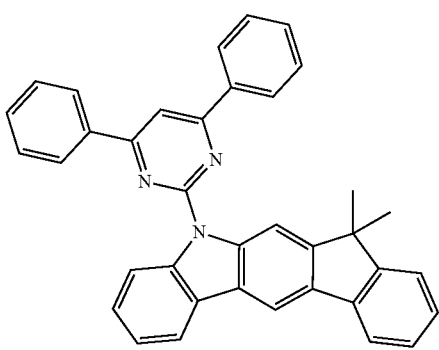

B-95
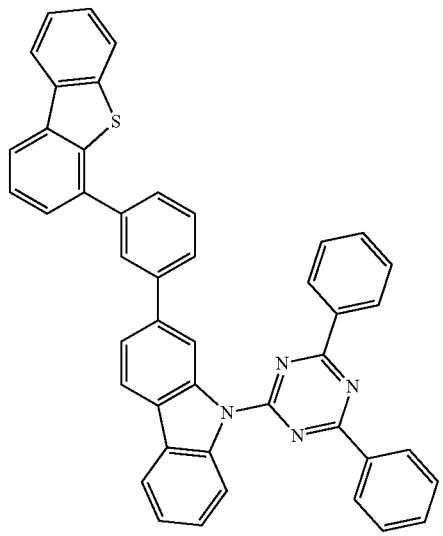
B-96
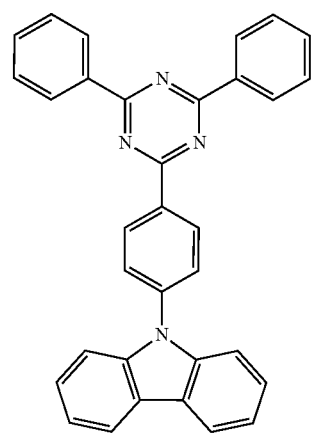
B-97
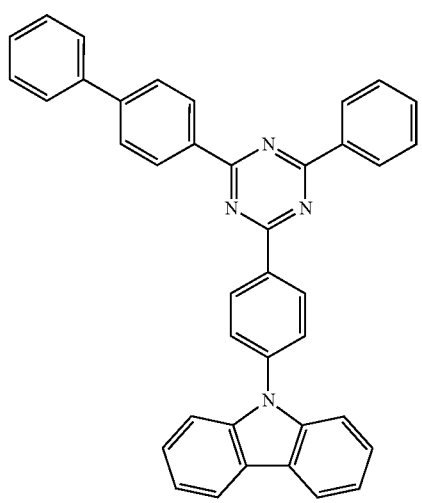
B-98
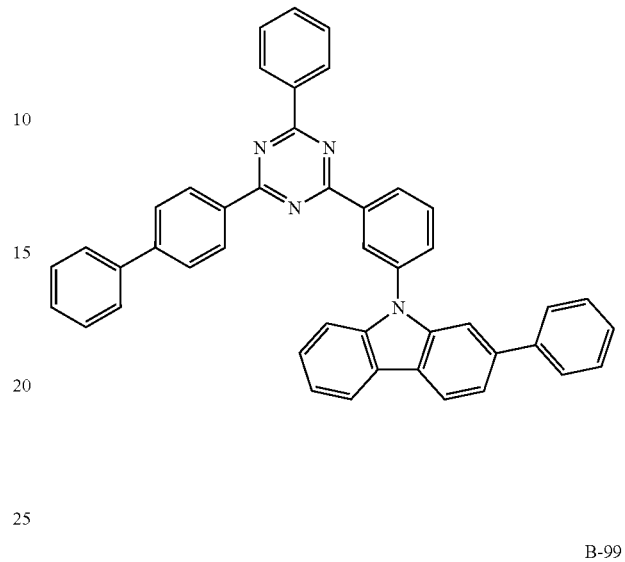
B-99
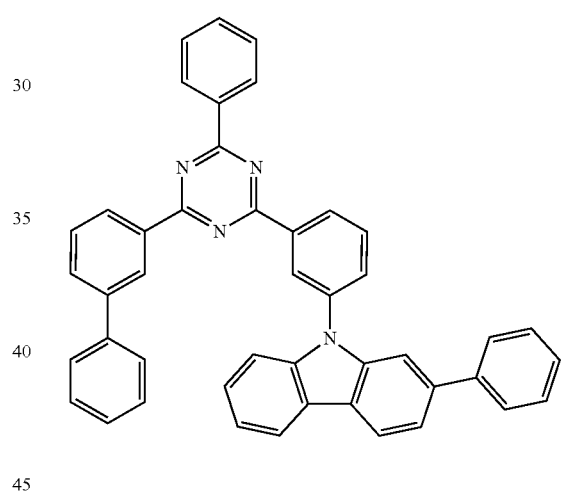
B-100
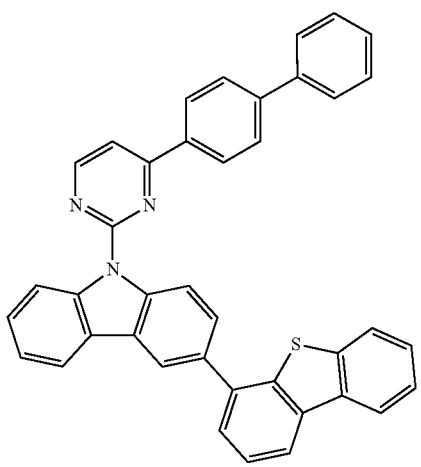

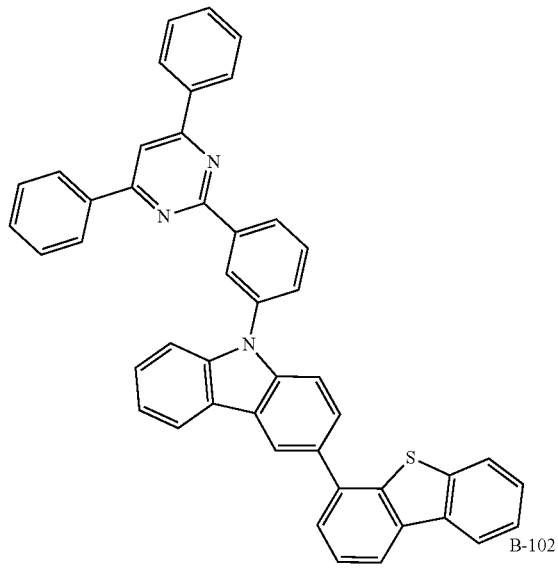
B-101
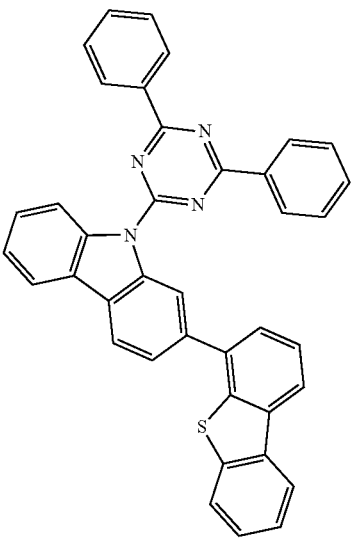
B-104
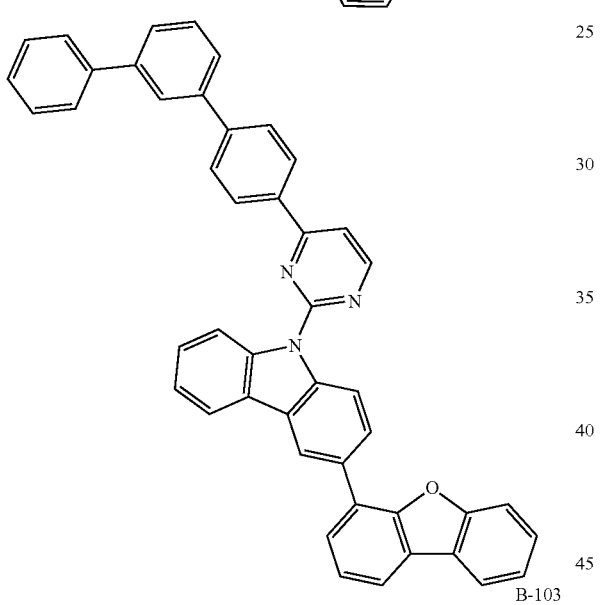
B-102
B-105
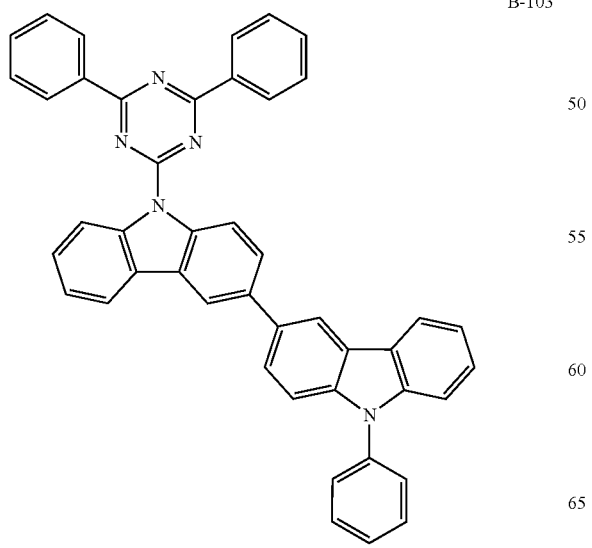
B-103
B-106

B-107
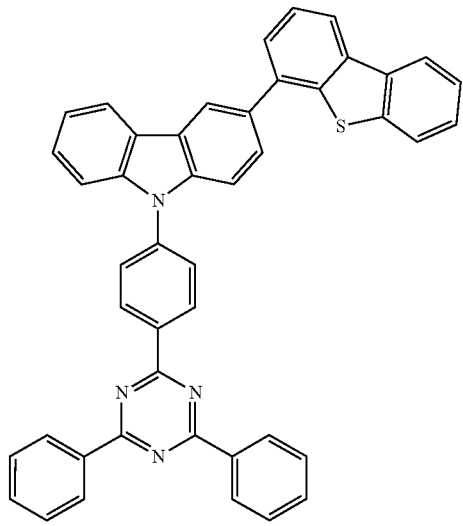
B-108
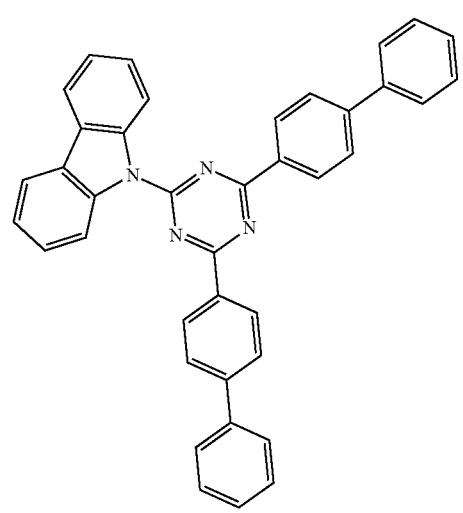
B-109
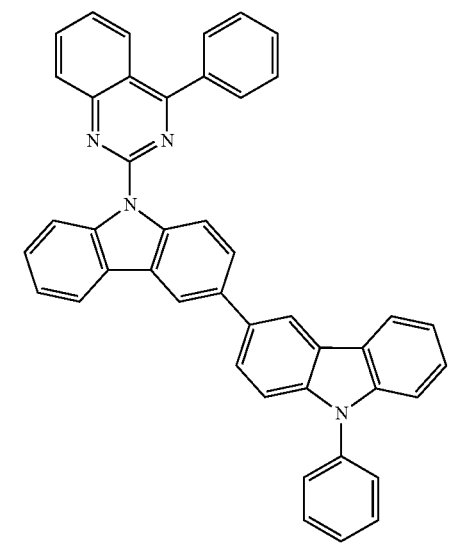
B-110
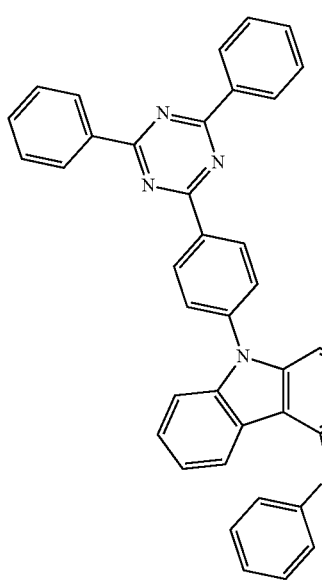
B-111
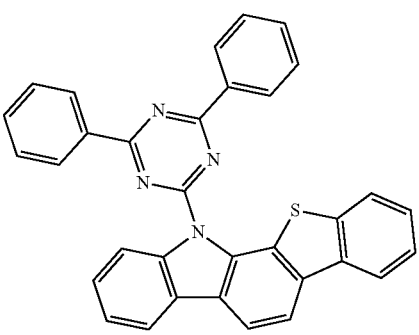
B-112
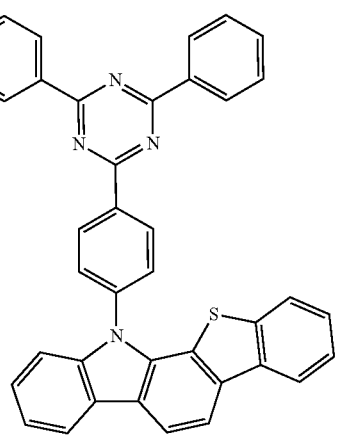

B-113
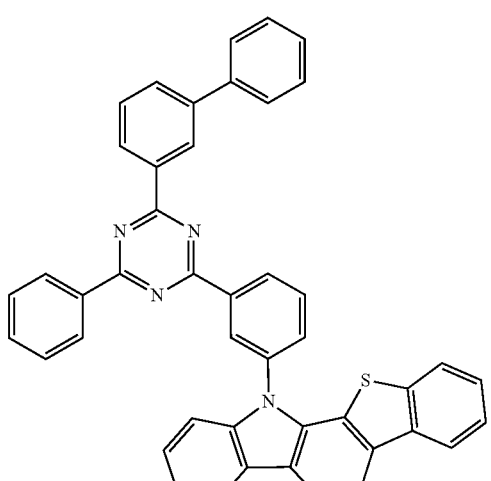
B-114
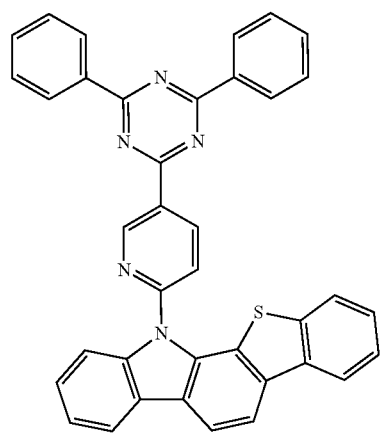
B-115
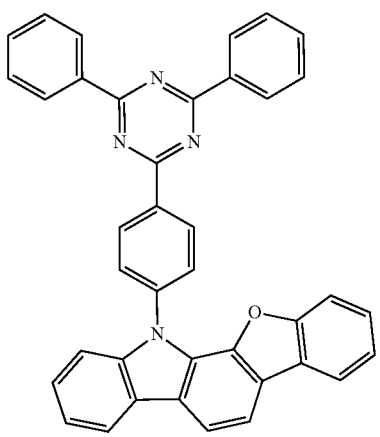
B-116
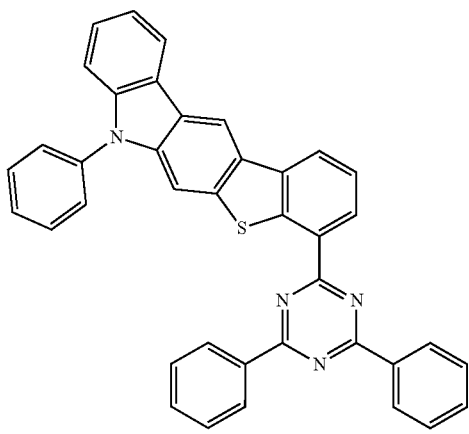
B-117
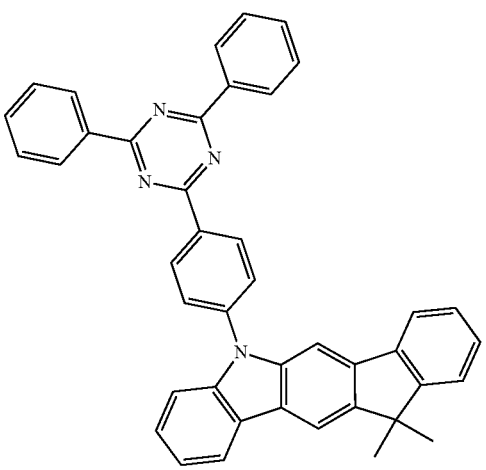
B-118
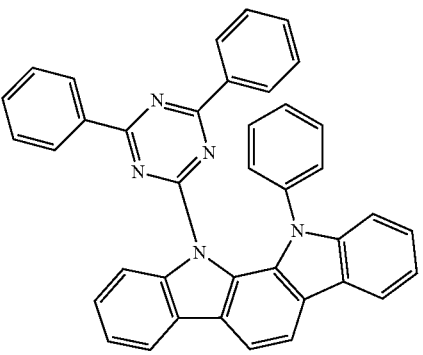

B-119
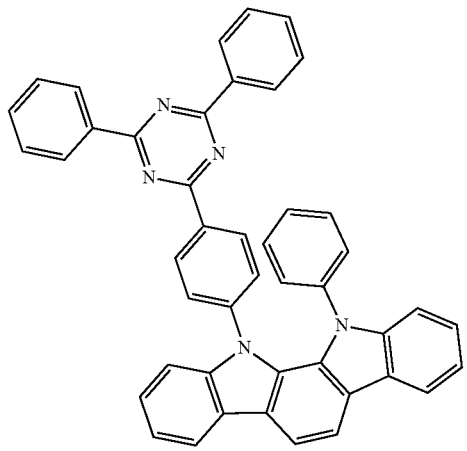
B-120
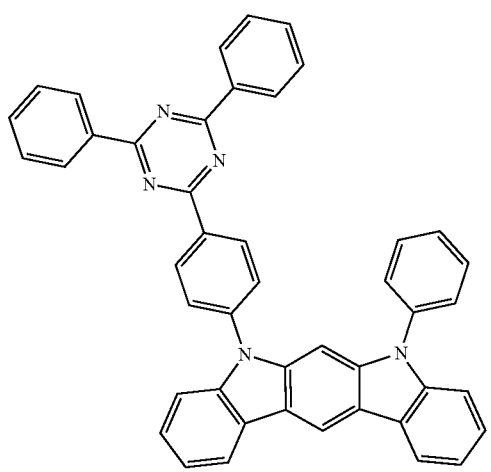
B-121
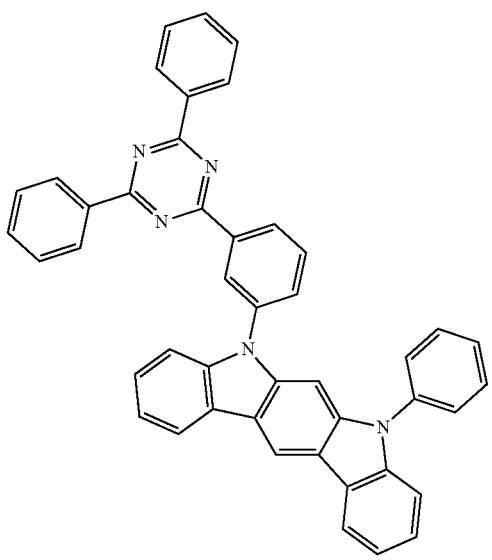
B-122
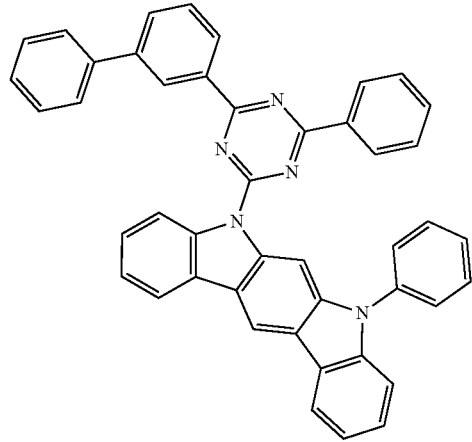
B-123
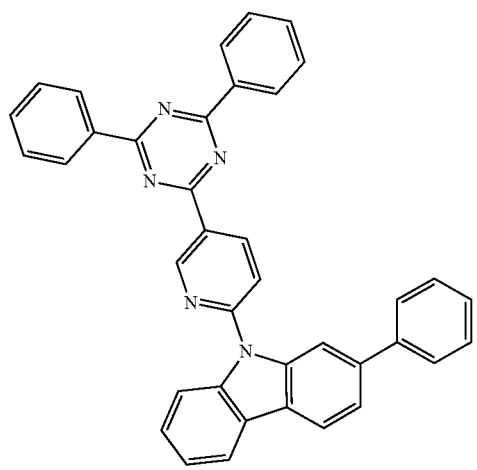
B-124
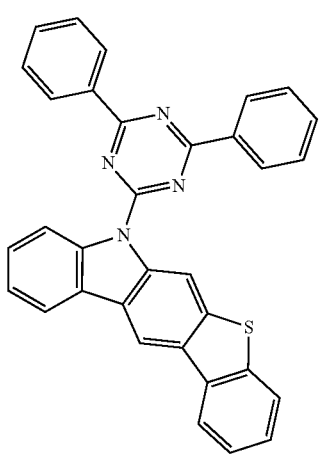

B-125
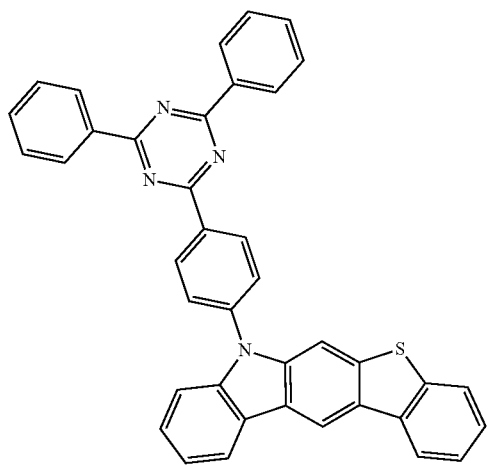
B-126
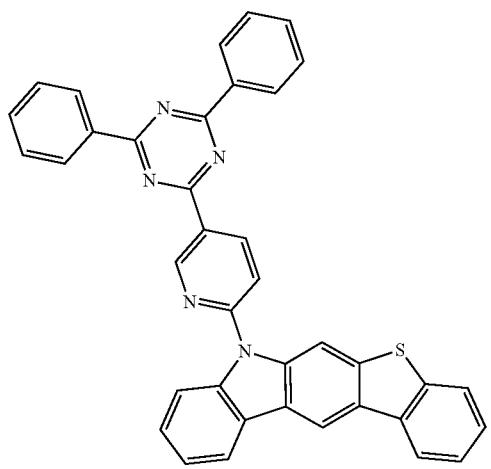
B-127
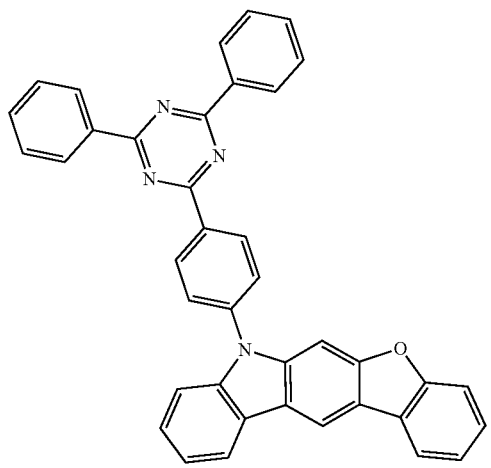
B-128
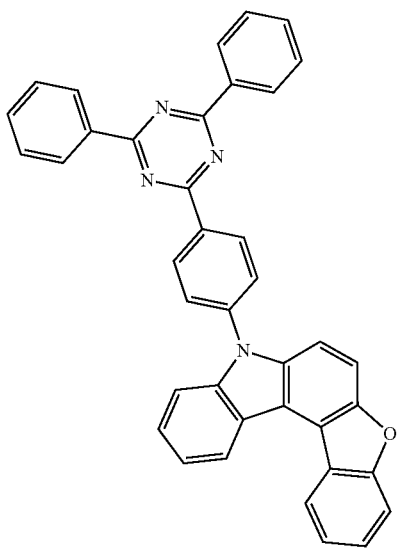
B-129
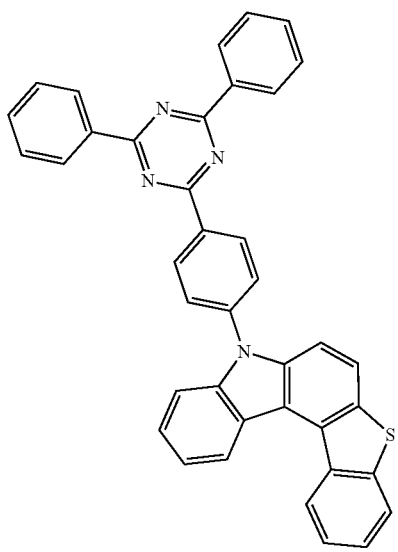
B-130
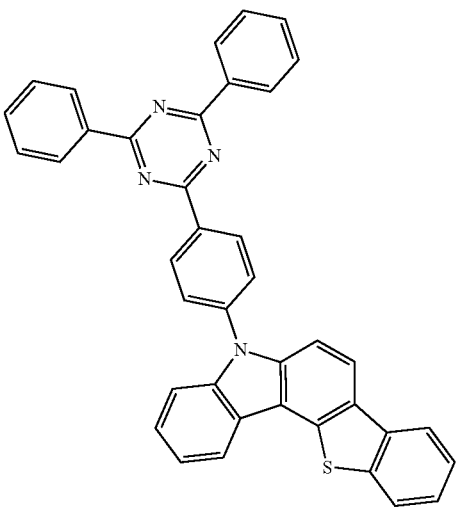

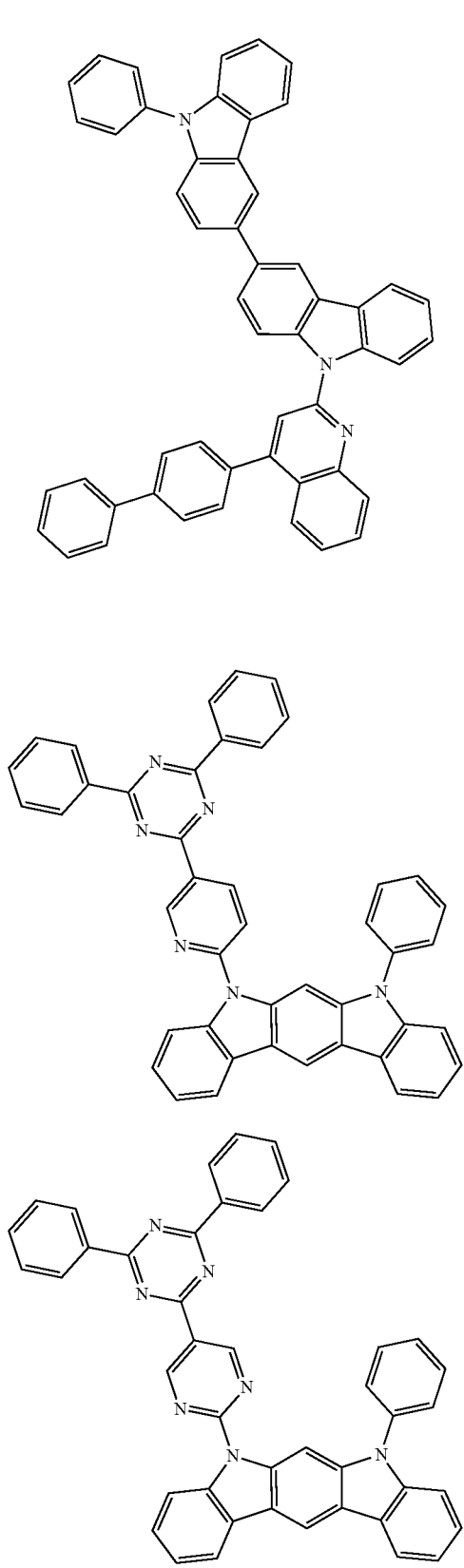
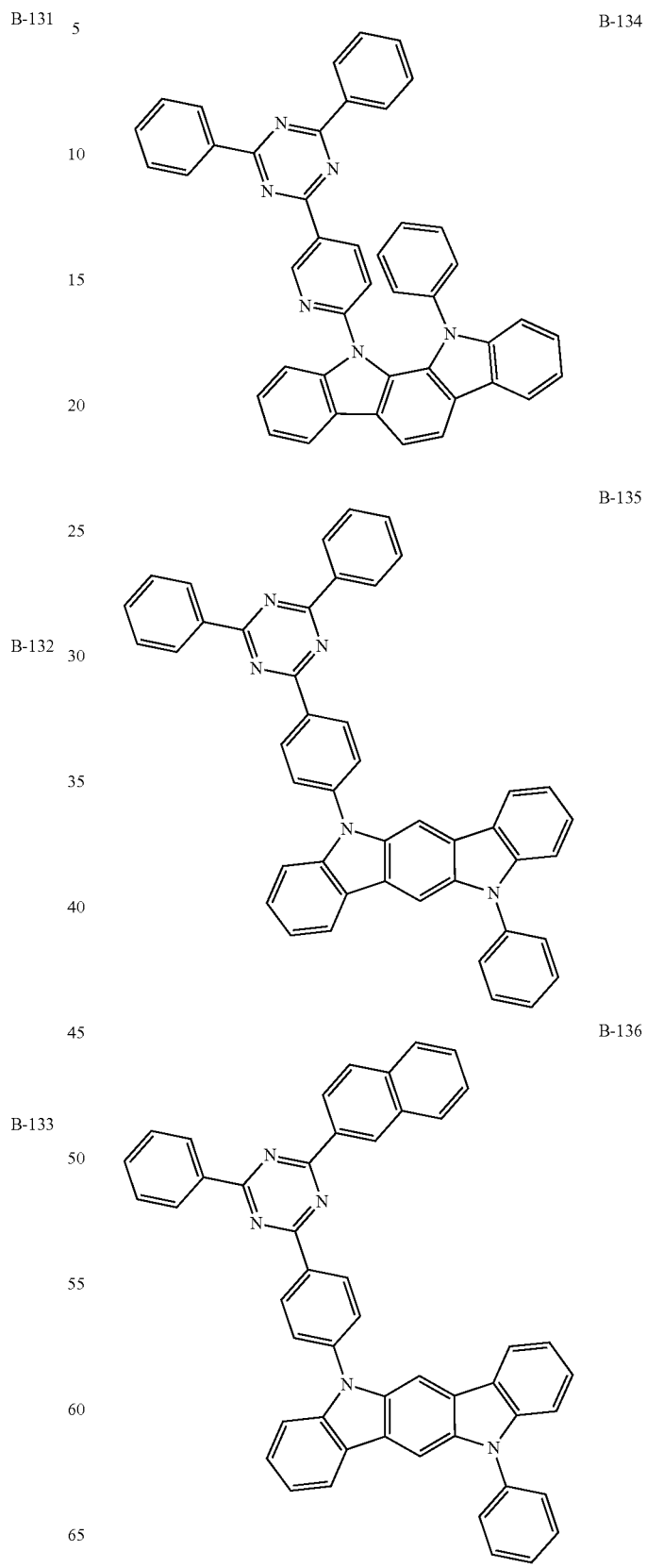

B-137
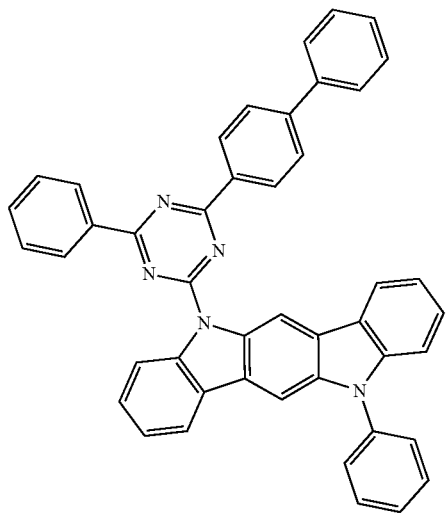
B-138
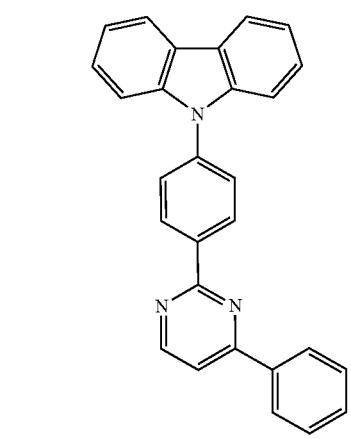
B-139
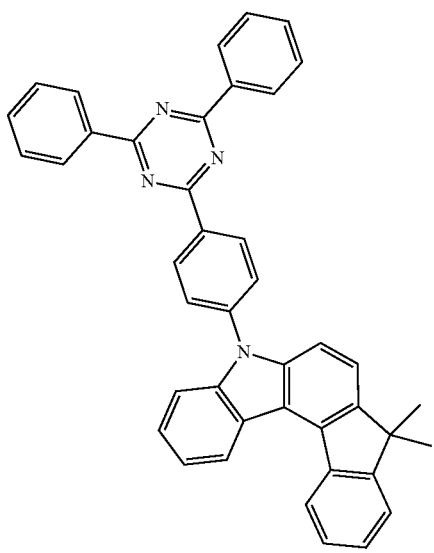
B-140
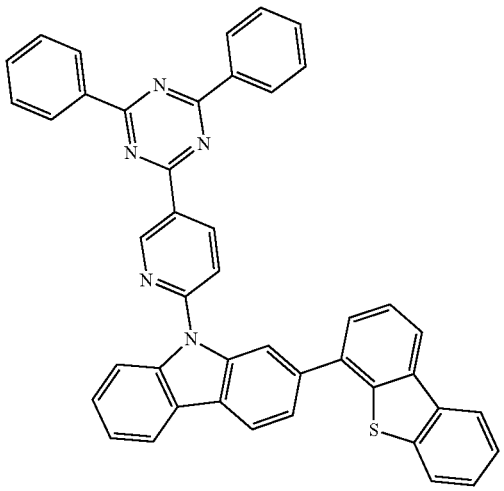
B-141
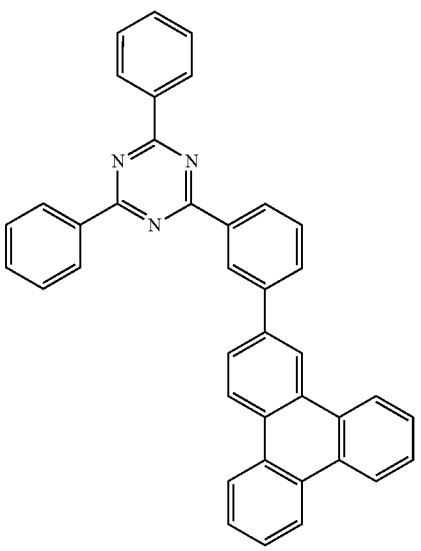
B-142
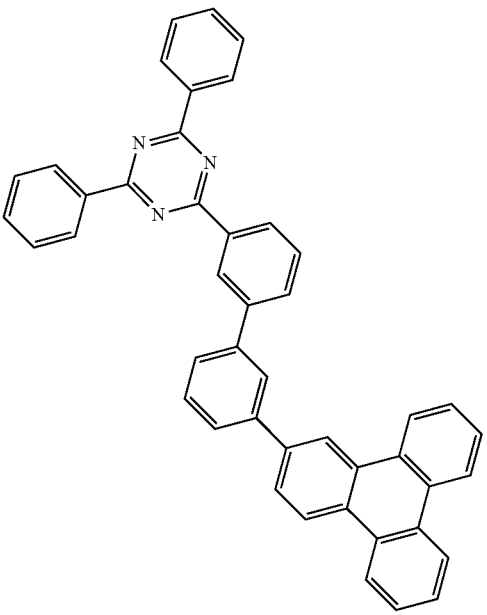

B-143
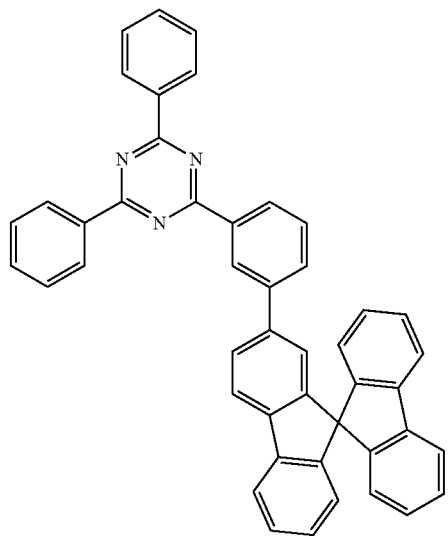
B-144
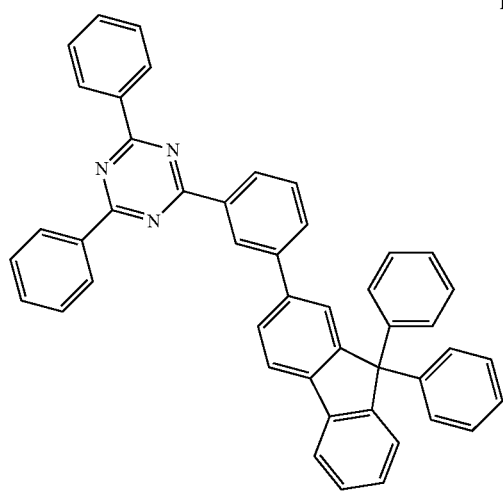
B-145
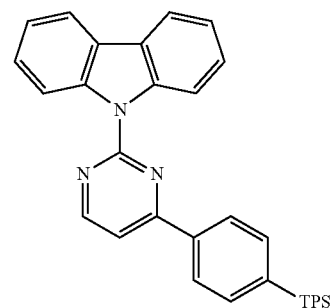
B-146
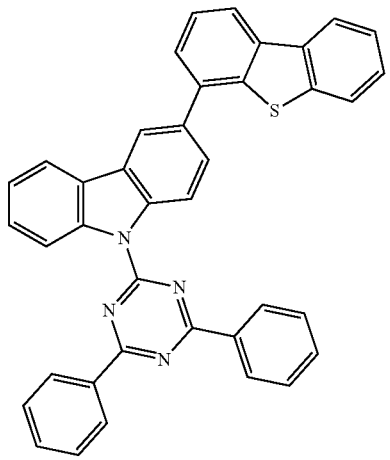
B-147
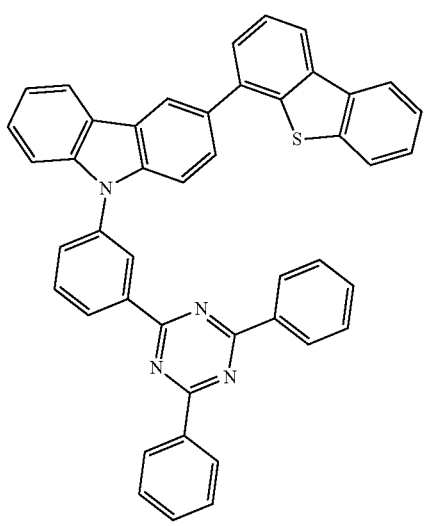
B-148
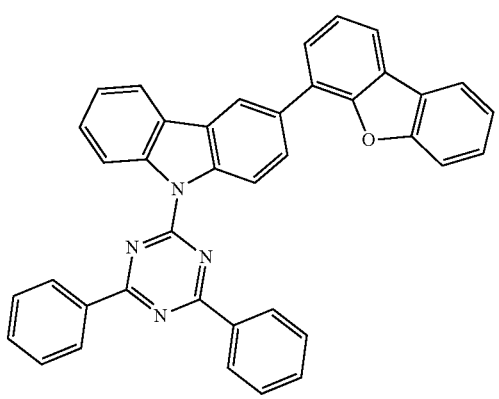

B-149
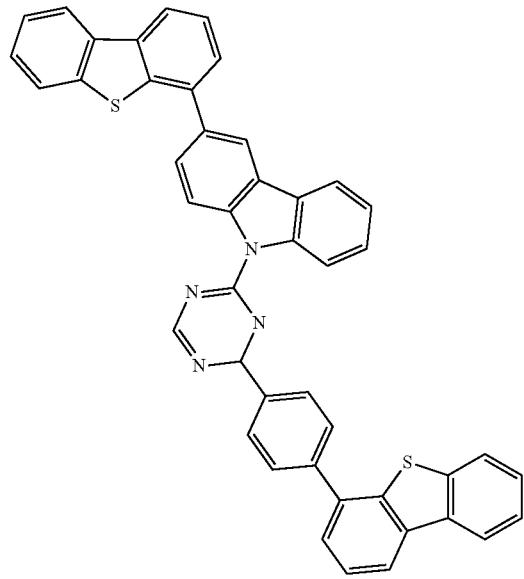
B-150
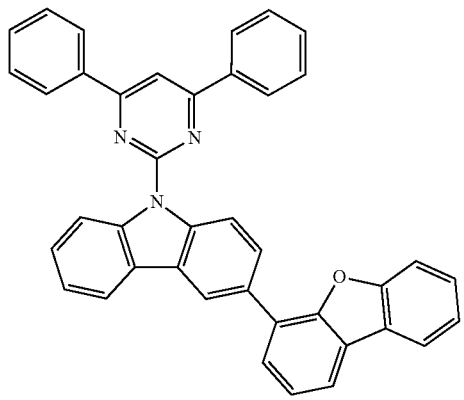
B-151
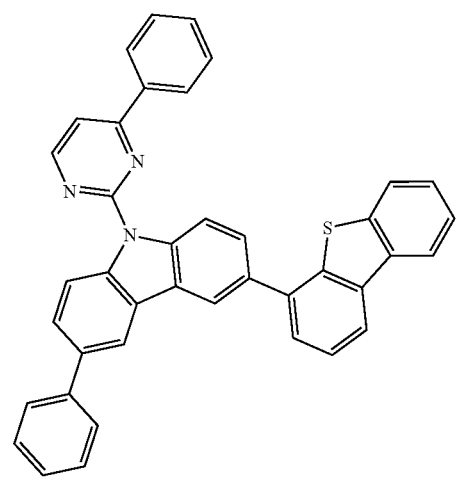
B-152
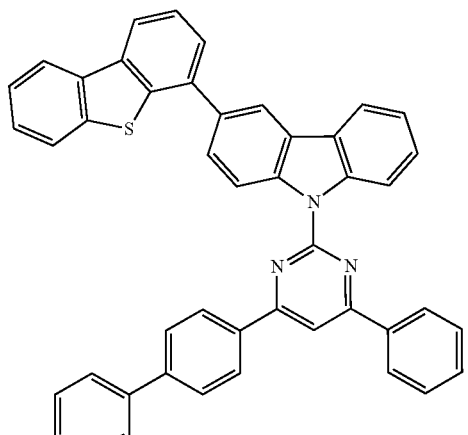
B-153
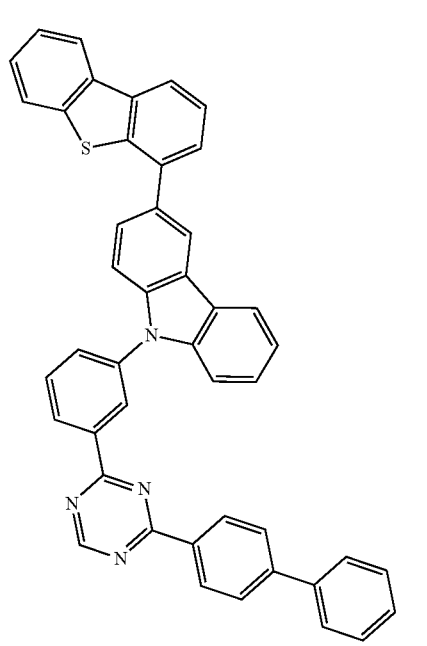
B-154
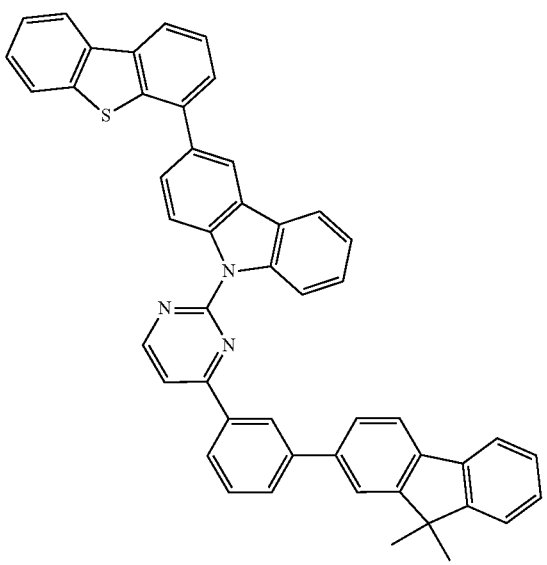

B-155
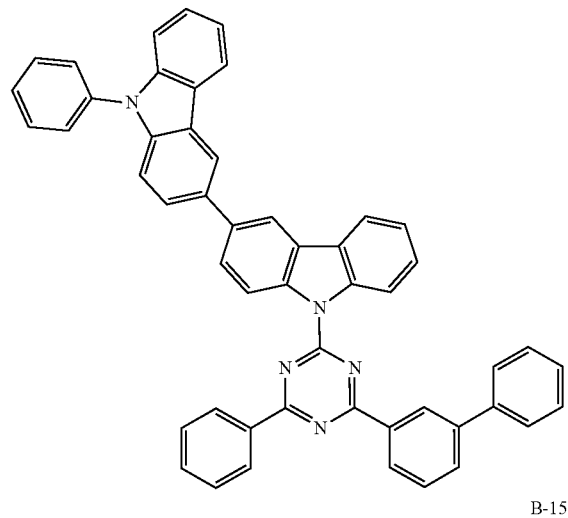
B-156
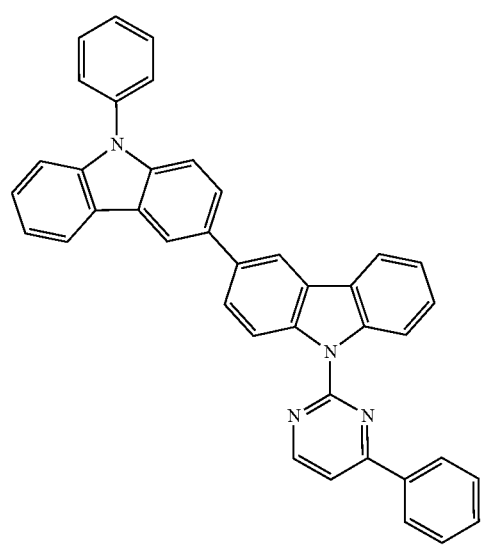
B-157
B-158
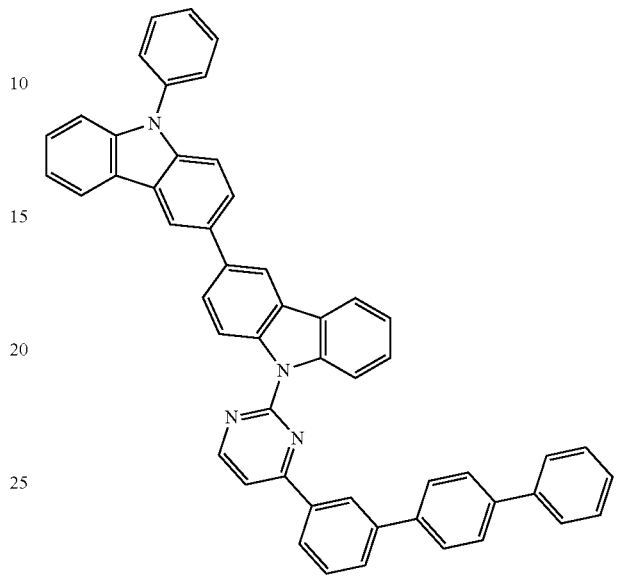
B-159
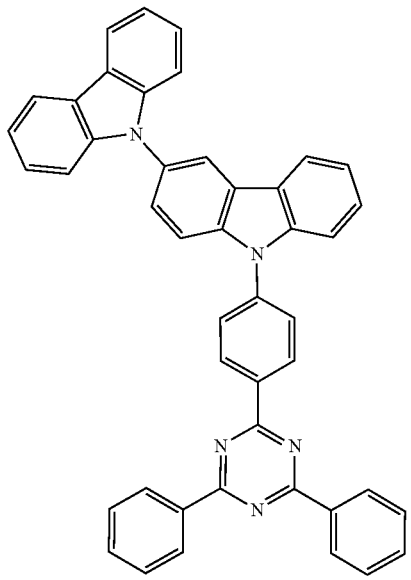

B-160
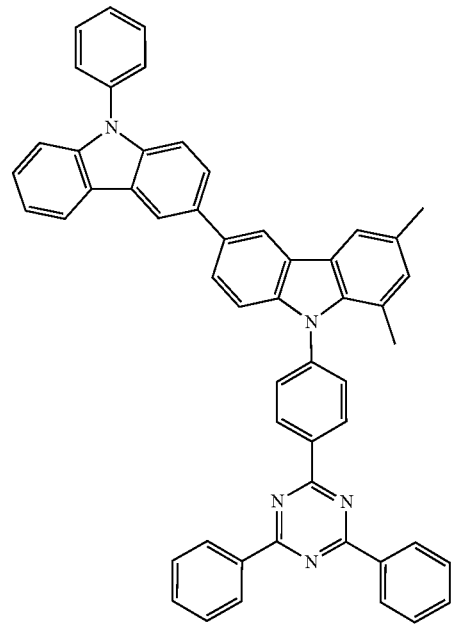
B-161
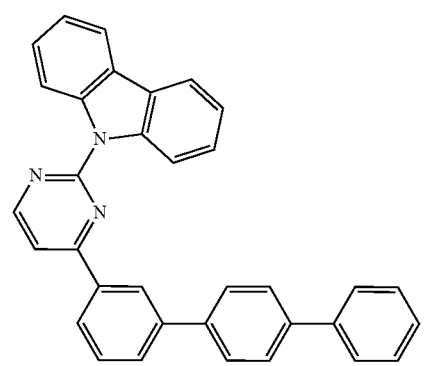
B-162
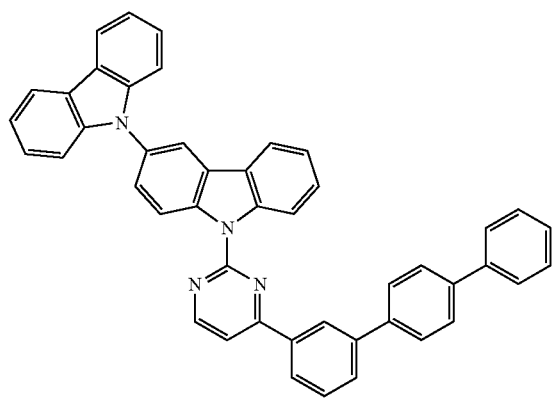
B-163
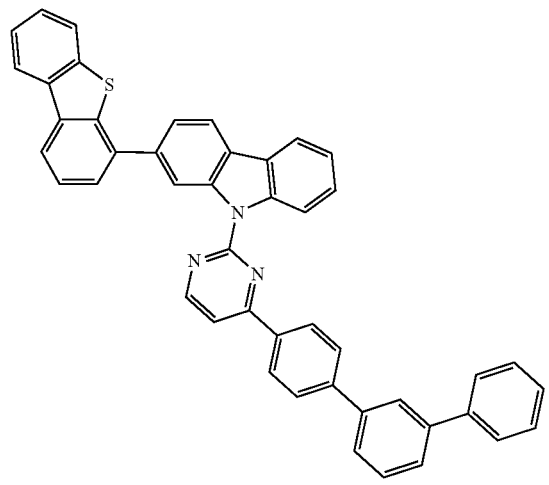
B-164
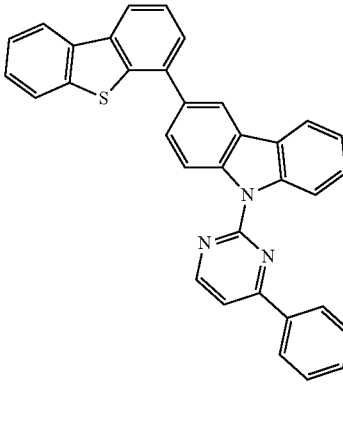
B-165
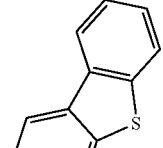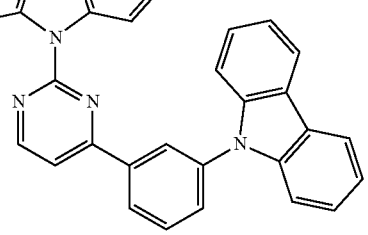

-continued
B-166
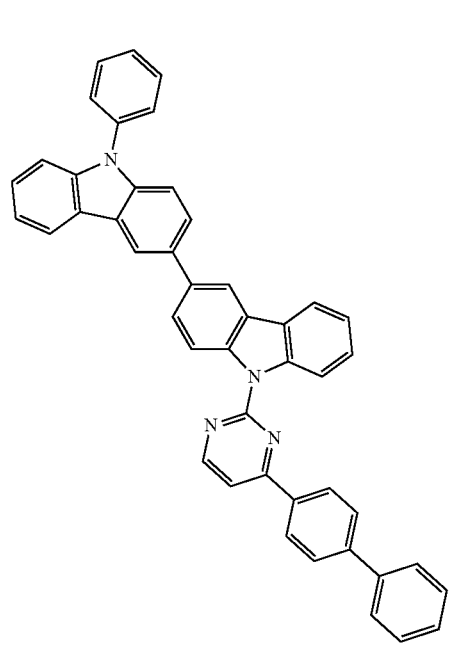
B-168
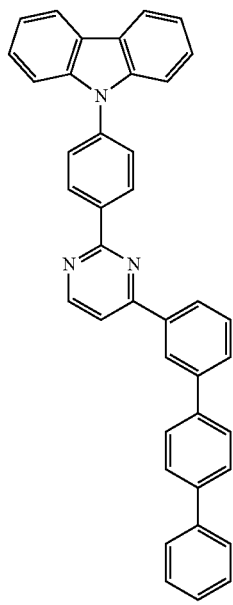
B-167
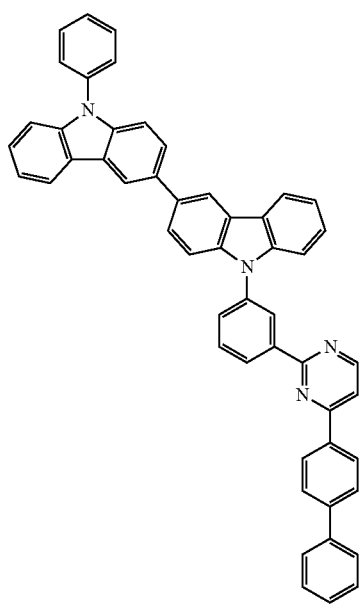
B-169
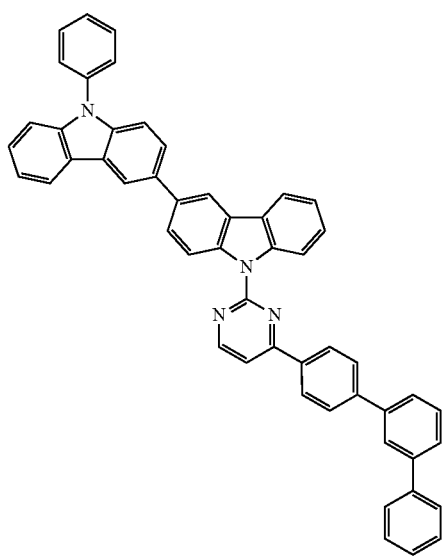

-continued
B-170
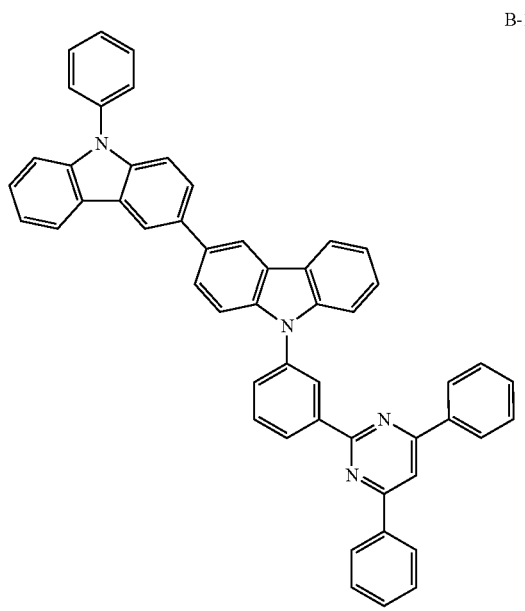
B-171
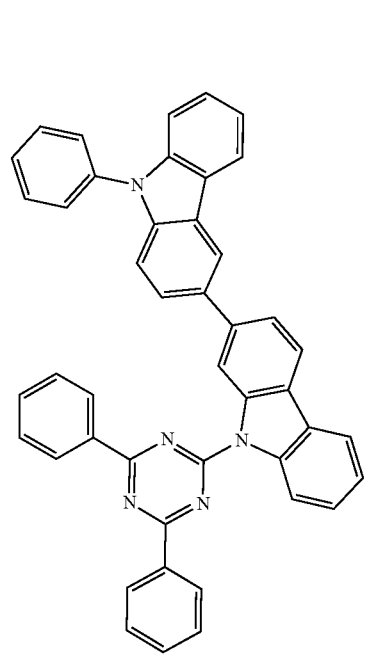
B-172
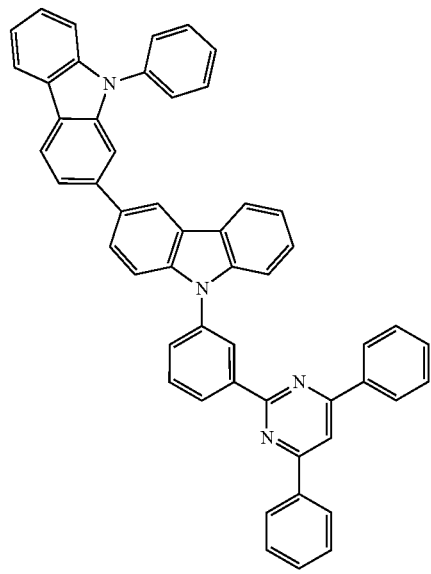
B-173
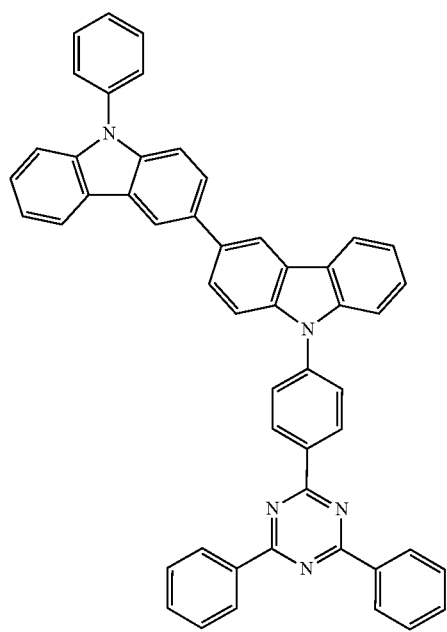

B-174
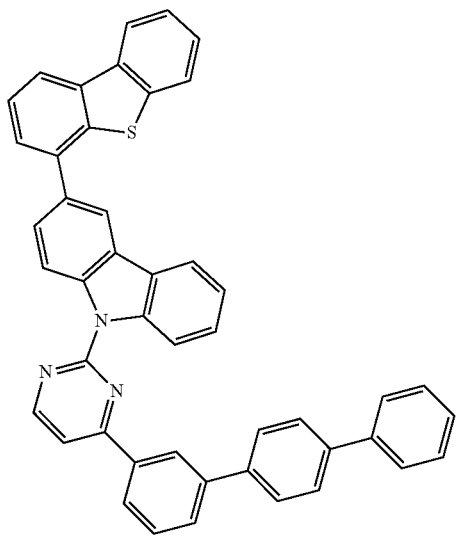
B-175
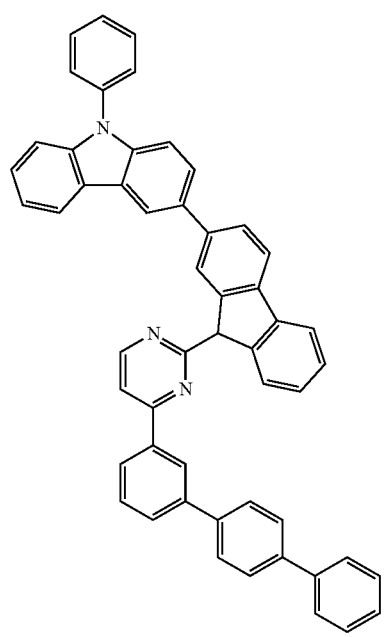
B-176
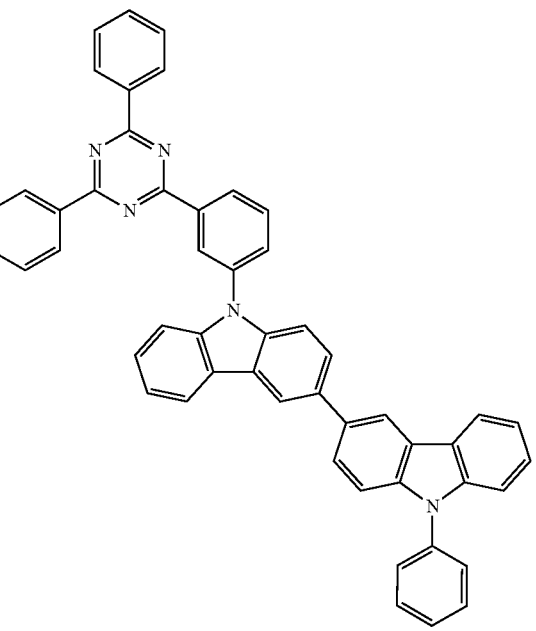
B-177
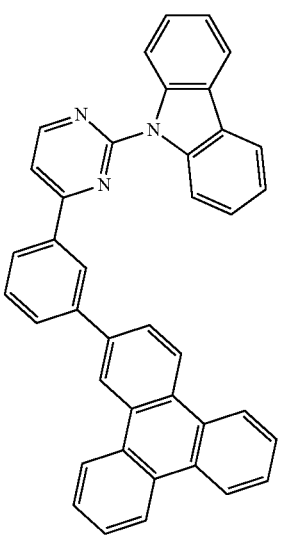

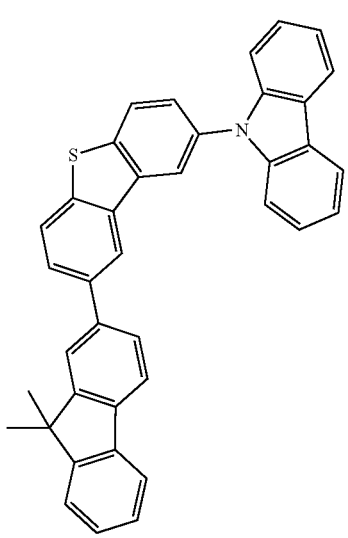
B-178
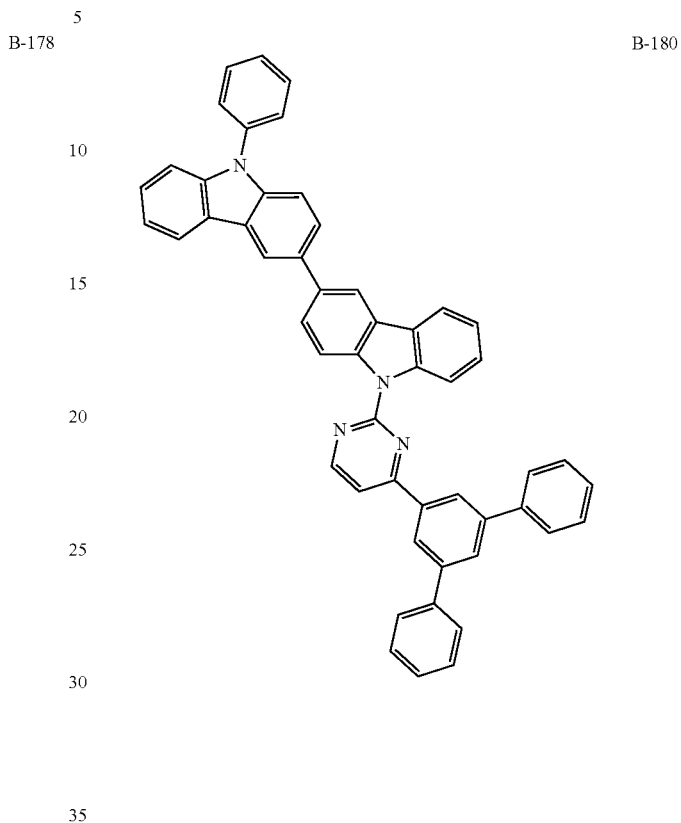
B-180
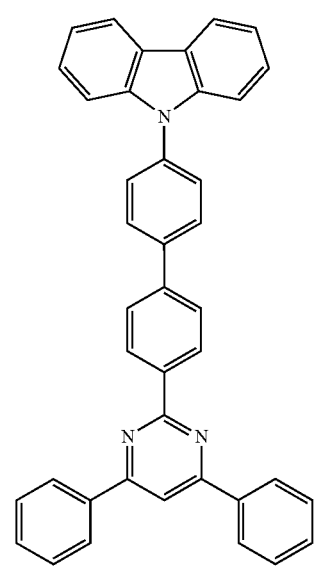
B-179
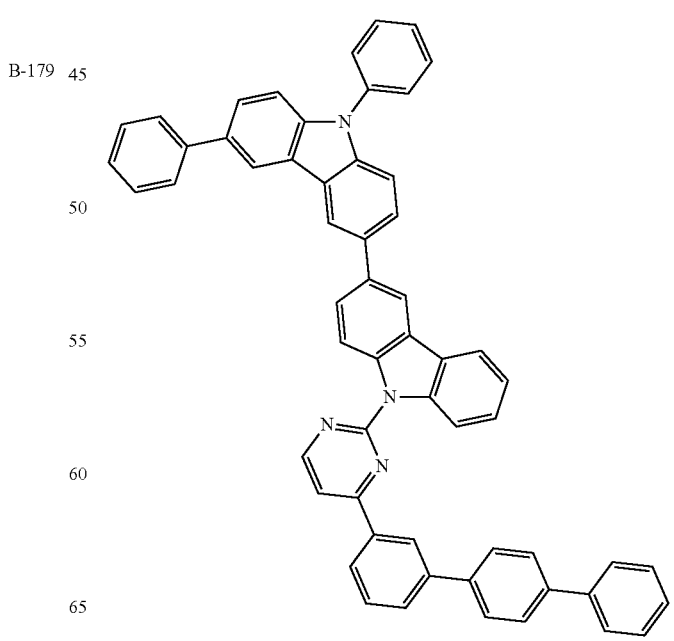
B-181

B-182
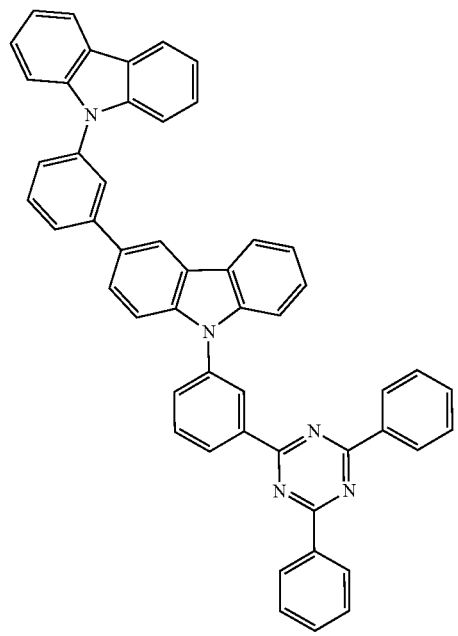
B-183
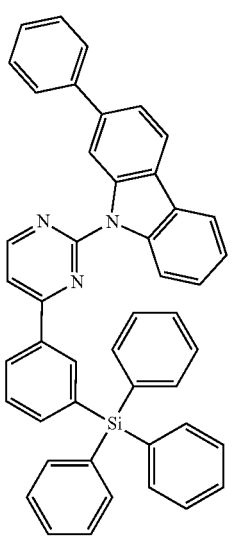
B-184
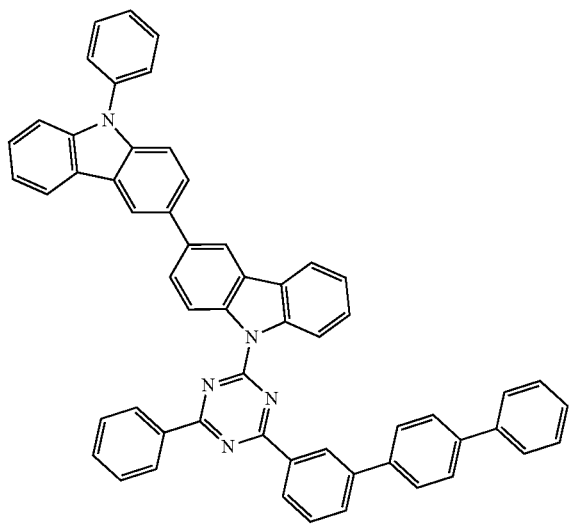
B-185
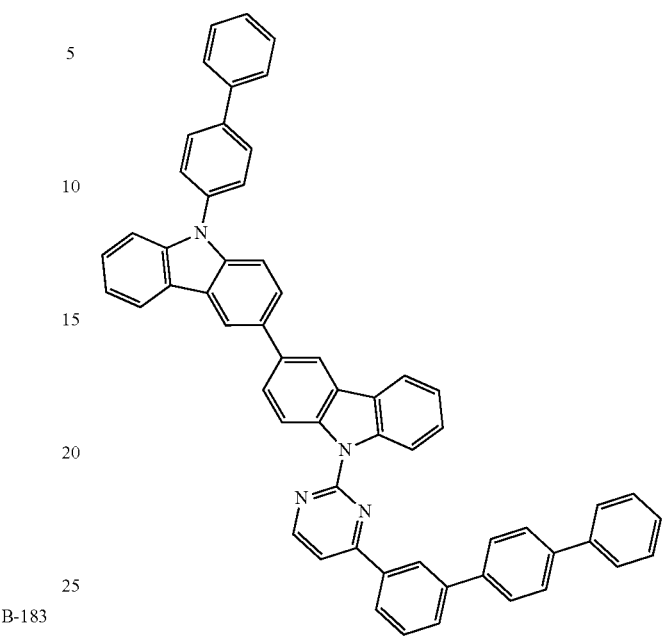
B-186
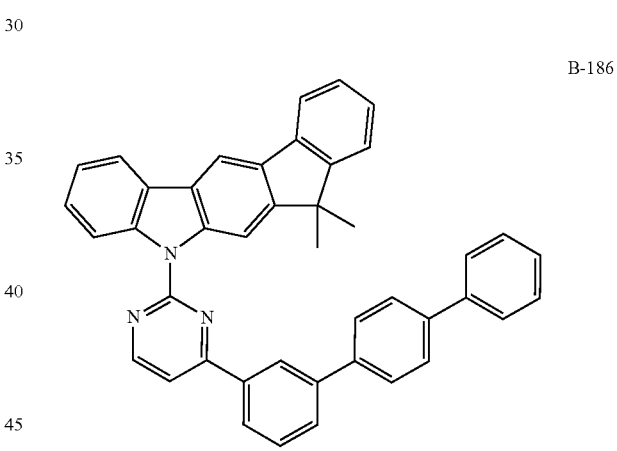
B-187
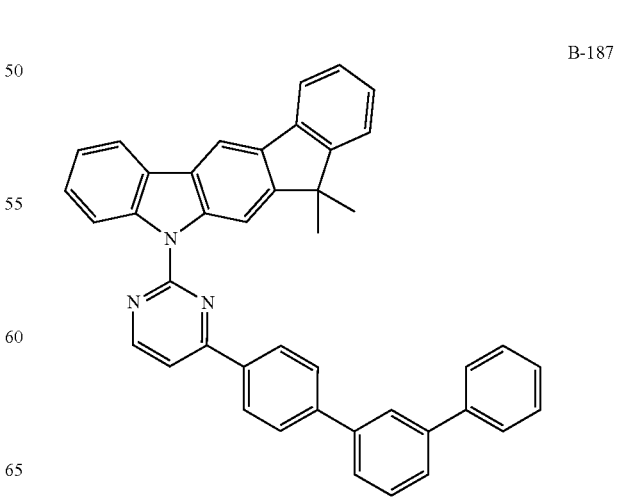

B-188
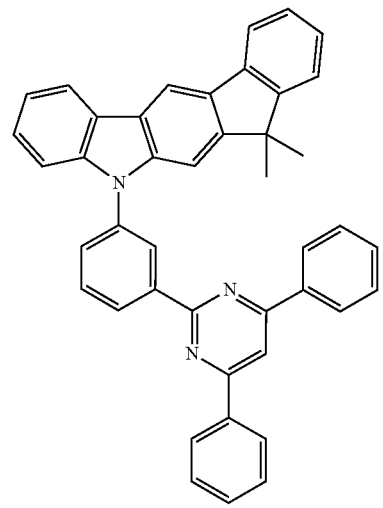
B-189
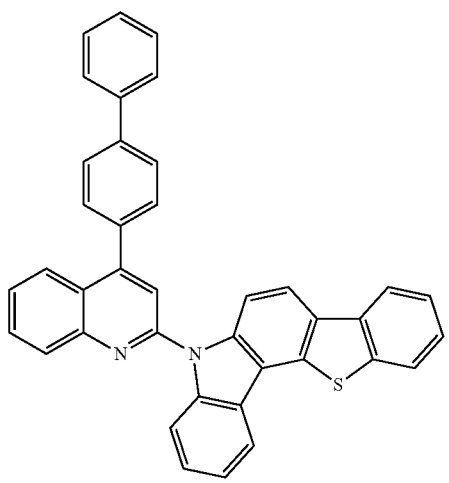
B-190
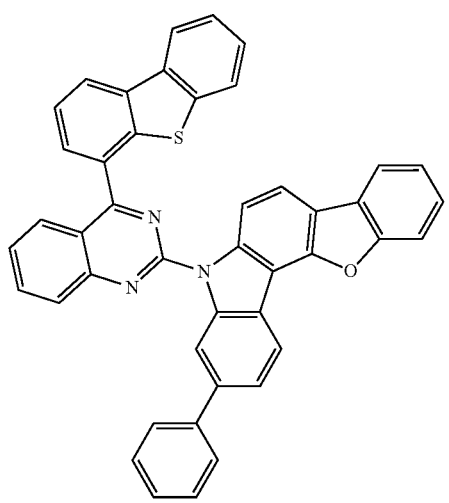
B-191
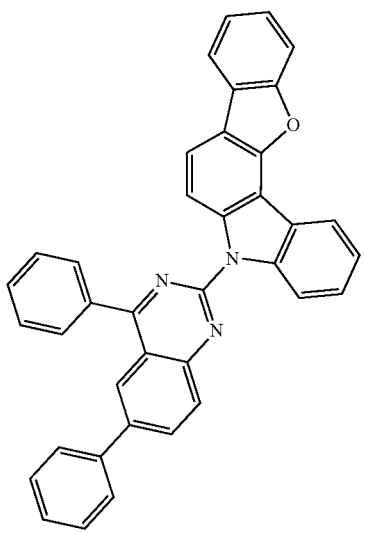
B-192
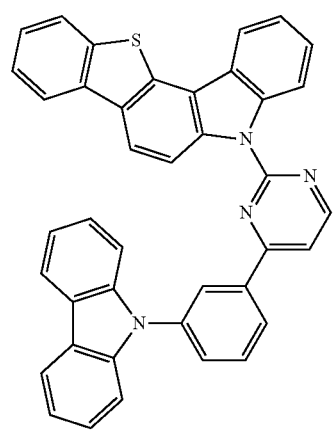
B-193
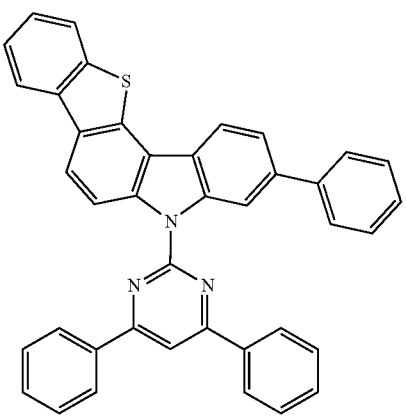

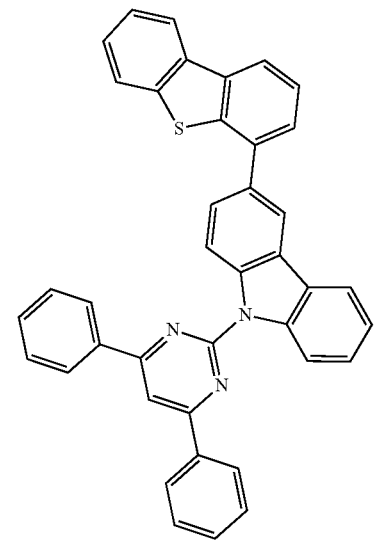

B-194

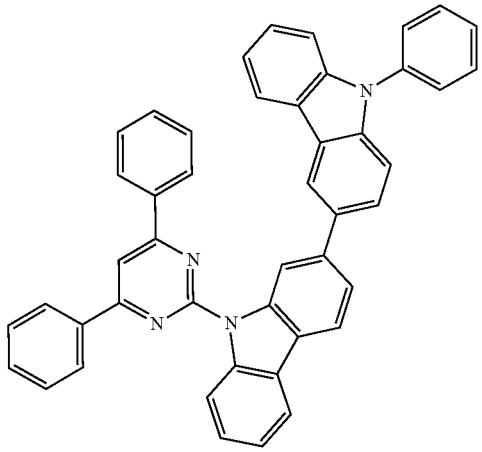

B-197

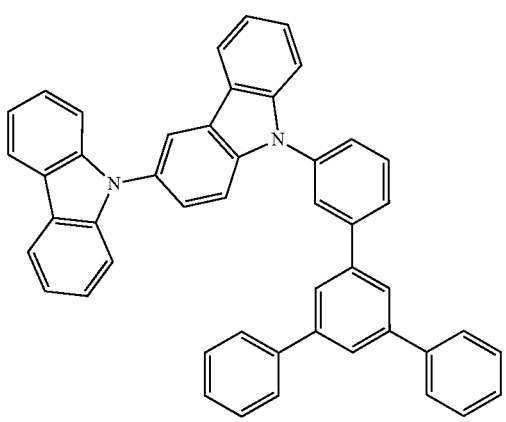

B-195

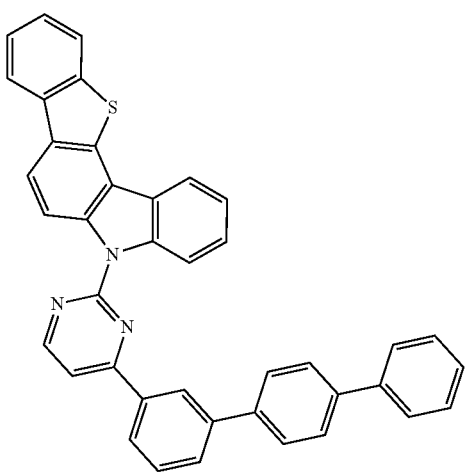

B-196

[Wherein, TPS represents a triphenylsilyl group.]

The dopant comprised in the organic electroluminescent device of the present disclosure is preferably at least one phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise the compound selected from the group consisting of the compounds represented by the following formulas 101 to 104, but are not limited thereto:

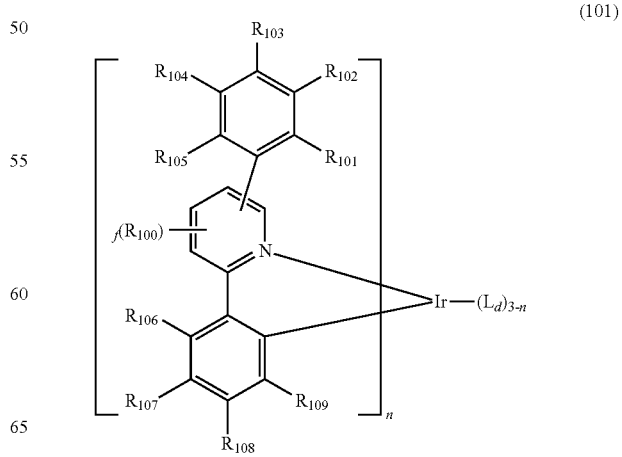

(101)

-continued

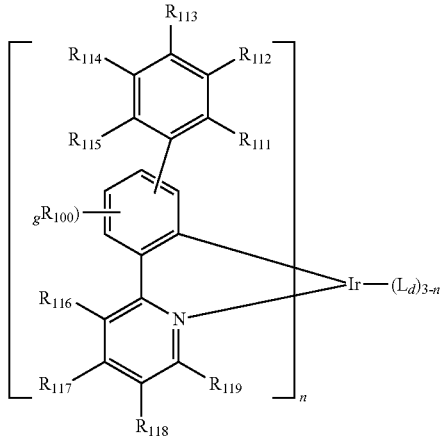
(102)

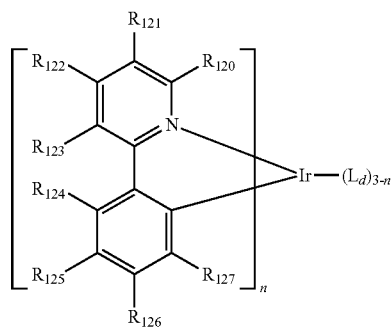
(103)

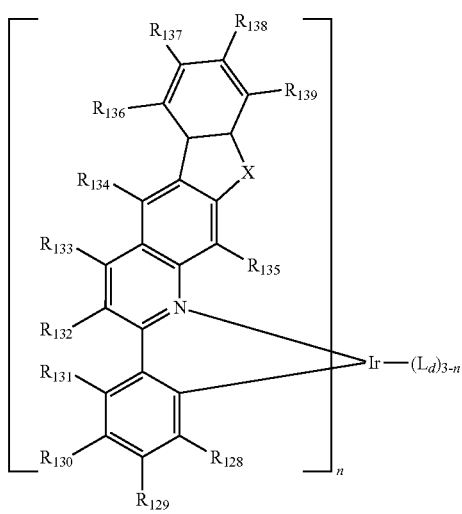
(104)

wherein, $L_d$ is selected from the following structures:

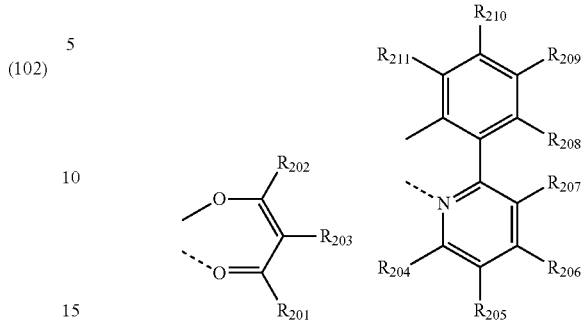

$R_{100}$, $R_{134}$ and $R_{135}$, each independently, represent hydrogen, deuterium, a substituted or unsubstituted (C1-C30) alkyl, or a substituted or unsubstituted (C3-C30)cycloalkyl;

$R_{101}$ to $R_{109}$ and $R_{111}$ to $R_{123}$, each independently, represent hydrogen, deuterium, a halogen, a (C1-C30)alkyl unsubstituted or substituted with deuterium or a halogen, a substituted or unsubstituted (C3-C30)cycloalkyl, a substituted or unsubstituted (C6-C30)aryl, a cyano, or a substituted or unsubstituted (C1-C30)alkoxy; $R_{106}$ to $R_{109}$ may be linked to adjacent $R_{106}$ to $R_{109}$, respectively, to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl; and $R_{120}$ to $R_{123}$ may be linked to adjacent $R_{120}$ to $R_{123}$, respectively, to form a substituted or unsubstituted fused ring, e.g., a quinoline unsubstituted or substituted with at least one of an alkyl, an aryl, an arylalkyl and an alkylaryl;

$R_{124}$ to $R_{133}$ and $R_{136}$ to $R_{139}$, each independently, represent hydrogen, deuterium, a halogen, a substituted or unsubstituted (C1-C30)alkyl, or a substituted or unsubstituted (C6-C30)aryl; and $R_{124}$ to $R_{127}$ may be linked to adjacent $R_{124}$ to $R_{127}$, respectively, to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

X represents $CR_{21}R_{22}$, O, or S;

$R_{21}$ and $R_{22}$, each independently, represent a substituted or unsubstituted (C1-C10)alkyl, or a substituted or unsubstituted (C6-C30)aryl;

$R_{201}$ to $R_{211}$, each independently, represent hydrogen, deuterium, a halogen, a (C1-C30)alkyl unsubstituted or substituted with deuterium or a halogen, a substituted or unsubstituted (C3-C30)cycloalkyl, or a (C6-C30)aryl unsubstituted or substituted with an alkyl or deuterium; and $R_{208}$ to $R_{211}$ may be linked to adjacent $R_{208}$ to $R_{211}$, respectively, to form a substituted or unsubstituted fused ring, e.g., a fluorene unsubstituted or substituted with an alkyl, a dibenzothiophene unsubstituted or substituted with an alkyl, or a dibenzofuran unsubstituted or substituted with an alkyl;

f and g, each independently, represent an integer of 1 to 3; where if f or g is an integer of 2 or more, each $R_{100}$ may be the same or different; and s represents an integer of 1 to 3.

The specific examples of the compound used as a dopant are as follows, but are not limited thereto.

D-1 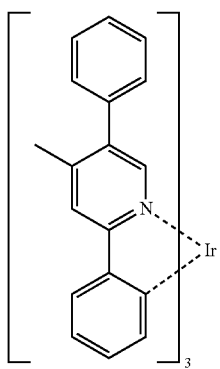
D-5 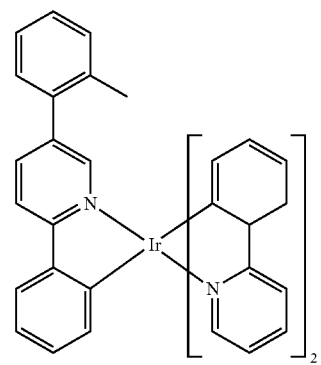
D-2 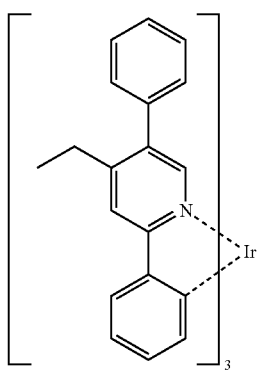
D-6 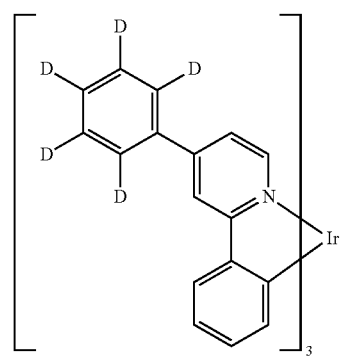
D-3 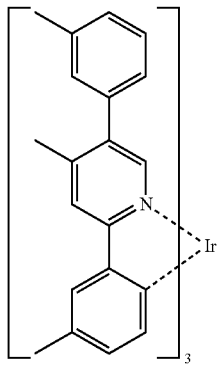
D-7 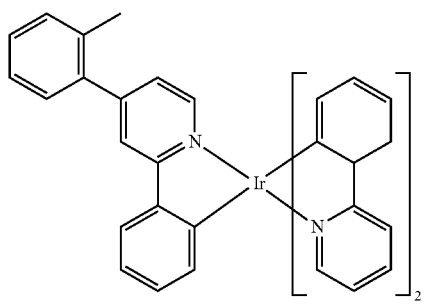
D-4 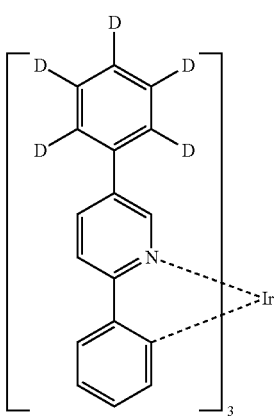
D-8 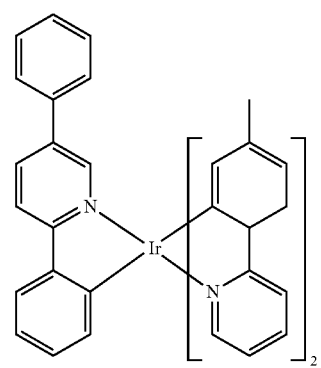

-continued
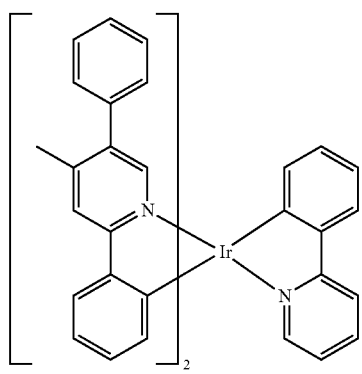
D-9
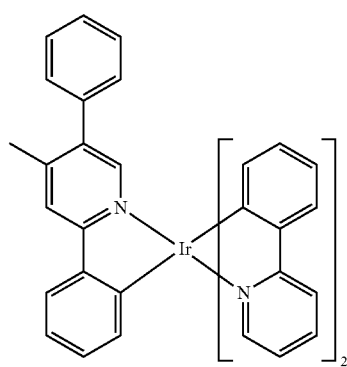
D-13
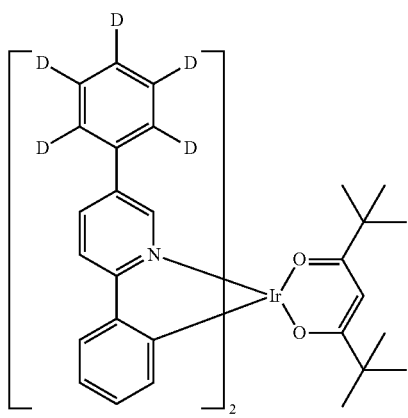
D-10
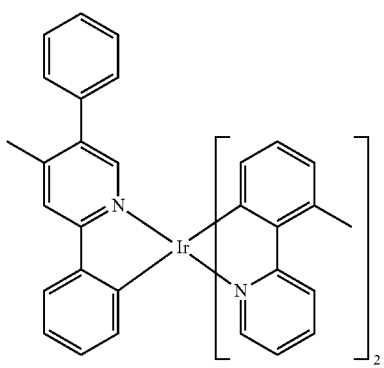
D-14
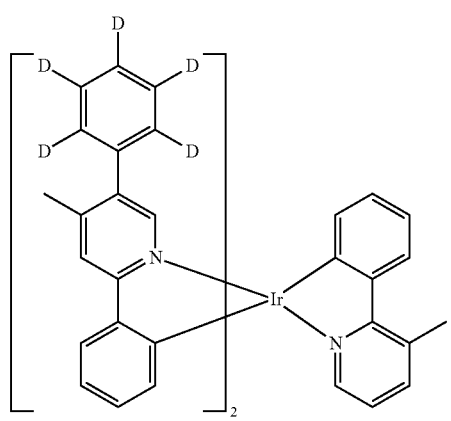
D-11
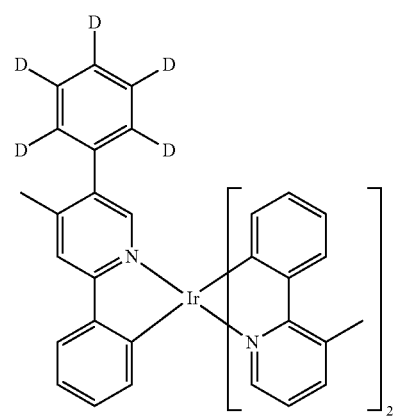
D-15
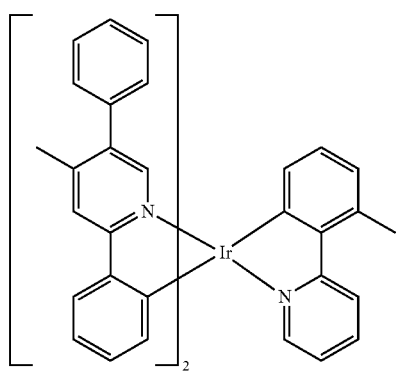
D-12
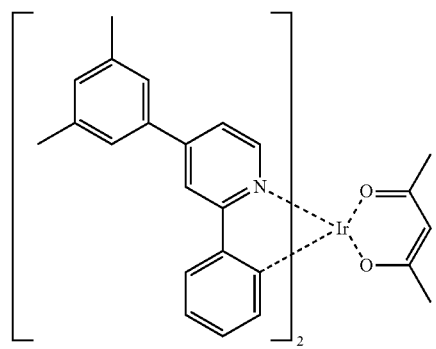
D-16

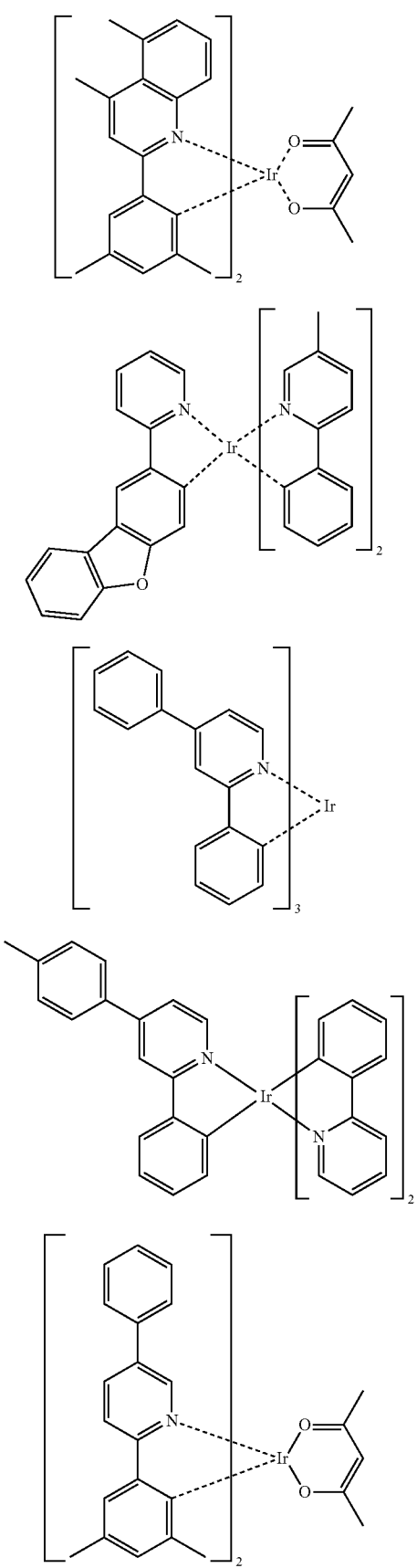
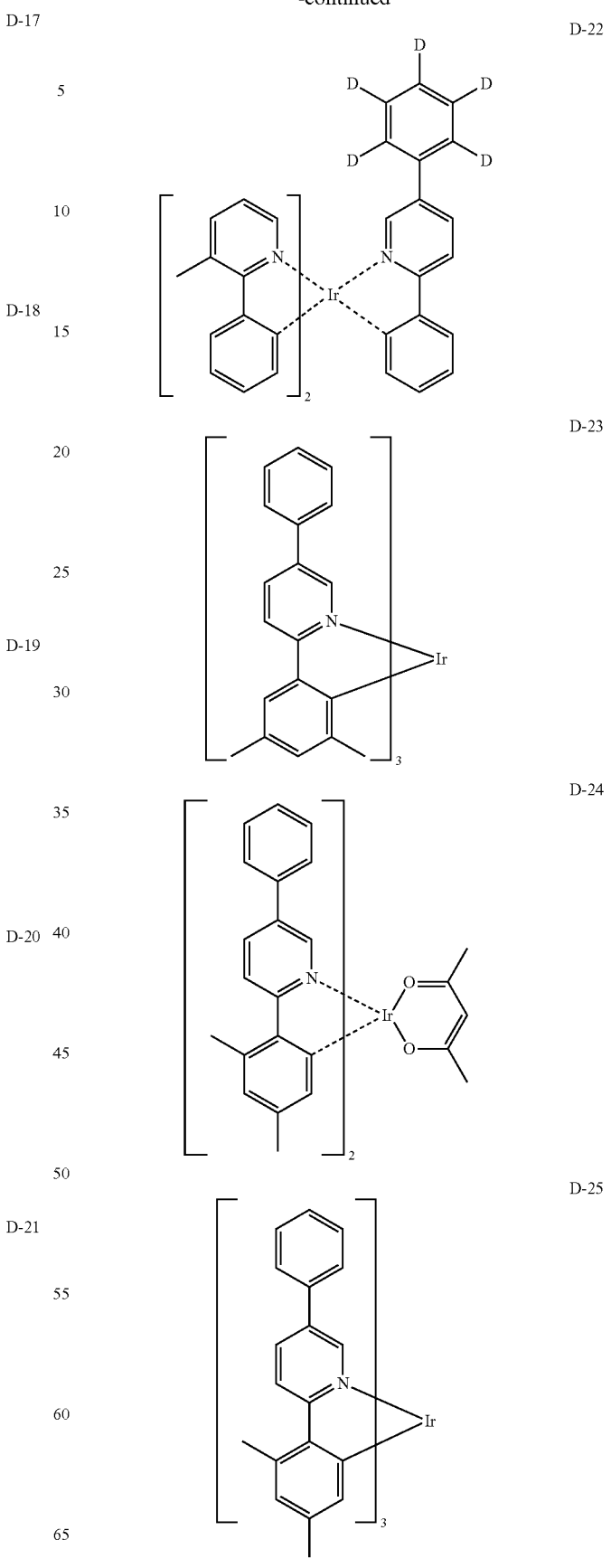

D-26
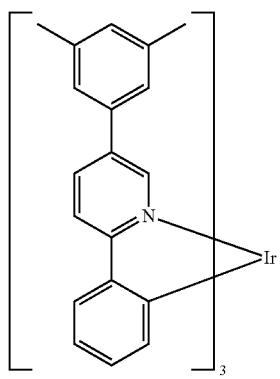
D-27
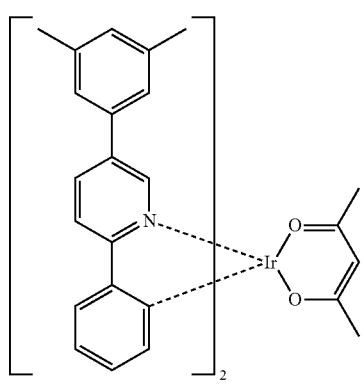
D-28
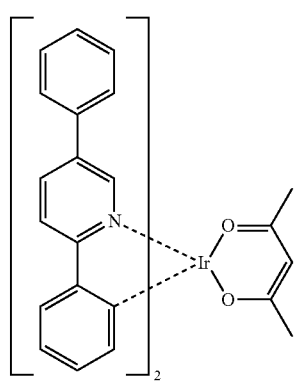
D-29
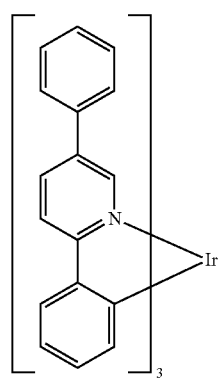
D-30
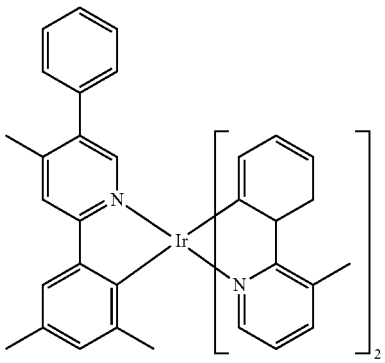
D-31
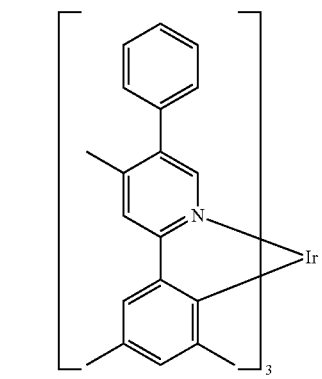
D-32
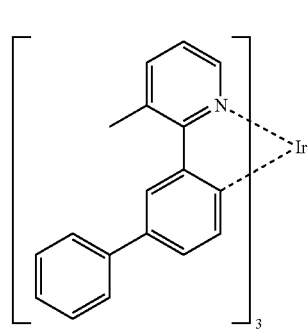
D-33
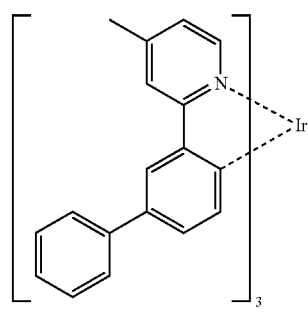

D-34 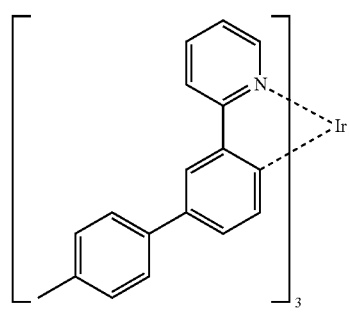
D-35 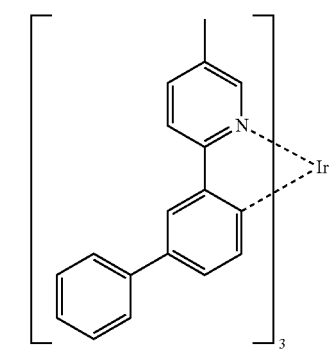
D-36 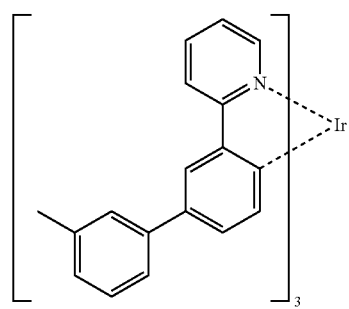
D-37 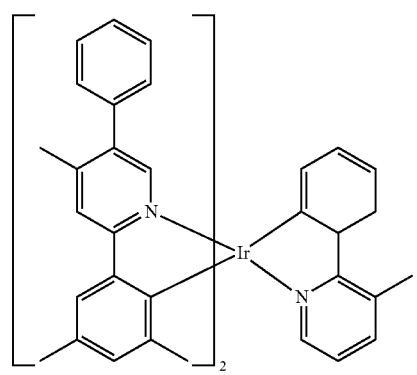
D-38 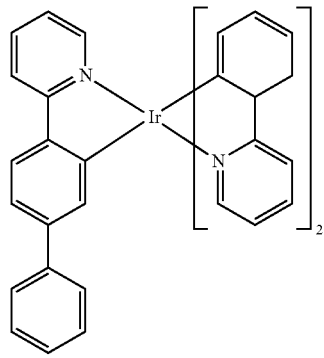
D-39 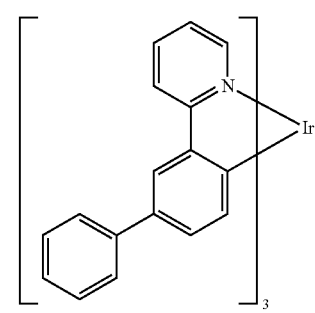
D-40 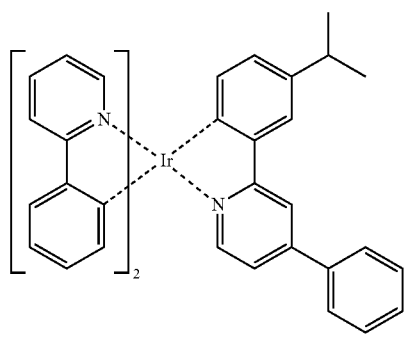
D-41 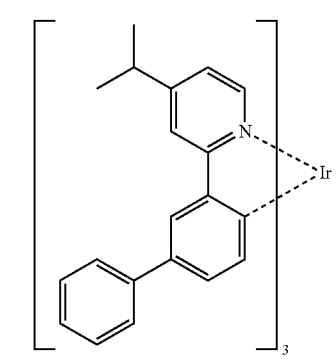
D-42 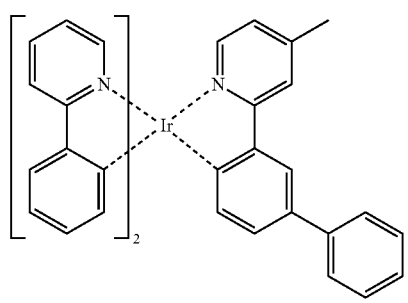

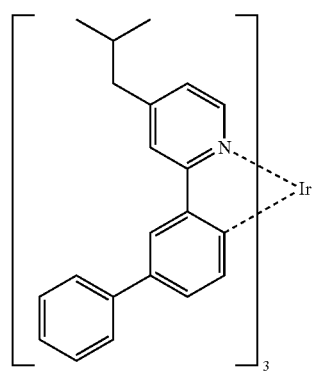
D-43
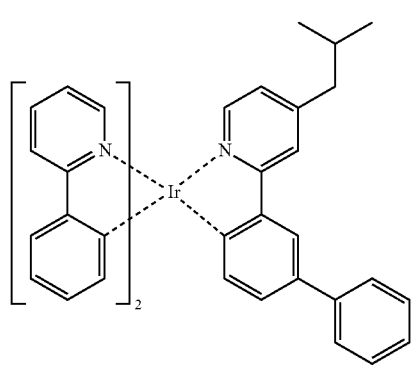
D-44
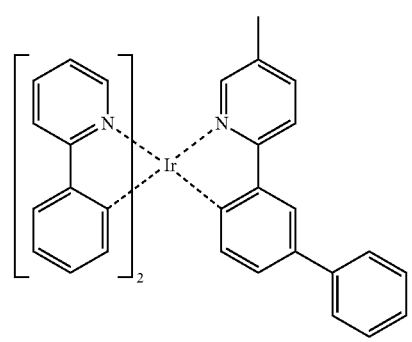
D-45
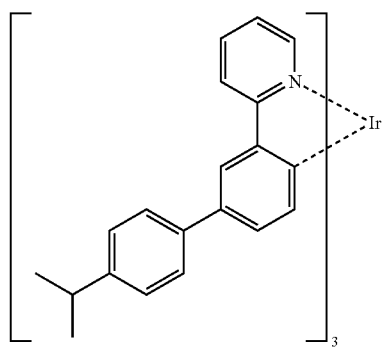
D-46
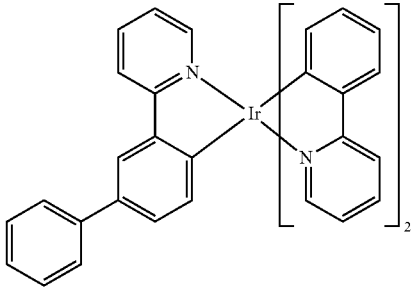
D-47
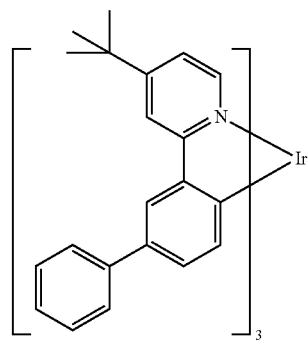
D-48
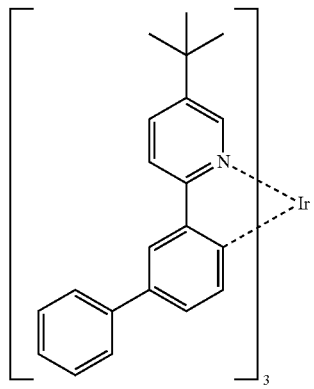
D-49
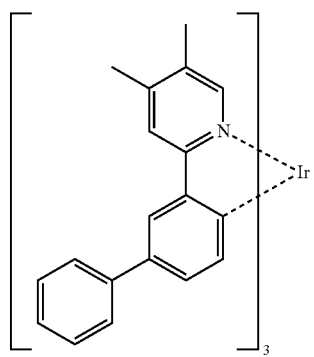
D-50

D-51 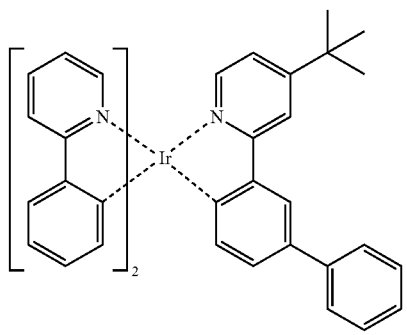
D-52 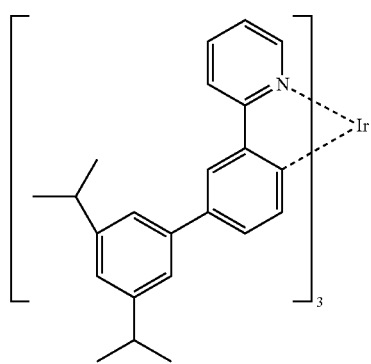
D-53 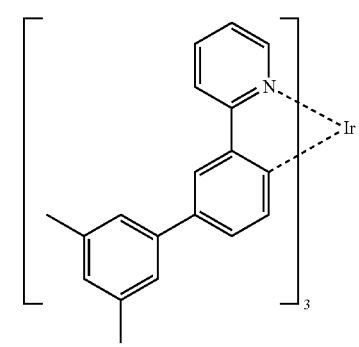
D-54 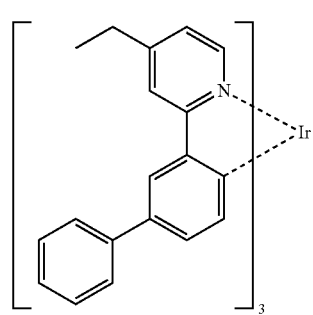
D-55 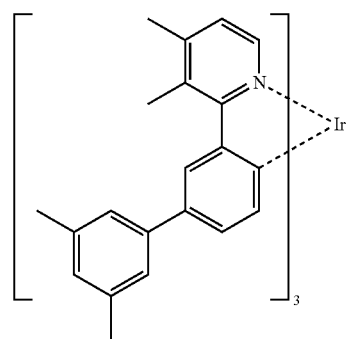
D-56 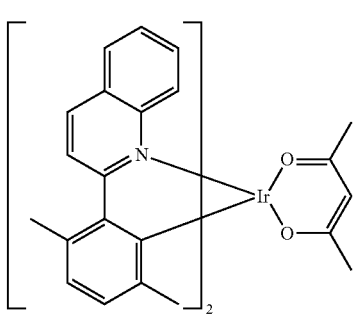
D-57 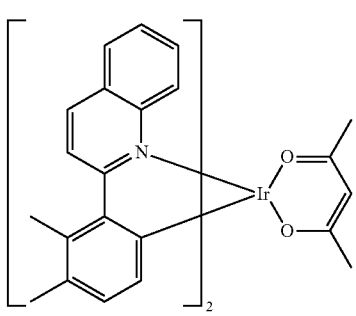
D-58 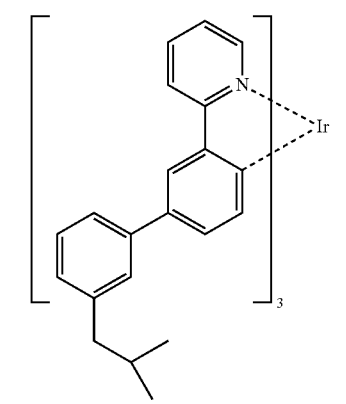

-continued
D-59
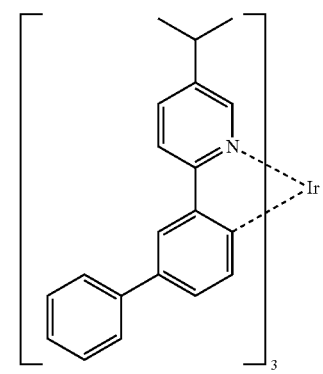
D-60
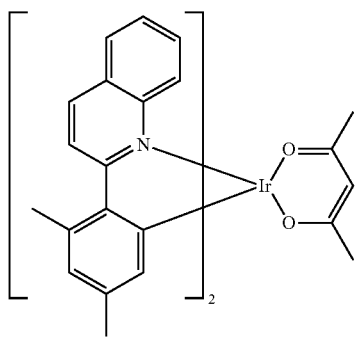
D-61
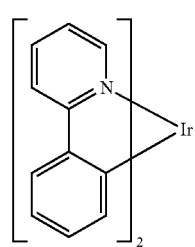
D-62
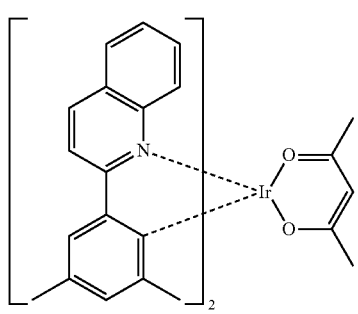
-continued
D-63
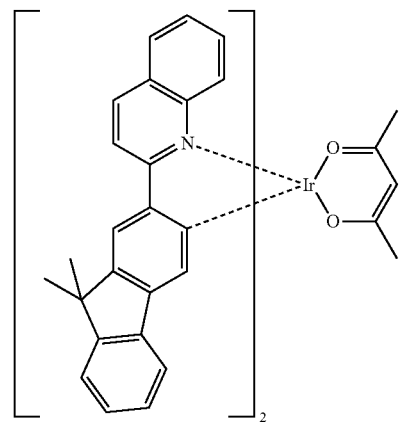
D-64
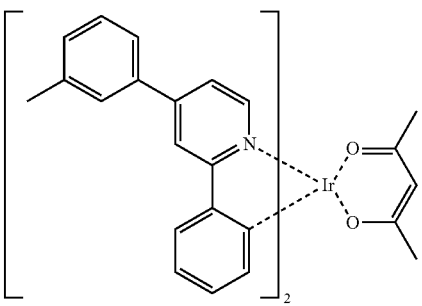
D-65
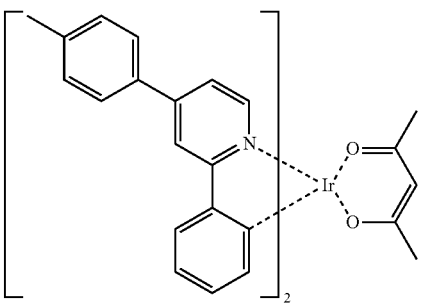
D-66
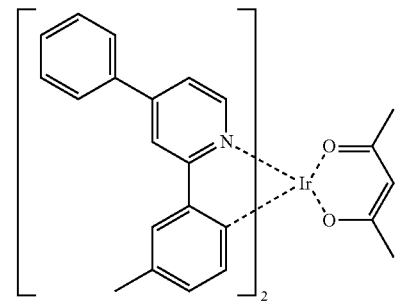
D-67
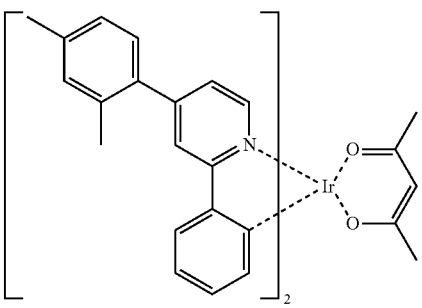

-continued
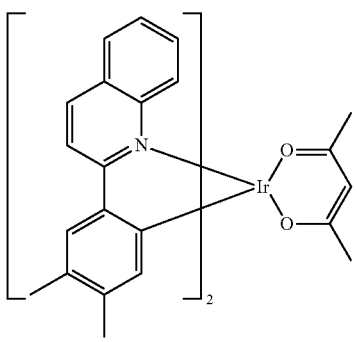
D-68
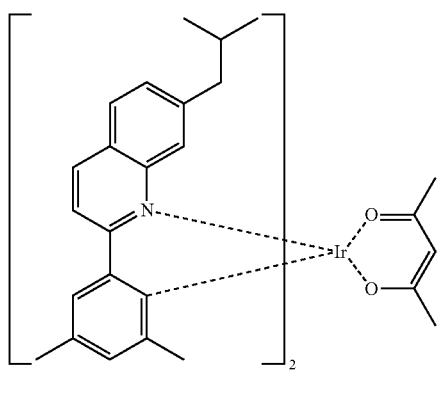
D-69
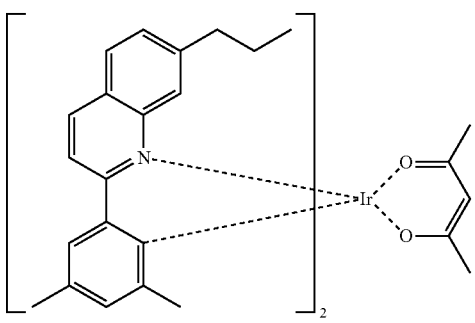
D-70
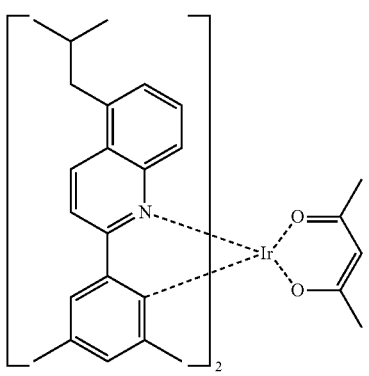
D-71
-continued
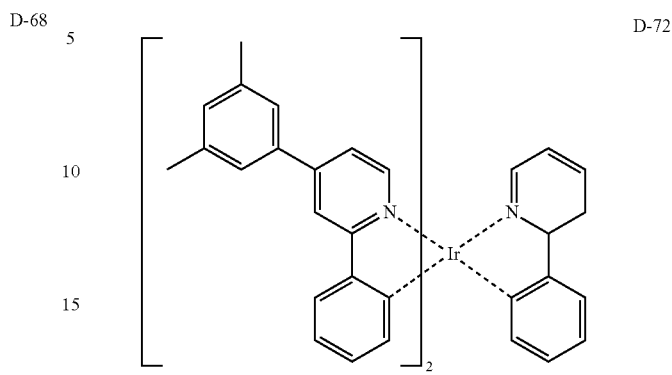
D-72
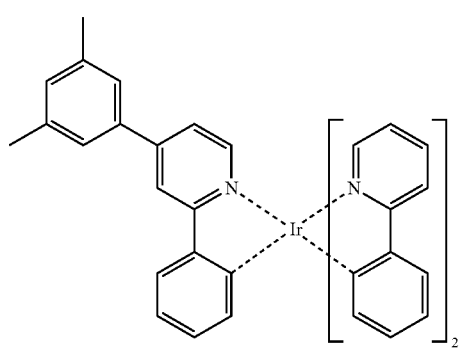
D-73
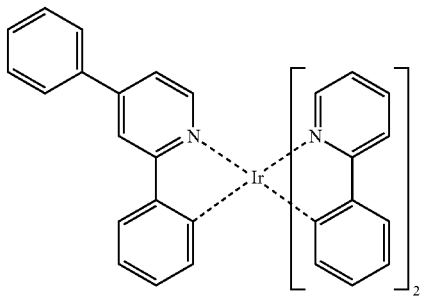
D-74
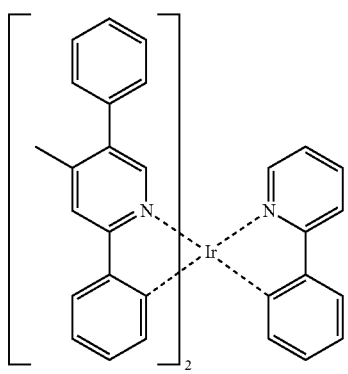
D-75

-continued
D-76
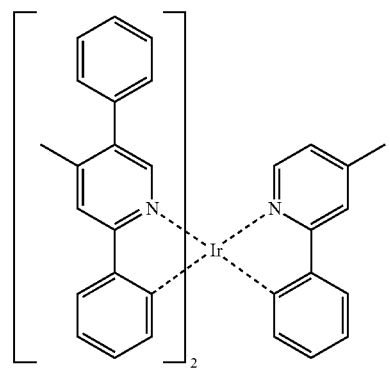
D-77
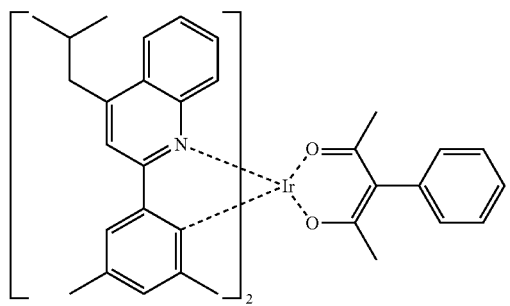
D-78
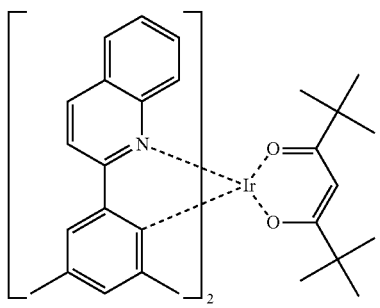
D-79
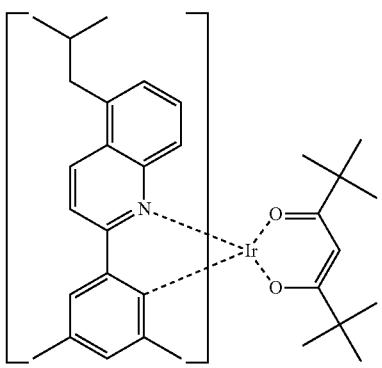
-continued
D-80
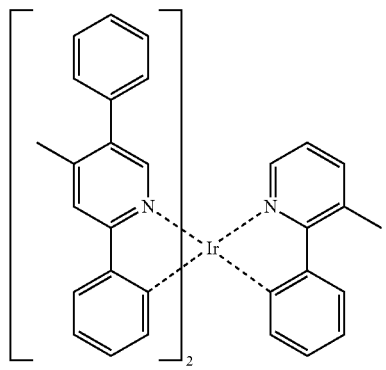
D-81
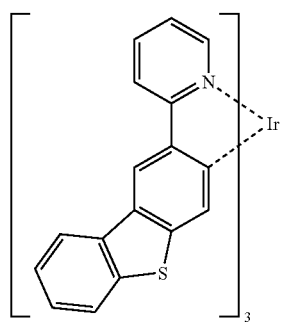
D-82
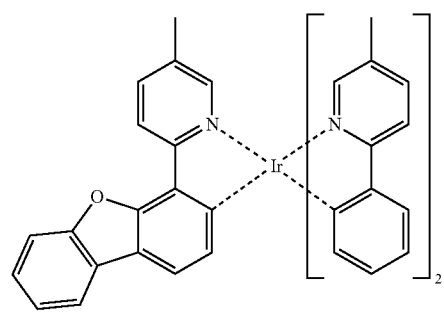
D-83
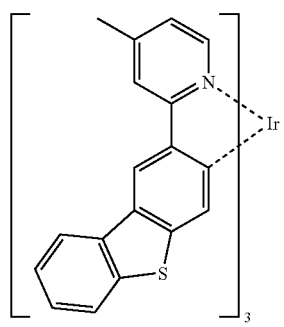
D-84
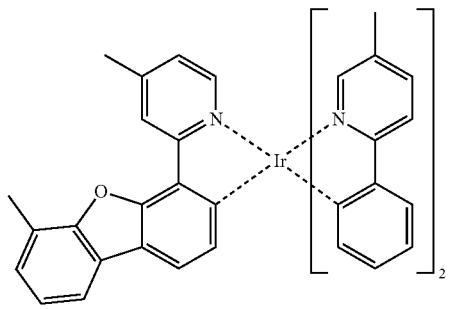

D-85
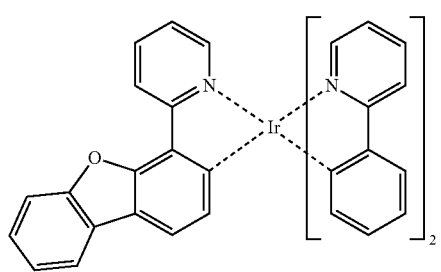
D-86
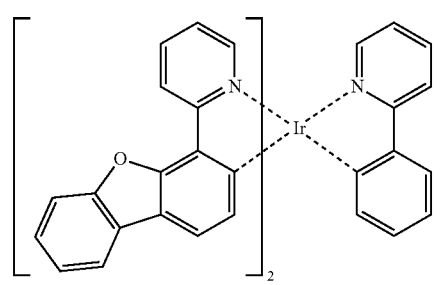
D-87
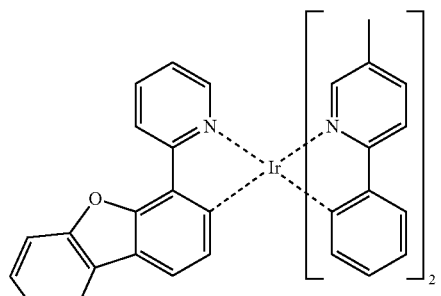
D-88
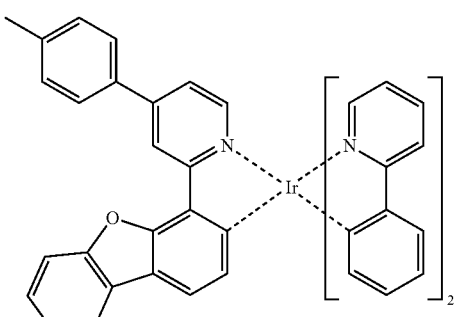
D-89
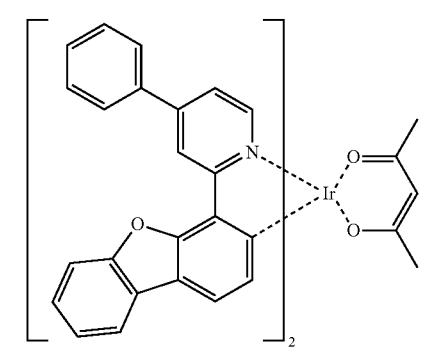
D-90
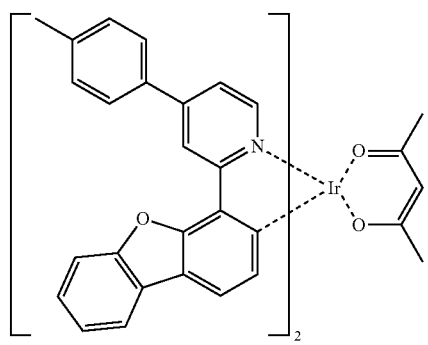
D-91
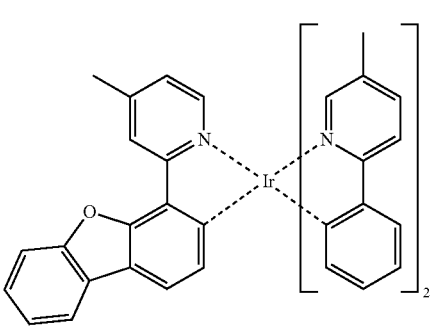
D-92
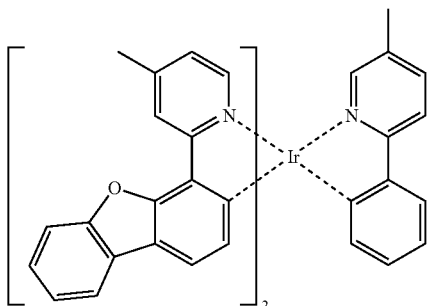
D-93
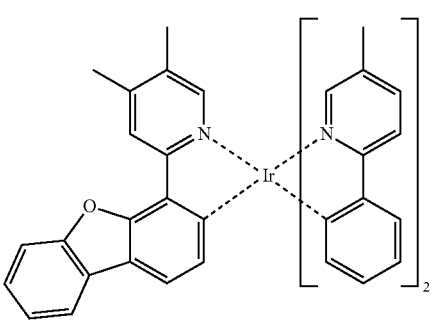
D-94
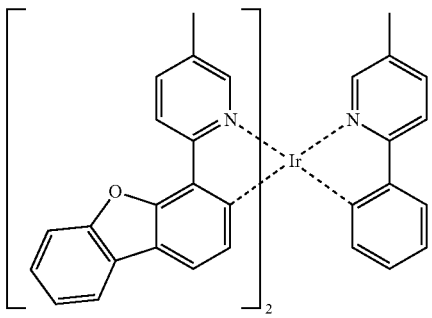

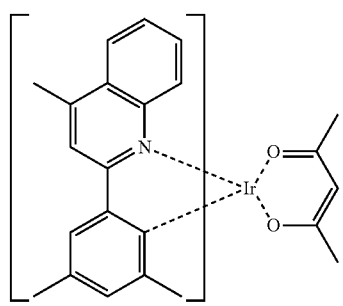
D-95
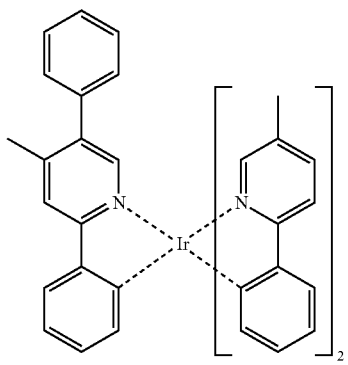
D-99
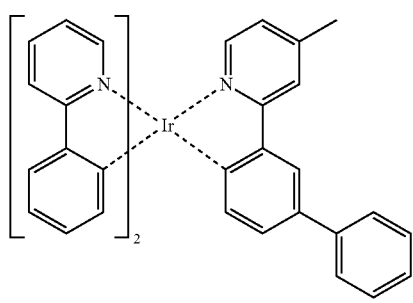
D-96
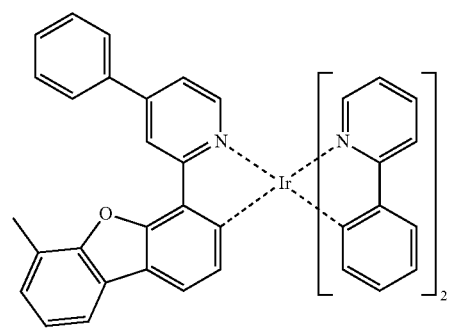
D-100
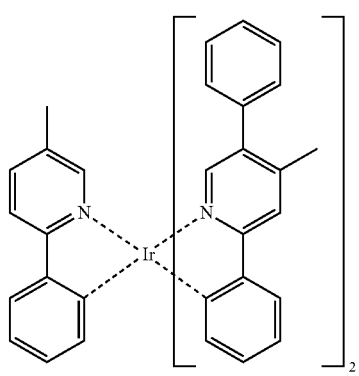
D-97
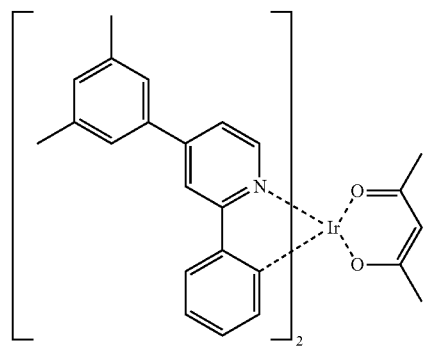
D-101
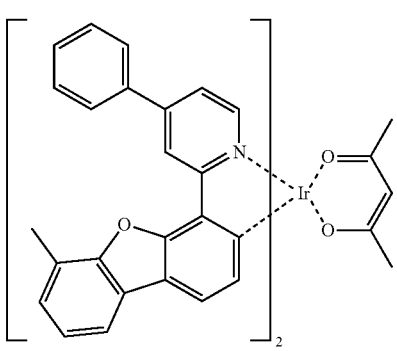
D-98
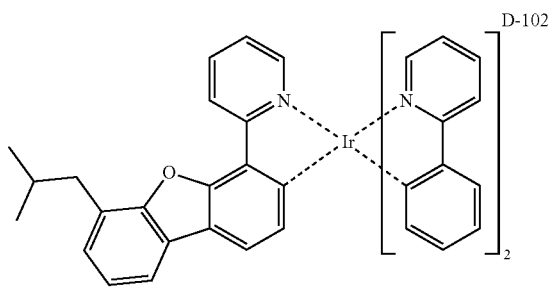
D-102

D-103 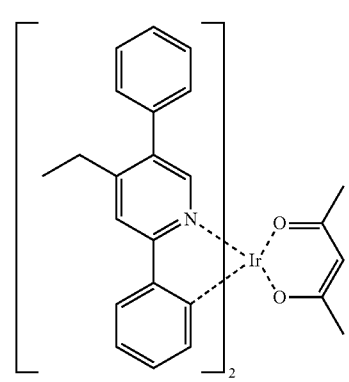
D-107 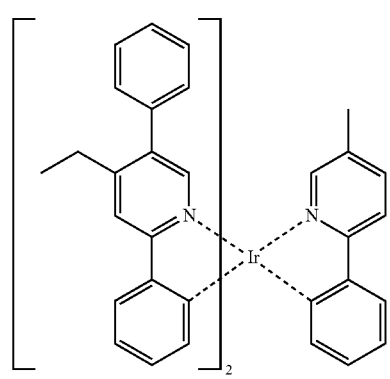
D-104 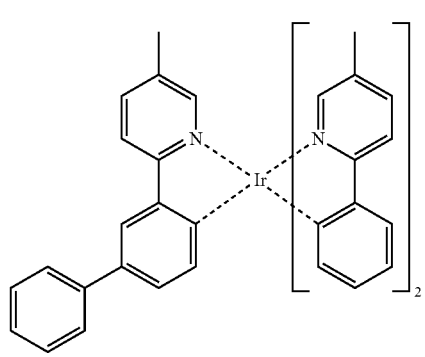
D-108 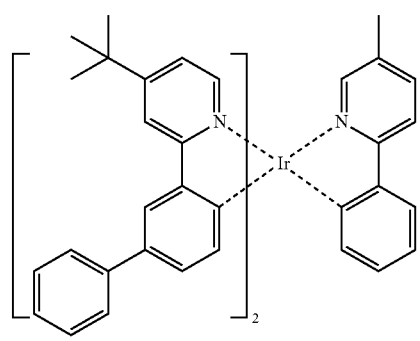
D-105 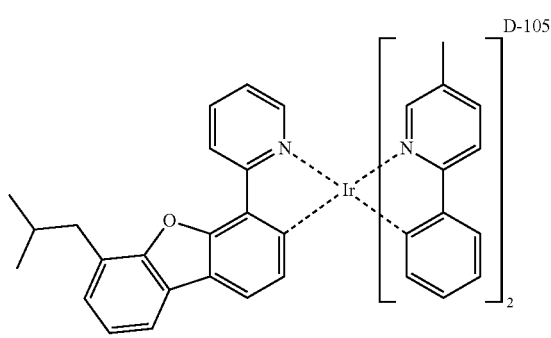
D-109 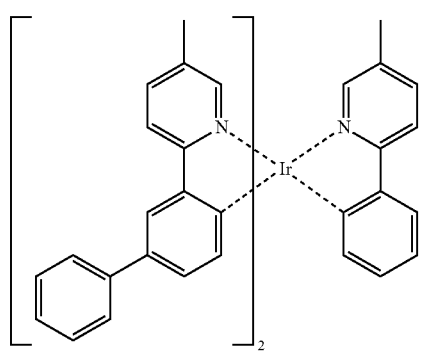
D-106 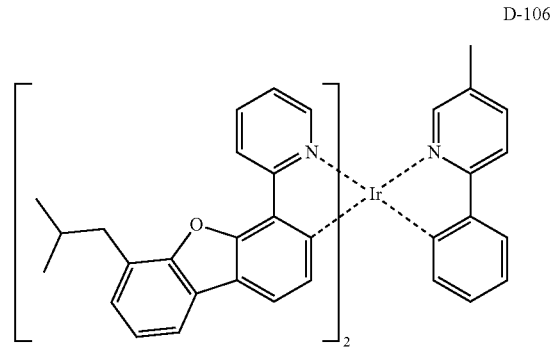
D-110 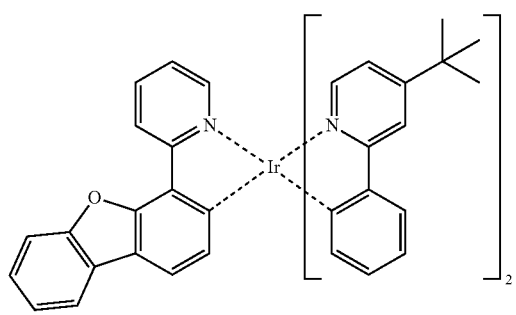

-continued
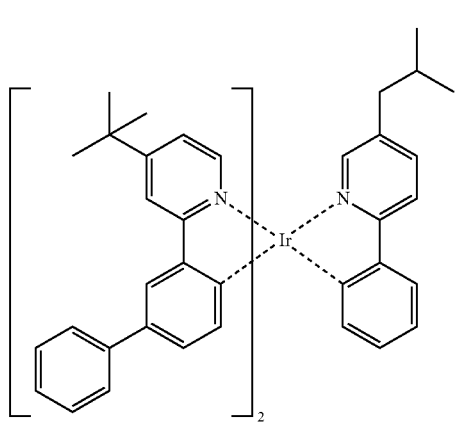
D-111
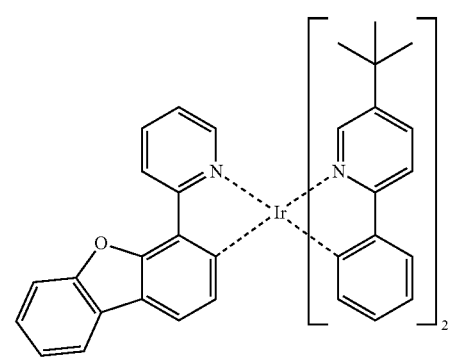
D-112
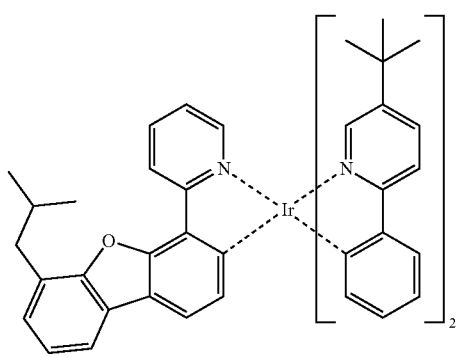
D-113
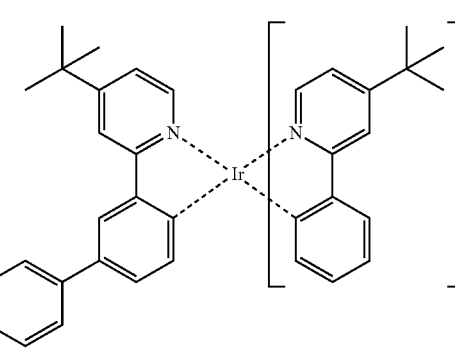
D-114
-continued
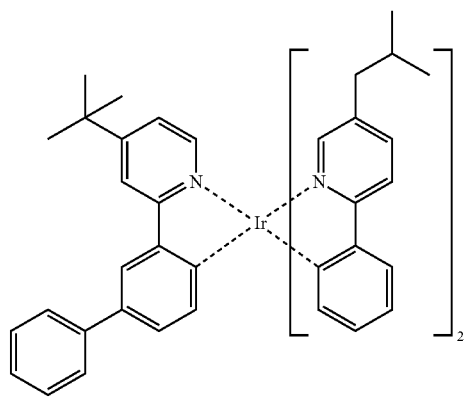
D-115
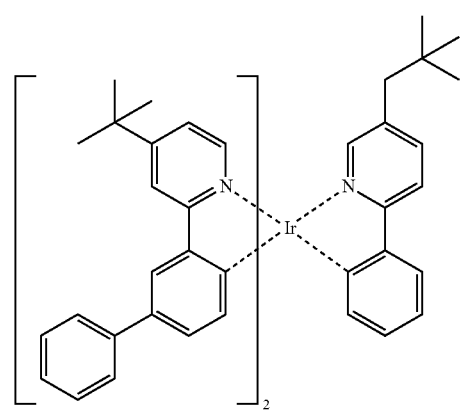
D-116
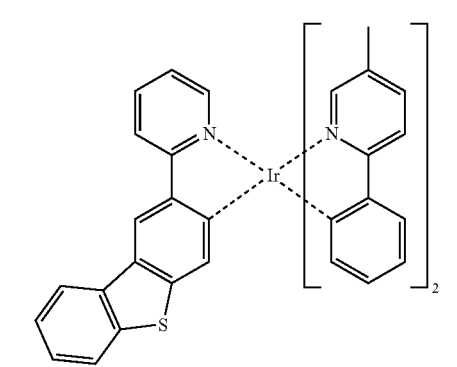
D-117
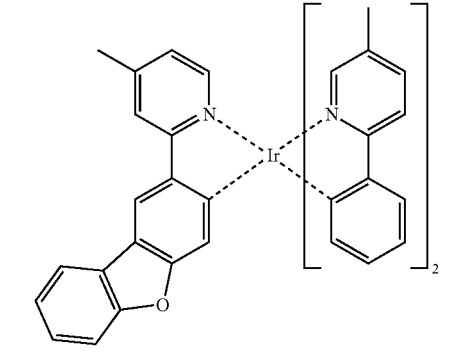
D-118

D-119
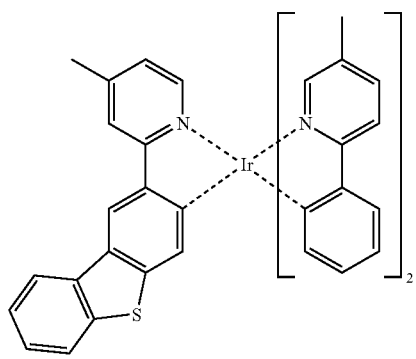
D-120
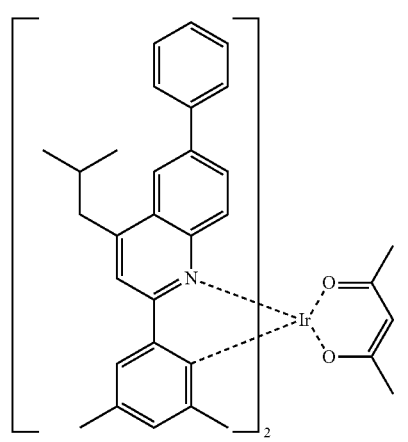
D-121
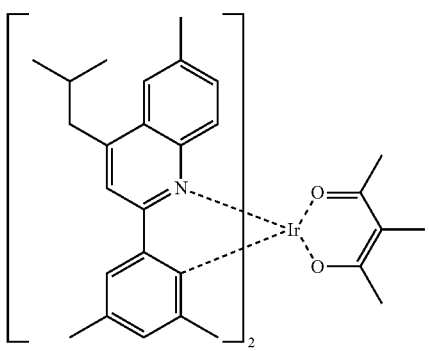
D-122
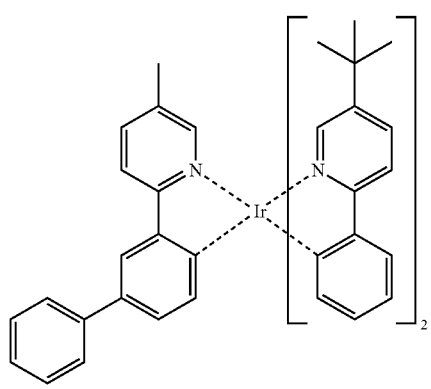
D-123
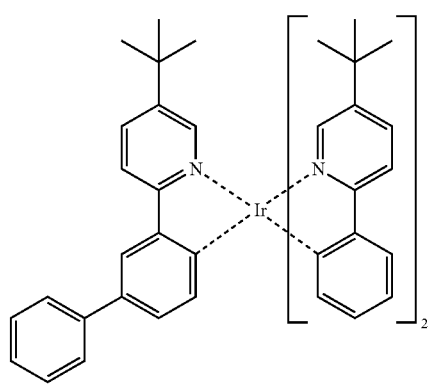
D-124
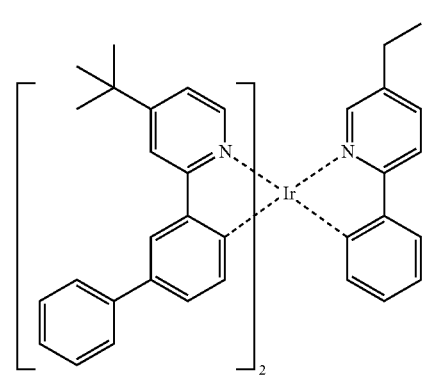
D-125
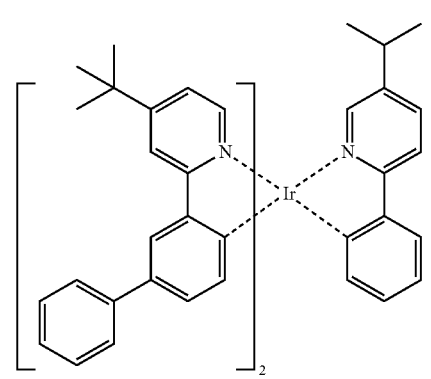
D-126
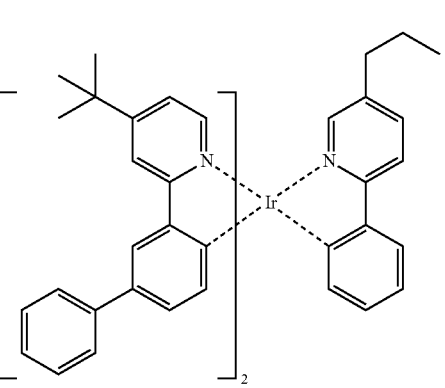

-continued
D-127
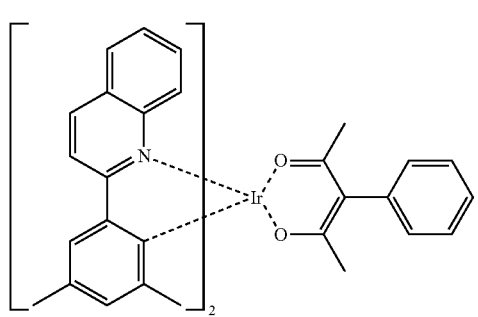
D-128
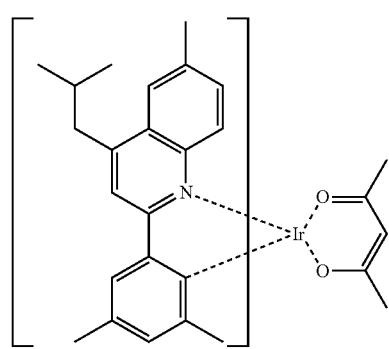
D-129
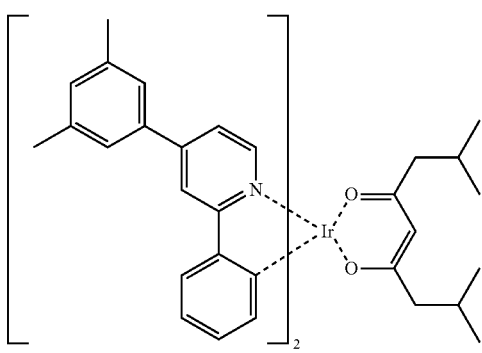
D-130
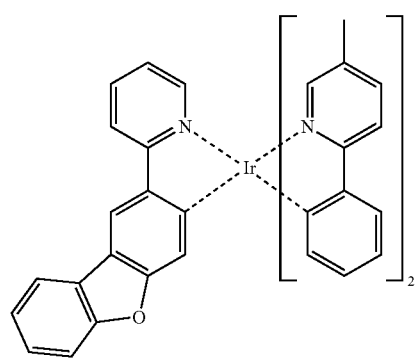
-continued
D-131
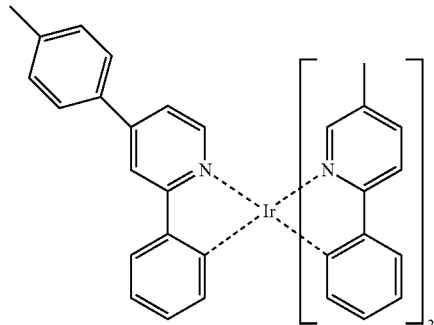
D-132
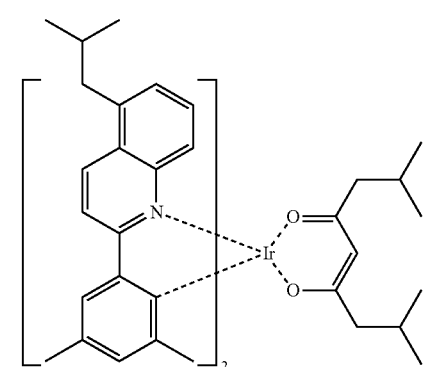
D-133
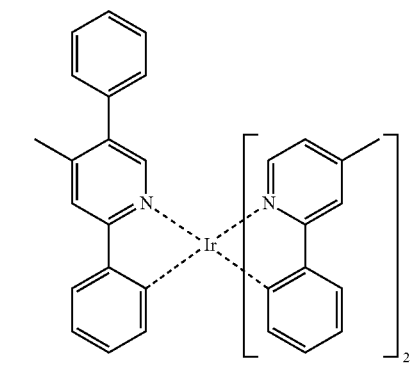
D-134
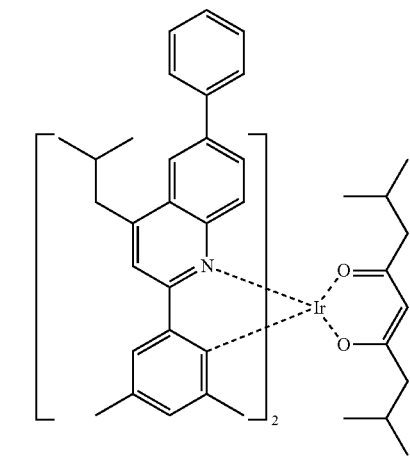

-continued
D-135
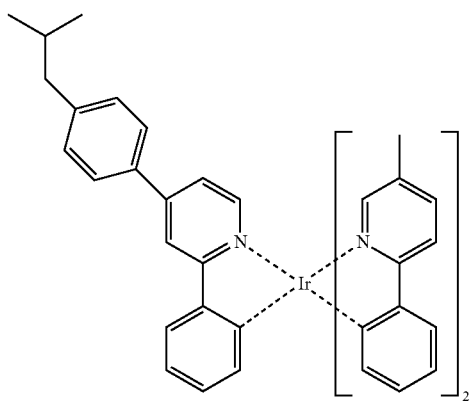
D-136
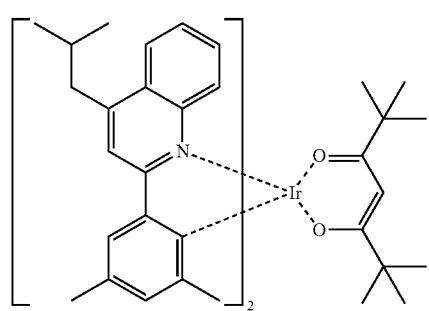
D-137
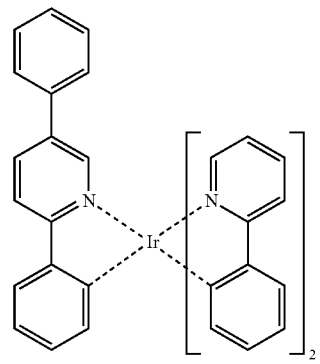
D-138
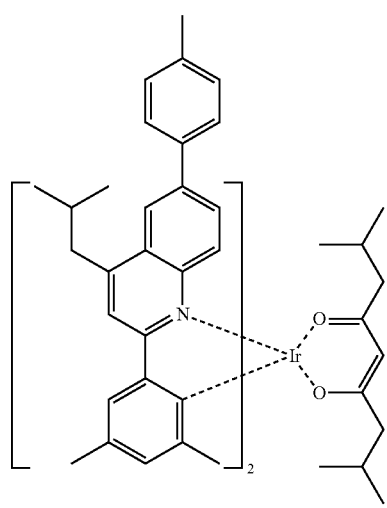
-continued
D-139
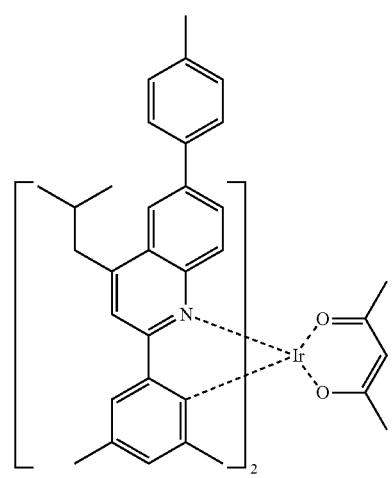
D-140
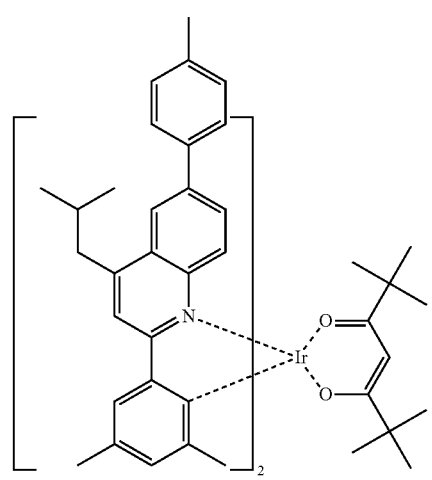
D-141
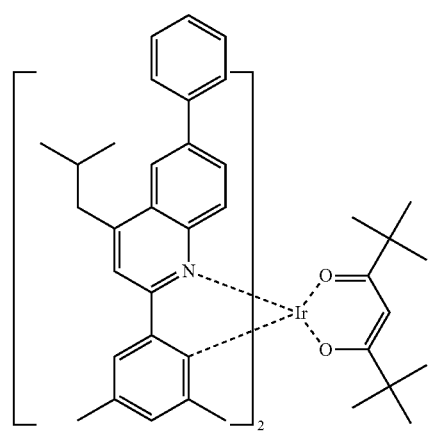

D-142 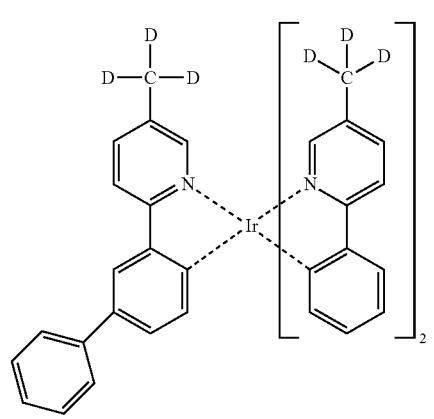
D-143 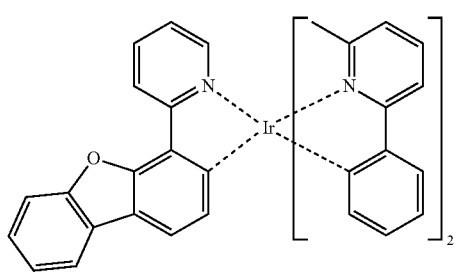
D-144 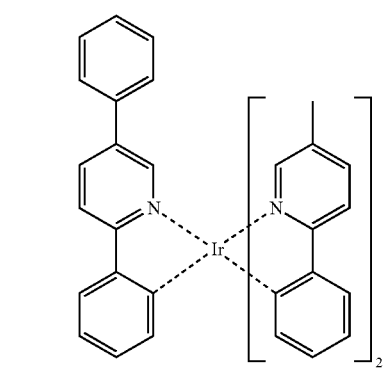
D-145 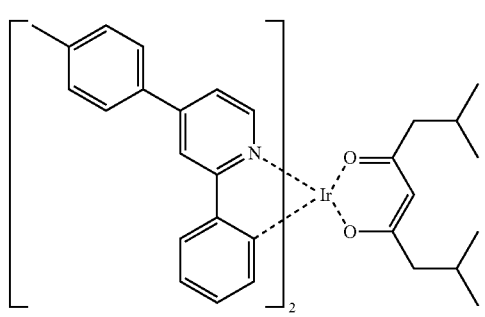
D-146 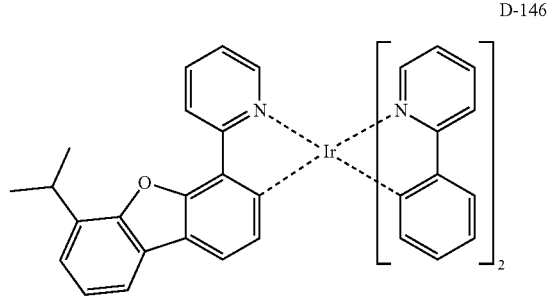
D-147 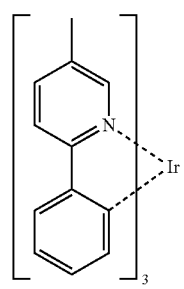
D-148 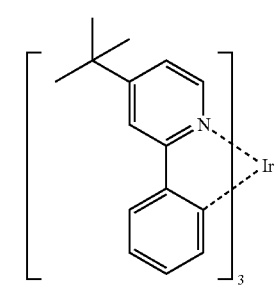
D-149 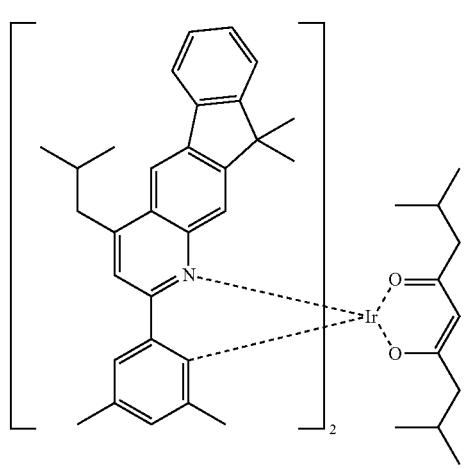

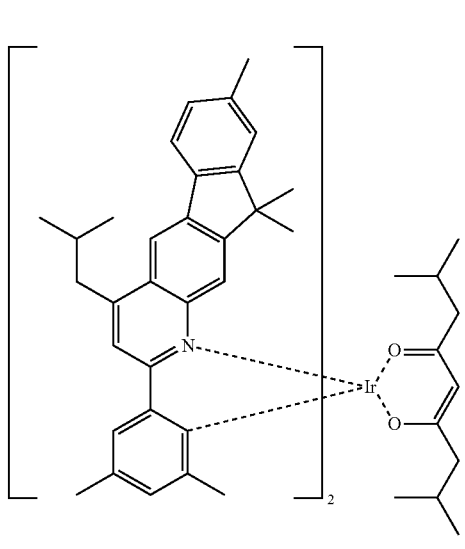
D-150
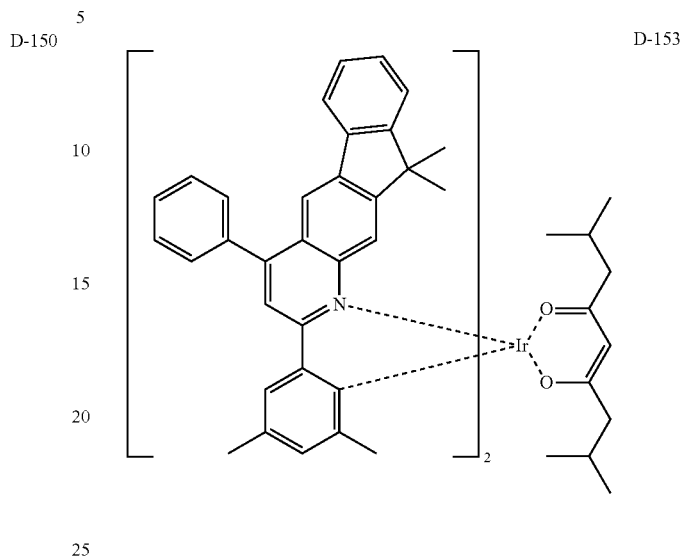
D-153
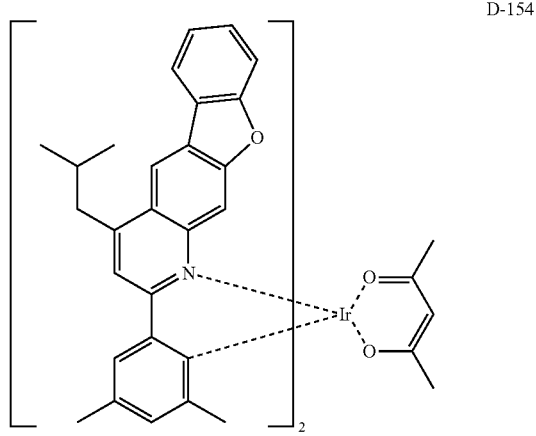
D-151
D-154
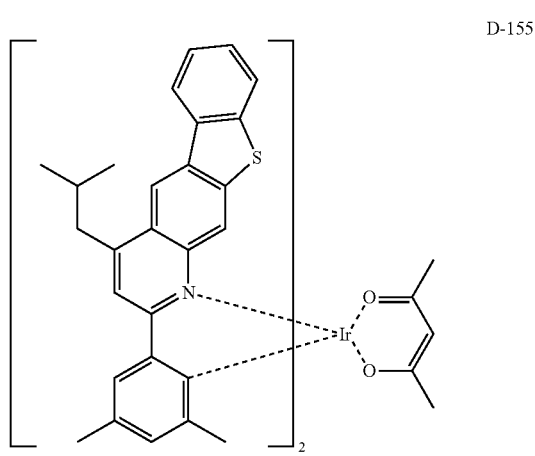
D-152
D-155
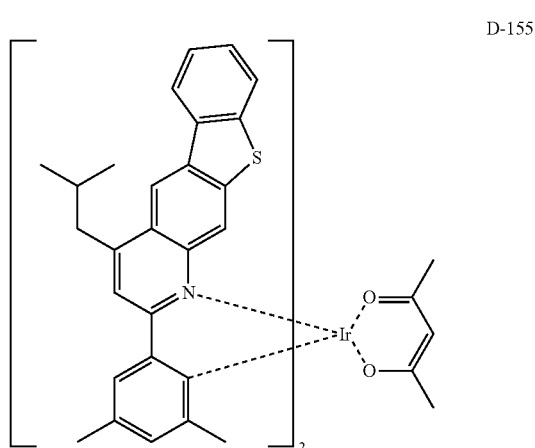

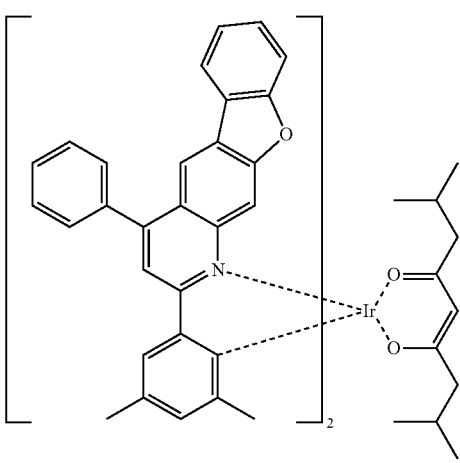

D-156

D-157

The organic electroluminescent device of the present disclosure may further comprise at least one compound selected from the group consisting of arylamine-based compounds and styrylarylamine-based compounds in the organic layer.

In addition, in the organic electroluminescent device of the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

In the organic electroluminescent device of the present disclosure, at least one layer (hereinafter, "a surface layer") selected from a chalcogenide layer, a metal halide layer and a metal oxide layer may be preferably placed on an inner surface(s) of one or both electrodes. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer may provide operation stability for the organic electroluminescent device. Preferably, the chalcogenide includes $SiO_X$ ($1 \leq X \leq 2$), $AlO_X$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

Between the anode and the light-emitting layer, a hole injection layer, a hole transport layer, a hole auxiliary layer, a light-emitting auxiliary layer, or an electron blocking layer, or a combination thereof may be used. Multi-layers can be used for the hole injection layer in order to lower the hole injection barrier (or hole injection voltage) from the anode to the hole transport layer or the electron blocking layer. Two compounds can be simultaneously used in each layer. The hole transport layer or the electron blocking layer may also be formed of multi-layers.

Between the light-emitting layer and the cathode, a layer selected from an electron buffer layer, a hole blocking layer, an electron transport layer, or an electron injection layer, or a combination thereof can be used. Multi-layers can be used for the electron buffer layer in order to control the injection of the electrons and enhance the interfacial characteristics between the light-emitting layer and the electron injection layer. Two compounds may be simultaneously used in each layer. The hole blocking layer or the electron transport layer may also be formed of multi-layers, and each layer can comprise two or more compounds.

In the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an organic electroluminescent device having two or more light-emitting layers and emitting white light.

In order to form each layer of the organic electroluminescent device of the present disclosure, dry film-forming methods such as vacuum evaporation, sputtering, plasma and ion plating methods, or wet film-forming methods such as spin coating, dip coating, and flow coating methods may be used. The first and second host compounds of the present disclosure may be co-evaporated or mixture-evaporated.

When using a wet film-forming method, a thin film may be formed by dissolving or diffusing materials forming each layer into any suitable solvent such as ethanol, chloroform, tetrahydrofuran, dioxane, etc. The solvent may be any solvent where the materials forming each layer can be dissolved or diffused, and where there are no problems in film-formation capability.

Also, by using the organic electroluminescent device of the present disclosure, a display system, for example smart phones, tablets, notebooks, PCs, TVs, or display system for car; or a lighting system, for example an outdoor or indoor lighting system, can be produced.

Hereinafter, the preparation method of the compound of the present disclosure, and the properties thereof will be explained in detail with reference to the representative compounds of the present disclosure. However, the present disclosure is not limited by the following examples.

Example 1: Preparation of Compound H-1

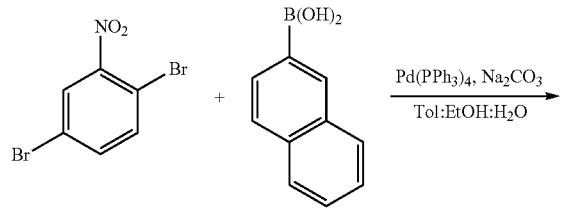

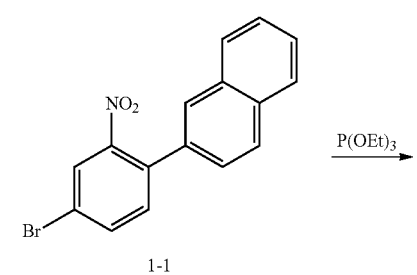

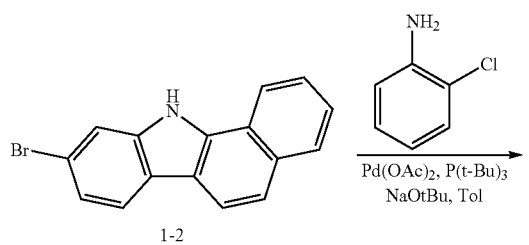

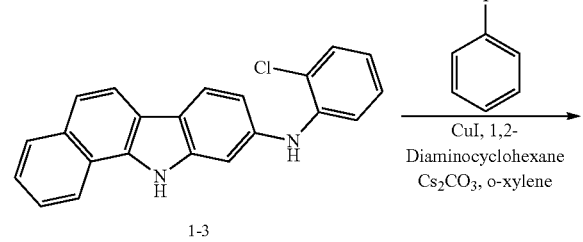

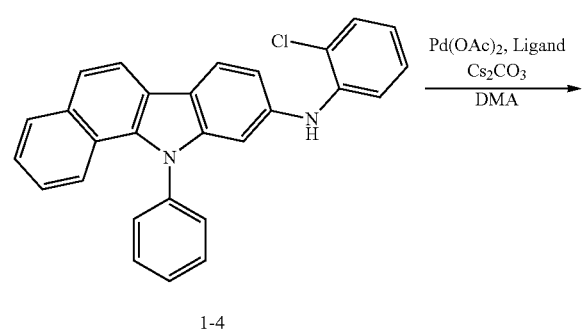

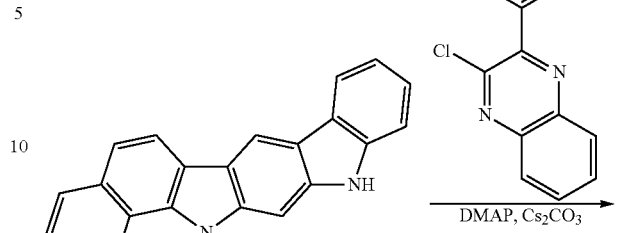

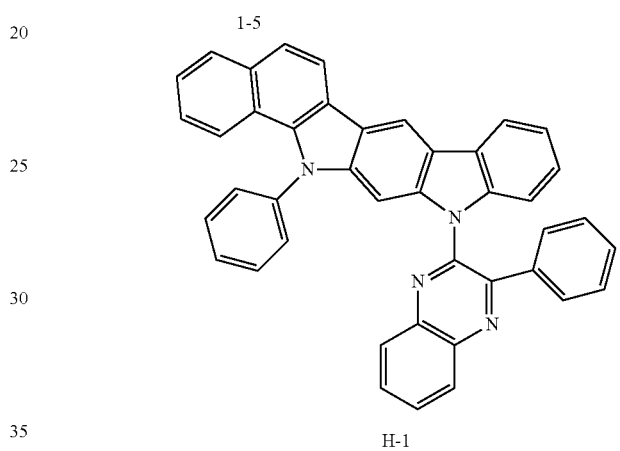

Preparation of Compound 1-1

80 g of 2,5-dibromonitrobenzene (465 mmol), 170 g of 2-naphthylboronic acid (604 mmol), 16.2 g of tetrakis(triphenylphosphine)palladium (Pd(PPh$_3$)$_4$) (13.95 mmol), and 123 g of sodium carbonate (Na$_2$CO$_3$) (1163 mmol) were poured into 1000 mL of toluene, 160 mL of ethanol (EtOH), and 500 mL of distilled water, and the mixture was stirred under reflux for one day. After completion of the reaction, the reaction product was cooled at room temperature, and extracted with distilled water and ethyl acetate (EA). The organic layer was distilled under reduced pressure and then purified by column chromatography using MC/Hex to obtain 88 g of compound 1-1 (58%).

Preparation of Compound 1-2

88 g of compound 1-1 (268 mmol) was poured into 1.3 L of triethylphosphite (P(OEt)$_3$), and the mixture was stirred for one day at 150° C. After completion of the reaction, the reaction product was concentrated under reduced pressure, extracted with methylene chloride (MC), and then the organic layer was concentrated. The organic layer was purified by column chromatography using MC/Hex to obtain 55 g of compound 1-2 (69%).

Preparation of Compound 1-3

40 g of compound 1-2 (135 mmol), 21 mL of chloroaniline (202 mmol), 1.2 g of palladium acetate (Pd(OAc)$_2$) (5.4 mmol), 5.4 mL of tri-tert-butylphosphine (P(t-Bu)$_3$) (50%) (10.8 mmol), and 32.5 g of sodium tert-butoxide (NaOt-Bu) (338 mmol) were poured into 390 mL of toluene, and the mixture was stirred under reflux for one day. After completion of the reaction, the reaction product was cooled at room temperature, and extracted with distilled water and MC. The organic layer was distilled under reduced pressure and then purified by column chromatography using MC/Hex to obtain 22 g of compound 1-3 (48%).

Preparation of Compound 1-4

22 g of compound 1-3 (64.2 mmol), 13 mL of iodobenzene (115.5 mmol), 6.1 g of copper iodide (32 mmol), 7.7 mL of 1,2-diaminocyclohexane (64.17 mmol), and 41.8 g of cesium carbonate (128.3 mmol) were poured into 350 mL of o-xylene, and the mixture was stirred under reflux for one day. The reaction product was extracted with MC. The organic layer was distilled under reduced pressure and then purified by column chromatography using MC/Hex to obtain 16 g of compound 1-4 (58%).

Preparation of Compound 1-5

15.4 g of compound 1-4 (36.76 mmol), 0.83 g of Pd(OAc)$_2$ (3.7 mmol), 2.7 g of tricyclohexylphosphonium tetrafluoroborate ($C_{18}H_{34}P.BF_4$) (7.35 mol), and 36 g of $Cs_2CO_3$ (110.2 mmol) were poured into 150 mL of dimethylacetamide (DMA), and the mixture was stirred for one day at 180° C. After completion of the reaction, the reaction product was extracted with ethyl acetate. The organic layer was dried with magnesium sulfate (MgSO$_4$), filtered, and then the solvent was removed under reduced pressure. The resulting product was purified by column chromatography to obtain 10.5 g of compound 1-5 (75%).

Preparation of Compound H-1

30.0 g of compound 1-5 (78.4 mmol), 23.0 g of 2-chloro-3-phenylquinoxaline (94.1 mmol), 4.8 g of 4-dimethylaminopyridine (39.2 mmol), and 25.5 g of $Cs_2CO_3$ (78.4 mmol) were dissolved in 392 mL of dimethylsulfoxide (DMSO), stirred for 4 hours at 135° C., and then poured into distilled water. The resulting solid was filtered under reduced pressure. The solid was dissolved in MC and purified by column chromatography to obtain 11.7 g of compound H-1 (19.94 mmol, 25%).

$^1$H NMR (600 MHz, CDCl$_3$, δ) 8.767 (s, 1H), 8.316-8.302 (d, 1H), 8.273-8.242 (t, 2H), 8.139-8.123 (d, 1H), 7.976-7.962 (d, 1H), 7.860-7.810 (m, 2H), 7.743-7.729 (d, 1H), 7.691-7.667 (t, 1H), 7.604-7.550 (m, 3H), 7.383-7.380 (d, 1H), 7.375-7.360 (m, 3H), 7.321-7.301 (m, 3H), 7.278-7.264 (d, 1H), 7.179-7.154 (t, 1H), 7.099-7.078 (t, 1H), 7.055-7.031 (t, 2H), 6.632 (s, 1H)

| | MW | UV | PL | M.P. |
|---|---|---|---|---|
| H-1 | 586.68 | 280 nm | 594 nm | 312-356° C. |

Example 2: Preparation of Compound H-131

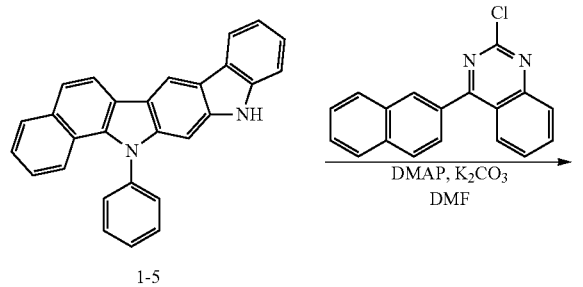

1-5

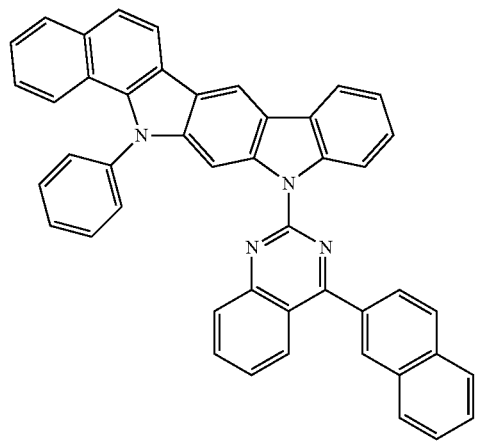

H-131

3.5 g of compound 1-5 (9.15 mmol), 3.2 g of 2-chloro-4-(naphthalene-2-yl)quinazoline (10.98 mmol), 0.6 g of 4-dimethylaminopyridine (DMAP) (4.58 mmol), and 3.2 g of K$_2$CO$_3$ (22.88 mmol) were dissolved in 46 mL of N,N-dimethylformamide (DMF), stirred for 3 hours at 120° C., and then poured into distilled water. The resulting solid was filtered under reduced pressure. The solid was dissolved in MC and purified by column chromatography to obtain 3.47 g of compound H-131 (5.45 mmol, 60%).

$^1$H NMR (600 MHz, CDCl$_3$, δ) 9.086-9.072 (d, 1H), 8.878 (s, 1H), 8.811 (s, 1H), 8.373-8.359 (d, 1H), 8.309 (s, 1H), 8.254-8.243 (d, 1H), 8.160-8.147 (d, 1H), 8.074-8.060 (d, 2H), 8.010-7.960 (m, 3H), 7.907-7.879 (m, 2H), 7.768-7.754 (d, 1H), 7.712-7.687 (t, 1H), 7.665-7.651 (t, 1H), 7.518-7.479 (m, 4H), 7.433-7.379 (m, 3H), 7.272-7.247 (m, 2H), 7.205-7.166 (m, 2H)

| | MW | UV | PL | M.P. |
|---|---|---|---|---|
| H-131 | 636.74 | 344 nm | 607 nm | 318° C. |

Example 3: Preparation of Compound H-26

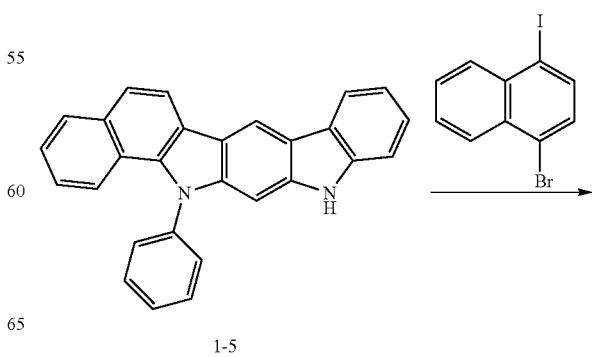

1-5

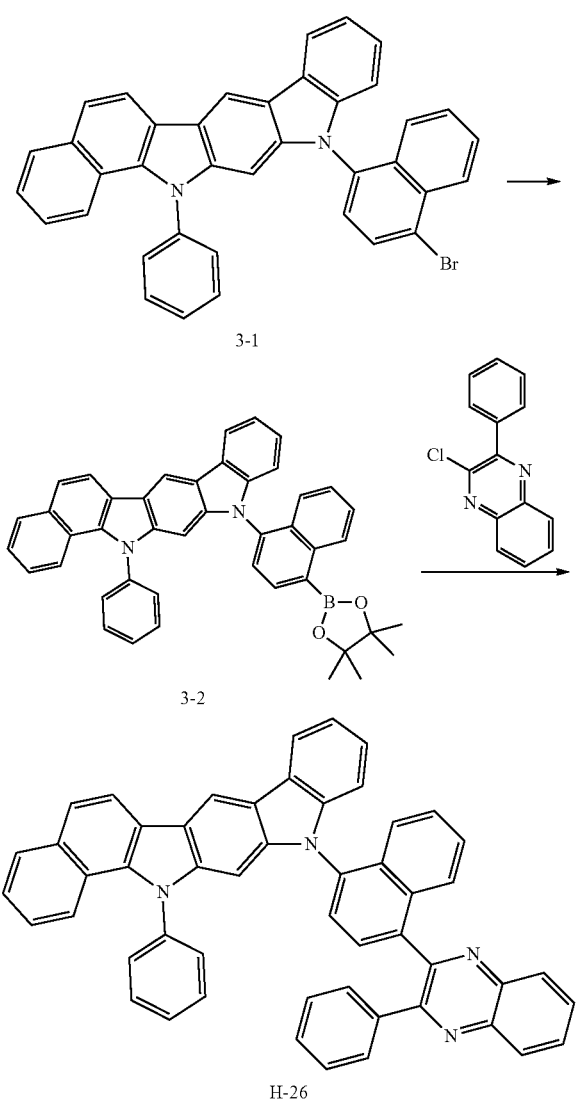

Preparation of Compound 31-1

40 g of compound 1-5 (101.4 mmol), 87 g of 1-bromo-4-iodonaphthalene (26.1 mmol), 367 mg of CuSO₄ (3.01 mmol), and 28 g of K₂CO₃ (202.8 mmol) were dissolved in 500 mL of dichlorobenzene, stirred for 12 hours at 200° C. After completion of the reaction, the reaction solvent was removed by distillation, and the resulting product was dried and then purified by column chromatography to obtain 18 g of compound 3-1 (yield: 30%).

Preparation of Compound 31-2

18 g of compound 3-1 (30.6 mmol), 9.3 g of bis(pinacolato)diboron (36.6 mmol), 2.1 g of PdCl₂(PPh₃)₂ (3.06 mmol), and 6 g of KOAc (61.2 mmol) were dissolved in 150 mL of 1,4-dioxane, and refluxed for 12 hours at 120° C. After completion of the reaction, the organic layer was extracted with ethyl acetate, and the residual water was removed using magnesium sulfate. The residue was dried and then purified by column chromatography to obtain 11 g of compound 3-2 (yield: 56.6%).

Preparation of Compound H-26

5.6 g of compound 3-2 (8.8 mmol), 2.5 g of 2-chloro-3-phenylquinoxaline (10.6 mmol), 3.6 g of K₂CO₃ (26.4 mmol), and 0.5 g of Pd(PPh₃)₄ (0.44 mmol) were dissolved in 25 mL of H₂O, 50 mL of toluene, and 25 mL of ethanol, and refluxed 3 hours at 120° C. After completion of the reaction, the organic layer was extracted with ethyl acetate, and the residual water was removed using magnesium sulfate. The residue was dried, and then purified by column chromatography to obtain 1.3 g of compound H-26 (yield: 20.7%).

¹H NMR (600 MHz, CDCl₃, δ) 8.95 (s, 1H), 8.40-8.26 (m, 4H), 7.98-7.76 (m, 5H), 7.59-7.53 (m, 5H) 7.43-7.07 (m, 17H)

| | MW | UV | PL | M.P. |
|---|---|---|---|---|
| H-26 | 712.86 | 342 nm | 604 nm | 198° C. |

Example 4: Preparation of Compound H-118

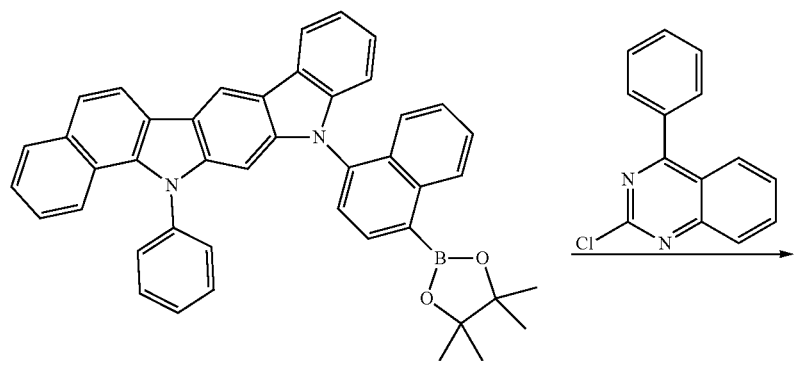

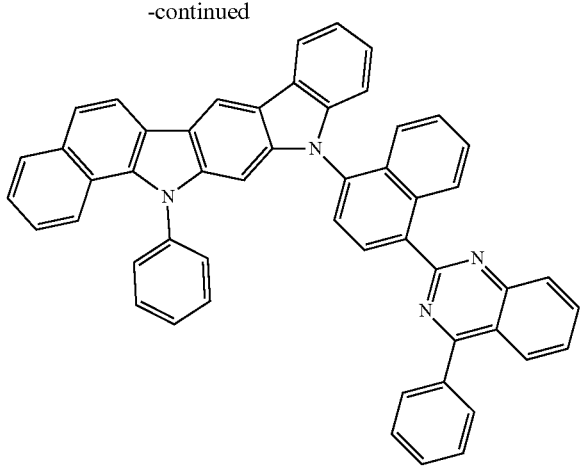

H-118

6 g of compound 3-2 (9.4 mmol), 2.73 g of 2-chloro-4-phenylquinazoline (11.3 mmol), 3.9 g of K$_2$CO$_3$ (28.2 mmol), and 0.54 g of Pd(PPh$_3$)$_4$ (0.47 mmol) were dissolved in 25 mL of H$_2$O, 50 mL of toluene, and 25 mL of ethanol in a flask, and refluxed for 3 hours at 120° C. After completion of the reaction, the organic layer was extracted with ethyl acetate, and the residual water was removed using magnesium sulfate. The residue was dried and then purified by column chromatography to obtain 1.7 g of compound H-118 (yield: 25%).

$^1$H NMR (600 MHz, CDCl$_3$, δ) 8.95 (s, 1H), 8.78-8.76 (d, J=12 Hz, 1H), 8.39-8.23 (m, 5H), 8.00-7.90 (m, 4H), 7.76-0.46 (m, 8H) 7.43~7.28 (m, 11H), 6.91-6.90 (d, J=6.0 Hz, 1H), 6.72 (s, 1H)

|       | MW     | UV     | PL     | M.P.    |
|-------|--------|--------|--------|---------|
| H-118 | 712.86 | 338 nm | 556 nm | 162° C. |

Example 5: Preparation of Compound H-37

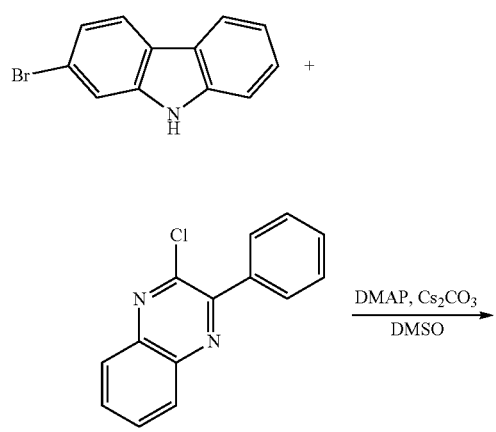

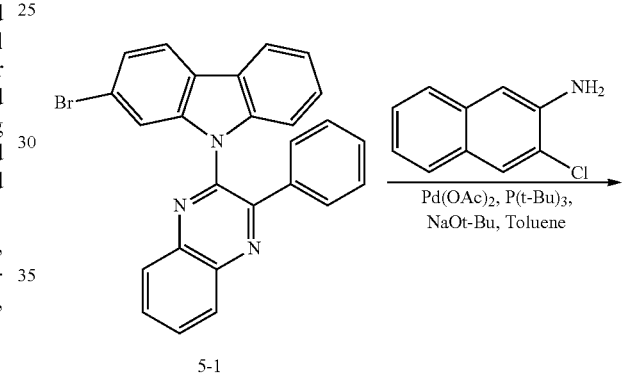

5-1

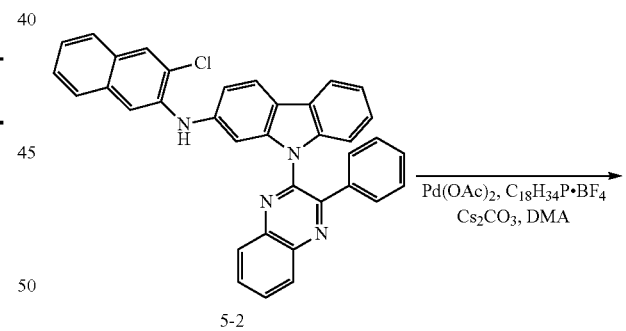

5-2

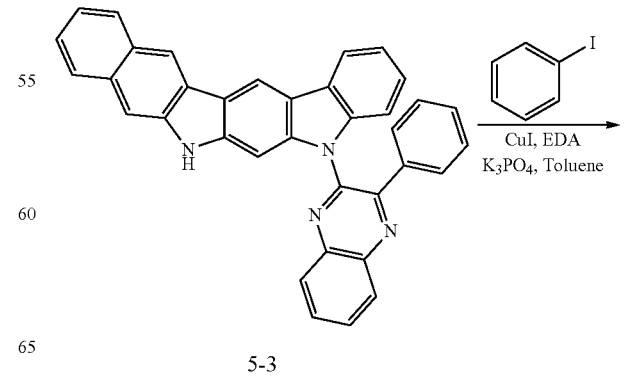

5-3

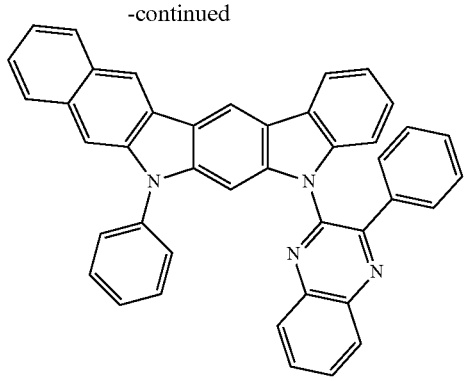

H-37

Preparation of Compound 51-1

25.0 g of 2-bromo-9H-carbazole (102 mmol), 29.4 g of 2-chloro-3-phenylquinoxaline (122 mmol), 6.3 g of 4-dimethylaminopyridine (51 mmol), and 33.0 g of $Cs_2CO_3$ (102 mmol) were dissolved in 510 mL of dimethylsulfoxide (DMSO), stirred for 2 hours at 110° C., and then poured into distilled water. The resulting solid was filtered under reduced pressure. The solid was dissolved in MC and purified by column chromatography to obtain 30.0 g of compound 5-1 (66%).

Preparation of Compound 51-2

14.4 g of compound 5-1 (32 mmol), 6.8 g of 3-chloronaphthalene-2-amine (38.3 mmol), 0.36 g of $Pd(OAc)_2$ (1.6 mmol), 1.6 mL of $P(t-Bu)_3$ (50%) (3.2 mmol), and 7.7 g of NaOt-Bu (80 mmol) were poured into 90 mL of toluene, and stirred under reflux for 6 hours. After completion of the reaction, the reaction product was cooled at room temperature, and extracted with distilled water and MC. The organic layer was distilled under reduced pressure and then purified by column chromatography using MC/Hex to obtain 13.5 g of compound 5-2 (77%).

Preparation of Compound 51-3

12.5 g of compound 5-2 (22.9 mmol), 0.51 g of $Pd(OAc)_2$ (2.3 mmol), 1.7 g of $C_{18}H_{34}P·BF_4$ (4.6 mol), and 18.6 g of $Cs_2CO_3$ (58 mmol) were poured into 92 mL of dimethylacetamide (DMA), and stirred for one day at 195° C. After completion of the reaction, the reaction product was extracted with ethyl acetate. The organic layer was dried with magnesium sulfate ($MgSO_4$), filtered, and then the solvent was removed under reduced pressure. The resulting solid was dissolved in MC and purified by column chromatography obtain 6.6 g of compound 5-3 (56%).

Preparation of Compound H-37

6.6 g of compound 5-3 (12.9 mmol), 2.9 mL of iodobenzene (25.9 mmol), 1.3 g of CuI (6.45 mmol), 0.9 mL of ethylenediamine (12.9 mmol), and 6.9 g of $K_3PO_4$ (32.3 mmol) were poured into 70 mL of toluene, and stirred under reflux for 6 hours. The reaction product was extracted with MC, distilled under reduced pressure, and then purified by column chromatography using MC/Hex to obtain 16 g of compound H-37 (58%).

$^1$H NMR (600 MHz, $CDCl_3$, δ) 8.84 (s, 1H), 8.63 (s, 1H), 8.27-8.26 (d, 1H), 8.23-8.21 (m, 1H), 8.13-8.12 (d, 1H), 8.07-8.06 (d, 1H), 7.86-7.80 (m, 3H), 7.63-7.60 (t, 2H), 7.58 (s, 1H), 7.50-7.35 (m, 10H), 7.16-7.10 (m, 3H), 6.84 (s, 1H)

|  | MW | M.P. |
|---|---|---|
| H-37 | 586.7 | 247° C. |

Example 6: Preparation of Compound H-80

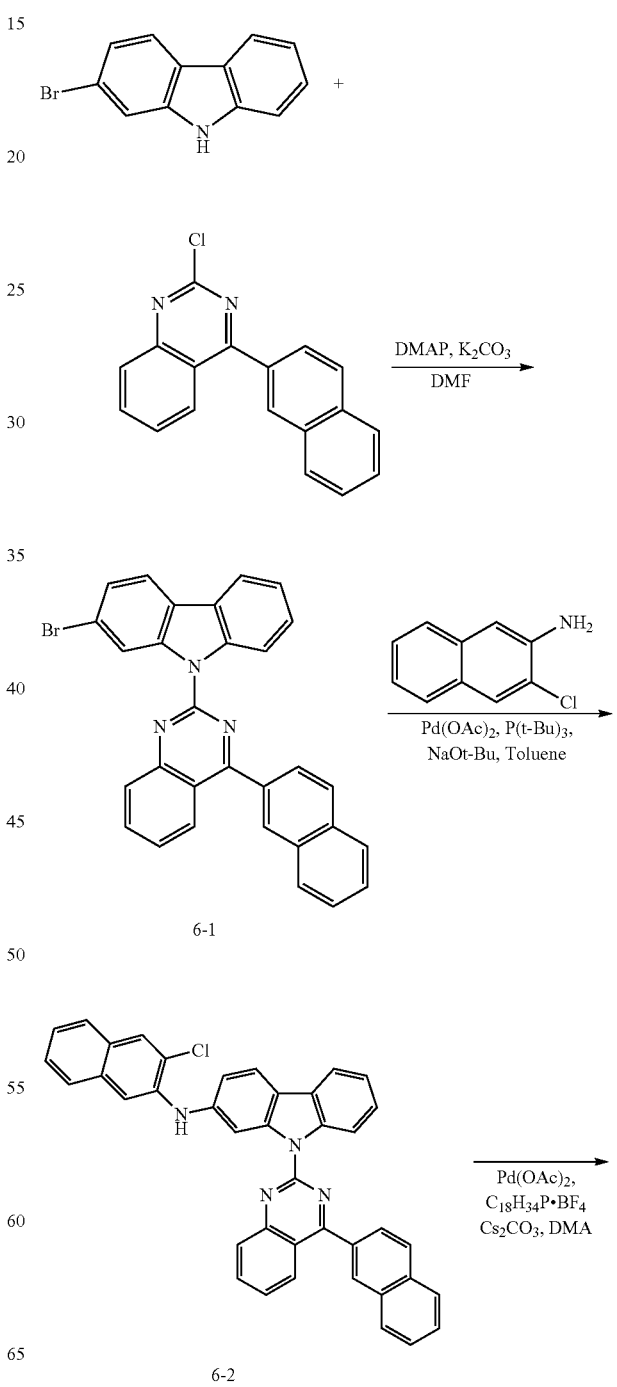

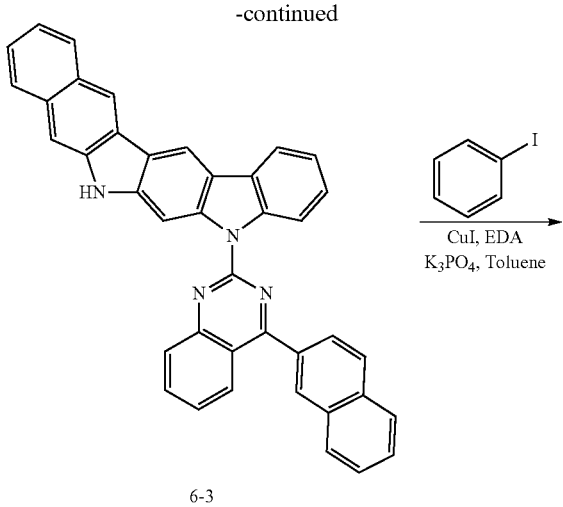

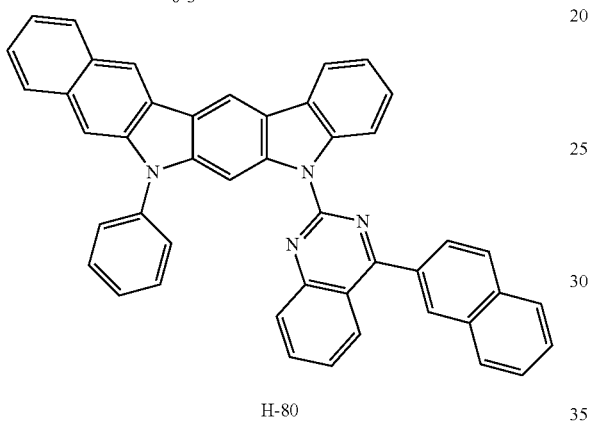

6-3

H-80

Preparation of Compound 61-1

15.0 g of 2-bromo-9H-carbazole (61 mmol), 21.2 g of 2-chloro-4-(naphthalene-2-yl)quinazoline (73 mmol), 3.8 g of 4-dimethylaminopyridine (31 mmol), and 40 g of $K_2CO_3$ (122 mmol) were dissolved in 300 mL of DMF, stirred for 3 hours at 120° C., and then poured into distilled water. The resulting solid was filtered under reduced pressure. The solid was dissolved in MC and purified by column chromatography to obtain 10.3 g of compound 6-1 (34%).

Preparation of Compound 61-2

10.3 g of compound 6-1 (20.5 mmol), 4.38 g of 3-chloronaphthalene-2-amine (24.7 mmol), 0.24 g of $Pd(OAc)_2$ (1.0 mmol), 1.0 mL of $P(t-Bu)_3$ (50%) (2.1 mmol), and 4.93 g of NaOt-Bu (51.3 mmol) were poured into 70 mL of toluene, and stirred under reflux for 6 hours. After completion of the reaction, the reaction product was cooled at room temperature, and extracted with distilled water and MC. The organic layer was distilled under reduced pressure and then purified by column chromatography using MC/Hex to obtain 9.7 g of compound 6-2 (78%).

Preparation of Compound 61-3

9.7 g of compound 6-2 (16.2 mmol), 0.4 g of $Pd(OAc)_2$ (1.6 mmol), 1.2 g of $C_{18}H_{34}P.BF_4$ (3.2 mol), and 13.0 g of $Cs_2CO_3$ (40.4 mmol) were poured into 65 mL of DMA, and stirred for one day at 195° C. After completion of the reaction, the reaction product was extracted with ethyl acetate. The organic layer was dried with $MgSO_4$, filtered, and then the solvent was removed under reduced pressure. The solid was dissolved in MC and purified by column chromatography to obtain 5.8 g of compound 6-3 (64%).

Preparation of Compound H-80

2.8 g of compound 6-3 (5.0 mmol), 1.1 mL of iodobenzene (10.0 mmol), 0.5 g of CuI (2.5 mmol), 0.4 mL of ethylenediamine (5.0 mmol), and 2.7 g of $K_3PO_4$ (12.5 mmol) were poured into 25 mL of toluene, and stirred under reflux for 6 hours. The reaction product was extracted with MC, distilled under reduced pressure, and then purified by column chromatography using MC/Hex to obtain 1.0 g of compound H-80 (31%).

$^1$H NMR (600 MHz, $CDCl_3$, δ) 9.116 (s, 1H), 9.105-9.092 (d, 1H), 8.874 (s, 1H), 8.694 (s, 1H), 8.312 (s, 1H), 8.234-8.222 (d, 1H), 8.192-8.178 (d, 1H), 8.105-8.092 (d, 1H), 8.055-8.036 (m, 2H), 8.009-7.995 (d, 1H), 7.976-7.963 (d, 1H), 7.929-7.895 (m, 2H), 7.860-7.847 (d, 1H), 7.707 (s, 1H), 7.693-7.626 (m, 4H), 7.530-7.493 (q, 2H), 7.459-7.408 (m, 3H), 7.301-7.275 (t, 2H), 7.165-7.140 (t, 1H)

|      | MW    | M.P.    |
|------|-------|---------|
| H-80 | 636.7 | 263° C. |

Example 7: Preparation of Compound H-3

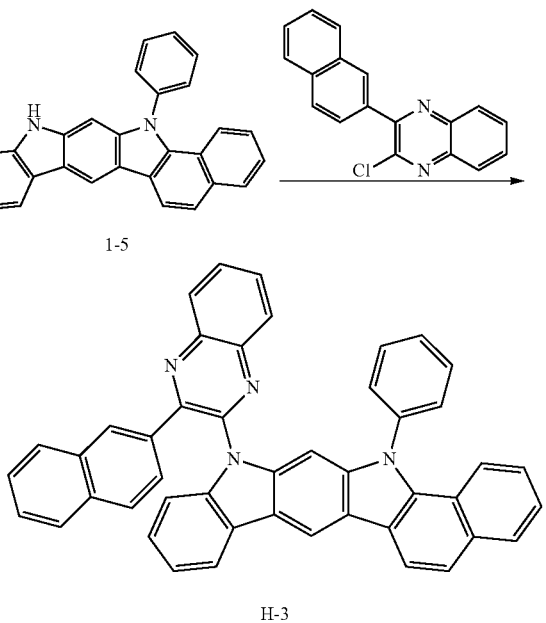

1-5

H-3

5.5 g of compound 1-5 (14 mmol), 5.0 g of 2-chloro-3-(naphthalene-2-yl)quinoxaline (17 mmol), 9.3 g of $Cs_2CO_3$ (29 mmol), and 0.88 g of DMAP (7 mmol) were dissolved in 71 mL of DMSO, and refluxed for 18 hours at 100° C. After completion of the reaction, the reaction product was cooled at room temperature, and poured into distilled water. The reaction product was extracted with MC and dried with magnesium sulfate. The resulting product was distilled under reduced pressure and then purified by column chromatography to obtain 3.4 g of compound H-3 (37%).

$^1$H NMR (600 MHz, CDCl3, δ) 8.75 (s, 1H), 8.30 (m, 1H), 8.28-8.26 (m, 2H), 8.15 (m, 1H), 8.07 (s, 1H), 7.93 (d, J=8.18 Hz, 1H), 7.85-7.82 (m, 2H), 7.69 (d, J=8.41 Hz, 2H), 7.64-7.58 (m, 5H), 7.41-7.32 (m, 7H), 7.27-7.24 (m, 1H), 7.19 (d, J=8.57 Hz, 1H), 7.13-7.10 (m, 1H), 6.88 (d, J=6.83 Hz, 1H), 6.64 (s, 1H)

| | MW | UV | PL | M.P. |
|---|---|---|---|---|
| H-3 | 636.76 | 615 nm | 470 nm | 354° C. |

Example 8: Preparation of Compound H-6

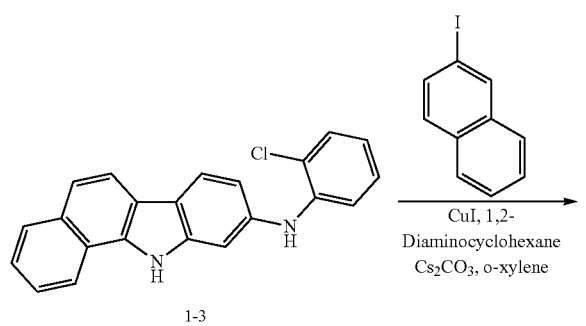

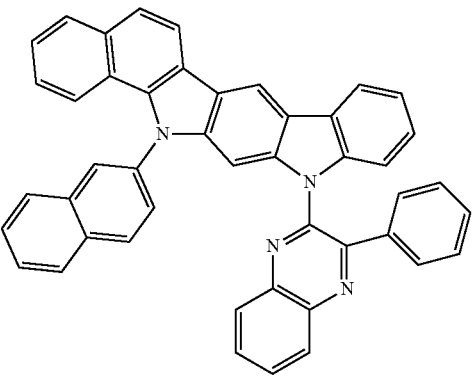

H-6

Preparation of Compound 81-1

19 g of compound 1-3 (55.42 mmol), 21 g of 2-iodonaphthalene (83.13 mmol), 6.6 mL of 1,2-cyclohexanediamine (55.42 mmol), 36 g of $Cs_2CO_3$ (110.84 mmol), and 5.2 g of CuI (27.71 mmol) were dissolved in 280 mL of o-xylene, and refluxed for 5 hours at 150° C. After completion of the reaction, the organic layer was extracted with ethyl acetate, and the residual water was removed using magnesium sulfate. The residue was dried and then purified by column chromatography to obtain 17.7 g of compound 8-1 (77%).

Preparation of Compound 81-2

15.7 g of compound 8-1 (36.29 mmol), 1.6 g of $Pd(OAc)_2$ (7.259 mmol), 35 g of $Cs_2CO_3$ (108.8 mmol), and 4 g of $PCy_3.HBF_4$ (10.88 mmol) were dissolved in 300 mL of DMA, and refluxed for 5 hours at 150° C. After completion of the reaction, the organic layer was extracted with ethyl acetate, and the residual water was removed using magnesium sulfate. The residue was dried and then purified by column chromatography to obtain 3.3 g of compound 8-2 (23%).

Preparation of Compound H-6

3.3 g of compound 8-2 (7.63 mmol), 2.2 g of 2-chloro-3-phenylquinoxaline (9.16 mmol), 2.4 g of $Cs_2CO_3$ (7.63 mmol), and 0.46 g of DMAP (3.81 mmol) were dissolved in 40 mL of DMSO, and refluxed for 6 hours at 135° C. After completion of the reaction, the reaction product was cooled at room temperature and poured into distilled water. The reaction product was extracted with MC and dried with magnesium sulfate. The resulting product was distilled under reduced pressure and then purified by column chromatography to obtain 2.3 g of compound H-6 (47%).

$^1$H NMR (600 MHz, CDCl3, δ) 8.78 (s, 1H), 8.33-8.32 (d, J=6.0 Hz, 1H), 8.25-7.95 (m, 7H), 7.81-7.77 (m, 4H), 7.76-7.54 (m, 3H), 7.37-7.23 (m, 6H), 7.07-6.64 (m, 5H)

| | MW | UV | PL | M.P. |
|---|---|---|---|---|
| H-6 | 636.76 | 354 nm | 530 nm | 188° C. |

Hereinafter, the luminescent properties of the organic light-emitting diode (OLED) device comprising the compound of the present disclosure will be explained in detail.

However, the following examples merely illustrate the characteristics of the OLED device according to the present invention for a detailed understanding of the present disclosure, but the present disclosure is not limited by the following examples.

Device Example 1: Producing an OLED Device Comprising the Organic Electroluminescent Compound of the Present Disclosure as a Host OLED devices were produced by using the organic electroluminescent compound according to the present disclosure. A transparent electrode indium tin oxide (ITO) thin film (10 Ω/sq) on a glass substrate for an OLED device (GEOMATEC CO., LTD., Japan) was subjected to an ultrasonic washing with trichloroethylene, acetone, ethanol, and distilled water, sequentially, and then was stored in isopropanol. The ITO substrate was then mounted on a substrate holder of a vacuum vapor deposition apparatus. The first hole injection layer material HI-1 was introduced into a cell of the vacuum vapor deposition apparatus, and then the pressure in the chamber of the apparatus was controlled to $10^{-6}$ torr. Thereafter, an electric current was applied to the cell to evaporate the above-introduced material, thereby forming a first hole injection layer having a thickness of 80 nm on the ITO substrate. Next, the second hole injection layer material HI-2 was introduced into another cell of the vacuum vapor deposition apparatus and was evaporated by applying an electric current to the cell, thereby forming a second hole injection layer having a thickness of 5 nm on the first hole injection layer. The first hole transport layer material HT-1 was then introduced into another cell of the vacuum vapor deposition apparatus and was evaporated by applying an electric current to the cell, thereby forming a first hole transport layer having a thickness of 10 nm on the second hole injection layer. The second hole transport layer material HT-4 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layer, a light-emitting layer was formed thereon as follows: Compound H-1 was introduced into one cell of the vacuum vapor depositing apparatus as a host, and compound D-71 was introduced into another cell as a dopant. The dopant was deposited in a doping amount of 3 wt % based on the total amount of the host and dopant to form a light-emitting layer having a thickness of 40 nm on the second hole transport layer. Compound ET-1 and compound EI-1 were then introduced into the other two cells and evaporated simultaneously to form an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED device was produced.

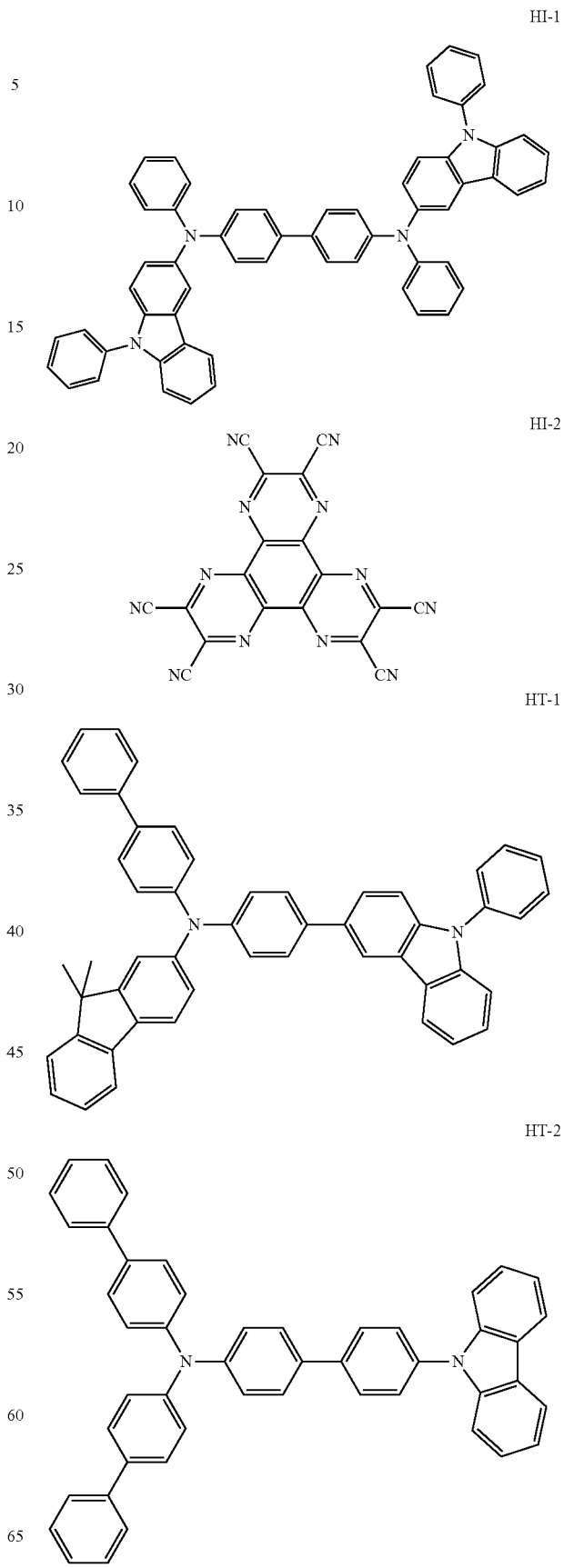

HT-4

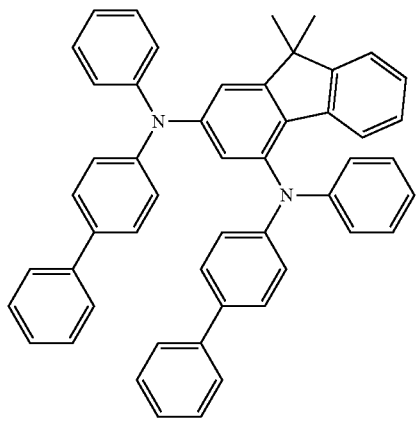

ET-1

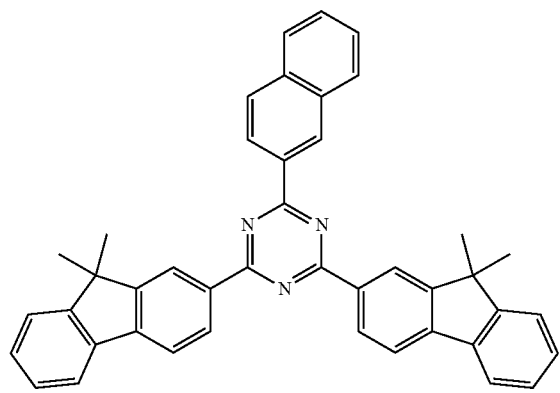

EI-1

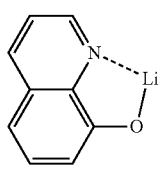

As a result, the power efficiency was 28.1 lm/W at a voltage of 2.8 V, and red luminescence of 1000 cd/m² was confirmed.

Comparative Example 1: Producing an OLED Device Comprising a Conventional Organic Electroluminescent Compound as a Host An OLED device was produced in the same manner as in Device Example 1, except for using the following compound X as a host.

X

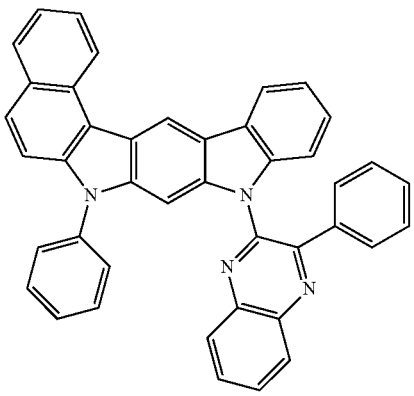

As a result, the power efficiency was 26.0 lm/W at a voltage of 3.2 V, and red luminescence of 1000 cd/m² was confirmed.

Device Example 2: Producing an OLED Device Comprising the Organic Electroluminescent Compound of the Present Disclosure as a Host An OLED device was produced in the same manner as in Device Example 1, except that compound HT-2 was used as the second hole transport layer material, and compound ET-1 and compound EI-1 as the electron transport layer material were deposited to a thickness of 30 nm.

As a result, the power efficiency was 23.5 lm/W at a voltage of 3.4 V, and red luminescence of 1000 cd/m² was confirmed.

Comparative Example 2: Producing an OLED Device Comprising a Conventional Organic Electroluminescent Compound as a Host An OLED device was produced in the same manner as in Device Example 2, except for using the following compound Y as a host.

Y

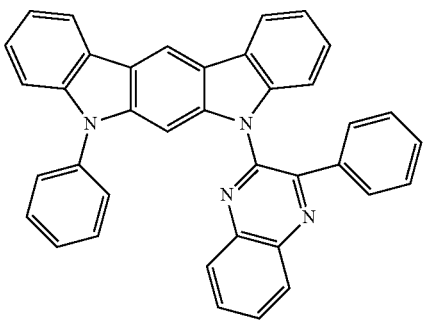

As a result, the power efficiency was 21.0 lm/W at a voltage of 3.9 V, and red luminescence of 1000 cd/m² was confirmed.

Device Example 3: Producing an OLED Device Comprising the Organic Electroluminescent Compound of the Present Disclosure as a Host An OLED device was produced in the same manner as in Device Example 1, except for using compound H-131 as a host.

As a result, the power efficiency was 19.1 lm/W at a voltage of 2.9 V, and red luminescence of 1000 cd/m² was confirmed.

Device Example 4: Producing an OLED Device Comprising the Organic Electroluminescent Compound of the Present Disclosure as a Host An OLED device was produced in the same manner as in Device Example 1, except for using compound H-37 as a host.

As a result, the power efficiency was 23.3 lm/W at a voltage of 3.1 V, and red luminescence of 1000 cd/m² was confirmed.

Device Example 5: Producing an OLED Device Comprising the Organic Electroluminescent Compound of the Present Disclosure as a Host An OLED device was produced in the same manner as in Device Example 1, except for using compound H-6 as a host.

As a result, the power efficiency was 28.2 lm/W at a voltage of 2.9 V, and red luminescence of 1000 cd/m² was confirmed.

Device Example 6: Producing an OLED Device Comprising the Organic Electroluminescent Compound of the Present Disclosure as a Host An OLED device was produced in the same manner as in Device Example 1, except for using compound H-3 as a host.

As a result, the power efficiency was 28.6 lm/W at a voltage of 2.9 V, and red luminescence of 1000 cd/m² was confirmed.

Comparative Example 3: Producing an OLED Device Comprising a Conventional Organic Electroluminescent Compound as a Host An OLED device was produced in the same manner as in Device Example 1, except for using the following compound Z as a host.

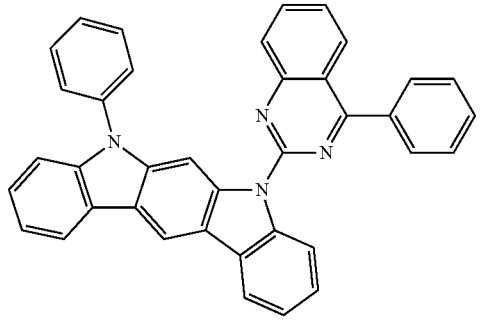

Z

As a result, the power efficiency was 18.9 lm/W at a voltage of 3.4 V, and red luminescence of 1000 cd/m² was confirmed.

From Device Examples 1 to 6 and Comparative Examples 1 to 3 above, the organic electroluminescent device comprising the organic electroluminescent compound according to the present disclosure as a host has a lower driving voltage property and a higher power efficiency property than an organic electroluminescent device using a conventional organic electroluminescent compound. It is understood that this is because the hole injection is possible by the enhanced harmonization of high HOMO of the compound according to the present disclosure and the HOMO of the hole transport layer (HTL), resulting in the increased hole mobility which lowers driving voltage.

Accordingly, it can be seen that using the organic electroluminescent compound according to the present disclosure has an advantage of lowering the power consumption since the voltage used to emit light of the same luminance is low. Further, it can be seen that it may have an advantage of increasing the battery usage time in portable display systems where OLED panels are mainly used.

The invention claimed is:
1. An organic electroluminescent device comprising an organic electroluminescent compound represented by the following formula 1:

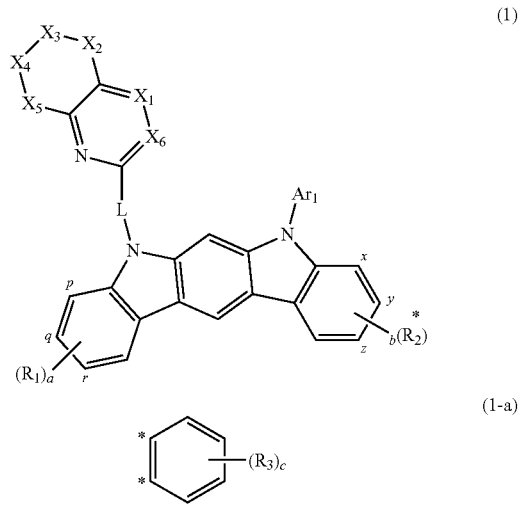

wherein
at least one of both x and y, both y and z, both p and q, and both q and r are fused with the * positions in formula 1-a, with the proviso that the case where both x and y, and both y and z are simultaneously fused with the * positions in formula 1-a, and the case where both p and q, and both q and r are simultaneously fused with the * positions in formula 1-a, are excluded;

L represents a single bond, a substituted or unsubstituted (C6-C30)arylene, or a substituted or unsubstituted (5- to 30-membered)heteroarylene;

$X_1$ to $X_6$, each independently, represent N or $CR_4$ with the proviso, at least one of $X_1$ to $X_6$ represents N;

$Ar_1$ represents a substituted or unsubstituted (C6-C30) aryl, or a substituted or unsubstituted (5- to 30-membered)heteroaryl;

$R_1$ to $R_4$, each independently, represent hydrogen, deuterium, a halogen, a substituted or unsubstituted (C1-C30)alkyl, a substituted or unsubstituted (C6-C30)aryl, a substituted or unsubstituted (5- to 30-membered) heteroaryl, a substituted or unsubstituted (C3-C30) cycloalkyl, a substituted or unsubstituted (3- to 7-membered)heterocycloalkyl, a substituted or unsubstituted (C6-C30)aryl(C1-C30)alkyl, —NR₁₁R₁₂, —SiR₁₃R₁₄R₁₅, —SR₁₆, —OR₁₇, a cyano, a nitro, or a hydroxyl;

R₁₁ to R₁₇, each independently, represent hydrogen, deuterium, a halogen, a substituted or unsubstituted (C1-C30)alkyl, a substituted or unsubstituted (C6-C30)aryl, a substituted or unsubstituted (5- to 30-membered) heteroaryl, a substituted or unsubstituted (3- to 7-membered)heterocycloalkyl, or a substituted or unsubstituted (C3-C30)cycloalkyl; or are linked to an adjacent substituent to form a substituted or unsubstituted, mono- or polycyclic, (3- to 30-membered) alicyclic or aromatic ring, or the combination thereof, which may comprise at least one heteroatom selected from nitrogen, oxygen, and sulfur;

a to c, each independently, represent an integer of 1 to 4, where if a to c, each independently, are an integer of 2 or more, each of R₁ to R₃ may be the same or different; and the heteroaryl(ene) or the heterocycloalkyl contains at least one heteroatom selected from B, N, O, S, Si, and P, wherein the organic electroluminescent compound is comprised as a host material of a light-emitting layer.

2. The organic electroluminescent device according to claim 1, wherein formula 1 is represented by any one of the following formulas 2 to 5:

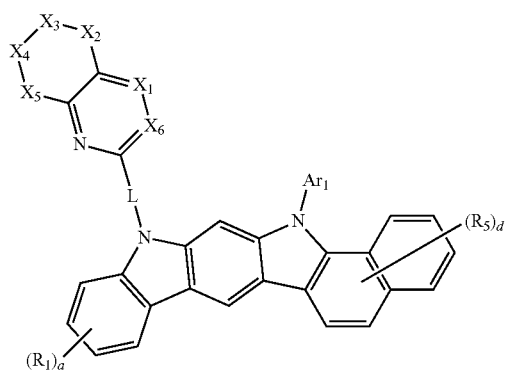

(2)

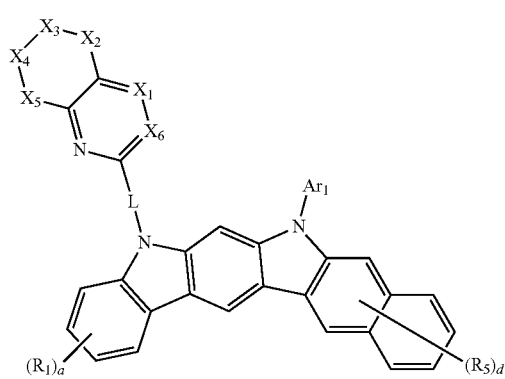

(3)

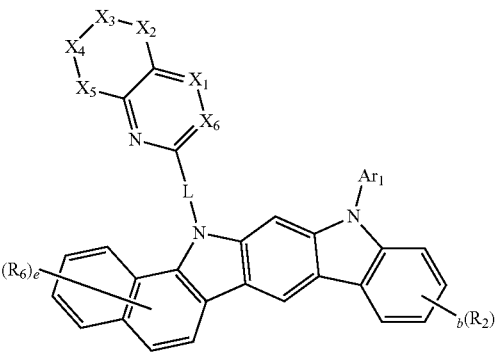

(4)

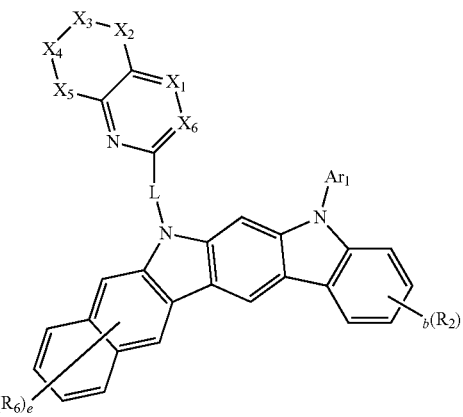

(5)

wherein
L, Ar₁, R₁, R₂, X₁ to X₆, a and b are as defined in claim 1,
R₅ and R₆, each independently, are as defined in R₁ and R₂,
d and e, each independently, represent an integer of 1 to 6, where if d and e, each independently, are an integer of 2 or more, each of R₅ and R₆ may be the same or different.

3. The organic electroluminescent device according to claim 1, wherein the substituents of the substituted alkyl, the substituted aryl(ene), the substituted heteroaryl(ene), the substituted cycloalkyl, the substituted heterocycloalkyl, the substituted aralkyl, and the substituted mono- or polycyclic, alicyclic or aromatic ring, or the combination thereof, in L, Ar₁, R₁ to R₄, and R₁₁ to R₁₇, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (C6-C30)aryl; a (5- to 30-membered)heteroaryl; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

4. The organic electroluminescent device according to claim 1, wherein the compound represented by formula 1 is selected from the group consisting of:

H-1
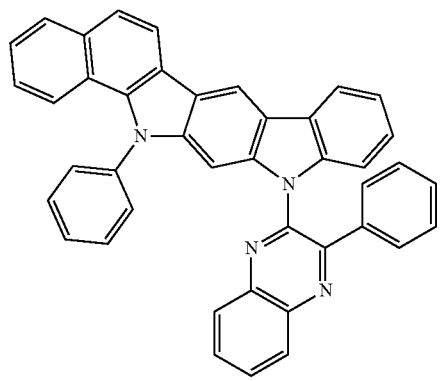
H-2
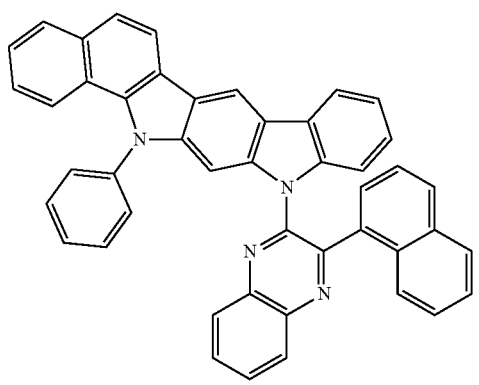
H-3
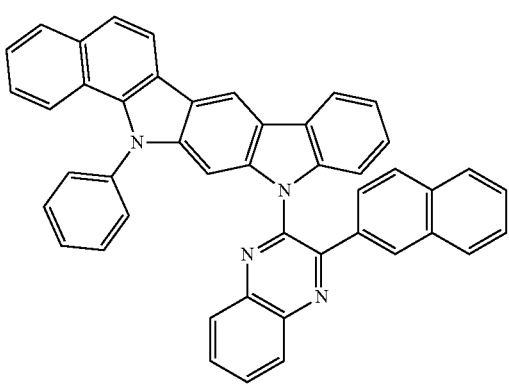
H-4
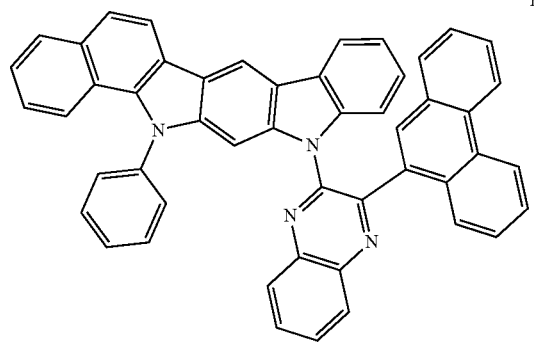
-continued
H-5
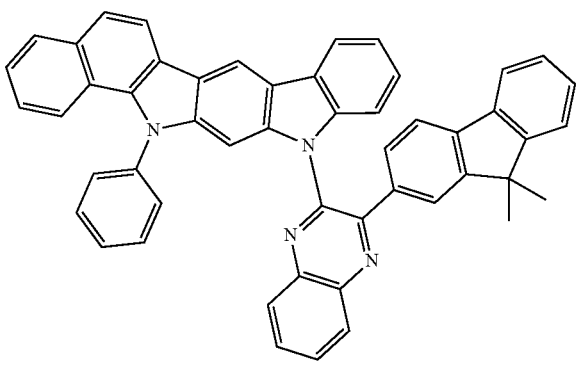
H-6
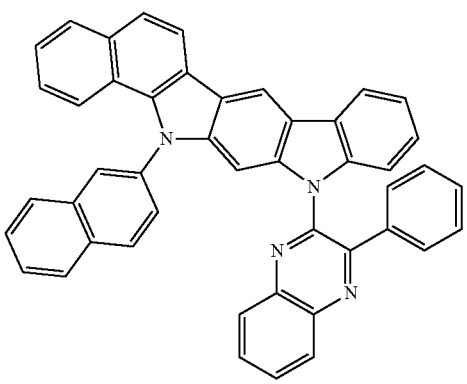
H-7
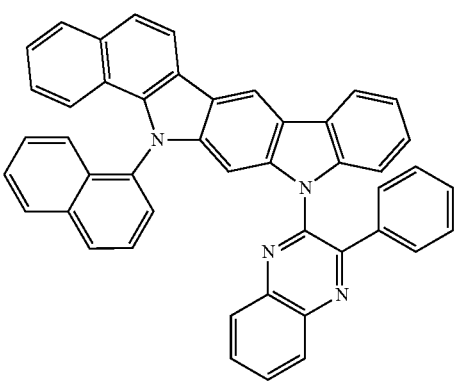
H-8
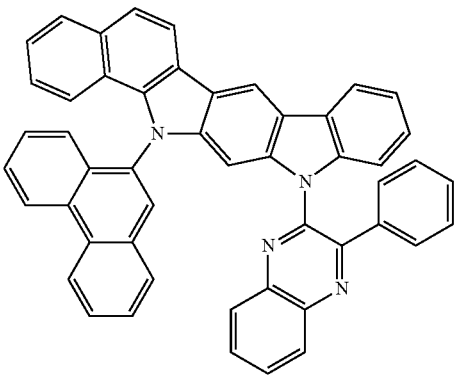

-continued
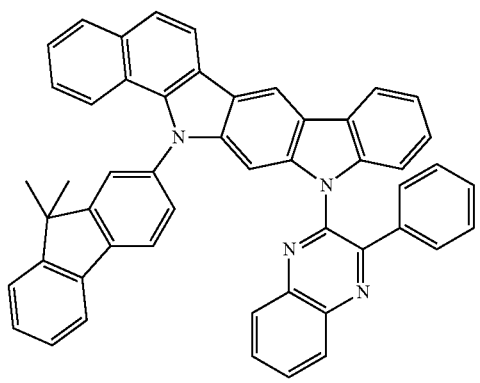
H-9
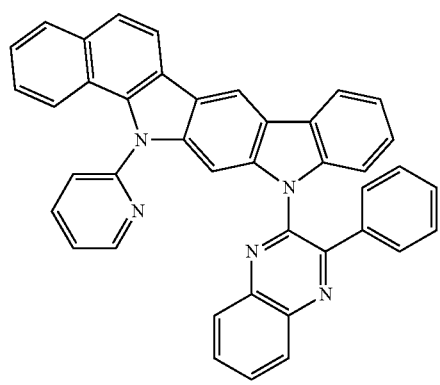
H-10
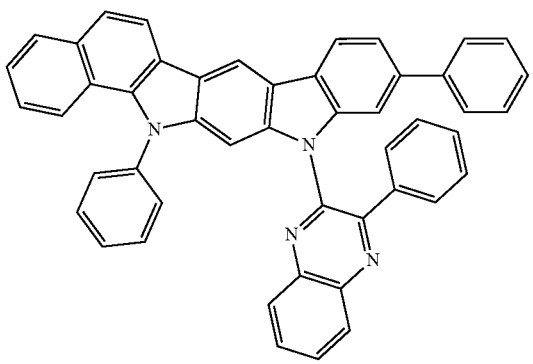
H-11
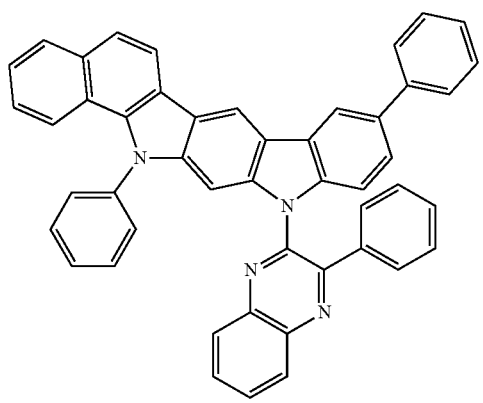
H-12
-continued
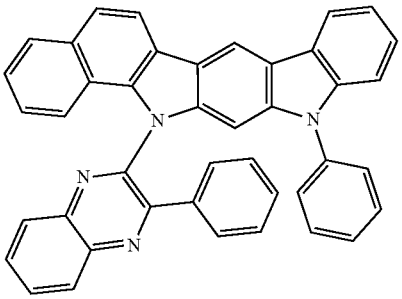
H-13
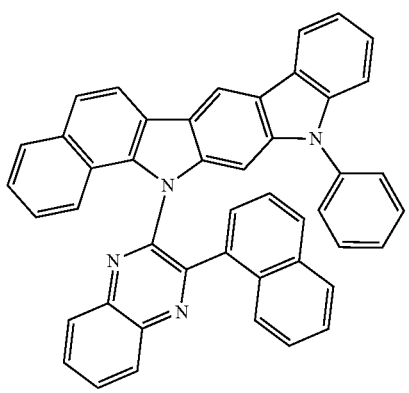
H-14
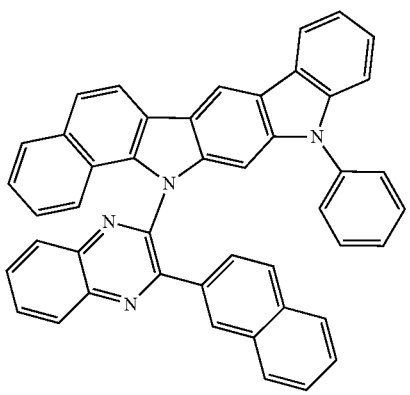
H-15
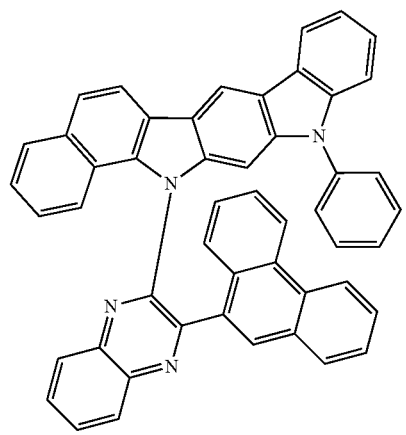
H-16

H-17
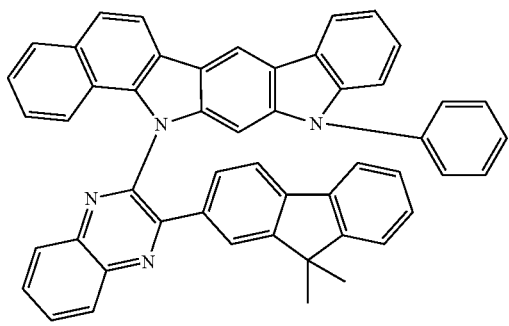
H-18
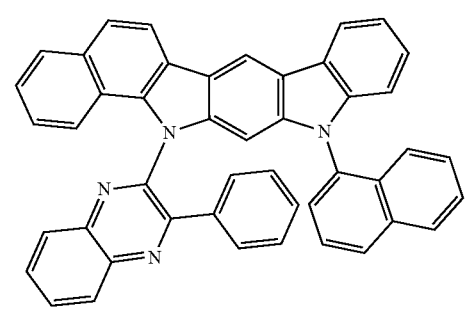
H-19
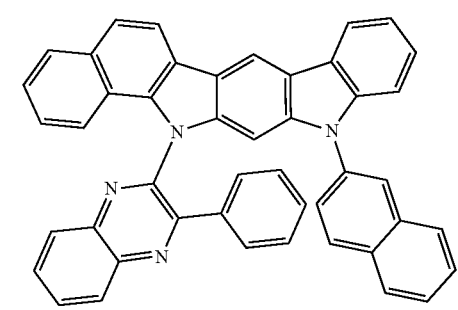
H-20
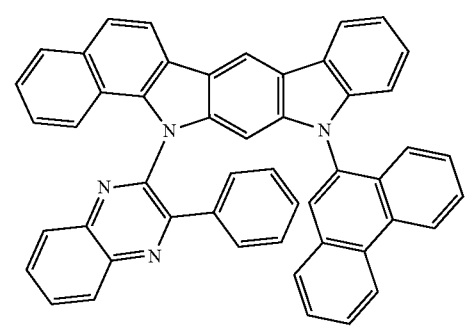
H-21
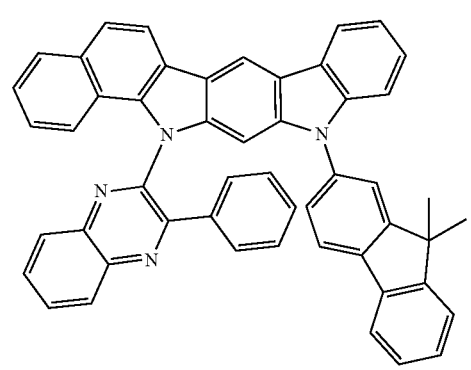
H-22
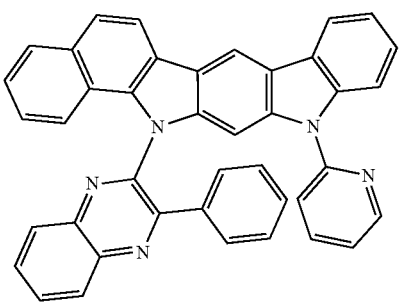
H-23
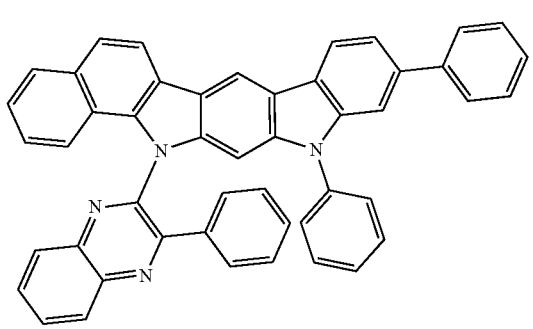
H-24
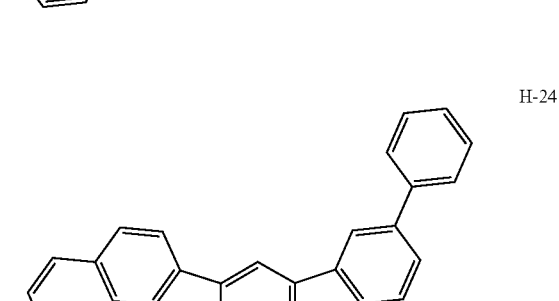
H-25
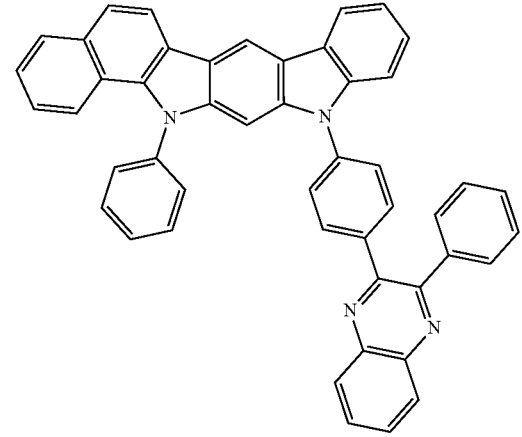

H-26
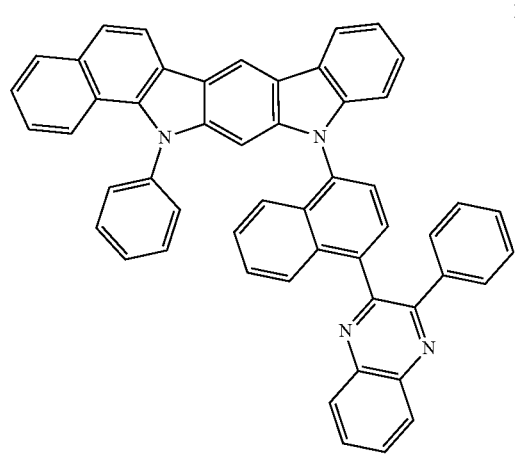
H-27
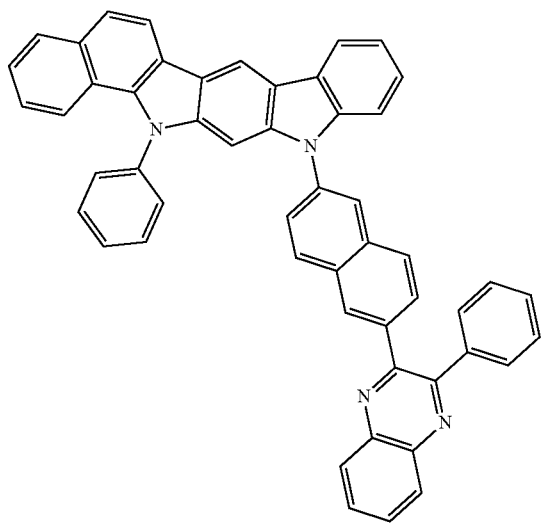
H-28
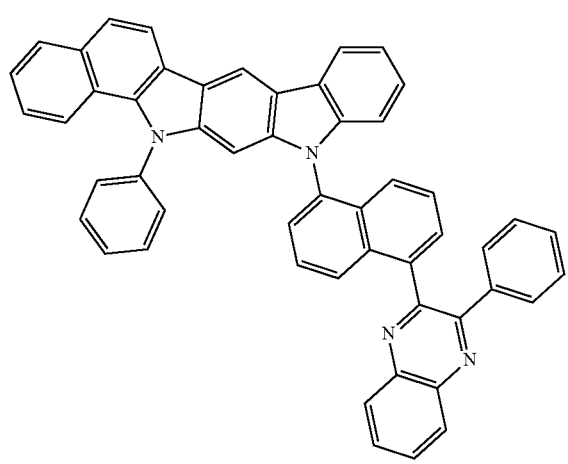
H-29
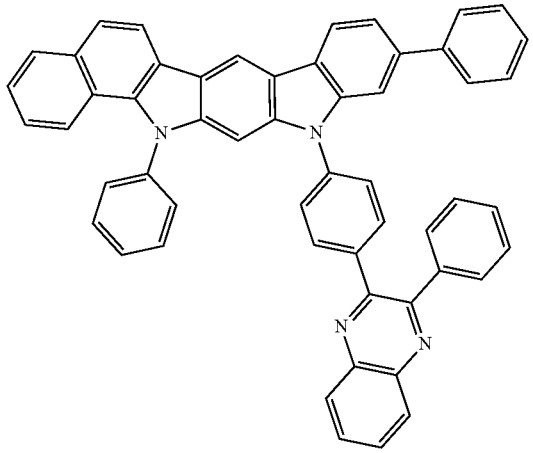
H-30
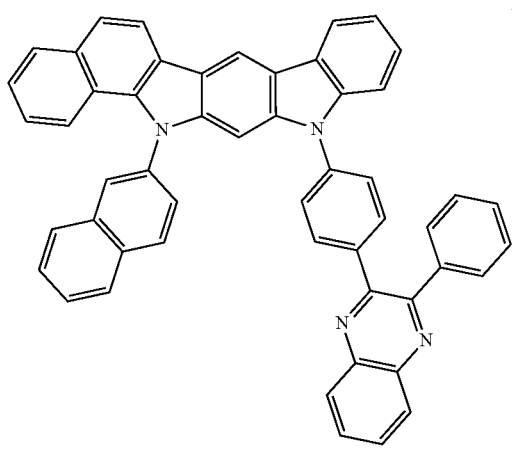
H-31
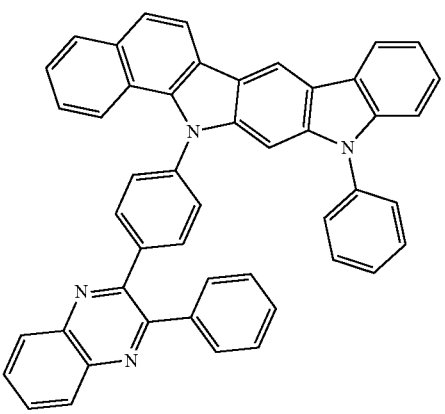

-continued
H-32
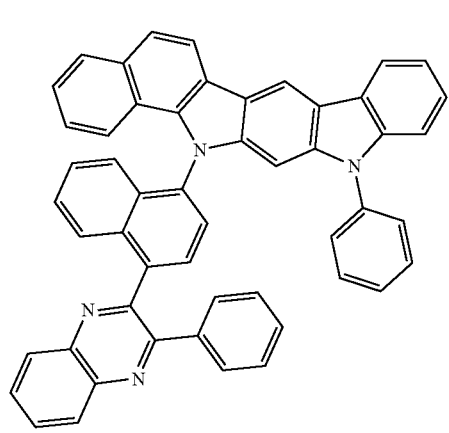
H-33
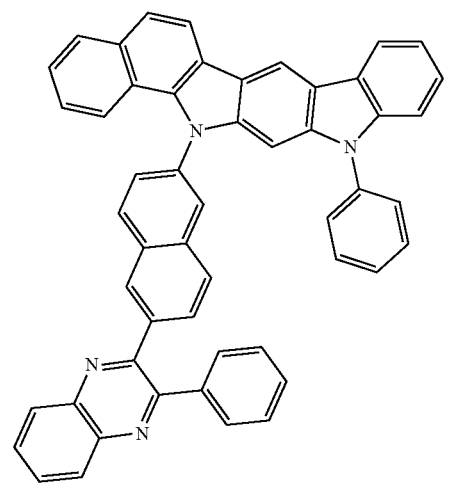
H-34
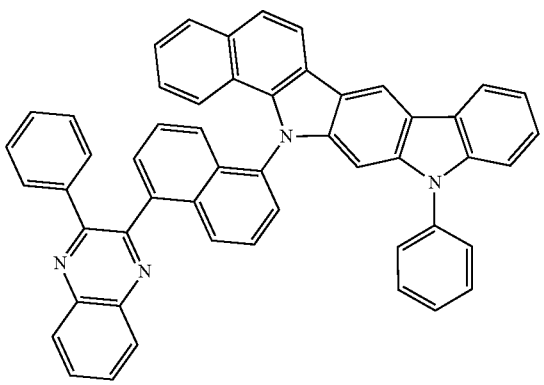
-continued
H-35
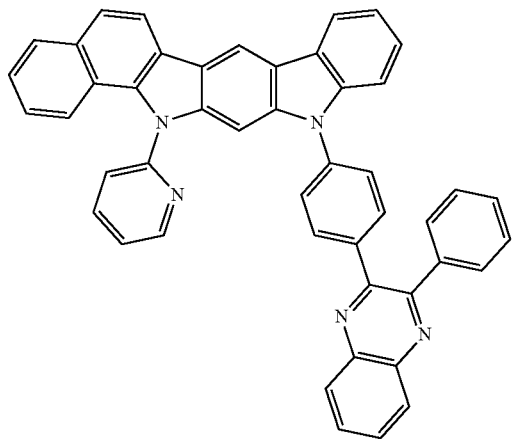
H-36
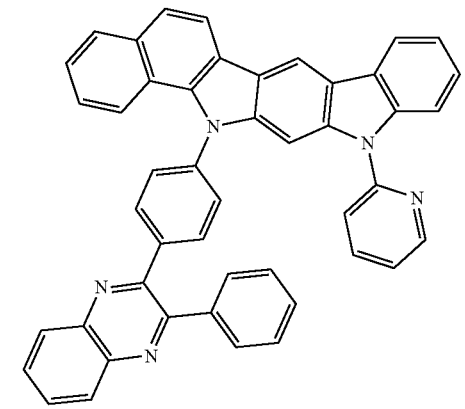
H-37
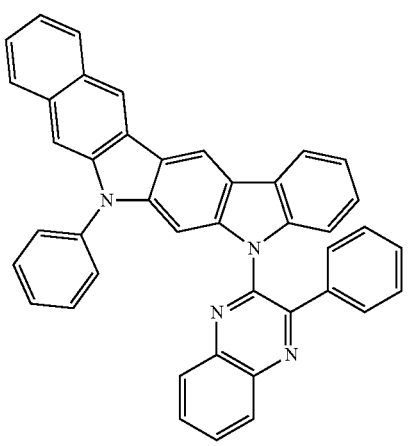

-continued
H-38
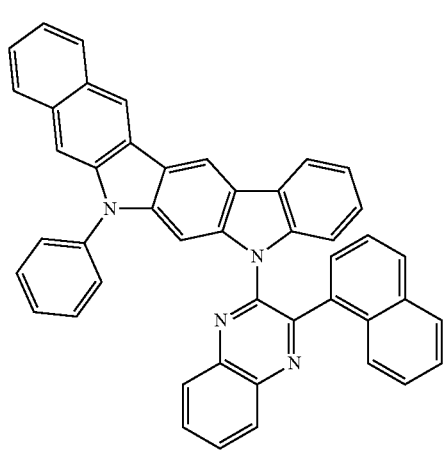
H-41
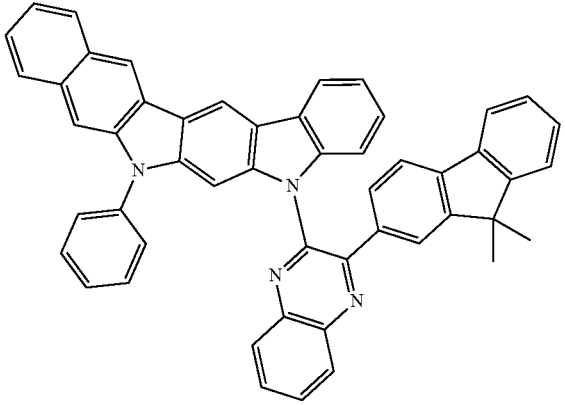
H-39
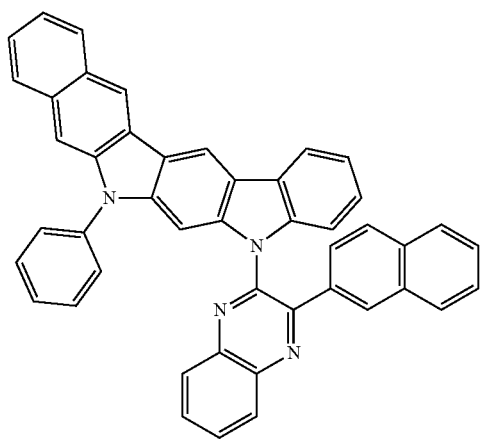
H-42
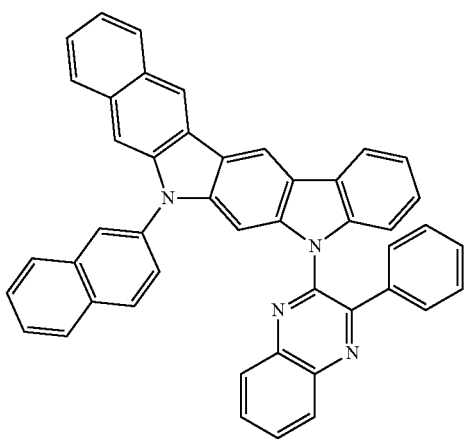
H-40
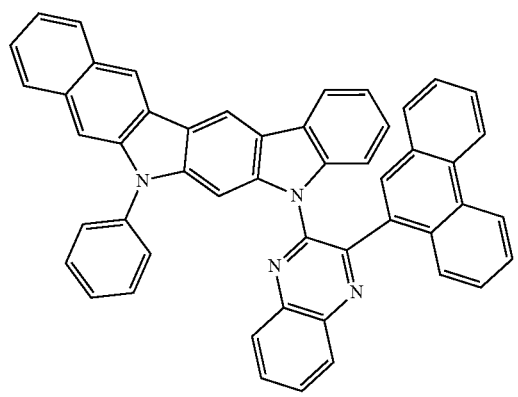
H-43
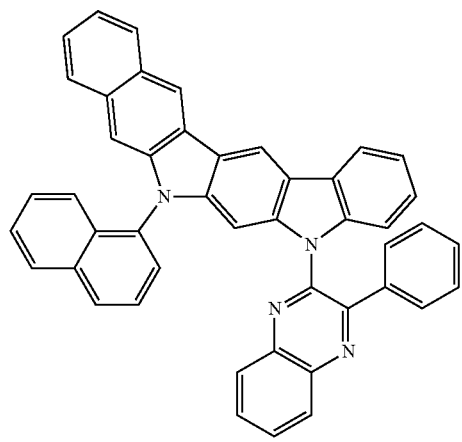

H-44
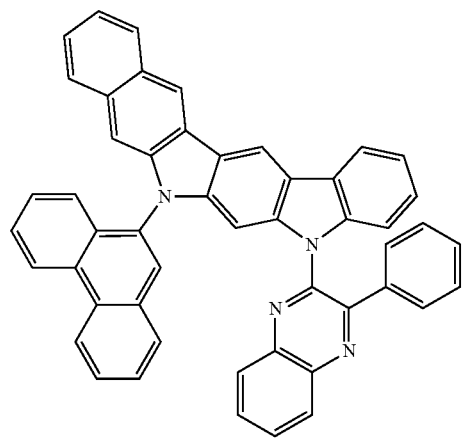
H-45
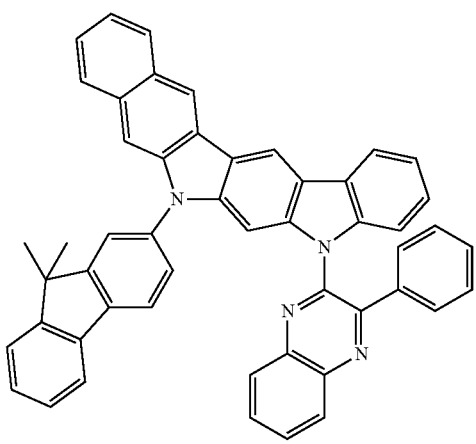
H-46
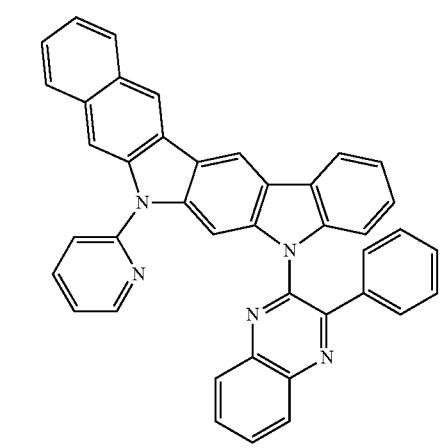
H-47
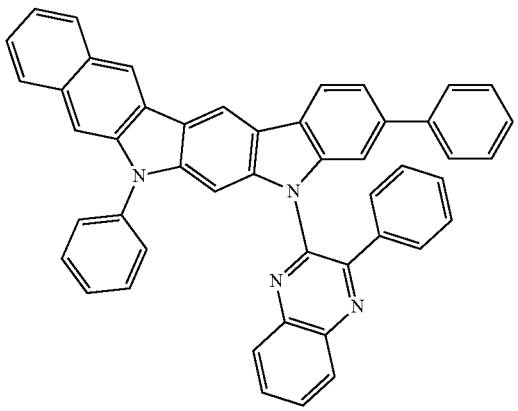
H-48
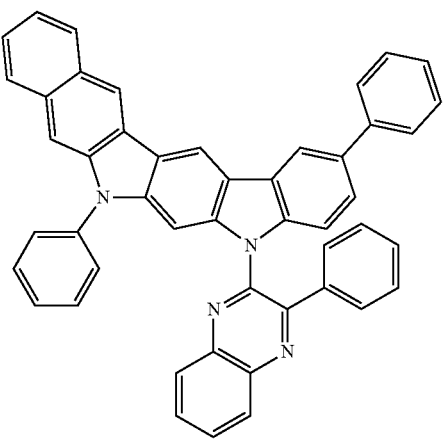
H-49
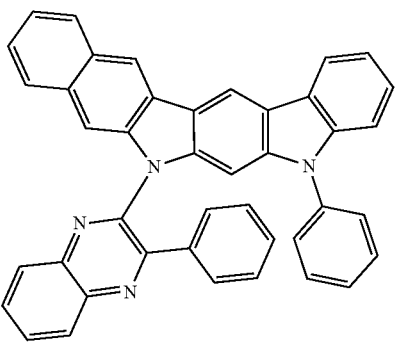
H-50
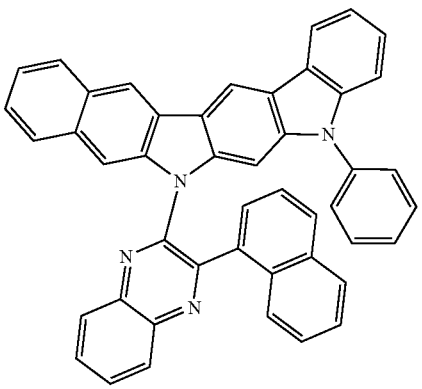

H-51
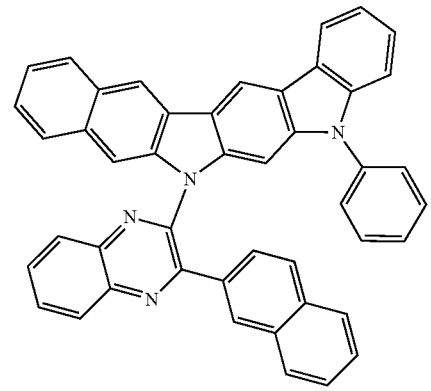
H-52
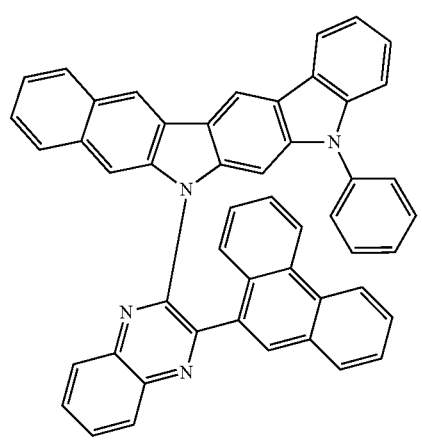
H-53
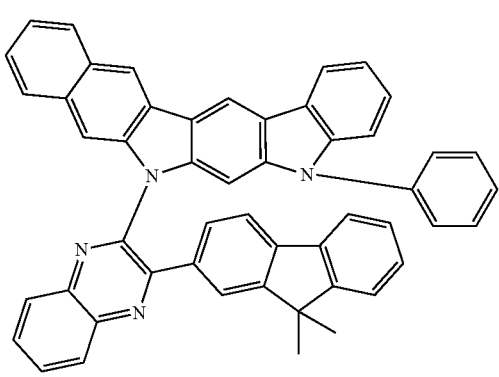
H-54
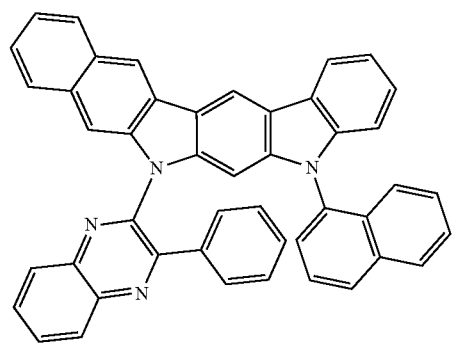
H-55
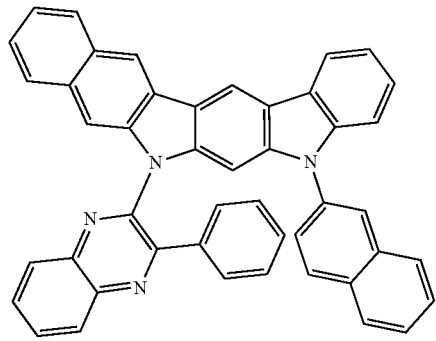
H-56
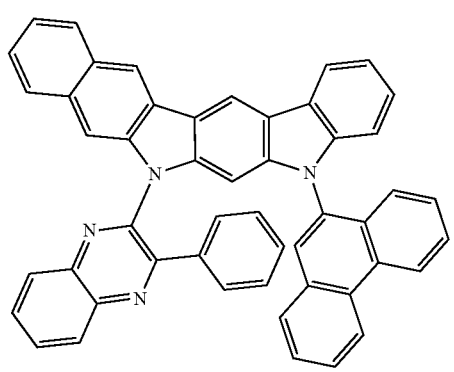
H-57
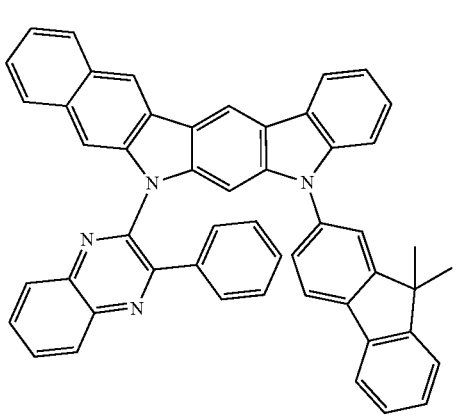
H-58
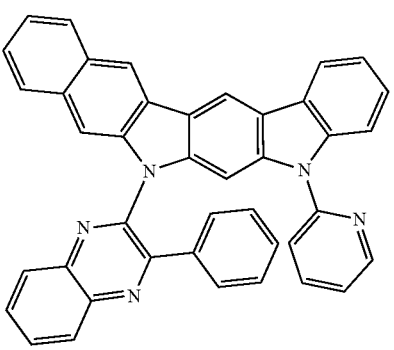

-continued
H-59
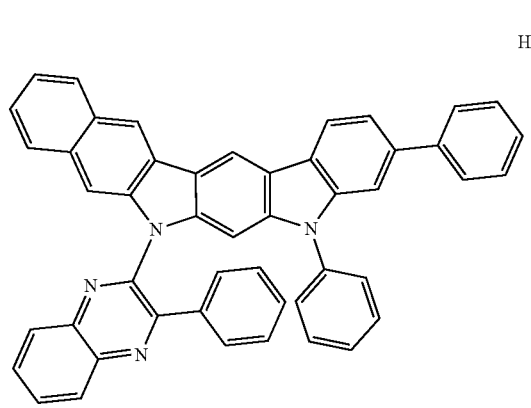
H-60
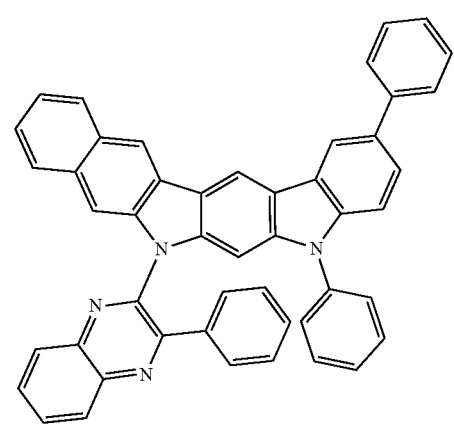
H-61
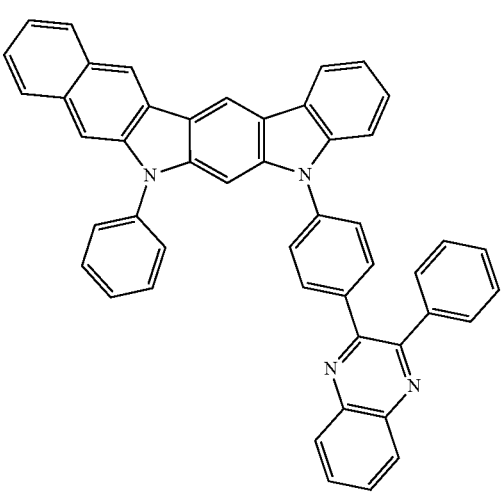
-continued
H-62
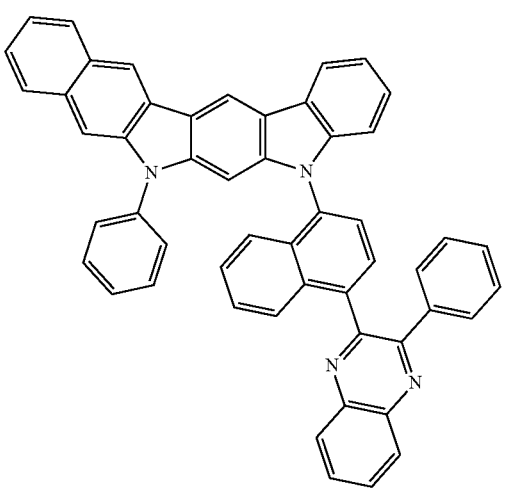
H-63
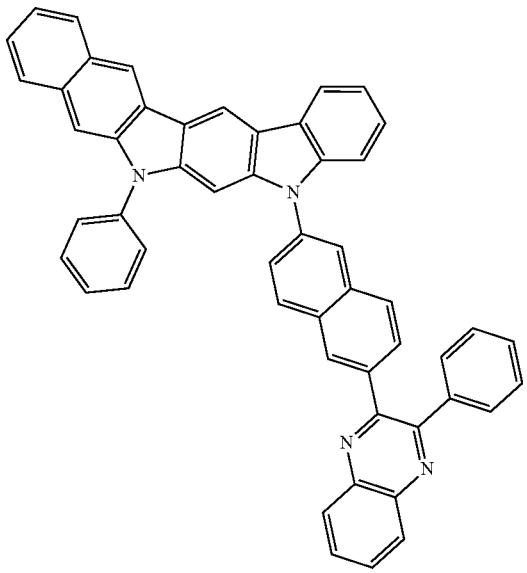
H-64
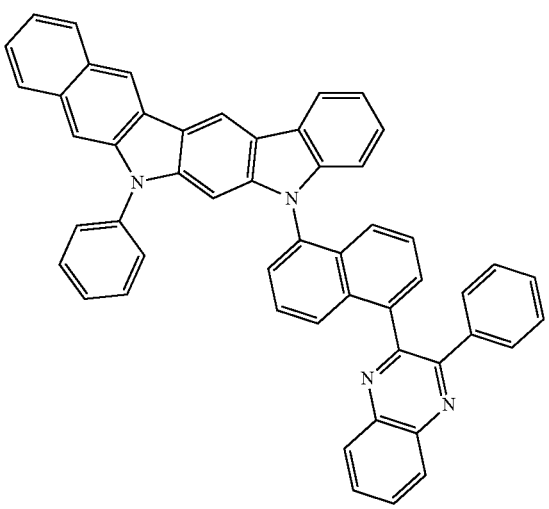

H-65
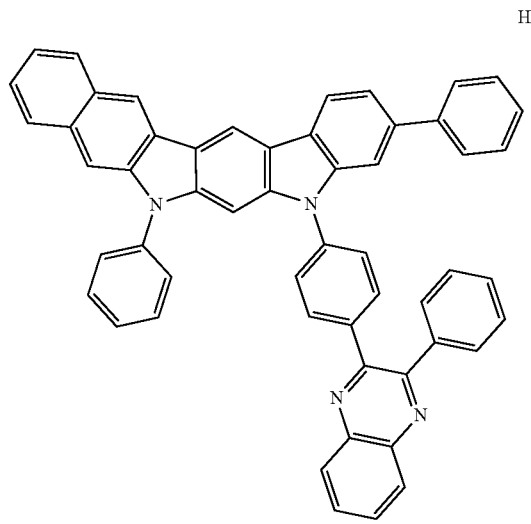
H-66
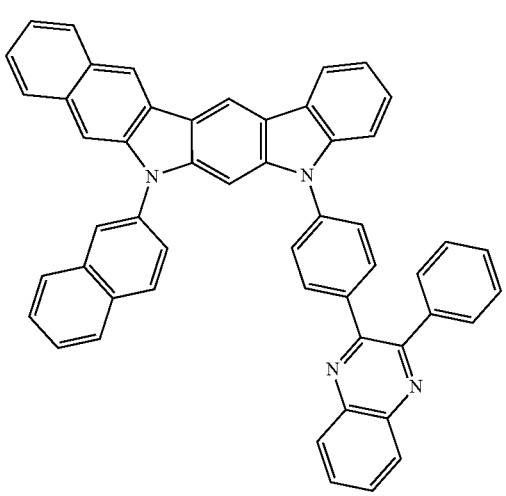
H-67
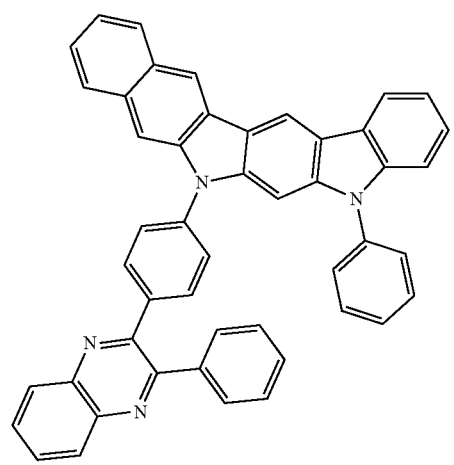
H-68
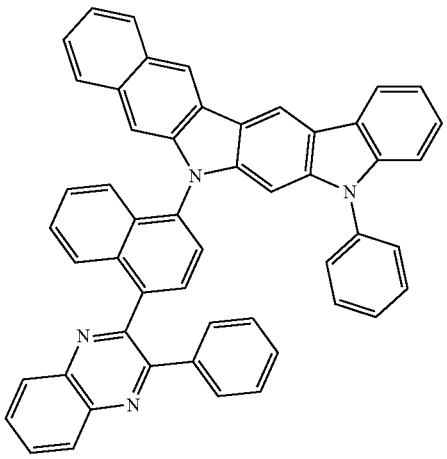
H-69
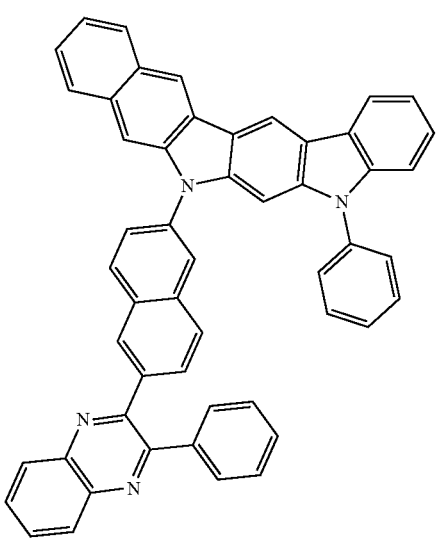
H-70
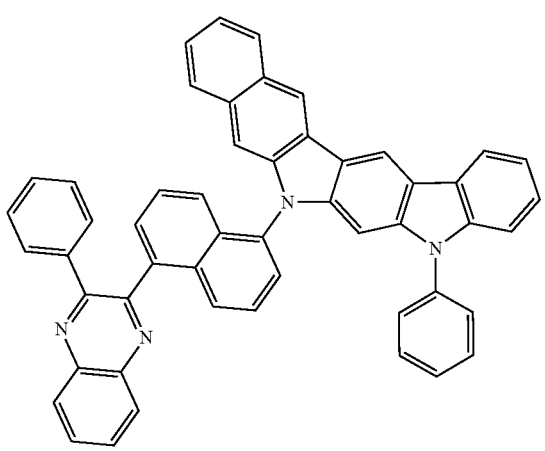

H-71
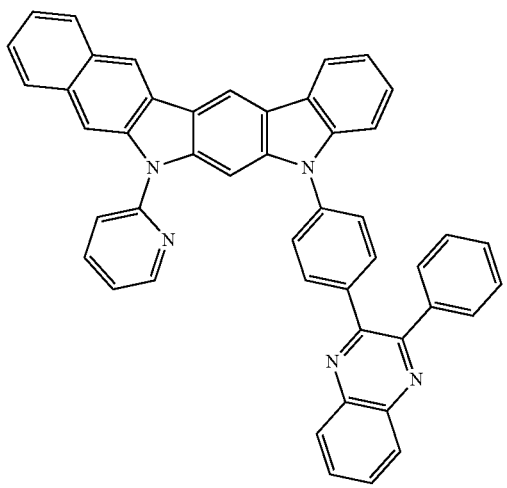
H-72
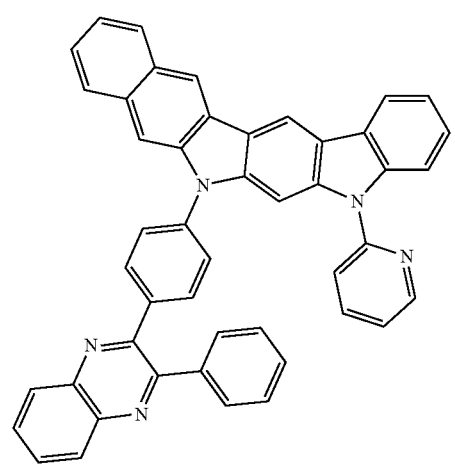
H-73
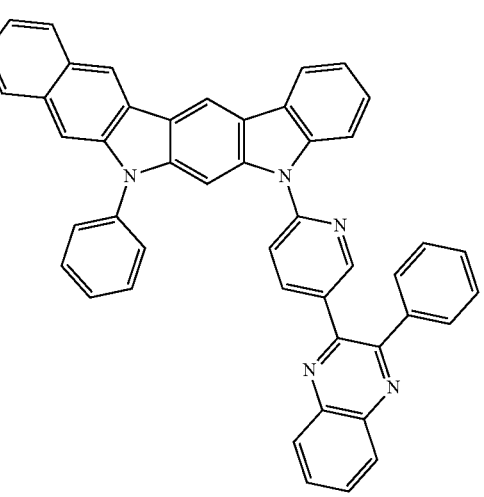
H-74
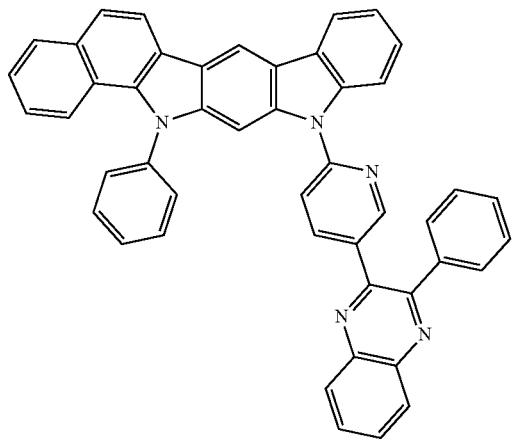
H-75
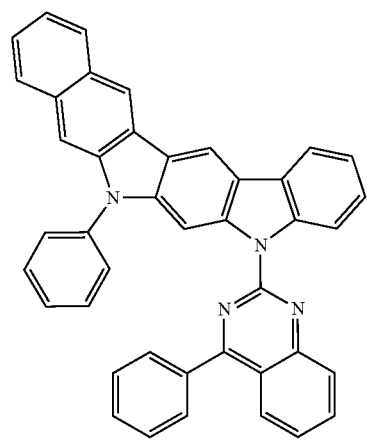
H-76
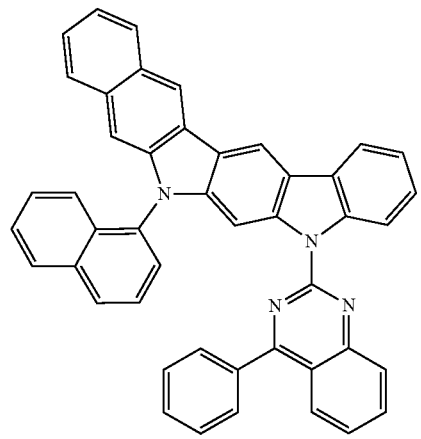

H-77
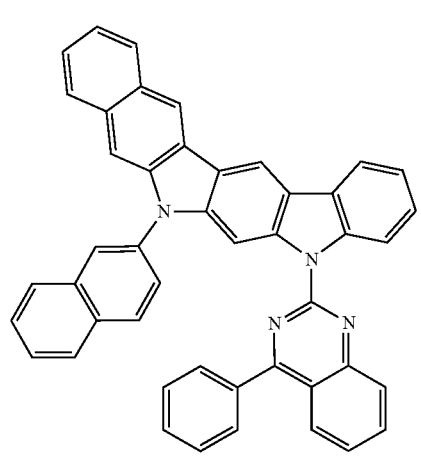
H-78
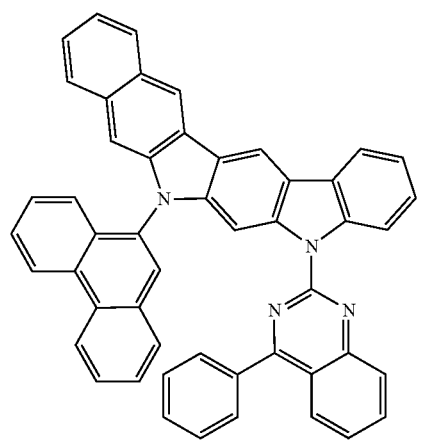
H-79
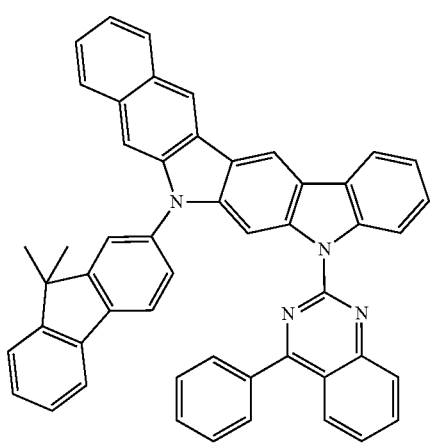
H-80
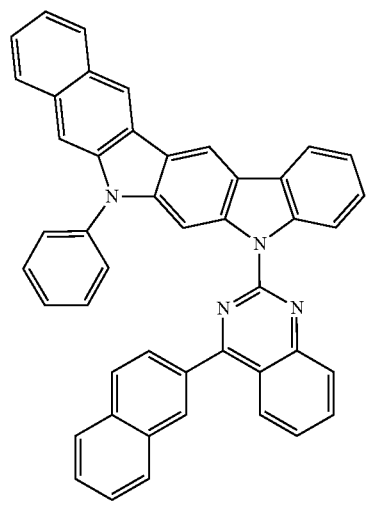
H-81
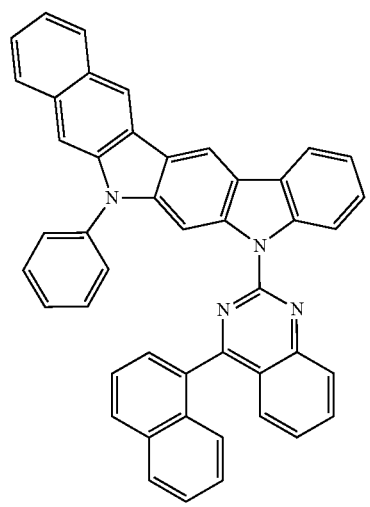
H-82
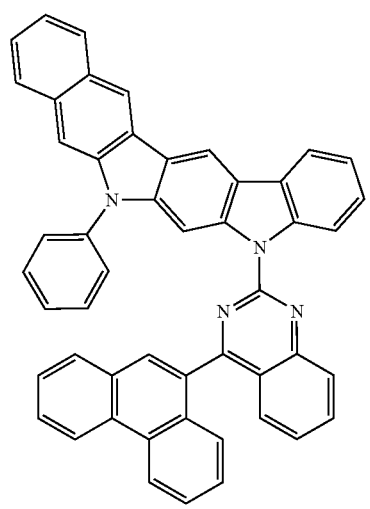

H-83
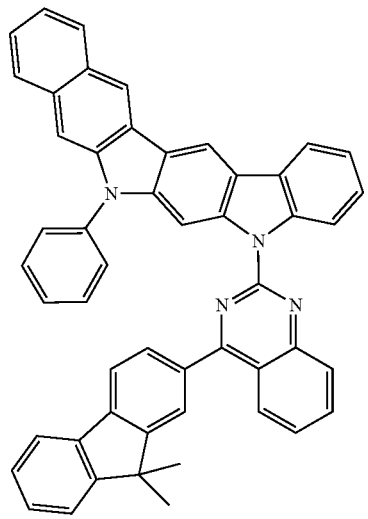
H-84
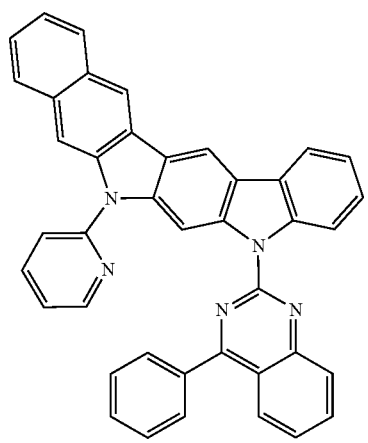
H-85
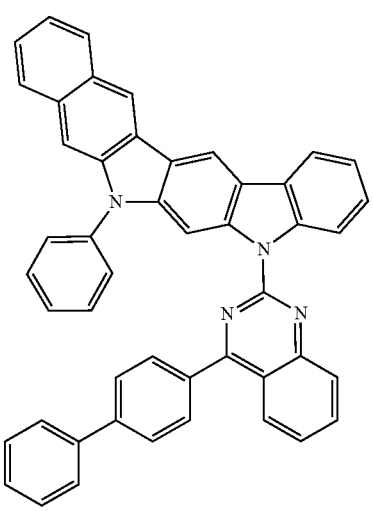
H-86
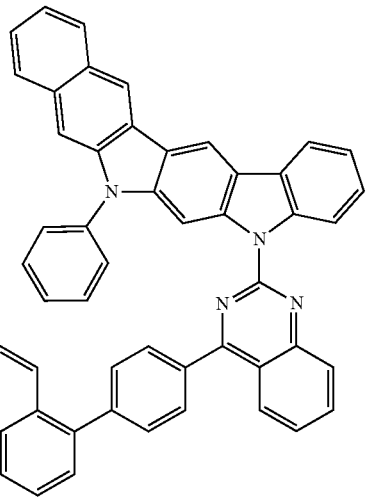
H-87
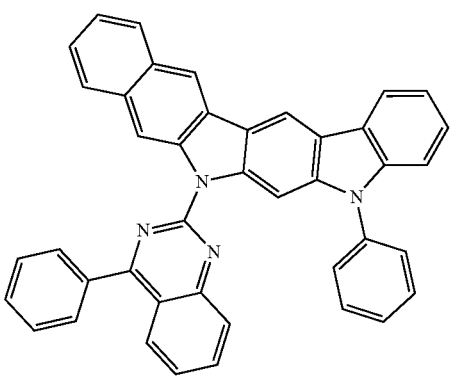
H-88
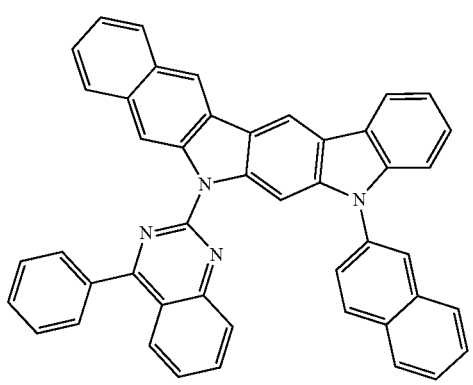
H-89
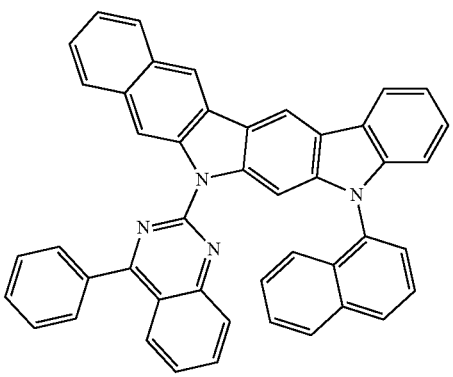

H-90
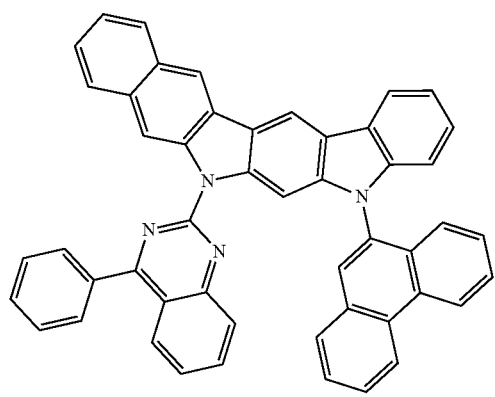
H-91
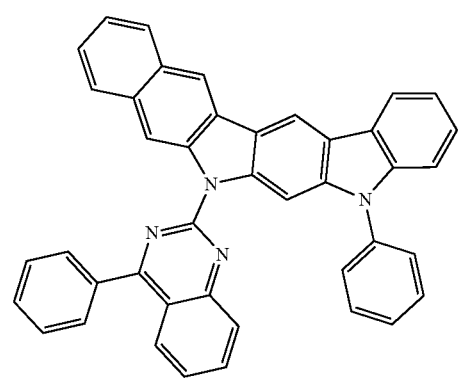
H-92
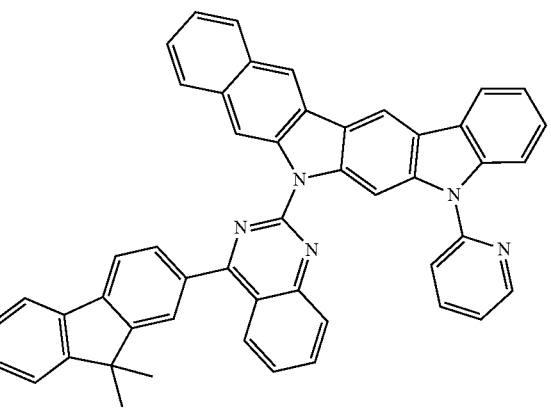
H-93
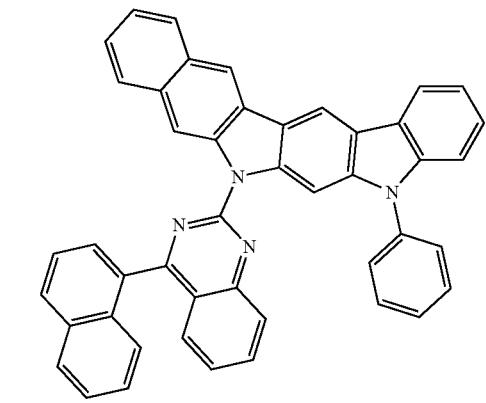
H-94
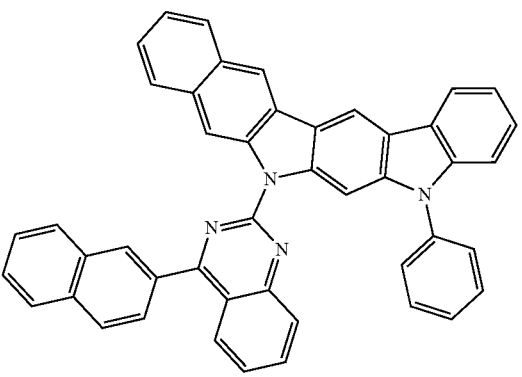
H-95
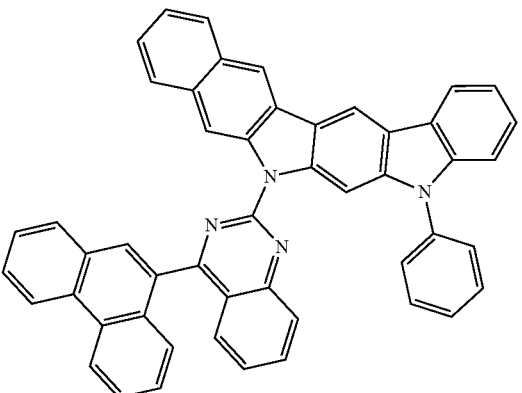
H-96
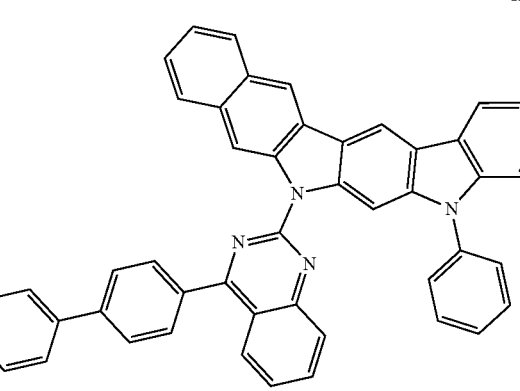
H-97
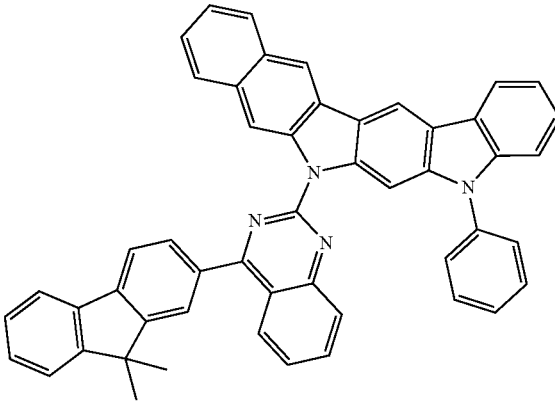

H-98
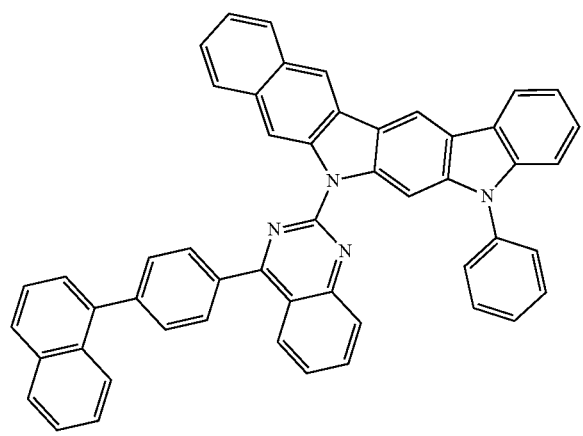
H-99
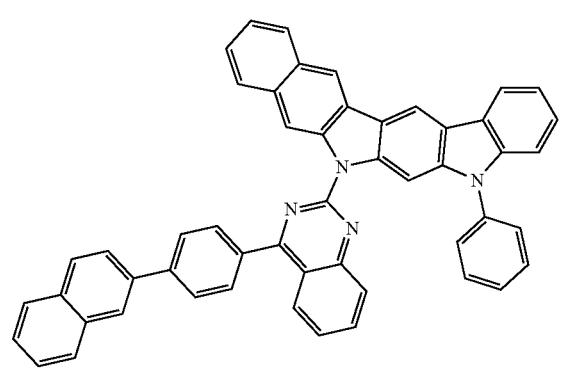
H-100
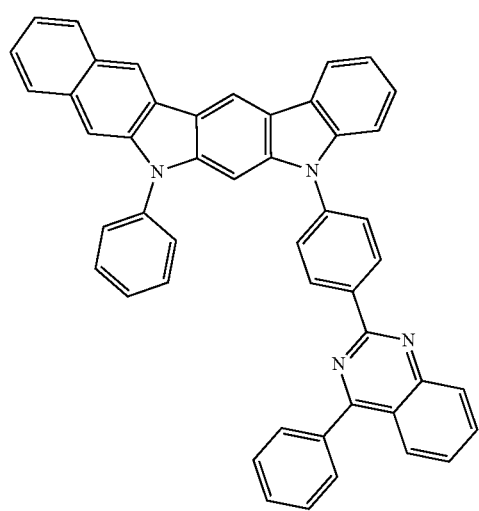
H-101
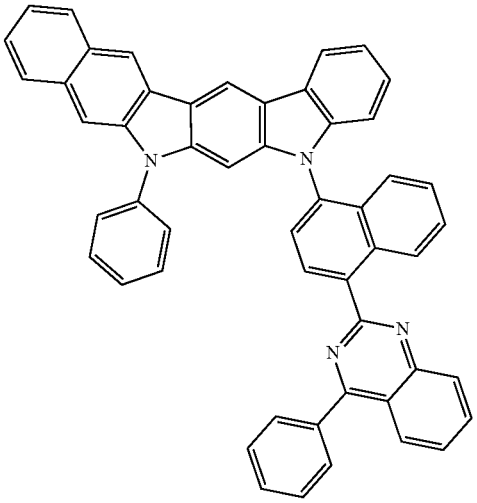
H-102
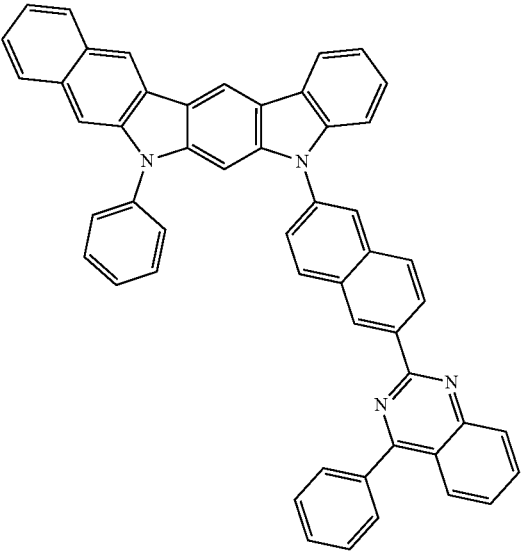
H-103
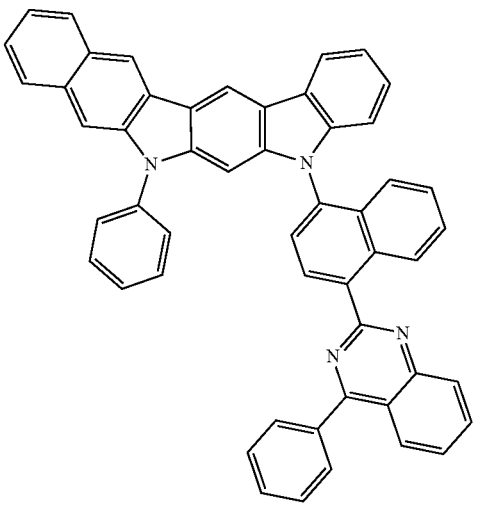

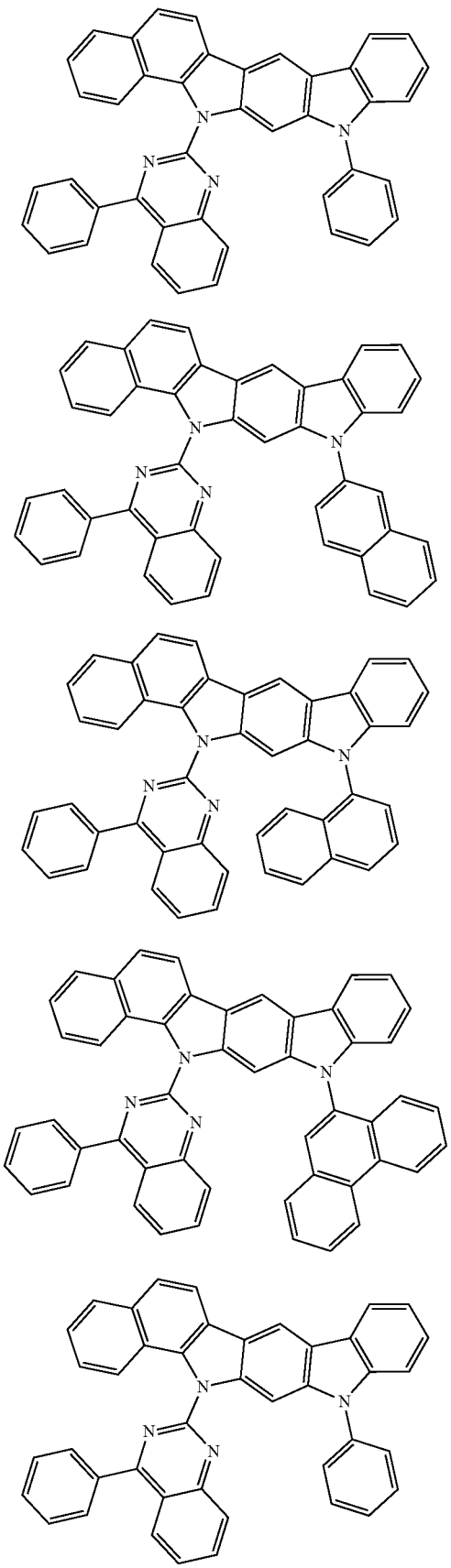
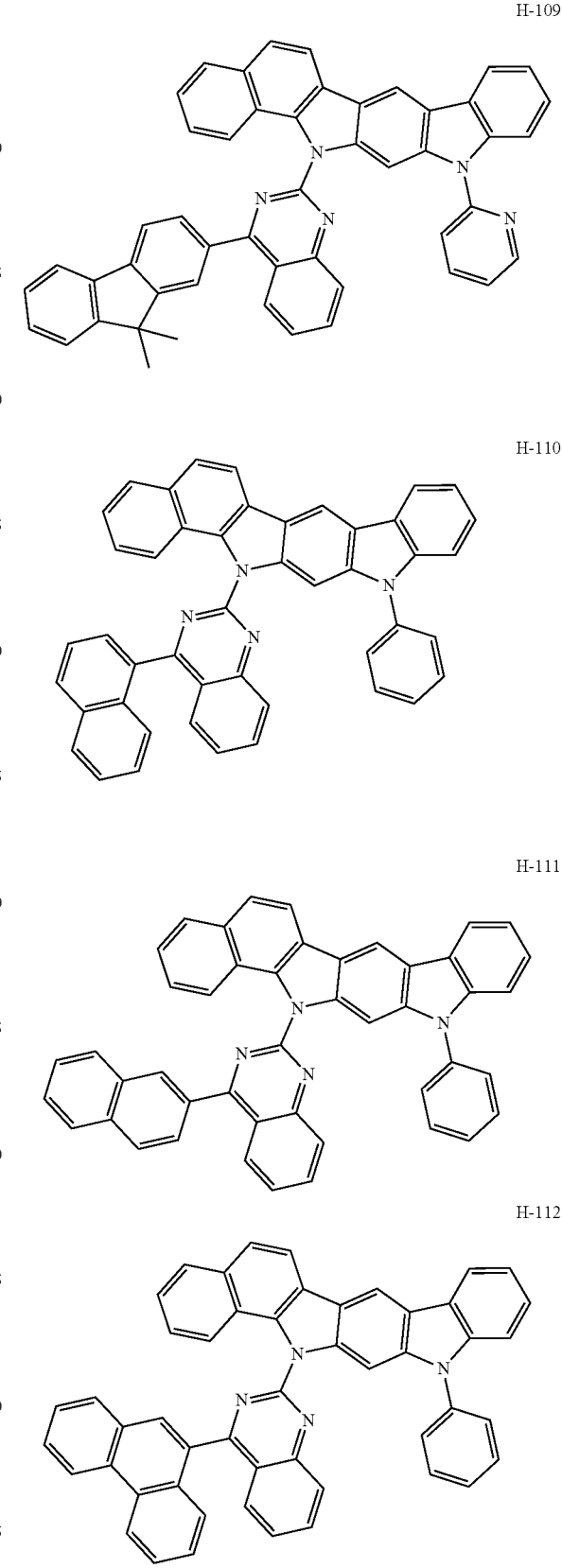

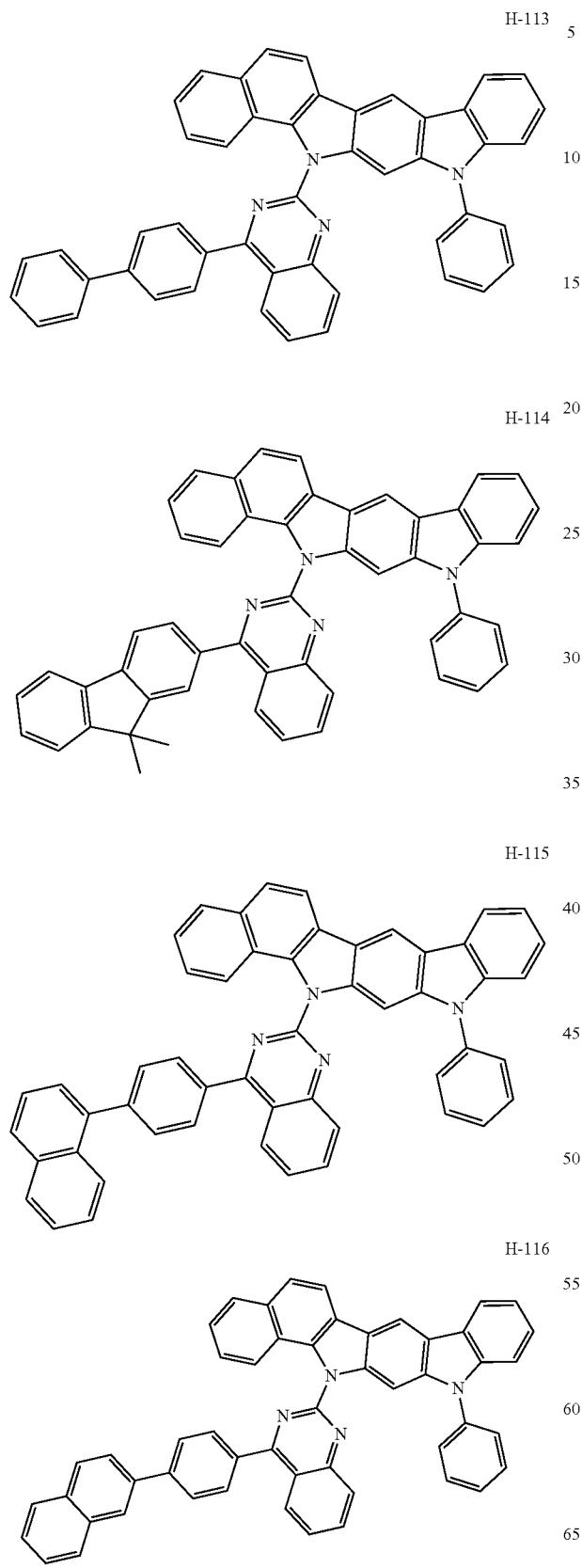
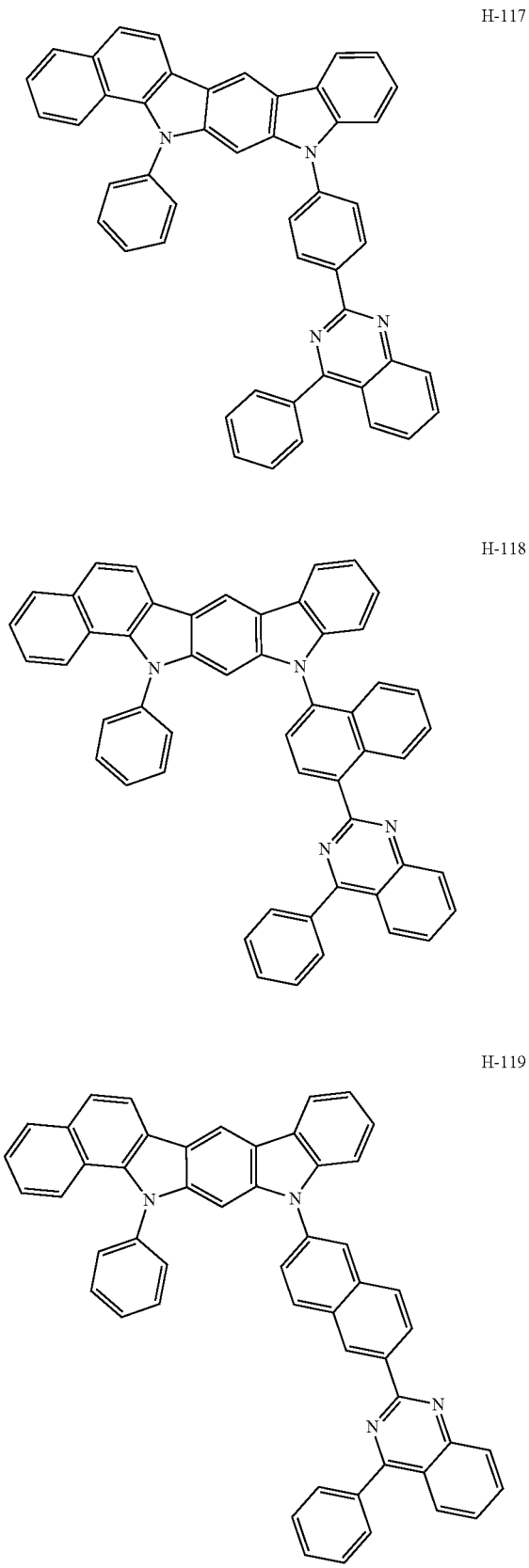

H-120
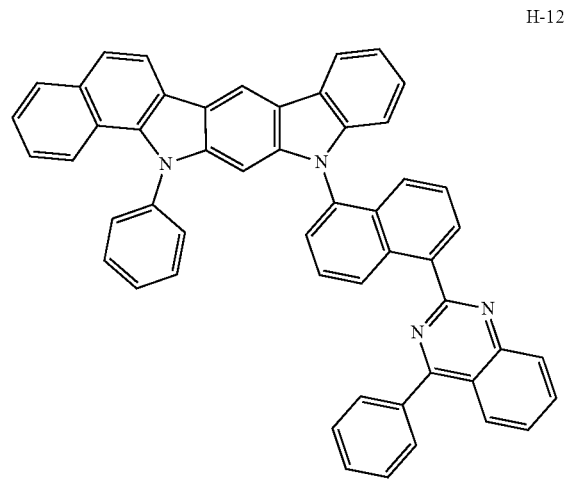
H-121
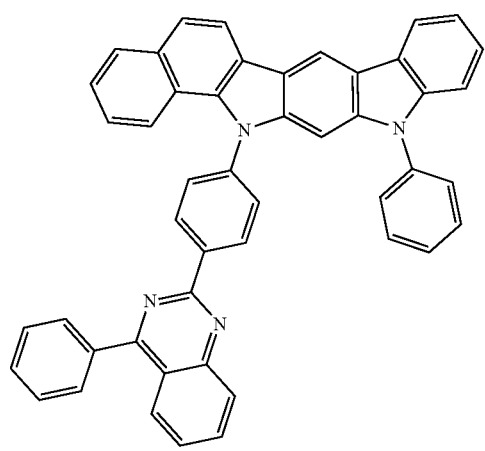
H-122
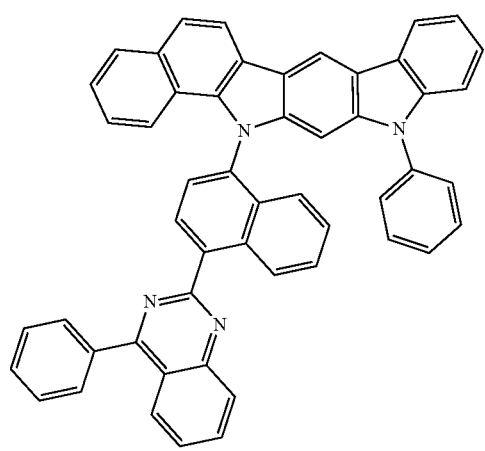
H-123
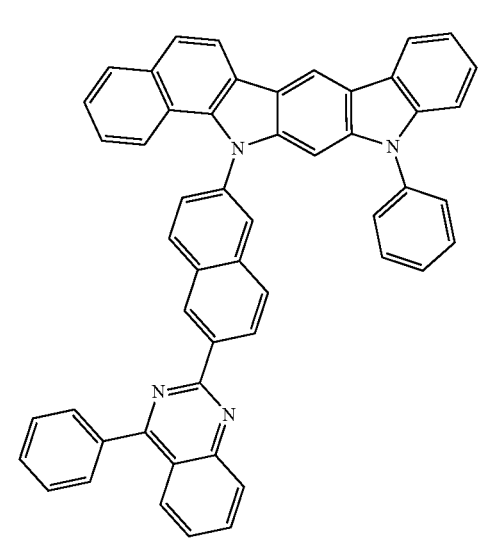
H-124
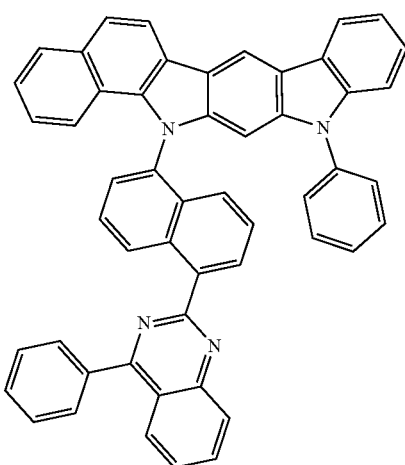
H-125
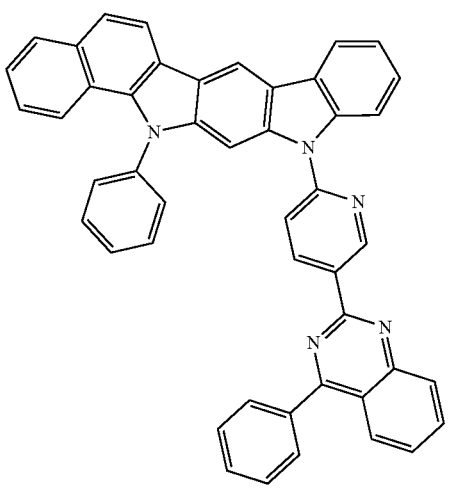

231
-continued
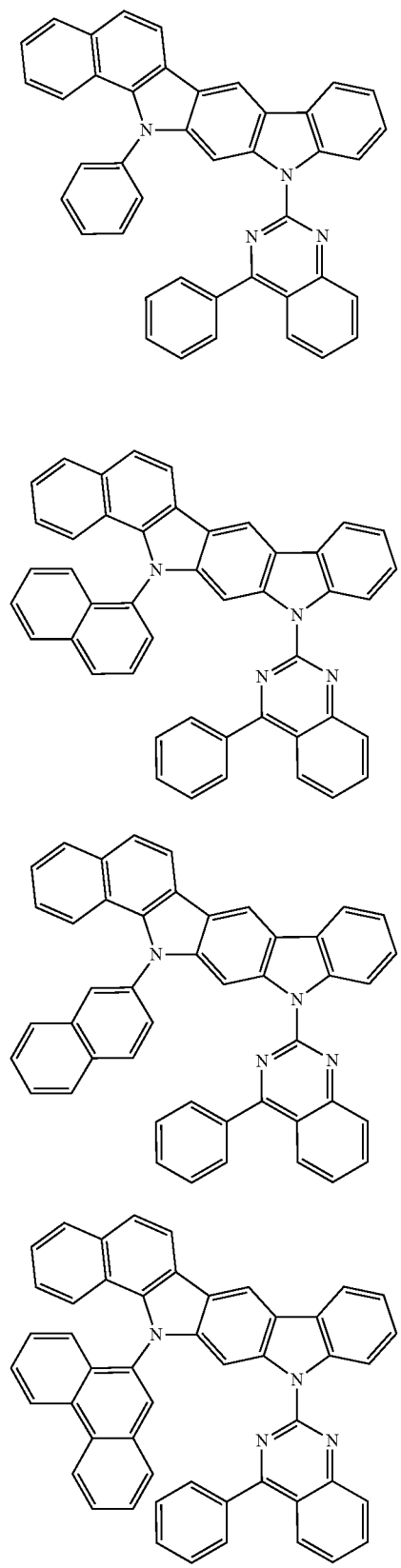
H-126
H-127
H-128
H-129
232
-continued
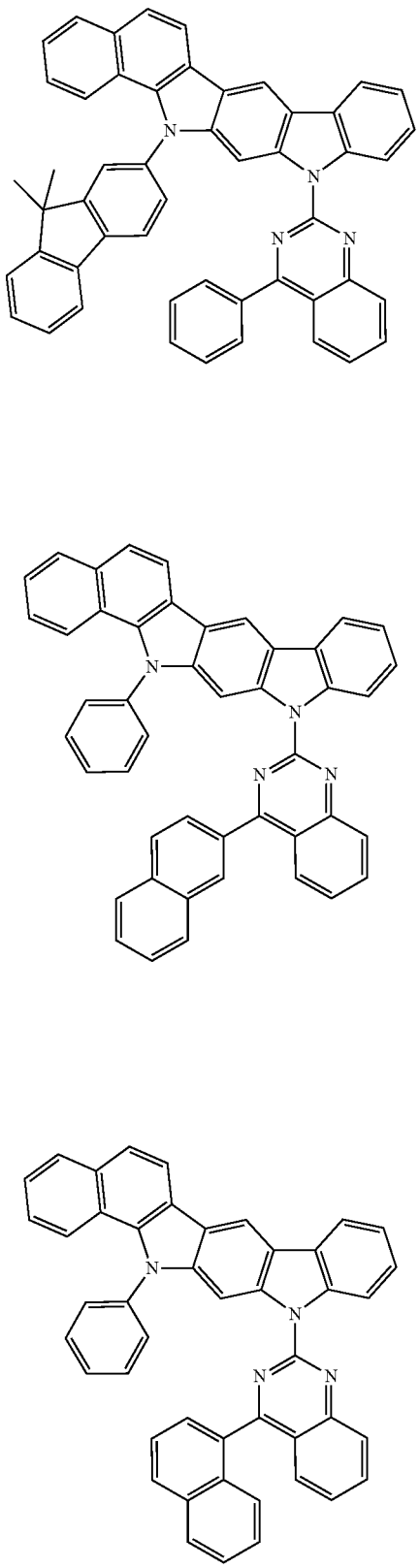
H-130
H-131
H-132

-continued
H-133
H-134
H-135
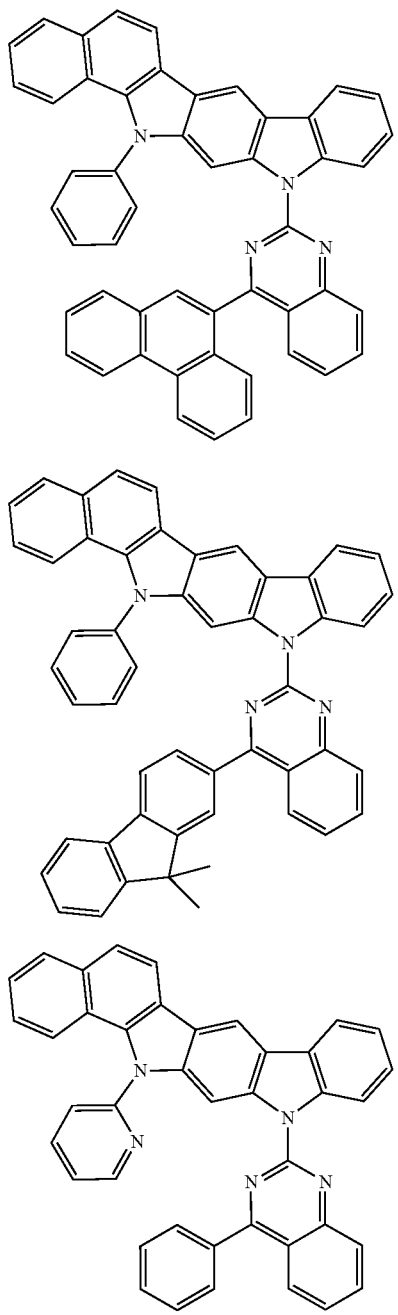
-continued
H-136
H-137
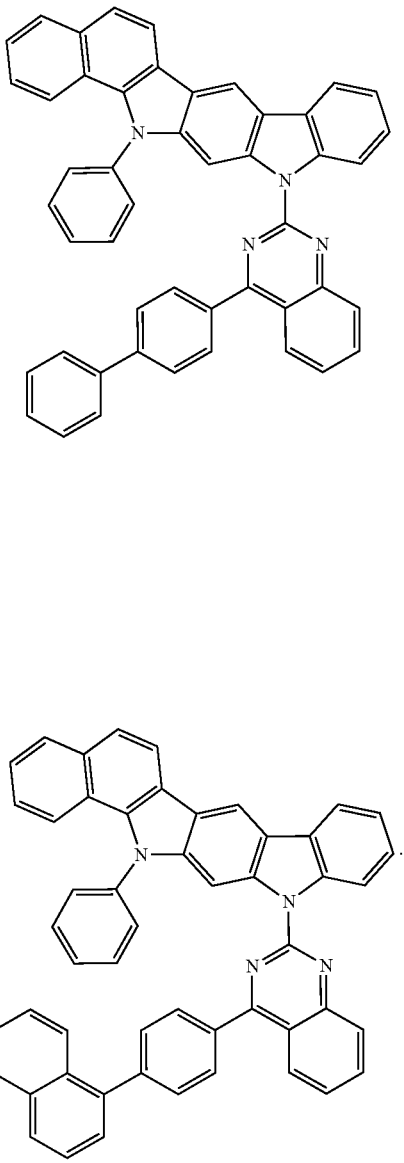
* * * * *